United States Patent
Chan et al.

(10) Patent No.: US 11,236,103 B2
(45) Date of Patent: Feb. 1, 2022

(54) BIFUNCTIONAL COMPOUNDS

(71) Applicant: BioTheryX, Inc., Chappaqua, NY (US)

(72) Inventors: Kyle W. H. Chan, San Diego, CA (US); Aparajita Hoskote Chourasia, San Diego, CA (US); Paul E. Erdman, San Diego, CA (US); Leah Fung, San Diego, CA (US); David Aaron Hecht, Chula Vista, CA (US); Frank Mercurio, Rancho Santa Fe, CA (US); Robert Sullivan, Vista, CA (US); Joseph P. Vacca, Telford, PA (US)

(73) Assignee: BioTheryX, Inc., Chappaqua, NY (US)

( * ) Notice: Subject to any disclaimer, the term of this patent is extended or adjusted under 35 U.S.C. 154(b) by 34 days.

(21) Appl. No.: 16/522,481

(22) Filed: Jul. 25, 2019

(65) Prior Publication Data
US 2020/0048277 A1 Feb. 13, 2020

Related U.S. Application Data

(60) Provisional application No. 62/711,164, filed on Jul. 27, 2018.

(51) Int. Cl.
| | | |
|---|---|---|
| C07D 495/04 | (2006.01) | |
| A61P 35/00 | (2006.01) | |
| C07D 417/14 | (2006.01) | |
| C07D 401/14 | (2006.01) | |
| C07D 403/14 | (2006.01) | |

(52) U.S. Cl.
CPC ............ *C07D 495/04* (2013.01); *A61P 35/00* (2018.01); *C07D 401/14* (2013.01); *C07D 403/14* (2013.01); *C07D 417/14* (2013.01)

(58) Field of Classification Search
CPC ..... A61P 35/00; C07D 495/04; C07D 417/14; C07D 401/14; C07D 403/14
USPC ........................................................ 514/212
See application file for complete search history.

(56) References Cited

U.S. PATENT DOCUMENTS

| | | |
|---|---|---|
| 3,331,835 A | 7/1967 | Bassiri et al. |
| 3,920,632 A | 11/1975 | Hohmann et al. |
| 4,339,600 A | 7/1982 | Ondetti et al. |
| 4,415,496 A | 11/1983 | Harris et al. |
| 4,644,069 A | 2/1987 | Baumann et al. |
| 5,015,650 A | 5/1991 | Stoltefuss et al. |
| 5,272,143 A | 12/1993 | Benson et al. |
| 5,272,158 A | 12/1993 | Hartman et al. |
| 5,376,522 A | 12/1994 | Takiguchi et al. |
| 5,463,063 A | 10/1995 | Muller |
| 5,504,080 A | 4/1996 | Karanewsky |
| 5,629,327 A | 5/1997 | D'Amato |
| 5,631,280 A | 5/1997 | Ciccarone et al. |
| 5,635,502 A | 6/1997 | Flynn |
| 5,845,025 A | 12/1998 | Garito et al. |
| 5,856,384 A | 1/1999 | Garito et al. |
| 5,932,582 A | 8/1999 | Young et al. |
| 5,977,134 A | 11/1999 | Ciccarone et al. |
| 6,207,697 B1 | 3/2001 | Han et al. |
| 6,248,740 B1 | 6/2001 | Kawano et al. |
| 6,284,755 B1 | 9/2001 | deSolms et al. |
| 6,388,090 B2 | 5/2002 | Huhtala et al. |
| 6,429,212 B1 | 8/2002 | Hashimoto |
| 6,476,052 B1 | 11/2002 | Muller et al. |
| 6,492,380 B1 | 12/2002 | Ross et al. |
| 6,569,858 B2 | 5/2003 | Prudhomme et al. |
| 6,686,477 B2 | 2/2004 | Boaz et al. |
| 6,719,925 B1 | 4/2004 | Breyne et al. |
| 7,071,181 B2 | 7/2006 | Davis et al. |
| 7,164,014 B2 | 1/2007 | Huang et al. |
| 7,189,738 B2 | 3/2007 | Straub et al. |
| 7,320,992 B2 | 1/2008 | Tegley et al. |
| 7,342,007 B2 | 3/2008 | Herzog et al. |
| 7,405,215 B2 | 7/2008 | Bennani et al. |
| 7,435,745 B2 | 10/2008 | D'Amato et al. |
| 7,569,580 B2 | 8/2009 | Thota et al. |
| 7,592,467 B2 | 9/2009 | Niestroj et al. |
| 7,700,641 B2 | 4/2010 | Chafeev et al. |
| 7,893,096 B2 | 2/2011 | Valiante, Jr. |
| 7,893,265 B2 | 2/2011 | Facchetti et al. |
| 8,063,225 B2 | 11/2011 | Gregor et al. |
| 8,143,284 B2 | 3/2012 | Gandhi et al. |
| 8,222,248 B2 | 7/2012 | Sung et al. |
| 8,362,234 B2 | 1/2013 | Hatala et al. |
| 8,383,139 B2 | 2/2013 | Kunz et al. |

(Continued)

FOREIGN PATENT DOCUMENTS

| | | |
|---|---|---|
| CA | 793864 | 9/1968 |
| CN | 104004122 | 8/2014 |

(Continued)

OTHER PUBLICATIONS

Audit, 1994, Thalidomide-induced polymine acylation: a new insight into the acylation mechanism, Biogenic Amines, 10(6):543-554.
Belyaev et al., 1992, A novel synthetic route to L-α-aminoadipic acid, Izsvestiya Akademi Nauk, Seriya Khimicheskaya, 7:1692-1693.
Belyaev et al., May 1991, A novel synthetic route to $N^6$-methyl-L-lysine and $N^5$-methyl-L-ornithine via $N^3$-protected (S)-3-aminolactams, Synthesis, 417-420.
Belyaev, Jan. 16, 1995, A novel synthetic route to enantiomers of epsilon-hydroxynorleucine and epsilon-chloronorleucine from L- and D,L-lysine, Tetrahedron Letters, 36(3):439-440.
CAS Registry 1212527-87-1, entered STN: Mar. 21, 2010.
David et al., 2004, Electrooxidation based strategy towards the core 3-amino-6-hydroxy-azepan-2-one, Synlett, 6:1029-1033.

(Continued)

*Primary Examiner* — Tracy Vivlemore
*Assistant Examiner* — Ebenezer O Sackey
(74) *Attorney, Agent, or Firm* — Lin Yu; Juniv LLP

(57) ABSTRACT

The present application provides compounds that modulate CDK protein function. Methods of making the compounds, compositions containing the compounds, and uses of the compounds for treating or ameliorating of diseases, disorders, or conditions associated with CDK proteins, are also disclosed.

33 Claims, No Drawings

(56) References Cited

U.S. PATENT DOCUMENTS

| | | |
|---|---|---|
| 8,697,690 B2 | 4/2014 | Beshore et al. |
| 8,742,097 B2 | 6/2014 | Hernandez et al. |
| 8,815,906 B2 | 8/2014 | Gregor et al. |
| 8,822,500 B2 | 9/2014 | Gregor |
| 2003/0114448 A1 | 6/2003 | Zhang et al. |
| 2004/0110757 A1 | 6/2004 | Arrhenius et al. |
| 2004/0127482 A1 | 7/2004 | Robichaud et al. |
| 2006/0211724 A1 | 9/2006 | Verschueren et al. |
| 2008/0318998 A1 | 12/2008 | Prince et al. |
| 2009/0082368 A1 | 3/2009 | Vohra et al. |
| 2009/0286775 A1 | 11/2009 | Almansa Rosales et al. |
| 2010/0152240 A1 | 6/2010 | Zhang |
| 2010/0222363 A1 | 9/2010 | Almansa Rosales et al. |
| 2011/0196150 A1 | 8/2011 | Man et al. |
| 2011/0319411 A1 | 12/2011 | Vu et al. |
| 2012/0192297 A1 | 7/2012 | Handa et al. |
| 2012/0301398 A1 | 11/2012 | Heiser et al. |
| 2013/0310555 A1 | 11/2013 | Chong |
| 2013/0324518 A1 | 12/2013 | Man et al. |
| 2018/0037567 A1 | 2/2018 | Man et al. |
| 2019/0062320 A1 | 2/2019 | Chan |

FOREIGN PATENT DOCUMENTS

| | | |
|---|---|---|
| DE | 292451 | 8/1991 |
| EP | 0 595 610 | 5/1997 |
| GB | 2450771 | 1/2009 |
| JP | 2000-159761 | 6/2000 |
| JP | 2009-023986 | 2/2009 |
| JP | 2011-153279 | 8/2011 |
| JP | 2012-123292 | 6/2012 |
| KR | 2013131663 | 12/2013 |
| KR | 2014039383 | 4/2014 |
| KR | 2014103447 | 8/2014 |
| SU | 1708812 | 1/1992 |
| WO | WO 99/04390 | 1/1999 |
| WO | WO 00/064917 | 11/2000 |
| WO | WO 02/079147 | 10/2002 |
| WO | WO 04/092174 | 10/2004 |
| WO | WO 05/016326 | 2/2005 |
| WO | WO 07/000337 | 1/2007 |
| WO | WO 07/028789 | 3/2007 |
| WO | WO 07/117394 | 10/2007 |
| WO | WO 08/037266 | 4/2008 |
| WO | WO 08/073865 | 6/2008 |
| WO | WO 09/051417 | 4/2009 |
| WO | WO 09/070533 | 6/2009 |
| WO | WO 09/072581 | 6/2009 |
| WO | WO 09/083105 | 7/2009 |
| WO | WO 09/094668 | 7/2009 |
| WO | WO 09/112445 | 9/2009 |
| WO | WO 10/011924 | 1/2010 |
| WO | WO 11/136483 | 11/2011 |
| WO | WO 12/072019 | 6/2012 |
| WO | WO 12/129562 | 9/2012 |
| WO | WO 12/158475 | 11/2012 |
| WO | WO 13/010218 | 1/2013 |
| WO | WO 13/106409 | 7/2013 |
| WO | WO 14/055548 | 4/2014 |
| WO | WO 14/055634 | 4/2014 |
| WO | WO 14/106019 | 7/2014 |
| WO | WO 14/113485 | 7/2014 |
| WO | WO 16/065980 | 5/2016 |
| WO | WO 16/191178 | 12/2016 |
| WO | WO 17/024318 | 2/2017 |
| WO | WO 17/185023 | 10/2017 |
| WO | 2018/36661 A1 * | 7/2018 |

OTHER PUBLICATIONS

Eger et al., 1990, Synthesis, central nervous system activity and teratogenicity of a homothalidomide, Arzneimittel-Forschung, 40(10): 1073-1075.

Eger et al., Sep. 1988, Alpha-phthalimidoadipinimide—synthesis, teratogenic properties and effect on the central nervous-system of a homo-thalidomide, Archiv Der Pharmazie, 321(9):577.

Gutschow et al., Apr. 2001, Aza analogues of thalidomide: synthesis and evaluation as inhibitors of tumor necrosis factor-alpha production in vitro, Bioorganic & Medicinal Chemistry, 9(4):1059-1065.

Ito et al., 2018, Discovery of 3-benzyl-1-(trans-4-((5-cyanopyridin-2-yl)amino)cyclohexyl)-1-arylurea derivatives as novel and selective cyclin-dependent kinase 12(CDK12) inhibitors, Journal of Medicinal Chemistry, 61:7210-7278.

Kralj et al., 1975, Mass spectrometric identification of some nonvolatile organic compounds, Biomedical Mass Spectrometry, 2(4): 215-218.

Lee et al., Jun. 2011, Assessing chiral self-recognition using chiral stationary phases, Tetrahedron, 67:7143-7147.

Minzel et al., Aug. 23, 2018, Small molecules co-targeting CKIα and the transcriptional kinases CDK7/9 control AML in preclinical models, Cell, 175(1):171.

Olson et al., Dec. 18, 2017, Pharmacological perturbation of CDK9 using selecive CDK9 inhibition or degradation, Nature Chemical Biology, 14 pp.

International Search Report and Written Opinion dated Sep. 17, 2019 in application No. PCT/US2019/043500.

Amit et al., "Axin-mediated CKI phosphorylation of β-catenin at Ser 45: a molecular switch for the Wnt pathway," Genes Dev 2002, 16:1066-76.

Brito et al., "Polyglycine expansions in eRF3/GSPT 1 are associated with gastric cancer susceptibility," Carcinogenesis 2005, 26, 2046-9.

Chauvin et al., "Human eukaryotic release factor 3a depletion causes cell cycle arrest at G1 phase through inhibition of the mTOR pathway," Mol. Cell. Biol. 2007, 27, 5619-29.

Cheong and Virshup, "Casein kinase 1: Complexity in the family," J. Biochem. Cell Biol. 2011, 43, 465-9.

Elyada et al., "CK1α ablation highlights a critical role for p53 in invasiveness control," Nature 2011, 470, 409-13.

Hashimoto et al, "Translation termination factor eRF3 is targeted for caspase-mediated proteolytic cleavage and degradation during DNA damage-induced apoptosis," Apoptosis 2012, 17, 1287-99.

Huart et al., "CK1α plays a central role in mediating MDM2 control of p53 and E2F-1 protein stability," J. Biol. Chem. 2009, 284, 32384-94.

Ishii et al., "A Novel Rac1-GSPT1 signaling pathway controls astrogliosis following central nervous system injury," J. Biol. Chem. 2017, 292, 1240-50.

Levine and Oren, "The first 30 years of p53: growing ever more complex," Nat. Rev. Cancer 2009, 9, 749-58.

Li et al., "eRF3b, a biomarker for hepatocellular carcinoma, influences cell cycle and phosphoralation status of 4E-BP1," PLoS One 2014, 9, e86371.

Malta-Vacas et al., "Differential expression of GSPT1 GGCn alleles in cancer," Cancer Genet. Cytogenet. 2009, 195, 132-42.

Miri et al., "GGCn polymorphism of eRF3a/GSPT 1 gene and breast cancer susceptibility," Med. Oncol. 2012, 29, 1581-5.

Schittek and Sinnberg, "Biological functions of casein kinase 1 isoforms and putative roles in tumorigenesis," Mol Cancer 2014, 13, Article 231.

Schneider et al., "Role of casein kinase 1A1 in the biology and targeted therapy of del(5q) MDS," Cancer Cell 2014, 26, 509-20.

Stern, "Prevalence of a history of skin cancer in 2007: results of an incidence-based model," Arch. Dermatol. 2010, 146, 279-82.

Wright and Lange, "Newer potential biomarkers in prostate cancer," Rev. Urol. 2007, 9, 207-13.

\* cited by examiner

BIFUNCTIONAL COMPOUNDS

INCORPORATION BY REFERENCE TO PRIORITY APPLICATION

The present application claims the benefit of priority to U.S. Provisional Application No. 62/711,164, filed Jul. 27, 2018, which is hereby incorporated by reference in its entirety.

BACKGROUND

Field

Compounds, methods of making such compounds, pharmaceutical compositions and medicaments comprising such compounds, and methods of using such compounds to treat or diagnose diseases, disorders, or conditions associated with protein malfunctions are provided.

Description of the Related Technology

Protein kinases are critical components of the cell-signaling machinery. Kinases mediate cell-signaling by transferring a phosphoryl group from a nucleoside triphosphate (NTP) to a protein acceptor. These phosphorylation events function as molecular on/off switches that can regulate the biological function of the target protein. Phosphorylation can be triggered by a wide variety of extracellular and other stimuli, such as environmental and chemical stress signals, cytokines, and growth factors. Thus, kinases facilitate cellular responses to such stimuli, in, for example, cell growth, migration, differentiation, secretion of hormones, activation of transcription factors, metabolism, control of protein synthesis, and regulation of the cell cycle.

The initiation, progression through, and completion of the cell cycle are tightly regulated by various cyclin-dependent kinases (CDKs), which are critical for normal cell growth. CDKs act as a complex with a CDK subunit (the catalytic subunit) and a regulatory subunit (the cyclin). There are over ten known CDKs, many of which are involved in regulating cell cycle progression, as well as having other functions. Accordingly, modulating CDK activity may provide advantageous anti-proliferative activity. Indeed, inhibitors of CDK4/6 such a palbociclib and ribociclib are currently on the market for the treatment of breast cancer.

Aberrant protein function, and/or protein imbalance is a hallmark of many disease states. For example, the functioning of the immune system is finely balanced by the activities of pro-inflammatory and anti-inflammatory mediators or cytokines. Some cytokines promote inflammation (pro-inflammatory cytokines), whereas other cytokines suppress the activity of the pro-inflammatory cytokines (anti-inflammatory cytokines). For example, IL-4, IL-10, and IL-13 are potent activators of B lymphocytes, and also act as anti-inflammatory agents. They are anti-inflammatory cytokines by virtue of their ability to suppress genes for pro-inflammatory cytokines such as IL-1, TNF, and chemokines.

Unregulated activities of these mediators can lead to the development of serious inflammatory conditions. For example, autoimmune diseases arise when immune system cells (lymphocytes, macrophages) become sensitized against the "self." Lymphocytes, as well as macrophages, are usually under control in this system. However, a misdirection of the system toward the body's own tissues may happen in response to still unexplained triggers. One hypothesis is that lymphocytes recognize an antigen which mimics the "self" and a cascade of activation of different components of the immune system takes place, ultimately leading to tissue destruction. Genetic predisposition has also been postulated to be responsible for autoimmune disorders.

Tumor necrosis factor-alpha (TNF-alpha, or TNF-α) and interleukin-1 (IL-1) are pro-inflammatory cytokines that mediate inflammatory responses associated with infectious agents and other cellular stresses. Overproduction of these cytokines is believed to underlie the progression of many inflammatory diseases including rheumatoid arthritis (RA), Crohn's disease, inflammatory bowel disease, endotoxin shock, osteoporosis, neurodegenerative diseases (such as multiple sclerosis, Alzheimer's disease, Parkinson's disease), congestive heart failure, and psoriasis among others.

Recent data from clinical trials support the use of protein antagonists of cytokines, for example soluble TNF-α receptor fusion protein (etanercept) or the monoclonal TNF-α antibody (infliximab), for the treatment of rheumatoid arthritis, Crohn's disease, juvenile chronic arthritis and psoriatic arthritis. Thus, the reduction of pro-inflammatory cytokines such as TNF-α and interleukin-1 (IL-1) has become an accepted therapeutic approach for potential drug intervention in these conditions.

Moreover, IL-2 is now FDA approved for the treatment of renal cancer and melanoma patients, with durable, complete remissions achieved with IL-2 up to 148 months. However, the short half-life of IL-2 in serum requires that large amounts of IL-2 be injected to achieve therapeutic levels. Many attempts have been made to minimize side effects of systemic IL-2 treatment, for example, introducing IL-2 directly into the tumor, though this complicates treatment, and has largely been unsuccessful.

Local delivery of cytokines is appealing compared to systemic delivery for a variety of reasons. It takes advantage of the natural biology of cytokines that have evolved to act locally in a paracrine or autocrine fashion. Local expression also dramatically minimizes many of the side effects of systemic delivery of cytokines. Thus, compounds and methods to increase local expression of IL-2 would be better tolerated than high dose IL-2 treatment, which would expand therapeutic utility of strategies that increase IL-2.

Additional targets include several candidate genes involved in apoptosis and cell survival, including the translation termination factor GSPT1 (eRF3a), casein kinase 1α (CK1α), and the zinc-finger transcription factors aiolos, helios, and ikaros. Aiolos, helios, and ikaros are transcription factors whose expression is restricted to lymphoid lineages. For example, aiolos binds to the Bcl-2 promoter, and also interacts with the Bcl-2 and Bcl-XL proteins to promote cell survival. Upregulation of aiolos expression, for example, can reduce apoptosis of HIV-1 infected cells.

Likewise, expression of aiolos in lung and breast cancers predicts significantly reduced patient survival. Aiolos decreases expression of a large set of adhesion-related genes, disrupting cell-cell and cell-matrix interactions, facilitating metastasis. Aiolos may also function as an epigenetic driver of lymphocyte mimicry in certain metastatic epithelial cancers. Similarly, aberrant ikaros and helios expression may promote Bcl-XL expression, driving the development of hematopoietic malignancies. Thus, downregulation of aiolos, ikaros, and/or helios may reduce or eliminate metastasis.

GSPT1 mediates stop codon recognition and facilitates release of a nascent peptide from the ribosome and is also involved in several other critical cellular processes, such as cell cycle regulation, cytoskeleton organization and apoptosis. Accordingly, decreased levels of GSPT1 may impair control of cell proliferation and facilitate cell migration and scar formation. Indeed, GSPT1 has been implicated as an oncogenic driver of several different cancer types, including breast cancer, hepatocellular carcinoma, gastric cancer, and prostate cancer. See, e.g., Brito, et al., *Carcinogenesis*, Vol. 26, No. 12, pp. 2046-49 (2005); Brito, et al., *Canc. Geneti. Cytogen.*, Vol. 195, pp. 132-42 (2009); Tavassoli, et al., *Med. Oncol.*, Vol. 29, pp. 1581-85 (2011); Wright and Lange, *Rev. Urol.*, Vol. 9, No. 4, pp. 207-213 (2007); Hoshino, et al., *Apoptosis*, Vol. 17, pp. 1287-99 (2012); Liu, et. al., PLOS One, Vol. 9, No. 1, e86371 (2014); and Jean-Jean, et al., *Mol. Cell. Bio.*, Vol. 27, No. 16, pp. 5619-29 (2007). GSPT1 also contributes to glial scar formation and astrogliosis after a central nervous system (CNS) injury. See, e.g., Ishii et al., *J. Biol. Chem.*, Vol. 292, No. 4, pp. 1240-50 (2017).

Casein kinase 1α (CK1α) is a component of the β-catenin-degradation complex and a critical regulator of the Wnt signaling pathway, and its ablation induces both Wnt and p53 activation. Schittek and Sinnberg, *Mol. Cancer.* 2014, 13, 231; Cheong and Virshup, *J. Biochem. Cell Biol.* 2011, 43, 465-469; Elyada et al., *Nature* 2011, 470, 409-413. CK1α phosphorylates β-catenin, which is subsequently further phosphorylated by GSK-3β. This destabilizes β-catenin and marks the protein for ubiquitination and proteasomal degradation. Thus, CK1α functions as a molecular switch for the Wnt pathway. Amit et al., *Genes Dev.* 2002, 16, 1066-1076. CK1α is critical for embryogenesis and plays an important role in tissue development and response to DNA damage, at least partly coordinated with p53. Elyada et al., *Nature* 2011, 470, 409-413; Schneider et al., *Cancer Cell* 2014, 26, 509-520. Levine and Oren, *Nat. Rev. Cancer* 2009, 9, 749-758.

Indeed, CK1α also phosphorylates p53, which inhibits binding to MDM2 (a p53 inhibitor) and stabilizes p53's binding interactions with the transcriptional machinery. Huart, et al., *J. Biol. Chem.* 2009, 284, 32384-32394. Thus, inhibiting CK1α activity increases cellular levels of p53. This is of particular importance for skin cancer, which has killed more people since 1980 than all other types of cancer combined. Stern, *Arch Dermatol.* 2010, 146, 279-282.

Most kinase inhibitors function by blocking the NTP binding site on the kinase. However, given the structural similarity of endogenous NTPs, kinase inhibitors may produce undesirable off-target effects by unintended, non-specific interactions, or via pathway cross-talk. One mechanism to disrupt protein drivers of disease is to decrease the cellular concentration of these proteins. For example, proteolytic degradation of cellular proteins is essential to normal cell function. Hijacking this process, by targeting specific disease-related proteins, presents a novel mechanism for the treatment of disease. The irreversible nature of proteolysis makes it well-suited to serve as a regulatory switch for controlling unidirectional processes.

Ubiquitin-mediated proteolysis begins with ligation of one or more ubiquitin molecules to a particular protein substrate. Ubiquitination occurs through the activity of ubiquitin-activating enzymes (E1), ubiquitin-conjugating enzymes (E2), and ubiquitin-protein ligases (E3), acting sequentially to attach ubiquitin to lysine residues of substrate proteins. The E3 ligases confer specificity to ubiquitination reactions by binding directly to particular substrates.

SUMMARY

The compounds disclosed in the present application have been discovered to exert surprising and unexpected biological effects. In particular, the compounds disclosed in the present application modulate protein function and/or modulate protein levels to restore protein homeostasis.

Some embodiments provide a compound of Formula (I), or a pharmaceutically acceptable salt thereof:

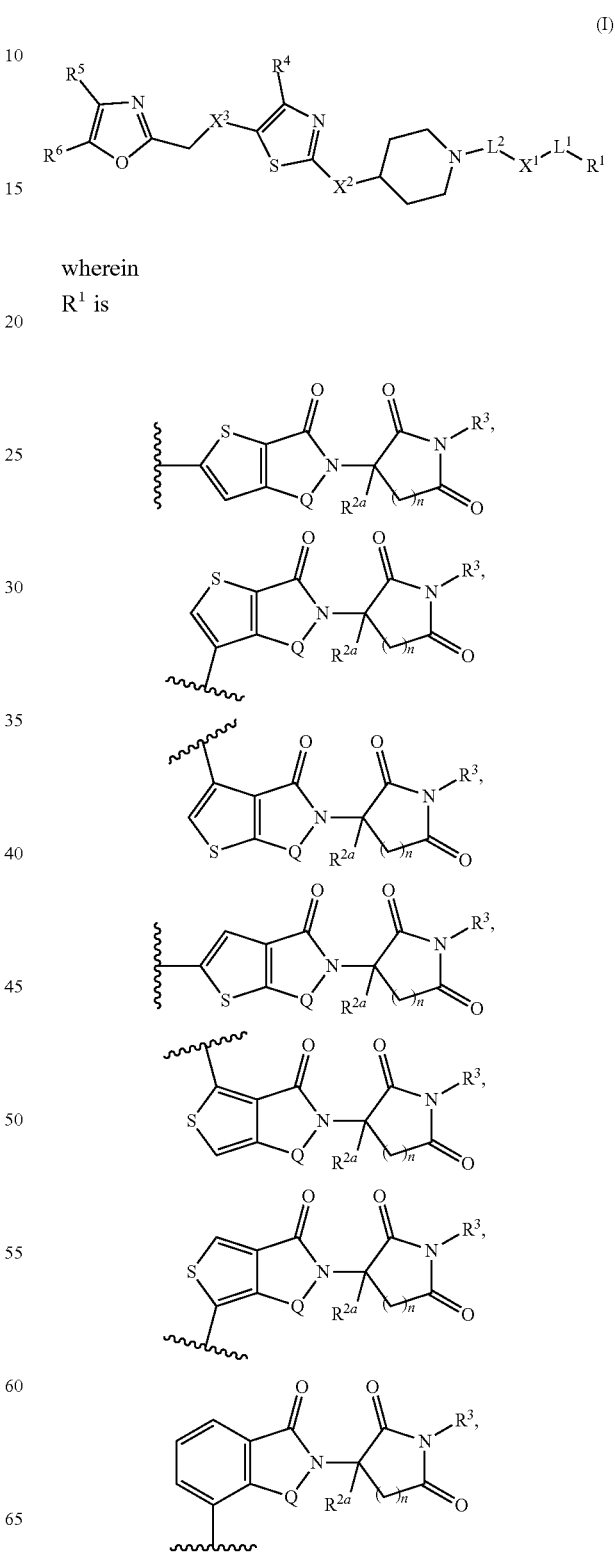

wherein
$R^1$ is

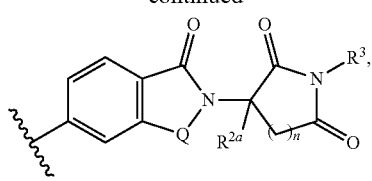

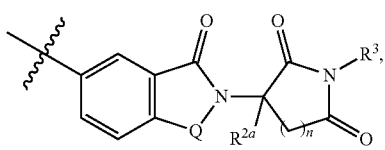

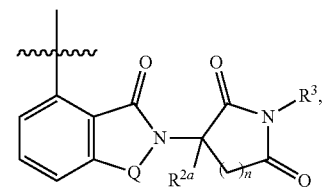

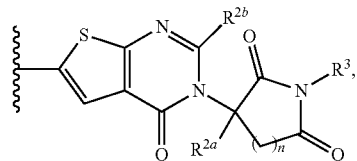

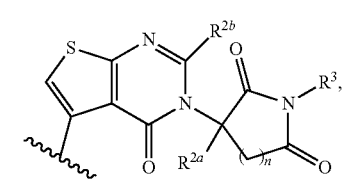

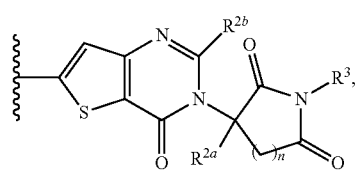

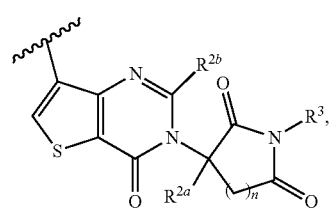

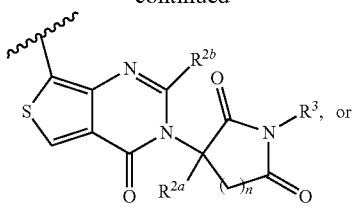

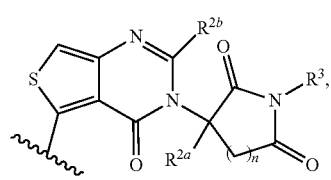

wherein $R^1$ is optionally substituted with one or more $R^4$;

n is 1, 2, or 3;

each $R^{2a}$ and $R^{2b}$ is independently H, deuterium, halogen, or $C_1$-$C_6$ alkyl;

each $R^3$ is independently H, deuterium, $C_1$-$C_6$ alkyl,

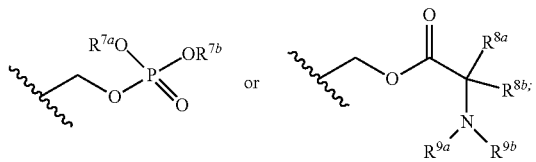

each $R^A$ is independently deuterium, hydroxyl, halogen, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, optionally substituted amino, $C_1$-$C_6$ alkylamino, amino($C_1$-$C_6$ alkyl), —(C=O)$NR^{10a}R^{10b}$, ($C_1$-$C_6$ alkoxy)$C_1$-$C_6$ alkyl, —O—($C_1$-$C_6$ alkoxy)$C_1$-$C_6$ alkyl, or optionally substituted $C_3$-$C_7$ cycloalkyl;

each of $R^4$, $R^5$ and $R^6$ is independently H, halogen, $C_1$-$C_6$ alkyl, $C_1$-$C_6$ haloalkyl, $C_1$-$C_6$ alkoxy, $C_1$-$C_6$ haloalkoxy, optionally substituted $C_3$-$C_7$ cycloalkyl($C_1$-$C_3$ alkyl), or optionally substituted $C_3$-$C_7$ cycloalkyl;

each of $R^{7a}$ and $R^{7b}$ is independently H, optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;

each of $R^{8a}$ and $R^{8b}$ is independently H, halogen, $C_1$-$C_6$ alkyl, $C_1$-$C_6$ alkoxy, $C_1$-$C_6$ haloalkyl, $C_1$-$C_6$ haloalkoxy, or $C_3$-$C_8$ carbocyclyl;

each of $R^{9a}$ and $R^{9b}$ is independently H, optionally substituted $C_1$-$C_6$ alkyl, optionally substituted $C_6$-$C_{10}$ aryl, optionally substituted $C_7$-$C_{14}$ aralkyl, or optionally substituted $C_3$-$C_8$ carbocyclyl;

each $R^{10a}$ and $R^{10b}$ is independently H or $C_1$-$C_6$ alkyl, or $R^{10a}$ and $R^{10b}$ together with the nitrogen atom to which they are attached form an optionally substituted 5 or 6 membered heterocyclyl optionally substituted with one or more $R^{11}$;

each $R^{11}$ is independently $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, —O—($C_1$-$C_6$ alkoxy)$C_1$-$C_6$ alkyl, optionally substituted amino, halogen, or cyano; or two geminal $R^{11}$ form oxo;

Q is $CH_2$ or C=O;

$L^1$ is a bond, wherein the asterisk * indicates the point of connection to $X^1$;

each of $Z^{1a}$, $Z^{1b}$, $Z^{1c}$, $Z^{1d}$, $Z^{1e}$, and $Z^{1f}$ is independently a bond or —$(CR^aR^b)_{q1}$—;

$Z^2$ is —$(CR^cR^d)_{q2}$—;

$Z^3$ is a bond, O or $NR^{12g}$;

each of $R^a$, $R^b$, $R^c$ and $R^d$ is independently H, halogen, hydroxy, $C_1$-$C_6$ alkyl, $C_1$-$C_6$ haloalkyl, $C_1$-$C_6$ alkoxy, $C_1$-$C_6$ haloalkoxy, or optionally substituted $C_3$-$C_6$ cycloalkyl;

each q1 and q2 is independently 1, 2 or 3;

each $X^a$ and $X^b$ is independently O or S;

each Ring A is independently phenyl or a five to six membered heteroaryl, each optionally substituted with one or more $R^{11}$;

each of $Y^1$, $Y^2$, $Y^3$, $Y^4$, $Y^5$ and $Y^6$ is —$NR^{12h}$—, —O—, or —S—;

each $R^{12a}$, $R^{12b}$, $R^{12c}$, $R^{12d}$, $R^{12e}$, $R^{12f}$, $R^{12g}$ and $R^{12h}$ is independently H or $C_1$-$C_6$ alkyl;

each of m1, m2, m3, m4, m5, m6, k1, k2, k3, k4, k5, k6, p1, p2, p3, p4, p5, and p6 is independently 0, 1, 2, or 3;

$L^2$ is a bond, —C(=O)—, or —$(CH_2)_{0-3}$—C(=O)NR$^{13}$—; $R^{13}$ is H or $C_1$-$C_6$ alkyl;

$X^1$ is alkylene or heteroalkylene; $X^2$ is —NHC(=O)—, —NH—, —O—, —NHC(=O)NH—, —NHCH$_2$— or —S—; and $X^3$ is —NH—, —O—, or —S—. In some embodiments, when the compound has the structure $R^1$ is Q is C=O, n is 2, $R^3$ is H, then $R^{2a}$ is deuterium, halogen, or $C_1$-$C_6$ alkyl.

Some embodiments provide a compound of Formula (II), or a pharmaceutically acceptable salt thereof:
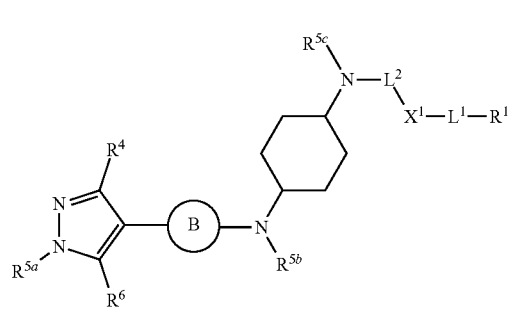
wherein:
R[1] is
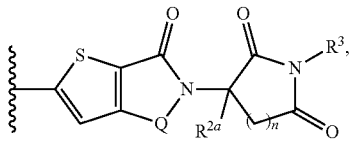
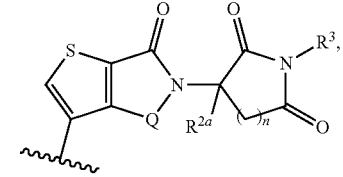
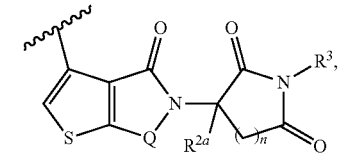
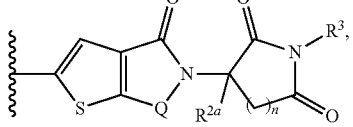
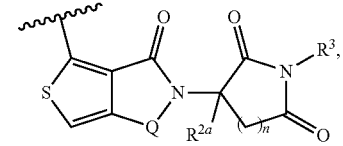
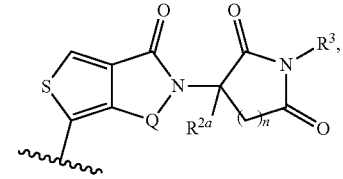
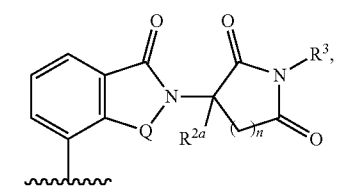
-continued
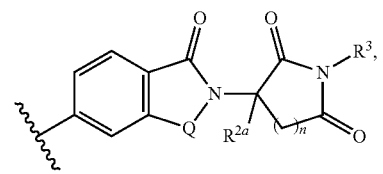
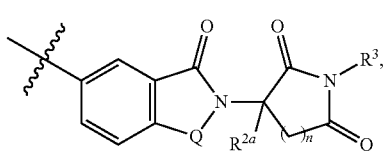
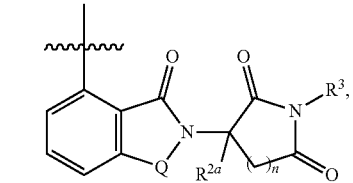
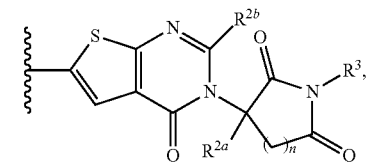
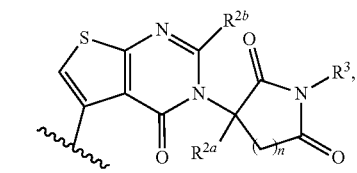
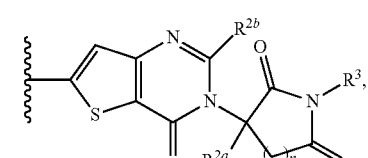
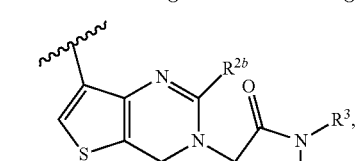
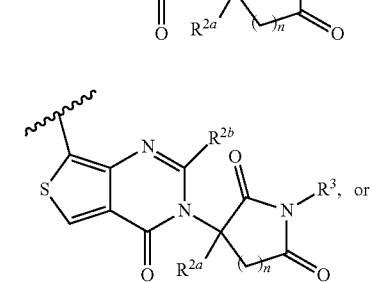
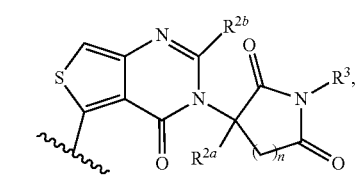

wherein $R^1$ is optionally substituted with one or more $R^A$;

n is 1, 2 or 3;

each $R^{2a}$ and $R^{2b}$ is independently H, deuterium, halogen or $C_1$-$C_6$ alkyl;

each $R^3$ is independently H, deuterium, $C_1$-$C_6$ alkyl,

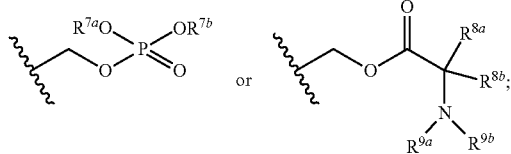

or each $R^A$ is independently deuterium, hydroxyl, halogen, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, optionally substituted amino, $C_1$-$C_6$ alkylamino, amino($C_1$-$C_6$ alkyl), —(C=O)$NR^{10a}R^{10b}$, ($C_1$-$C_6$ alkoxy) $C_1$-$C_6$ alkyl, —O—($C_1$-$C_6$ alkoxy)$C_1$-$C_6$ alkyl, or optionally substituted $C_3$-$C_7$ cycloalkyl;

each of $R^4$ and $R^6$ is independently H, halogen, $C_1$-$C_6$ alkyl, $C_1$-$C_6$ haloalkyl, $C_1$-$C_6$ alkoxy, $C_1$-$C_6$ haloalkoxy, optionally substituted $C_3$-$C_7$ cycloalkyl($C_1$-$C_3$ alkyl), or optionally substituted $C_3$-$C_7$ cycloalkyl;

each of $R^{5a}$, $R^{5b}$ and $R^{5c}$ is independently H or $C_1$-$C_6$ alkyl;

each of $R^{7a}$ and $R^{7b}$ is independently H, optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;

each of $R^{8a}$ and $R^{8b}$ is independently H, halogen, $C_1$-$C_6$ alkyl, $C_1$-$C_6$ alkoxy, $C_1$-$C_6$ haloalkyl, $C_1$-$C_6$ haloalkoxy, or $C_3$-$C_8$ carbocyclyl;

each of $R^{9a}$ and $R^{9b}$ is independently H, optionally substituted $C_1$-$C_6$ alkyl, optionally substituted $C_6$-$C_{10}$ aryl, optionally substituted $C_7$-$C_{14}$ aralkyl, or optionally substituted $C_3$-$C_8$ carbocyclyl;

each $R^{10a}$ and $R^{10b}$ is independently H or $C_1$-$C_6$ alkyl, or $R^{10a}$ and $R^{10b}$ together with the nitrogen atom to which they are attached form an optionally substituted 5 or 6 membered heterocyclyl optionally substituted with one or more $R^{11}$;

each $R^{11}$ is independently $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, —O—($C_1$-$C_6$ alkoxy)$C_1$-$C_6$ alkyl, optionally substituted amino, halogen, or cyano; or two geminal $R^{11}$ form oxo;

Q is $CH_2$ or C=O;

$L^1$ is

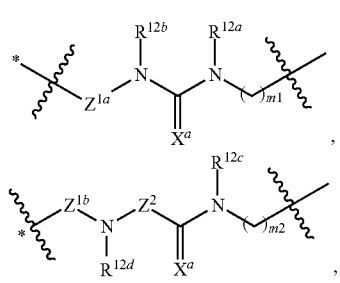

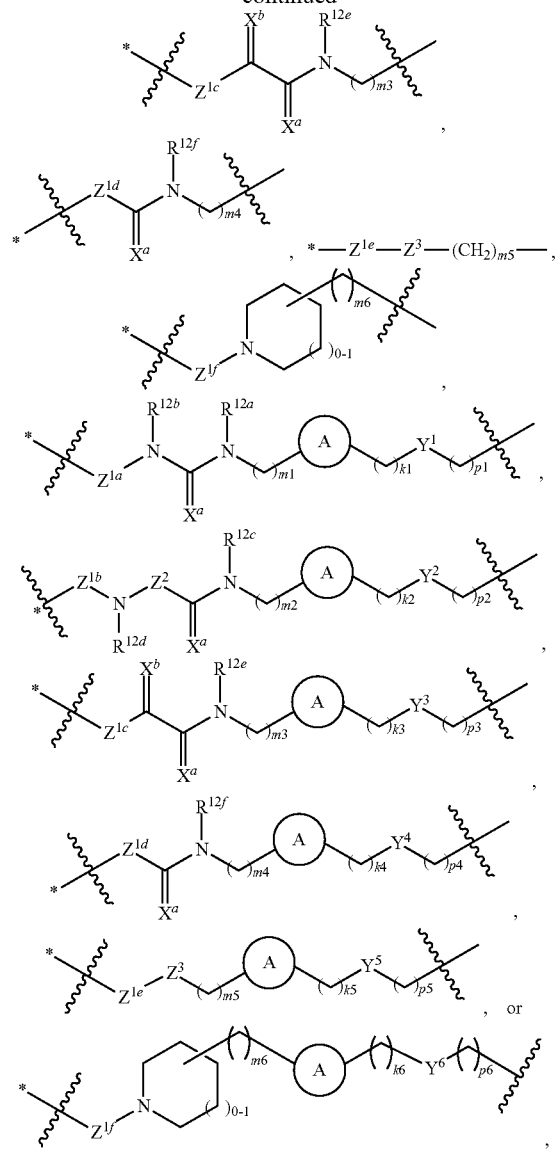

wherein the asterisk * indicates the point of connection to $X^1$;

each of $Z^{1a}$, $Z^{1b}$, $Z^{1c}$, $Z^{1d}$, $Z^{1e}$, and $Z^{1f}$ is independently a bond or —$(CR^aR^b)_{q1}$—;

$Z^2$ is —$(CR^cR^d)_{q2}$—;

$Z^3$ is a bond, O or $NR^{12g}$;

each of $R^a$, $R^b$, $R^c$ and $R^d$ is independently H, halogen, hydroxy, $C_1$-$C_6$ alkyl, $C_1$-$C_6$ haloalkyl, $C_1$-$C_6$ alkoxy, $C_1$-$C_6$ haloalkoxy, or optionally substituted $C_3$-$C_6$ cycloalkyl;

each q1 and q2 is independently 1, 2 or 3;

each $X^a$ and $X^b$ is independently O or S;

each Ring A is independently phenyl or a five to six membered heteroaryl, each optionally substituted with one or more $R^1$;

each of $Y^1$, $Y^2$, $Y^3$, $Y^4$, $Y^5$ and $Y^6$ is —$NR^{12h}$—, —O—, or —S—;

each $R^{12a}$, $R^{12b}$, $R^{12c}$, $R^{12d}$, $R^{12e}$, $R^{12f}$, $R^{12g}$ and $R^{12h}$ is independently H or $C_1$-$C_6$ alkyl;

each of m1, m2, m3, m4, m5, m6, k1, k2, k3, k4, k5, k6, p1, p2, p3, p4, p5, and p6 is independently 0, 1, 2, or 3;

L² is a bond, —(CH₂)₁₋₆NH—, —(CH₂)₀₋₆—C(=O)—, or —(CH₂)₀₋₃—C(=O)NR¹³—;

R¹³ is H or C₁-C₆ alkyl;

X¹ is alkylene or heteroalkylene; and

Ring B is phenyl or a 6 membered heteroaryl, optionally substituted with one or more R¹¹.

Some embodiments provide a pharmaceutical composition, comprising a compound of Formula (I), a compound of Formula (II), or a pharmaceutically acceptable salt of any of the foregoing, and at least one pharmaceutically acceptable excipient or carrier.

Some embodiments provide a method of decreasing cellular levels of CDK, comprising contacting a cell with an effective amount of a compound of Formula (I), a compound of Formula (II), or a pharmaceutically acceptable salt of any of the foregoing. Some additional embodiments provide a method of inhibiting the activity of CDK in a biological sample, comprising contacting the biological sample with an effective amount of a compound of Formula (I), a compound of Formula (II), or a pharmaceutically acceptable salt of any of the foregoing. In some embodiments, the CDK is CDK9 or CDK16.

Some embodiments provide a method of treating or ameliorating a disease, disorder, or condition associated with CDK, comprising administering an effective amount of a compound of Formula (I), a compound of Formula (II), or a pharmaceutically acceptable salt of any of the foregoing, or a pharmaceutical composition of any of the foregoing, to a subject. In some such embodiments, the disease, disorder, or condition is cancer. Some additional embodiments provide a method or treating or ameliorating cancer, comprising administering an effective amount of a compound of Formula (I), a compound of Formula (II), or a pharmaceutically acceptable salt of any of the foregoing, or a pharmaceutical composition of any of the foregoing, to a subject. In some embodiments of the methods described herein, the cancer is small cell lung cancer, non-small cell lung cancer, breast cancer, prostate cancer, head and neck cancer, pancreatic cancer, colon cancer, rectal cancer, teratoma, gastric cancer, ovarian cancer, endometrial cancer, brain cancer, retinoblastoma, leukemia, skin cancer, melanoma, squamous cell carcinoma, liposarcoma, lymphoma, multiple myeloma, testicular cancer, liver cancer, esophageal cancer, kidney carcinoma, astrogliosis, relapsed/refractory multiple myeloma, or neuroblastoma, or combinations thereof. In some embodiments, the CDK is CDK9 or CDK16.

DETAILED DESCRIPTION

Disclosed herein are compounds useful for the treatment or amelioration of various diseases, disorders, or conditions associated with protein malfunctions, including various types of cancers. In some aspects, these compounds are inhibitors of CDK. In some other aspects, these compounds are inhibitors of GSPT1, CK1α, Ikaros, TNFα, or a cytokine such as IL-1β, IL-6 and IL-2. In other aspects, these compounds may also induce the production of IL-2.

The section headings used herein are for organizational purposes only and are not to be construed as limiting the subject matter described.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting.

While the disclosure has been illustrated and described in detail in the foregoing description, such description is to be considered illustrative or exemplary and not restrictive. The disclosure is not limited to the disclosed embodiments. Variations to the disclosed embodiments can be understood and effected by those skilled in the art in practicing the claimed disclosure, from a study of the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

As used herein, common organic abbreviations are defined as follows:

ACN acetonitrile
AcOH acetic acid
CCl₄ carbon tetrachloride
CDI 1,1'-carbonyldiimidazole, N,N'-carbonyldiimidazole
d day, days
DCM dichloromethane, methylene chloride
DEAD diethyl azodicarboxylate
DIEA DIEA
DMA N,N-dimethylamide
DMF N,N-dimethylformamide
DMSO dimethylsulfoxide
EDAC.HCl 1-(3-dimethylaminopropyl)-3-ethylcarbodiimide hydrochloride
EDCI 1-ethyl-3-(3-dimethylaminopropyl)carbodiimide
Ether diethyl ether
EA ethyl acetate
EtOH ethanol
K₂CO₃ potassium carbonate
LiAH lithium aluminium hydride
LiCl lithium chloride
LiOH lithium hydroxide
h hour, hours
H hydrogen atom H₂ hydrogen gas
HCl hydrochloric acid or hydrochloride
HOBt 1-hydroxybenzotriazole
MeOH methanol
m minute, minutes
NaHCO₃ sodium bicarbonate
Na₂SO₄ sodium sulfate
NBS N-bromosuccinimide
N₂ nitrogen
Pd/C palladium on activated carbon
PE petroleum ether
RT room temperature
T3P propylphosphonic anhydride
TEA triethylamine
TFA trifluoroacetic acid
THF tetrahydrofuran
quant quantitative yield As used herein, any "R" group(s) represent substituents that can be attached to the indicated atom. An R group may be substituted or unsubstituted. If two "R" groups are described as being "taken together" the R groups and the atoms they are attached to can form a cycloalkyl, aryl, heteroaryl, or heterocycle. For example, without limitation, if $R^2$ and $R^3$, and the atom to which it is attached, are indicated to be "taken together" or "joined together" it means that they are covalently bonded to one another to form a ring:

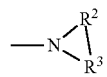

Whenever a group is described as being "optionally substituted" that group may be unsubstituted or substituted with one or more of the indicated substituents. Likewise, when a group is described as being "unsubstituted or substituted" if substituted, the substituent may be selected from one or more the indicated substituents. If no substituents are indicated, it is meant that the indicated "optionally substituted" or "substituted" group may be individually and independently substituted with one or more group(s) individually and independently selected from alkyl, cycloalkyl, aryl, heteroaryl, heterocyclyl, aralkyl, heteroaralkyl, heterocyclyl (alkyl), hydroxy, alkoxy, cycloalkoxy, aryloxy, acyl, mercapto, alkylthio, arylthio, cyano, halogen, C-amido, N-amido, C-carboxy, O-carboxy, isocyanato, thiocyanato, isothiocyanato, nitro, haloalkyl, haloalkoxy, amino, and alkylamino. When a group is not described as "optionally substituted," "unsubstituted" or "substituted," such group is unsubstituted unless the definition of such group states otherwise.

As used herein, "$C_a$ to $C_b$" in which "a" and "b" are integers refer to the number of carbon atoms in an alkyl group, or the number of ring atoms of a cycloalkyl, aryl, heteroaryl or heterocyclyl group. That is, the alkyl, ring of the cycloalkyl, and ring of the aryl, can contain from "a" to "b", inclusive, carbon atoms. Likewise, the ring of the heteroaryl and ring of the heterocyclyl can contain from "a" to "b", inclusive, total ring atoms. Thus, for example, a "$C_1$ to $C_4$ alkyl" group refers to all alkyl groups having from 1 to 4 carbons, that is, $CH_3-$, $CH_3CH_2-$, $CH_3CH_2CH_2-$, $(CH_3)_2CH-$, $CH_3CH_2CH_2CH_2-$, $CH_3CH_2CH(CH_3)-$ and $(CH_3)_3C-$; a $C_3$ to $C_4$ cycloalkyl group refers to all cycloalkyl groups having from 3 to 4 carbon atoms, that is, cyclopropyl and cyclobutyl. Similarly, a "4 to 6 membered heterocyclyl" group refers to all heterocyclyl groups with 4 to 6 total ring atoms, for example, azetidine, oxetane, oxazoline, pyrrolidine, piperidine, piperazine, morpholine, and the like. If no "a" and "b" are designated with regard to an alkyl, cycloalkyl aryl, heteroaryl or heterocyclyl group, the broadest range described in these definitions is to be assumed. As used herein, the term "$C_1$-$C_6$" includes $C_1$, $C_2$, $C_3$, $C_4$, $C_5$ and $C_6$, and a range defined by any of the two numbers. For example, $C_1$-$C_6$ alkyl includes $C_1$, $C_2$, $C_3$, $C_4$, $C_5$ and $C_6$ alkyl, $C_2$-$C_6$ alkyl, $C_1$-$C_3$ alkyl, etc. Similarly, $C_3$-$C_8$ carbocyclyl or cycloalkyl each includes hydrocarbon ring containing 3, 4, 5, 6, 7 and 8 carbon atoms, or a range defined by any of the two numbers, such as $C_3$-$C_7$ cycloalkyl or $C_5$-$C_6$ cycloalkyl.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, n-propyl, isopropyl, butyl, isobutyl, tertiary butyl, pentyl (straight chain or branched), and hexyl (straight chain or branched). The alkyl group may be substituted or unsubstituted.

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 10 atoms in the ring(s), 3 to 8 atoms in the ring(s), or 3 to 6 atoms in the ring(s). A cycloalkyl group may be unsubstituted or substituted. Examples of monocyclic cycloalkyl groups include, but are in no way limited to, cyclopropyl, cyclobutyl, cyclopentyl, cyclohexyl, cycloheptyl and cyclooctyl. Examples of bicyclic fused cycloalkyl groups are decahydronaphthalenyl, dodecahydro-1H-phenalenyl and tetradecahydroanthracenyl; examples of bicyclic bridged cycloalkyl groups are bicyclo[1.1.1]pentyl, adamantanyl and norbornanyl; and examples of bicyclic spiro cycloalkyl groups include spiro [3.3]heptane and spiro[4.5]decane.

As used herein, "carbocyclyl" refers to a non-aromatic a mono- or multi-cyclic hydrocarbon ring system. When composed of two or more rings, the rings may be joined together in a fused, bridged or spiro fashion, as described herein. Carbocyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A carbocyclyl group may be unsubstituted or substituted. Examples of carbocyclyl groups include, but are in no way limited to, cycloalkyl groups, as defined herein, and the non-aromatic portions of 1,2,3,4-tetrahydronaphthalene, 2,3-dihydro-1H-indene, 5,6,7,8-tetrahydroquinoline and 6,7-dihydro-5H-cyclopenta[b]pyridine.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$ aryl group, or a $C_{10}$ aryl group. Examples of aryl groups include, but are not limited to, benzene and naphthalene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 5 to 10 atoms in the ring(s), 6 to 10 atoms in the ring(s) or 5 to 6 atoms in the ring(s), such as nine carbon atoms and one heteroatom; eight carbon atoms and two heteroatoms; seven carbon atoms and three heteroatoms; eight carbon atoms and one heteroatom; seven carbon atoms and two heteroatoms; six carbon atoms and three heteroatoms; five carbon atoms and four heteroatoms; five carbon atoms and one heteroatom; four carbon atoms and two heteroatoms; three carbon atoms and three heteroatoms; four carbon atoms and one heteroatom; three carbon atoms and two heteroatoms; or two carbon atoms and three heteroatoms. Furthermore, the term "heteroaryl" includes fused ring systems where two rings, such as at least one aryl ring and at least one heteroaryl ring or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to three-, four-, five-, six-, seven-, eight-, nine-, and ten-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings (i.e., heterocyclyl groups are not aromatic). The heteroatom(s) is an element other than carbon including, but not limited to, oxygen, sulfur and nitrogen. A heterocycle may further contain one or more carbonyl functionalities, so as to make the definition include oxo-systems such as lactams, lactones, and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" refers to compounds wherein the heterocyclyl contains a linkage of one or more atoms connecting non-adjacent atoms. As used herein, the term "spiro" refers to two rings which have one atom in common and the two rings are not linked by a bridge. Heterocyclyl groups can contain 3 to 10 atoms in the ring(s), 3 to 8 atoms in the ring(s), 3 to 6 atoms in the ring(s), or 5 to 6 atoms in the ring(s). For example, five carbon atoms and one heteroatom; four carbon atoms and two heteroatoms; three carbon atoms and three heteroatoms; four carbon atoms and one heteroatom; three carbon atoms and two heteroatoms; two carbon atoms and three heteroatoms; one carbon atom and four heteroatoms; three carbon atoms and one heteroatom; or two carbon atoms and one heteroatom. Additionally, any nitrogens in a heterocyclyl group may be quaternized. Heterocyclyl groups can be linked to the rest of the molecule via a carbon atom in the heterocyclyl group (C-linked) or by a heteroatom in the heterocyclyl group, such as a nitrogen atom (N-linked). Heterocyclyl groups may be unsubstituted or substituted. Examples of such "heterocyclyl" groups include but are not limited to, aziridine, oxirane, thiirane, azetidine, oxetane, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, azepane, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

"Alkylene groups" are straight chained or branched saturated all-carbon tethering groups, forming bonds to connect molecular fragments via their terminal carbon atoms. Alkylene groups contain from 2 to 8 carbon atoms. Examples include but are not limited to ethylene (—$CH_2CH_2$—), propylene (—$CH_2CH_2CH_2$—), butylene (—$CH_2CH_2CH_2CH_2$—), and pentylene (—$CH_2CH_2CH_2CH_2CH_2$—).

As used herein, "heteroalkylene" refers to an alkylene group, as defined herein, containing one or more heteroatoms in the carbon back bone (i.e., an alkylene group in which one or more carbon atoms is replaced with a heteroatom). Heteroalkylene groups include, but are not limited to ether, thioether, amino-alkylene, and alkylene-amino-alkylene moieties.

As used herein, "lower alkylene groups" are straight-chained —$CH_2$— tethering groups, forming bonds to connect molecular fragments via their terminal carbon atoms. Lower alkylene groups contain from 1 to 4 carbon atoms.

Examples include but are not limited to methylene (—CH$_2$—), ethylene (—CH$_2$CH$_2$—), propylene (—CH$_2$CH$_2$CH$_2$—) and butylene (—CH$_2$CH$_2$CH$_2$CH$_2$—).

As used herein, "cycloalkylalkyl" and "cycloalkyl(alkyl)" refer to a cycloalkyl group (as defined herein) connected, as a substituent, via a lower alkylene group. Examples include but are not limited to cyclopropylmethyl, cyclobutylmethyl, cyclopentylethyl, and cyclohexylpropyl.

As used herein, "alkoxy" refers to the formula —OR wherein R is an alkyl group, as defined herein. A non-limiting list of alkoxys is methoxy, ethoxy, n-propoxy, 1-methylethoxy (isopropoxy), n-butoxy, iso-butoxy, sec-butoxy, and tert-butoxy. An alkoxy may be substituted or unsubstituted.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or unsubstituted.

The terms "amino" or "optionally substituted amino," as used herein refer to a —NR$_A$R$_B$ radical where R$_A$ and R$_B$ are independently hydrogen, alkyl, cycloalkyl, aryl, heteroaryl, heterocyclyl, aralkyl, or heterocyclyl(alkyl), as defined herein. An unsubstituted amino groups is an —NH$_2$ group.

As used herein, "alkylamino" or "(alkyl)amino" refers to a —NR$_A$R$_B$ group where R$_A$ and R$_B$ are hydrogen or alkyl as defined above, and at least one of R$_A$ and R$_B$ is alkyl. The alkyl portion of the (alkyl)amine, includes, for example, C$_1$-C$_6$ alkyl groups. Examples of alkylamino groups include, but are not limited to methylamino (—NHMe), ethylamino (—NHEt), dimethylamino (—N(Me)$_2$, methylethylamino (—N(Me)(Et)), and isopropylamino (—NHiPr).

As used herein, "aminoalkyl" or "amino(alkyl)" refers to an alkyl group in which one or more of the hydrogen atoms are replaced by an amino group or "—NR$_A$R$_B$" group as defined herein. The alkyl portion of the amino(alkyl), includes, for example, C$_1$-C$_6$ alkyl. Examples of aminoalkyl groups include, but are not limited to —(CH$_2$)$_{1-4}$NH$_2$, —(CH$_2$)$_{1-4}$—NHCH$_3$, —(CH$_2$)$_{1-4}$—NHC$_2$H$_5$, —(CH$_2$)$_{1-4}$—N(CH$_3$)$_2$, —(CH$_2$)$_{1-4}$—N(C$_2$H$_5$)$_2$, —(CH$_2$)$_{1-4}$—NH—CH(CH$_3$)$_2$, —(CH$_2$)$_{1-4}$N(CH$_3$)C$_2$H$_5$, and —CH(NH$_2$)CH$_3$.

The term "halogen atom" or "halogen" as used herein, means any one of the radio-stable atoms of column 7 of the Periodic Table of the Elements, such as, fluorine, chlorine, bromine, and iodine.

As used herein, "alkoxyalkyl" or "(alkoxy)alkyl" refers to an alkoxy group connected via an lower alkylene group, such as C$_2$-C$_8$ alkoxyalkyl, or (C$_1$-C$_6$ alkoxy)C$_1$-C$_6$ alkyl, for example, —(CH$_2$)$_{1-3}$—OCH$_3$.

As used herein, "—O-alkoxyalkyl" or "—O-(alkoxy)alkyl" refers to an alkoxy group connected via an —O-(lower alkylene) group, such as —O—(C$_1$-C$_6$ alkoxy)C$_1$-C$_6$ alkyl, for example, —O—(CH$_2$)$_{1-3}$—OCH$_3$.

Where the numbers of substituents is not specified (e.g., haloalkyl), there may be one or more substituents present. For example "haloalkyl" may include one or more of the same or different halogens. As another example, "C$_1$-C$_3$ alkoxyphenyl" may include one or more of the same or different alkoxy groups containing one, two, or three atoms.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition it is understood that, in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns.

Likewise, it is understood that, in any compound described, all tautomeric forms are also intended to be included.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

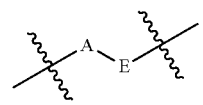

includes the substituent being oriented such that the A is attached at the leftmost attachment point of the molecule as well as the case in which A is attached at the rightmost attachment point of the molecule. In addition, if a group or substituent is depicted as

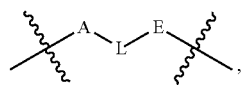

and when L is defined as a bond; such group or substituent is equivalent to

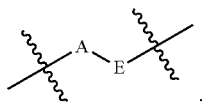

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

It is understood that the methods and formulations described herein include the use of pharmaceutically acceptable salts and/or conformers of compounds of preferred embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond. Likewise, it is understood that the compounds described herein, include the compound in any of the forms described herein (e.g., pharmaceutically acceptable salts, enantiomeric forms, tautomeric forms, and the like).

As used herein, the abbreviations for any protective groups, amino acids and other compounds, are, unless indicated otherwise, in accord with their common usage, recognized abbreviations, or the IUPAC-IUB Commission on Biochemical Nomenclature (See, *Biochem.* 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls (e.g., t-butoxycarbonyl (BOC), acetyl, or isobutyryl); arylalkylcarbonyls (e.g., benzyloxycarbonyl or benzoyl); substituted methyl ether (e.g., methoxymethyl ether); substituted ethyl ether; a substituted benzyl ether; tetrahydropyranyl ether; silyl ethers (e.g., trimethylsilyl, triethylsilyl, triisopropylsilyl, t-butyldimethylsilyl, or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMTr); 4,4'-dimethoxytrityl (DMTr); or 4,4',4''-trimethoxytrityl (TMTr)).

The term "leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, 5$^{th}$ ed., John McMurry (2000), pages 398 and 408; all of which are incorporated herein by reference for the limited purpose of disclosing characteristics and examples of leaving groups.

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid (AcOH), propionic acid, glycolic acid, pyruvic acid, malonic acid, maleic acid, fumaric acid, trifluoroacetic acid (TFA), benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluensulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, ($C_1$-$C_7$ alkyl)amine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

In some embodiments, the compounds described herein may be in the form of a trifluoroacetate salt.

The term "CDK protein," as used herein, refers to a protein in the cyclin-dependent kinase family, including, but not limited to CDK1, CDK2, CDK3, CDK4, CDK5, CDK6, CDK7, CDK8, CDK9, CDK10, CDK11, CDK12, CDK13, CDK14, CDK15, and CDK16.

The terms "effective amount" and "therapeutically effective amount" are broad terms, and are to be given their ordinary and customary meaning to a person of ordinary skill in the art (and are not to be limited to a special or customized meaning), and refer without limitation to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. Where a drug has been approved by the U.S. Food and Drug Administration (FDA) or a counterpart foreign medicines agency, a "therapeutically effective amount" optionally refers to the dosage approved by the FDA or its counterpart foreign agency for treatment of the identified disease or condition.

"Treat," "treatment," or "treating," as used herein refers to administering a compound or pharmaceutical composition to a subject for prophylactic and/or therapeutic purposes. The term "prophylactic treatment" refers to treating a subject who does not yet exhibit symptoms of a disease or condition, but who is susceptible to, or otherwise at risk of, a particular disease or condition, whereby the treatment reduces the likelihood that the patient will develop the disease or condition. The term "therapeutic treatment" refers to administering treatment to a subject already suffering from a disease or condition.

The terms "co-administration" and similar terms as used herein are broad terms, and are to be given their ordinary and customary meaning to a person of ordinary skill in the art (and are not to be limited to a special or customized meaning), and refer without limitation to administration of the selected therapeutic agents to a single patient, and are intended to include treatment regimens in which the agents are administered by the same or different route of administration or at the same or different time.

Compounds

Formula (I)

Some embodiments provide a compound of Formula (I), or a pharmaceutically acceptable salt thereof as described herein:

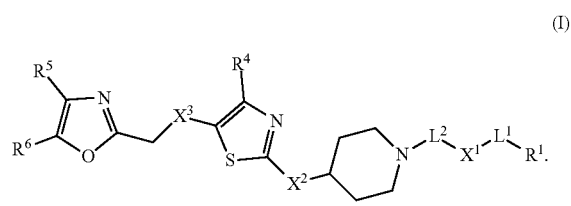

In some embodiments, when the compound has the structure of Formula (A):

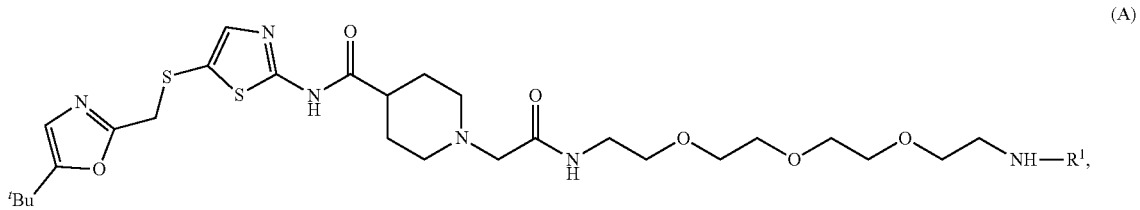

$R^1$ is

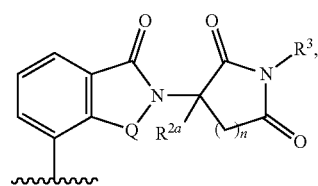

Q is C=O, n is 2, $R^3$ is H, then $R^{2a}$ is deuterium, halogen, or $C_1$-$C_6$ alkyl. In some further embodiments, when the compound is Formula (A), $R^1$ is

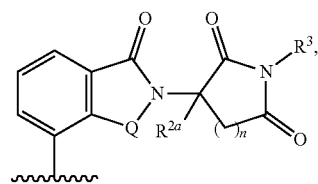

$R^3$ is H; then n is 1 or 3. In some further embodiments, when the compound has the structure of Formula (A), then $R^1$ is

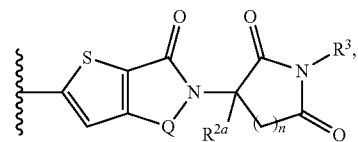
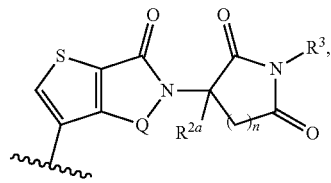
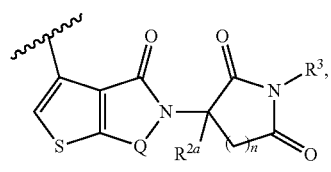
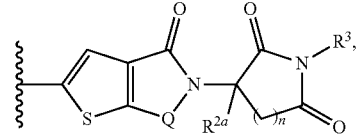
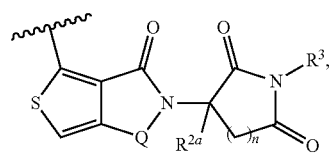
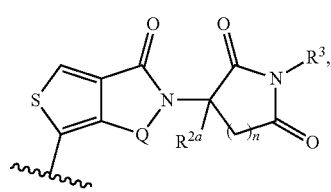
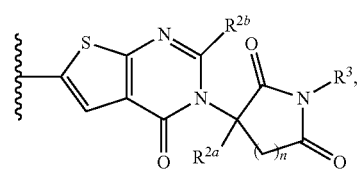
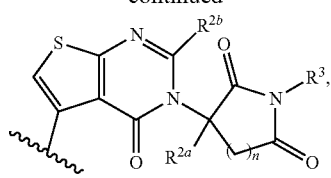
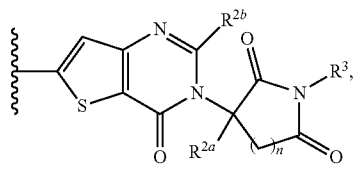
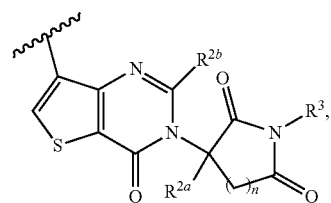
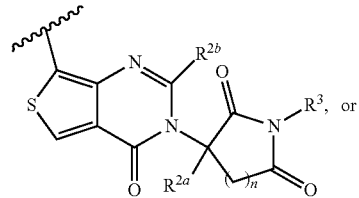
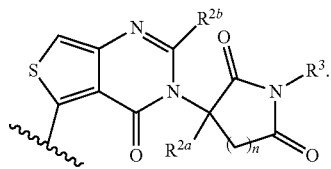
In some embodiments of the compound of Formula (I), $R^4$ is H.
In some further embodiments, the compound of Formula (I) is also represented by Formula (Ia):
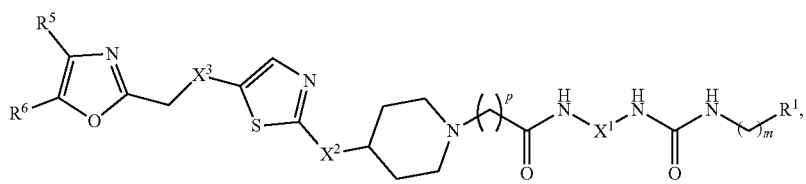
(Ia)

or a pharmaceutically acceptable salt thereof, wherein:
R¹ is

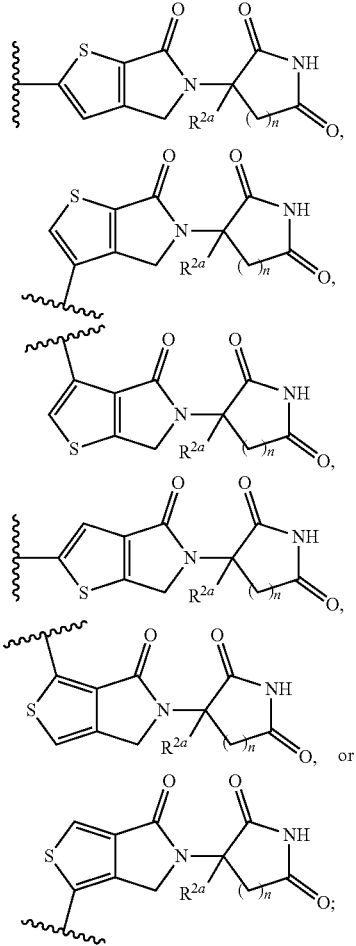

$R^{2a}$ is H, deuterium, fluoro, or methyl; n is 1, 2, or 3; each of m and p is independently 1, 2, 3, 4, or 5; $X^1$ is an unsubstituted alkylene or an unsubstituted heteroalkylene; $X^2$ is —(CO)NH—, —NH(CO)—, —NH—, —O—, —NH(CO)NH—, —NHCH$_2$—, —CH$_2$NH—, or —S—; $X^3$ is —NH—, —O—, or —S—; and $R^5$ and $R^6$ are independently H, $C_1$-$C_6$ alkyl, $C_1$-$C_6$ haloalkyl, $C_1$-$C_6$ alkoxy, $C_3$-$C_6$ cycloalkyl($C_1$-$C_3$ alkyl), $C_3$-$C_6$ cycloalkyl or $C_1$-$C_6$ haloalkoxy. In some embodiments, m is 1; and p is 1. In other embodiments, m is 1; and p is 2. In still other embodiments, m is 2; and p is 2.

In some embodiments of the compounds of Formula (I) or (Ia), one of $R^5$ and $R^6$ is H and the other of $R^5$ and $R^6$ is $C_1$-$C_6$ alkyl (for example, methyl, ethyl, n-propyl, isopropyl, n-butyl, sec-butyl, t-butyl, pentyl (straight chain or branched), or hexyl (straight chain or branched)), $C_1$-$C_6$ haloalkyl (for example, —CH$_2$F, —CHF$_2$, —CF$_3$, —CH$_2$CF$_3$, and —CF$_2$Cl), $C_1$-$C_6$ alkoxy (for example, methoxy, ethoxy, n-propoxy, isopropoxy, n-butoxy, sec-butoxy, t-butoxy, pentoxy (straight chain or branched), or hexoxy (straight chain or branched)), optionally substituted $C_3$-$C_7$ cycloalkyl($C_1$-$C_3$ alkyl) (for example, cyclopropylmethyl, cyclobutylmethyl, cyclopentylmethyl, cyclohexylmethyl, cyclopropylethyl, cyclobutylethyl, cyclopentylethyl, or cyclohexylethyl, halogen substituted $C_3$-$C_7$ cycloalkyl($C_1$-$C_3$ alkyl) (e.g., fluoro substituted cyclopropyl($C_1$-$C_3$ alkyl) such as

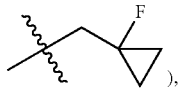

or $C_1$-$C_6$ haloalkyl substituted $C_3$-$C_7$ cycloalkyl($C_1$-$C_3$ alkyl) (e.g., trifluoromethyl substituted cyclopropyl($C_1$-$C_3$ alkyl) such as

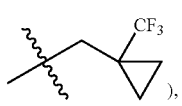 [SMILES: *CC1(C(F)(F)F)CC1]

optionally substituted $C_3$-$C_7$ cycloalkyl (for example, cyclopropyl, cyclobutyl, cyclopentyl, or cyclohexyl, halogen substituted $C_3$-$C_7$ cycloalkyl (e.g., fluoro substituted cyclopropyl such as

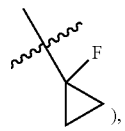

or $C_1$-$C_6$ haloalkyl substituted $C_3$-$C_7$ cycloalkyl (e.g., trifluoromethyl substituted cyclopropyl such as

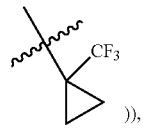 [SMILES: *C1(C(F)(F)F)CC1]

or $C_1$-$C_6$ haloalkoxy (for example, —OCH$_2$F, —OCHF$_2$, —OCF$_3$, —OCH$_2$CF$_3$, and —OCF$_2$Cl). In some embodiments, one of $R^5$ and $R^6$ is H and the other of $R^5$ and $R^6$ is $C_2$-$C_4$ alkyl, $C_2$-$C_4$ haloalkyl, $C_2$-$C_4$ alkoxy, or $C_2$-$C_4$ haloalkoxy. In some embodiments, one of $R^5$ and $R^6$ is H and the other of $R^5$ and $R^6$ is $C_1$-$C_6$ alkyl. In some embodiments, $R^5$ is H and $R^6$ is $C_1$-$C_6$ alkyl (e.g., t-butyl). In other embodiments, $R^5$ is $C_1$-$C_6$ alkyl (e.g., t-butyl) and $R^6$ is H. In some embodiments, one of $R^5$ and $R^6$ is H and the other of $R^5$ and $R^6$ is trifluoromethyl fluoro substituted cyclopropyl or cyclopropyl($C_1$-$C_3$ alkyl), such as

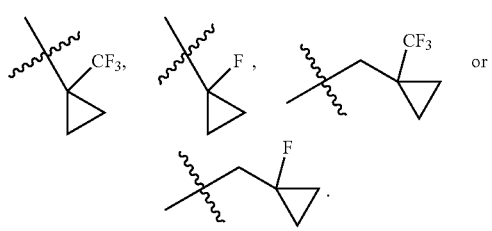

In some embodiments of the compounds of Formula (I) or (Ia), $X^3$ is —NH—. In other embodiments, $X^3$ is —O—. In still other embodiments, $X^3$ is —S—.

In some embodiments of the compounds of Formula (I) or (Ia), $X^2$ is —NH(CO)—. In some such embodiment, $X^2$ may connect to the adjacent thiazole moiety in either direction (i.g., either via the amine or the carbonyl). In other embodiments, $X^2$ is —NH—. In some embodiments, $X^2$ is —O—. In other embodiments, $X^2$ is —NH(CO)NH—. In still other embodiments, $X^2$ is —NHCH$_2$—. In other embodiments, $X^2$ is —S—.

In some embodiments, the compound of Formula (I) is also represented by Formula (Ib):

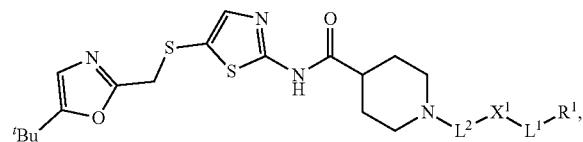

(Ib)

or a pharmaceutically acceptable salt thereof, wherein $R^1$, $X^1$, $L^1$ and $L^2$ are defined herein in Formula (I).

In some embodiments of the compounds of Formula (I) or (Ib), $R^1$ is unsubstituted. In other embodiments, $R^1$ is substituted with one or more $R^A$. In some further embodiments, $R^A$ is substituted at the thiophene moiety, isoindolinone moiety, or isoindolinedione moiety of $R^1$. In some further embodiments, $R^1$ is

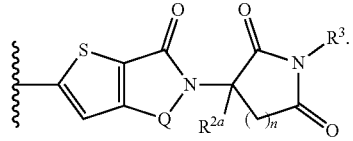

In other embodiments, $R^1$ is

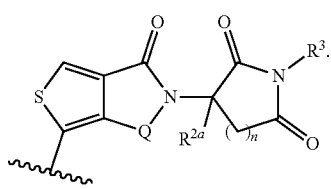

In still other embodiments, $R^1$ is

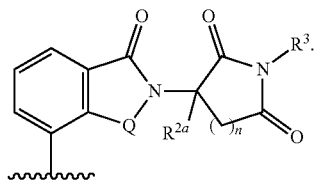

In some embodiments, wherein $R^1$ is

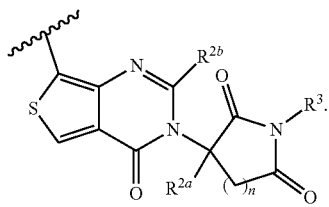

In some further embodiments, $R^1$ is substituted with one $R^A$, for example, $R^1$ is

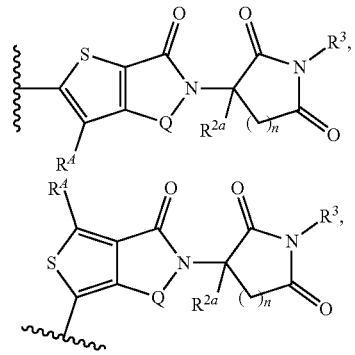

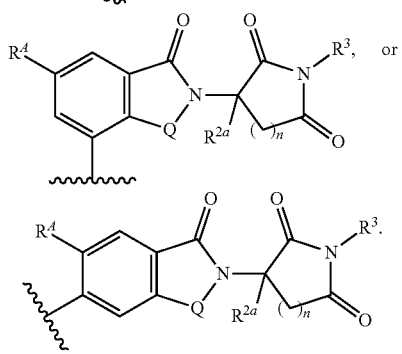

In some embodiments, $R^A$ is halogen (e.g., fluoro). In some embodiments, $R^3$ is H.

In some embodiments of the compounds of Formula (I), (Ia) or (Ib), $R^{2a}$ is H. In other embodiments, $R^{2a}$ is deuterium, fluoro or methyl. In some embodiments of the compounds of Formula (I) or (Ib), $R^{2b}$ is $C_1$-$C_6$ alkyl, for example, methyl, ethyl or isopropyl. In one embodiment, $R^{2b}$ is H. In another embodiment, $R^{2b}$ is methyl.

In some embodiments of the compounds of Formula (I), (Ia) or (Ib), n is 1. In other embodiments, n is 2. In still other embodiments, n is 3.

In some embodiments of the compounds of Formula (I), (Ia) or (Ib), $X^1$ is an alkylene, for example, $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, or $C_{15}$ alkylene (including both straight-chained or branched). In some embodiments, $X^1$ is methylene, ethylene, propylene, butylene, pentylene, hexylene, heptylene, or octylene. In some such embodiments, $X^1$ is unsubstituted. In some other embodiments, $X^1$ is heteroalkylene (including both straight-chained or branched), for example $C_1$-$C_{15}$ alkylene where one or more carbon atoms (including hydrogen atom(s) attached to the carbon atom) are replaced by a heteroatom. In some instances, the heteroatom in the heteroalkylene contains oxygen, nitrogen or sulfur, or combinations thereof. In some such embodiments, $X^1$ is a heteroalkylene containing carbon, hydrogen and oxygen atoms (where at least one methylene unit is replaced by oxygen), such as $[-(CH_2)_2O-]_{1-5}$ or $-[(CH_2)_2O]_{1-5}(CH_2)_2-$. In other embodiments, $X^1$ is a heteroalkylene containing carbon, hydrogen and nitrogen atoms (where at least one methylene unit is replaced by $NR^{14}$; such as $-(CH_2)_{1-5}-NR^{14}-(CH_2)_{1-5}-$, and wherein $R^{14}$ is H or $C_1$-$C_6$ alkyl (e.g., methyl). In one embodiment, $R^{14}$ is methyl. In still other embodiments, $X^1$ is an unsubstituted heteroalkylene containing carbon, hydrogen, oxygen, and nitrogen atoms. In some embodiments, $X^1$ is $-CH_2CH_2O-$, $-(CH_2CH_2O)_2-$, $-(CH_2CH_2O)_3-$, $-CH_2CH_2OCH_2CH_2-$, $-(CH_2CH_2O)_2CH_2CH_2-$, $-(CH_2CH_2O)_3CH_2CH_2-$, $-(CH_2CH_2O)_4CH_2CH_2-$, $-CH_2NR^{14}CH_2-$, $-CH_2CH_2NR^{14}CH_2CH_2-$, $-(CH_2)_2OCH_2(CH_2)_3-$, or $-(CH_2)_3NR^{14}(CH_2)_3-$. In some such embodiments, $R^{14}$ is H or methyl.

In some embodiments of the compounds of Formula (I) or (Ib), $L^1$ is

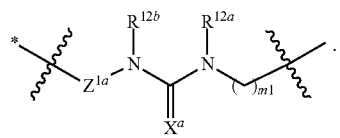

In some such embodiments, each of $R^{12a}$ and $R^{12b}$ is H; $X^a$ is O; $Z^{1a}$ is a bond or $-(CH_2)_{1-3}-$; and m1 is 0 or 1. In other embodiments, $L^1$ is

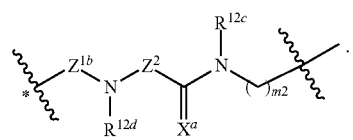

In some such embodiments, each of $R^{12c}$ and $R^{12d}$ is H; $X^a$ is O; $Z^2$ is $-CH_2-$; $Z^{1b}$ is a bond or $-(CH_2)_{1-3}-$; and m2 is 0 or 1. In other embodiments, $L^1$ is *$-Z^{1e}-Z^3-(CH_2)_{m5}-$, and wherein $Z^3$ is O or $NR^{12g}$. In some such embodiments, $Z^3$ is $NR^{12g}$; $R^{12g}$ is H; $Z^{1e}$ is a bond or $-(CH_2)_{1-3}-$; and m5 is 0 or 1. In other embodiments, $L^1$ is

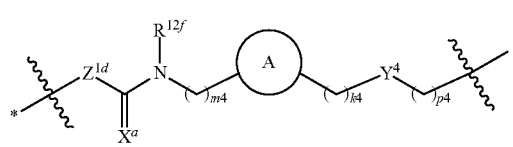

In some such embodiments, $R^{12f}$ is H; $Z^{1d}$ is a bond or $-(CH_2)_{1-3}-$; $X^a$ is O; Ring A is phenyl; $Y^4$ is $-O-$ or $-NH-$; each of k4, p4 and m4 is independently 0 or 1. In other embodiments, $L^1$ is

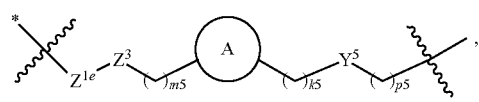

and wherein $Z^3$ is O or $NR^{12g}$. In some such embodiments, $Z^3$ is $NR^{12g}$; $R^{12g}$ is H; $Z^{1e}$ is a bond or $-(CH_2)_{1-3}-$; Ring A is phenyl; $Y^5$ is $-O-$ or $-NH-$; each of k5, p5 and m5 is independently 0 or 1. In some other such embodiments, $Z^3$ is a bond; $Z^{1e}$ is a bond or $-(CR^aR^b)_{1-3}-$; and m5 is 0. In still other embodiments, $L^1$ is

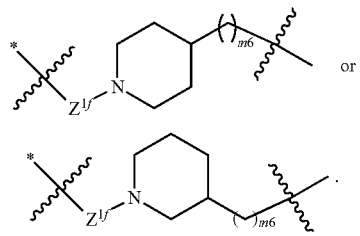

In some such embodiments, $Z^{1f}$ is a bond or $-(CH_2)_{1-3}-$; m6 is 0 or 1. In any embodiments of $L^1$ that contains Ring A, Ring A may be optionally substituted with one or more $R^{11}$. Additional non-limiting examples of $L^1$ include *$-NHC(=O)NHCH_2-$, *$-NHCH_2C(=O)NHCH_2-$, $-NH-$, *$-NHCH_2-$,

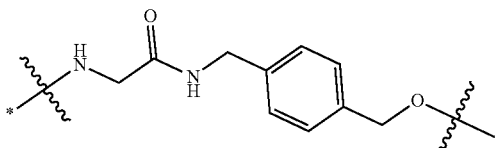

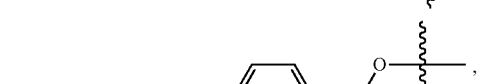

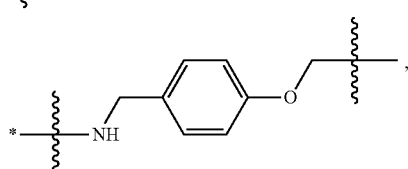

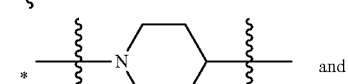 and

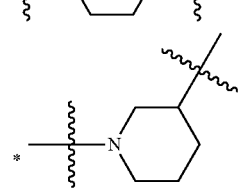

In some embodiments, * indicates the point of connection to $X^1$.

In some embodiments of the compounds of Formula (I) or (Ib), $L^2$ is a bond. In other embodiments, $L^2$ is $-C(=O)-$. In other embodiments, $L^2$ is $-CH_2-C(=O)NR^{13}-$. In some further embodiments, $L^2$ is $-CH_2-C(=O)NH-$ where  indicates the point of connection to $X^1$.

In some embodiments of the compounds of Formula (I) or (Ib), R¹ is
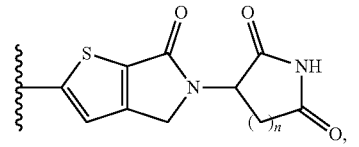
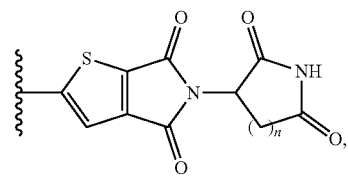
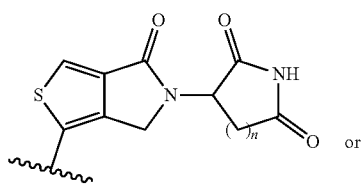
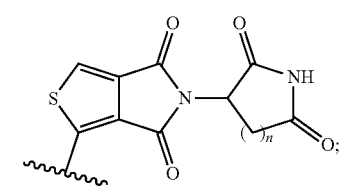
or
n is 2; and -L²-X¹-L¹- is listed in Table A. In other embodiments, R¹ is
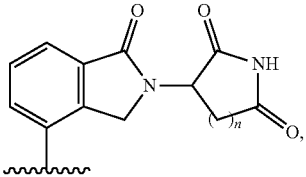
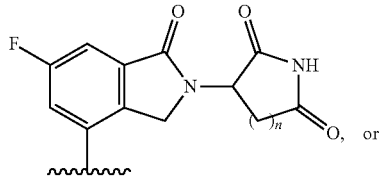
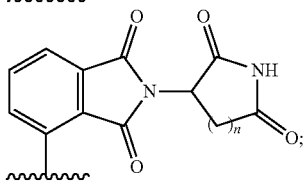
or
n is 2 or 3; and -L²-X¹-L¹- is listed in Table A. In other embodiments, R¹ is
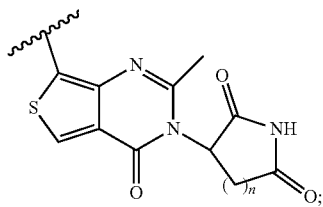
n is 2; and -L²-X¹-L¹- is listed in Table A.
TABLE A
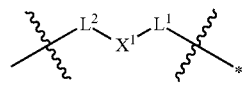
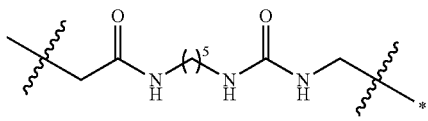
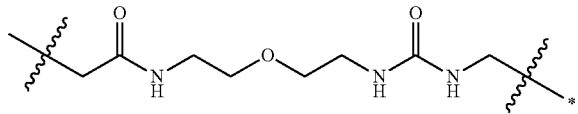 [SMILES: *CNC(=O)NCCOCCNC(=O)C*]
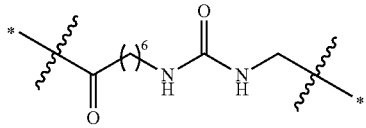

TABLE A-continued
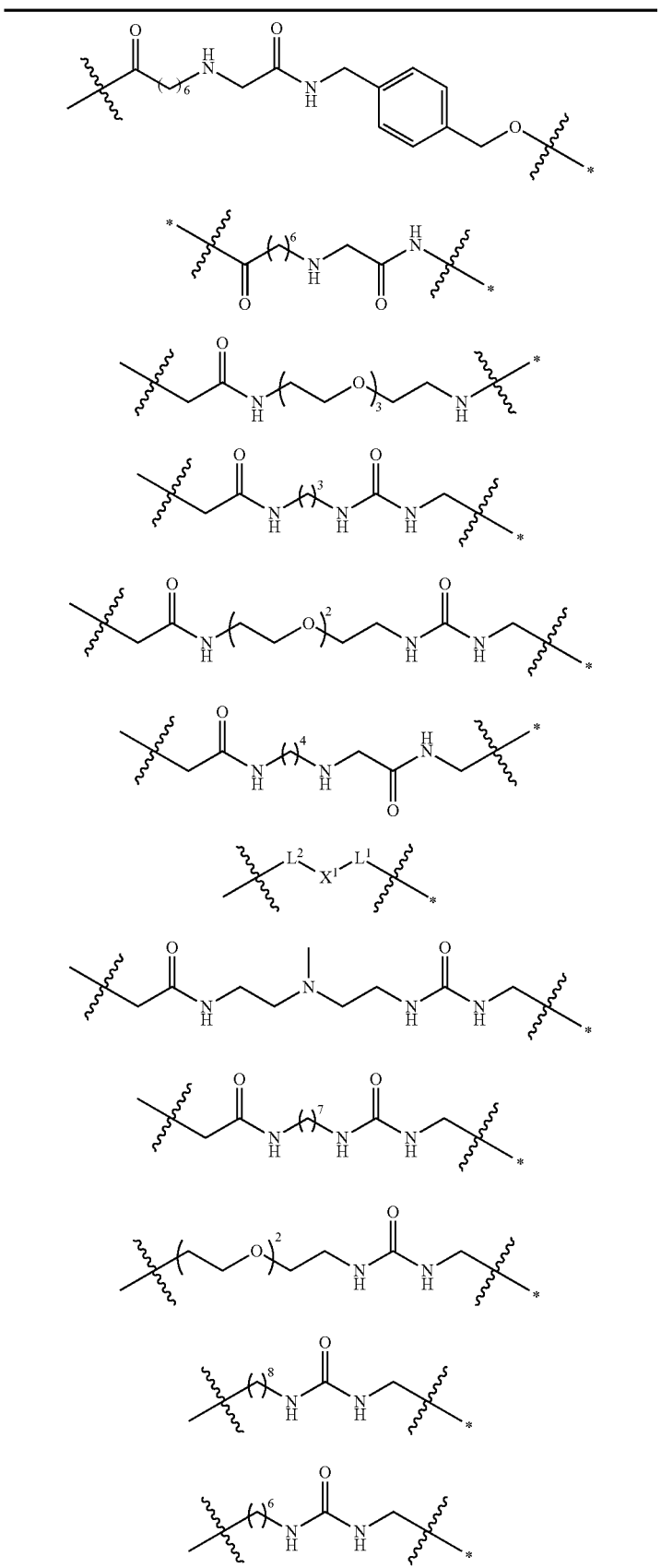

TABLE A-continued
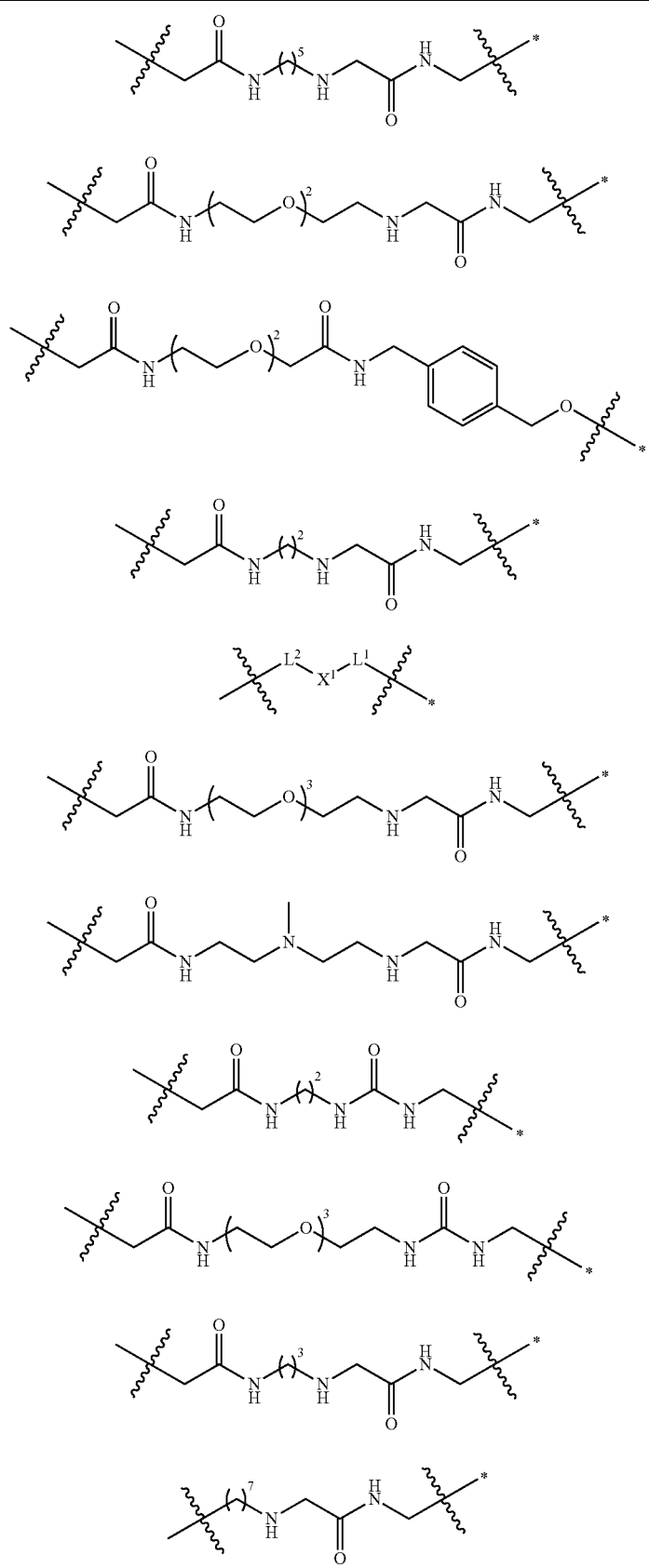

TABLE A-continued
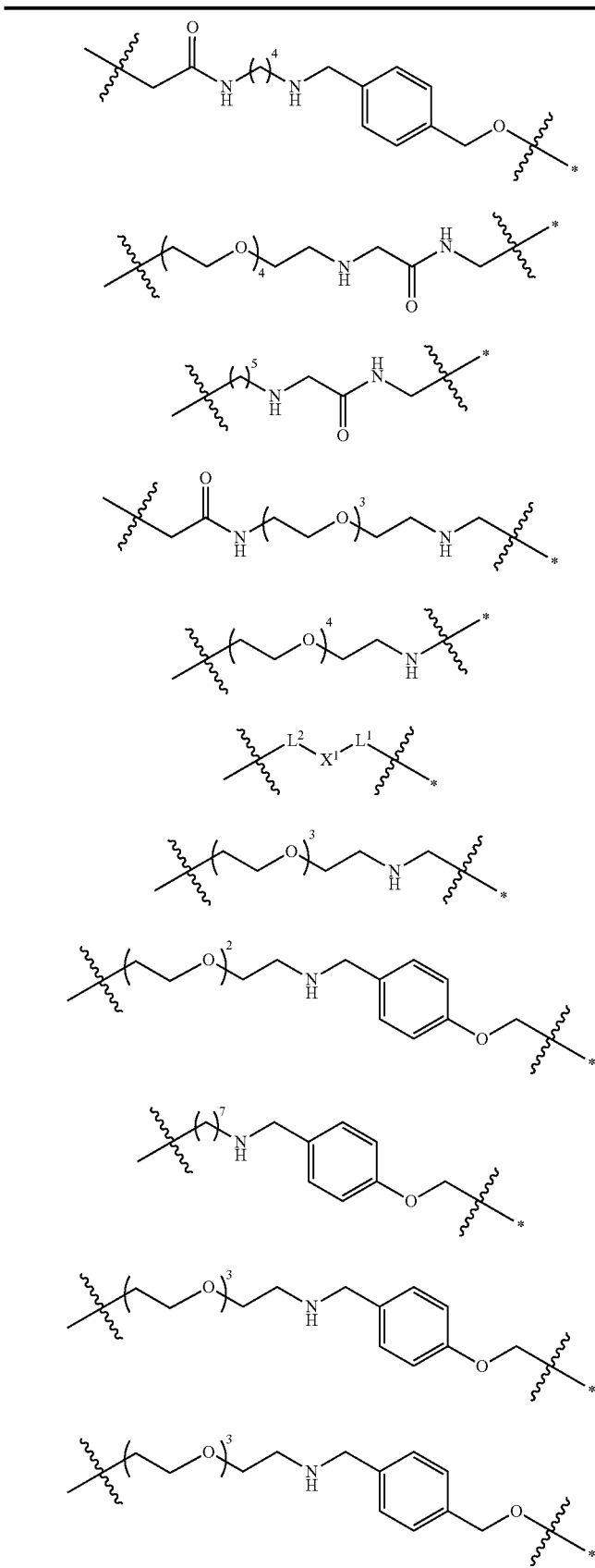

TABLE A-continued

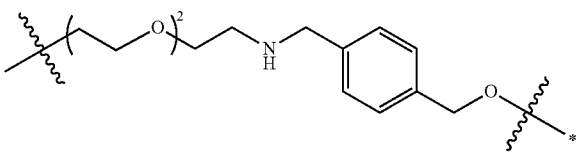

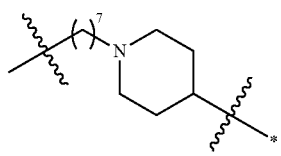

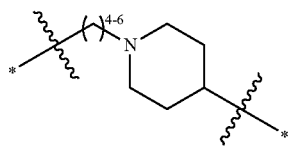

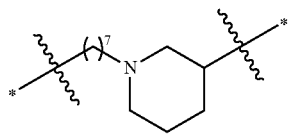

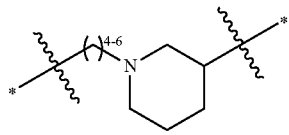

Additional exemplary embodiments of the compound of Formula (I) is selected from the group consisting of: 1-3, 6, 7, 11-15, 18-20, 26, 27, 33, 34, 41, 42, 44, 47, 52, 54, 57 and 58 of Table B, or a pharmaceutically acceptable salt thereof.

Formula (II)

Some embodiments provide a compound of Formula (II), or a pharmaceutically acceptable salt as described herein:

In some further embodiments, the compound of Formula (II) is also represented by Formula (II'):

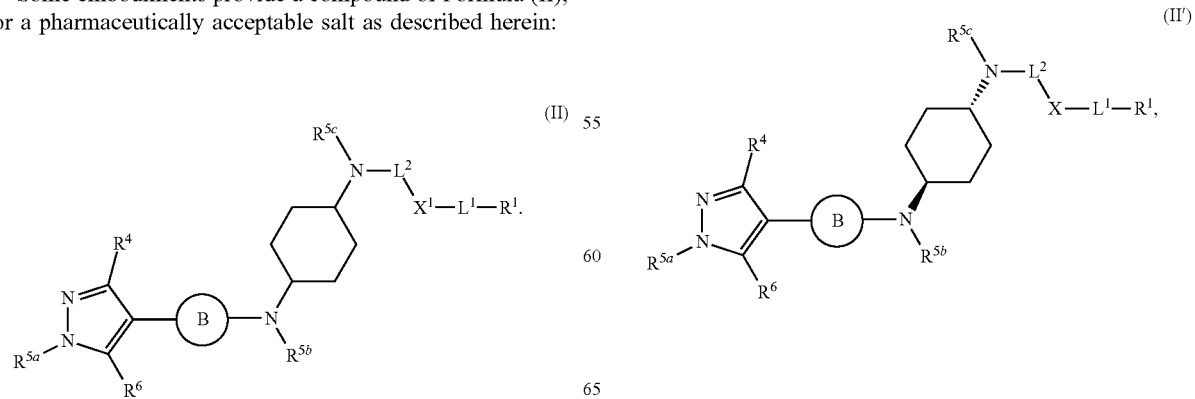

or a pharmaceutically acceptable salt thereof.

In some further embodiments, the compound of Formula (II) is also represented by Formula (IIa):

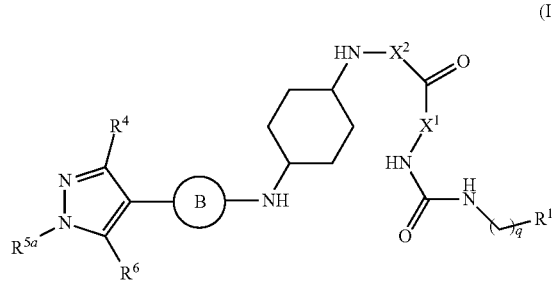

(IIa)

wherein:
R¹ is

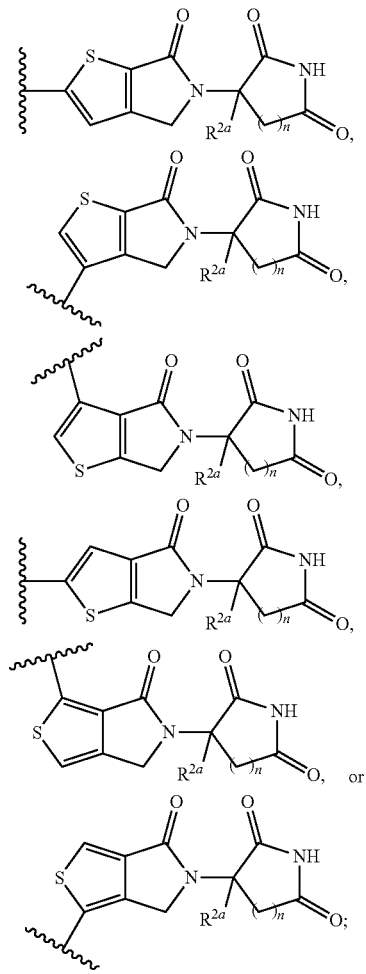

$R^{2a}$ is H or deuterium; n is 1, 2, or 3; q is 1, 2, 3, 4, or 5; $X^1$ is an unsubstituted alkylene or an unsubstituted heteroalkylene; $X^2$ is a bond, —(CH$_2$)$_{1-6}$NH—, —CH$_2$—, —CH$_2$CH$_2$—, —(CH$_2$)$_3$—, —(CH$_2$)$_4$—, —(CH$_2$)$_5$— or —(CH$_2$)$_6$—; Ring B is phenyl or 6 membered heteroaryl, optionally substituted with one to five substituents selected from the group consisting of halogen and C$_1$-C$_6$ alkyl; R$^4$ and R$^6$ are independently H, C$_1$-C$_6$ alkyl, or C$_3$-C$_7$ cycloalkyl(alkyl); and R$^{5a}$ is H or C$_1$-C$_6$ alkyl. In some further embodiments, q is 1.

In some embodiments of Formula (II), (II') or (IIa), Ring B is phenyl. In other embodiments, Ring B is a 6 membered heteroaryl containing 1 nitrogen atom. In other embodiments, Ring B is a 6 membered heteroaryl containing 2 nitrogen atoms. In other embodiments, Ring B is a 6 membered heteroaryl containing 3 nitrogen atoms. In some embodiments, Ring B is a pyridine. In other embodiments, Ring B is a pyrimidine. In other embodiments, Ring B is triazine. Ring B may be optionally substituted with one or more R$^1$. In some embodiments, Ring B is

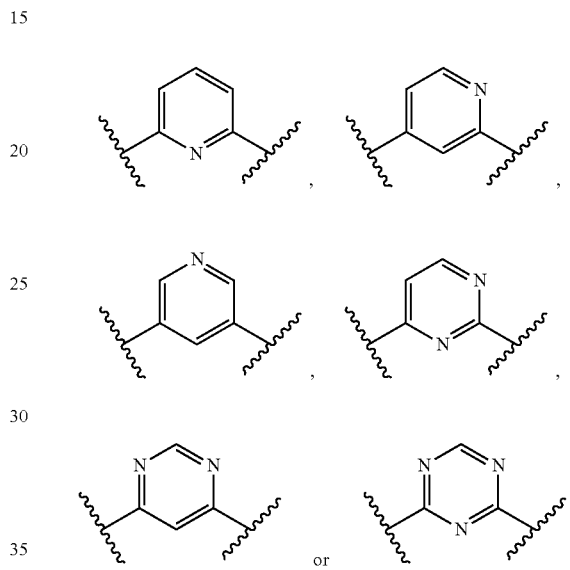

each optionally substituted with one R$^{11}$. In some further embodiments, Ring B is

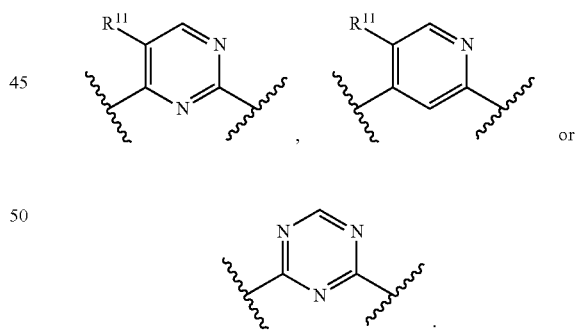

In some such embodiments, Ring B is

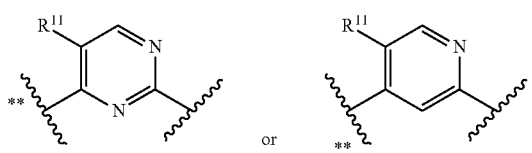

where ** indicate the point of attachment to

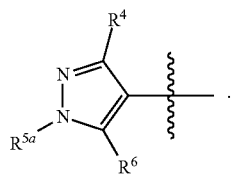

In some such embodiments, Ring B is unsubstituted. In other embodiments, $R^{11}$ is independently halogen (such as chloro or fluoro) or $C_1$-$C_6$ alkyl (e.g., methyl).

In some embodiments of Formula (II), (II') or (IIa), at least one of $R^4$ and $R^6$ is H. In other embodiments, one of $R^4$ and $R^6$ is H and the other of $R^4$ and $R^6$ is halogen, $C_1$-$C_6$ alkyl (for example, methyl, ethyl, n-propyl, isopropyl, n-butyl, sec-butyl, t-butyl, pentyl (straight chain or branched), or hexyl (straight chain or branched)), $C_1$-$C_6$ haloalkyl (for example, —$CH_2F$, —$CHF_2$, —$CF_3$, —$CH_2CF_3$, and —$CF_2Cl$), $C_1$-$C_6$ alkoxy (for example, methoxy, ethoxy, n-propoxy, isopropoxy, n-butoxy, sec-butoxy, t-butoxy, pentoxy (straight chain or branched), or hexoxy (straight chain or branched)), optionally substituted $C_3$-$C_7$ cycloalkyl($C_1$-$C_3$ alkyl) (for example, cyclopropylmethyl, cyclobutylmethyl, cyclopentylmethyl, cyclohexylmethyl, cyclopropylethyl, cyclobutylethyl, cyclopentylethyl, cyclohexylethyl, halogen substituted $C_3$-$C_7$ cycloalkyl($C_1$-$C_3$ alkyl) (e.g., fluoro substituted cyclopropyl($C_1$-$C_3$ alkyl) such as

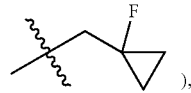

or $C_1$-$C_6$ haloalkyl substituted $C_3$-$C_7$ cycloalkyl($C_1$-$C_3$ alkyl) (e.g., trifluoromethyl substituted cyclopropyl($C_1$-$C_3$ alkyl) such as

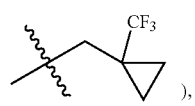 [SMILES: *CC1(C(F)(F)F)CC1]

optionally substituted $C_3$-$C_7$ cycloalkyl (for example, cyclopropyl, cyclobutyl, cyclopentyl, cyclohexyl, halogen substituted $C_3$-$C_7$ cycloalkyl (e.g., fluoro substituted cyclopropyl such as

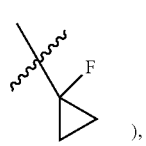

or $C_1$-$C_6$ haloalkyl substituted $C_3$-$C_7$ cycloalkyl (e.g., trifluoromethyl substituted cyclopropyl such as

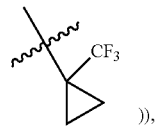 [SMILES: *C1(C(F)(F)F)CC1]

or $C_1$-$C_6$ haloalkoxy (for example, —$OCH_2F$, —$OCHF_2$, —$OCF_3$, —$OCH_2CF_3$, and —$OCF_2Cl$). In still other embodiments, one of $R^4$ and $R^6$ is H and the other $R^4$ and $R^6$ is $C_3$-$C_7$ cycloalkyl($C_1$-$C_2$ alkyl), e.g., cyclopropyl($C_1$-$C_2$ alkyl), cyclobutyl($C_1$-$C_2$ alkyl), cyclopentyl($C_1$-$C_2$ alkyl), or cyclohexyl($C_1$-$C_2$ alkyl). In further embodiments, $R^4$ is H and $R^6$ is cyclopropyl($C_1$-$C_3$ alkyl), e.g., —($CH_2$)-cyclopropyl. In some embodiments, one of $R^4$ and $R^6$ is H and the other $R^4$ and $R^6$ is trifluoromethyl or fluoro substituted cyclopropyl or cyclopropyl($C_1$-$C_3$ alkyl), such as

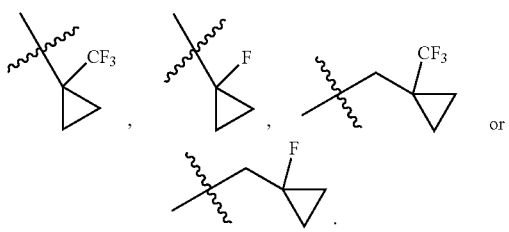

In some embodiments of Formula (II), (II') or (IIa), $R^{5a}$ is H. In other embodiments, $R^{5a}$ is $C_1$-$C_6$ alkyl. In some embodiments, $R^{5a}$ is methyl.

In some embodiments of Formula (II) or (II'), each of $R^{5b}$ and $R^{5c}$ is H. In other embodiments, at least one of $R^{5b}$ and $R^{5c}$ is $C_1$-$C_6$ alkyl. In some embodiments, one of $R^{5b}$ and $R^{5c}$ is $R^{5b}$ is methyl.

In some embodiments, the compound of Formula (II) is also represented by Formula (IIb):

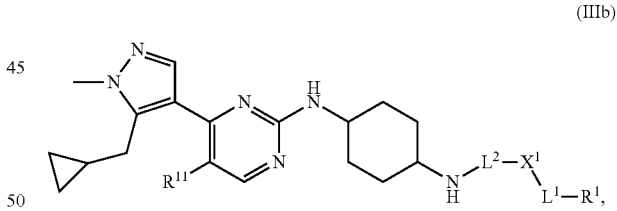
(IIIb)

or a pharmaceutically acceptable salt thereof, wherein $R^1$, $X^1$, $L^1$ and $L^2$ are defined herein in Formula (I); and $R^{11}$ is halogen (e.g., F or Cl). In some further embodiments, the compound of Formula (IIb) is also represented by Formula (IIb'):

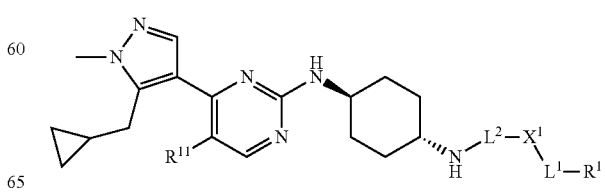

or a pharmaceutically acceptable salt thereof.

In some embodiments of the compounds of Formula (II), (II'), (IIb) or (IIb'), $R^1$ is unsubstituted. In other embodiments, $R^1$ is substituted with one or more $R^A$. In some further embodiments, $R^A$ is substituted at the thiophene moiety, isoindolinone moiety, or isoindolinedione moiety of $R^1$. In some further embodiments, $R^1$ is

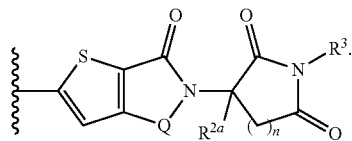

In other embodiments, $R^1$ is

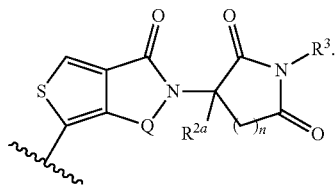

In still other embodiments, $R^1$ is

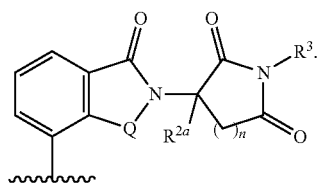

In some embodiments, wherein $R^1$ is

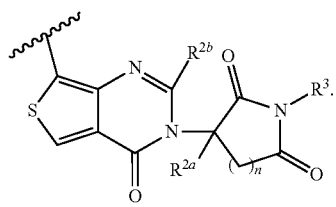

In some further embodiments, $R^1$ is substituted with one $R^A$, for example, $R^1$ is

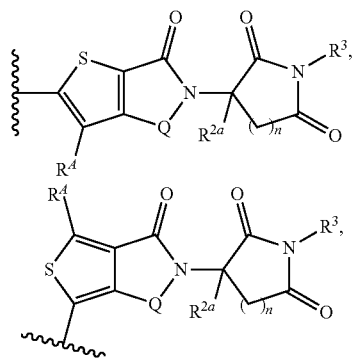

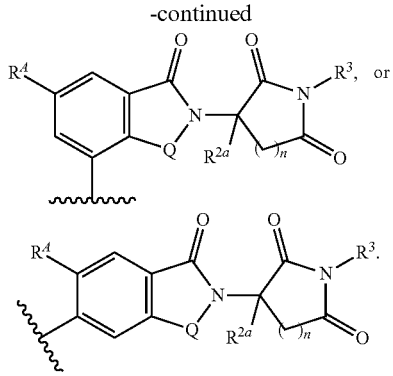

In some embodiments, $R^A$ is halogen (e.g., fluoro). In some embodiments, $R^3$ is H.

In some embodiments of the compounds of Formula (II), (II'), (IIa), (IIb) or (IIb'), $R^{2a}$ is H. In other embodiments, $R^{2a}$ is deuterium. In other embodiments, $R^{2a}$ is fluoro or methyl. In some embodiments of the compounds of Formula (I) or (Ib), $R^{2b}$ is $C_1$-$C_6$ alkyl, for example, methyl, ethyl or isopropyl. In one embodiment, $R^{2b}$ is H. In another embodiment, $R^{2b}$ is methyl.

In some embodiments of the compounds of Formula (II), (II'), (IIa), (IIb) or (IIb'), n is 1. In other embodiments, n is 2. In still other embodiments, n is 3.

In some embodiments of the compounds of Formula (II), (II'), (IIa), (IIb) or (IIb'), $X^1$ is an alkylene, for example, $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, or $C_{15}$ alkylene (including both straight-chained or branched). In some embodiments, $X^1$ is methylene, ethylene, propylene, butylene, pentylene, hexylene, heptylene, or octylene. In some such embodiments, $X^1$ is unsubstituted. In some other embodiments, $X^1$ is heteroalkylene (including both straight-chained or branched), for example $C_1$-$C_{15}$ alkylene where one or more carbon atoms (including hydrogen atom(s) attached to the carbon atom) are replaced by a heteroatom. In some instances, the heteroatom in the heteroalkylene contains oxygen, nitrogen or sulfur, or combinations thereof. In some such embodiments, $X^1$ is a heteroalkylene containing carbon, hydrogen and oxygen atoms (where at least one methylene unit is replaced by oxygen), such as $[-(CH_2)_2O-]_{1-5}$ or $-[(CH_2)_2O]_{1-5}(CH_2)_2-$. In other embodiments, $X^1$ is a heteroalkylene containing carbon, hydrogen and nitrogen atoms (where at least one methylene unit is replaced by $NR^{14}$; such as $-(CH_2)_{1-5}-NR^{14}-(CH_2)_{1-5}-$, and wherein $R^{14}$ is H or $C_1$-$C_6$ alkyl (e.g., methyl). In one embodiment, $R^{14}$ is methyl. In still other embodiments, $X^1$ is an unsubstituted heteroalkylene containing carbon, hydrogen, oxygen, and nitrogen atoms. In some embodiments, $X^1$ is $-CH_2CH_2O-$, $-(CH_2CH_2O)_2-$, $-(CH_2CH_2O)_3-$, $-CH_2CH_2OCH_2CH_2-$, $-(CH_2CH_2O)_2CH_2CH_2-$, $-(CH_2CH_2O)_3CH_2CH_2-$, $-(CH_2CH_2O)_4CH_2CH_2-$, $-CH_2NR^{14}CH_2-$, $-CH_2CH_2NR^{14}CH_2CH_2-$, $-(CH_2)_2OCH_2(CH_2)_3-$, or $-(CH_2)_3NR^{14}(CH_2)_3-$. In some such embodiments, $R^{14}$ is H or methyl.

In some embodiments of the compounds of Formula (II), (II'), (IIb) or (IIb'), $L^1$ is

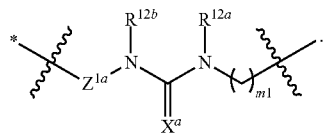

In some such embodiments, each of $R^{12a}$ and $R^{12b}$ is H; $X^a$ is O; $Z^{1a}$ is a bond or —$(CH_2)_{1-3}$—; and m1 is 0 or 1. In other embodiments, $L^1$ is

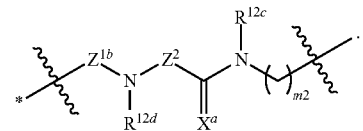

In some such embodiments, each of $R^{12c}$ and $R^{12d}$ is H; $X^a$ is O; $Z^2$ is —$CH_2$—; $Z^{1b}$ is a bond or —$(CH_2)_{1-3}$—; and m2 is 0 or 1. In other embodiments, $L^1$ is

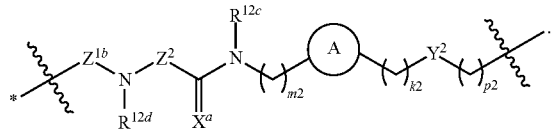

In some such embodiments, each of $R^{12c}$ and $R^{12d}$ is H; $X^a$ is O; $Z^{1b}$ is a bond or —$(CH_2)_{1-3}$—; $Z^2$ is —$(CH_2)_{1-3}$—; Ring A is phenyl; and each of k2, p2 and m2 is independently 0 or 1. In other embodiments, $L^1$ is *—$Z^{1e}$—$Z^3$—$(CH_2)_{m5}$— and wherein $Z^3$ is O or $NR^{12g}$. In some such embodiments, $Z^3$ is $NR^{12g}$; $R^{12g}$ is H; $Z^{1e}$ is a bond or —$(CH_2)_{1-3}$—; and m5 is 0 or 1. In other embodiments, $L^1$ is

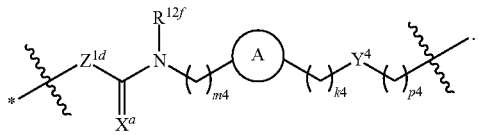

In some such embodiments, $R^{12f}$ is H; $Z^{1d}$ is a bond or —$(CH_2)_{1-3}$—; $X^a$ is O; Ring A is phenyl; $Y^4$ is —O— or —NH—; each of k4, p4 and m4 is independently 0 or 1. In other embodiments, $L^1$ is

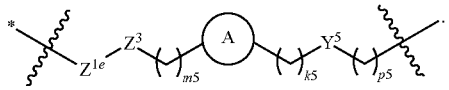

and wherein $Z^3$ is O or $NR^{12g}$. In some such embodiments, $Z^3$ is $NR^{12g}$; $R^{12g}$ is H; $Z^{1e}$ is a bond or —$(CH_2)_{1-3}$—; Ring A is phenyl; $Y^5$ is —O— or —NH—; each of k5, p5 and m5 is independently 0 or 1. In some other such embodiments, $Z^3$ is a bond; $Z^{1e}$ is a bond or —$(CR^aR^b)_{1-3}$—; and m5 is 0. In still other embodiments, $L^1$ is

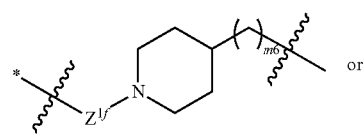

or

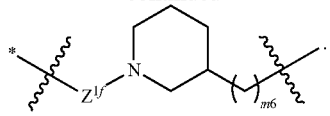

In some such embodiments, $Z^{1f}$ is a bond or —$(CH_2)_{1-3}$—; m6 is 0 or 1. In any embodiments of $L^1$ that contains Ring A, Ring A may be optionally substituted with one or more $R^{11}$. Additional non-limiting examples of $L^1$ include *—NHC(=O)NHCH$_2$—, *—NHCH$_2$C(=O)NHCH$_2$—,

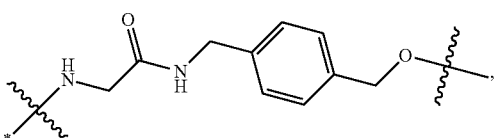

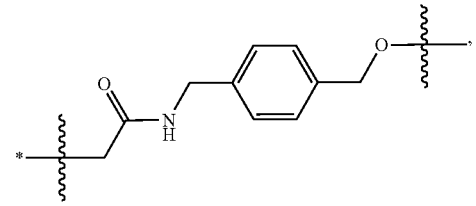

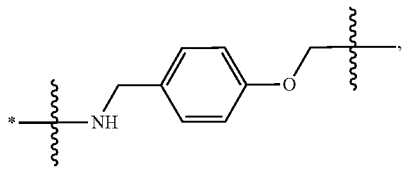

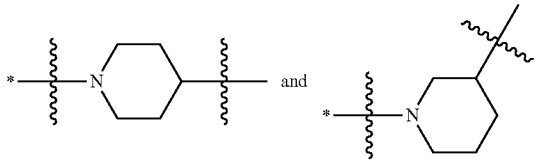

In some embodiments, * indicates the point of connection to $X^1$.

In some embodiments of the compounds of Formula (II), (II'), (IIb) or (IIb'), $L^2$ is a bond. In other embodiments, $L^2$ is —C(=O)—. In other embodiments, $L^2$ is —CH$_2$—C(=O)NR$^{13}$—. In some further embodiments, $L^2$ is —CH$_2$—C(=O)NH— where  indicates the point of connection to $X^1$.

In some embodiments of the compounds of Formula (II), (II'), (IIa), (IIb) or (IIb'), $R^1$ is

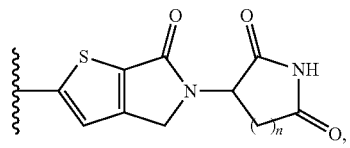

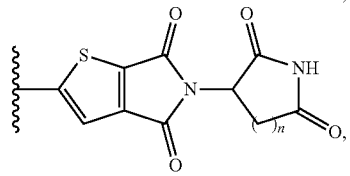

-continued

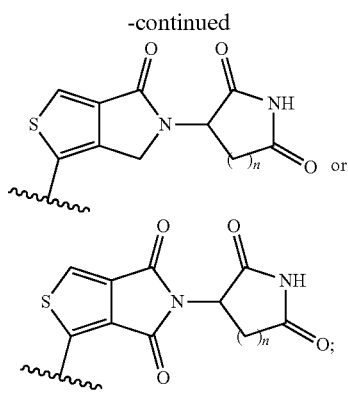

n is 2; and -L²-X¹-L¹- is listed in Table A. In other embodiments, R¹ is

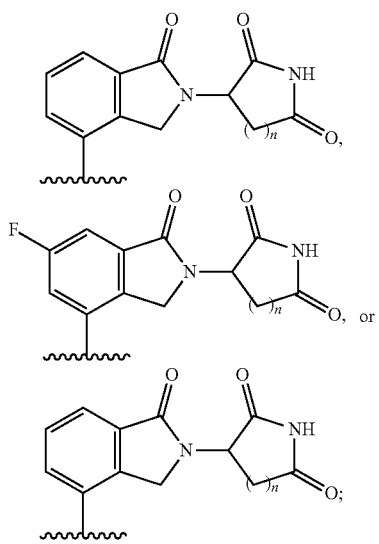

n is 2 or 3; and -L²-X¹-L¹- is listed in Table A. In other embodiments, R¹ is

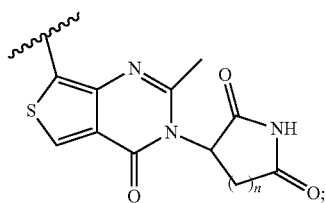

n is 2; and -L²-X¹-L¹- is listed in Table A.

In some embodiments, the compound of Formula (II) is selected from the group consisting of Compounds 4, 5, 8, 9, 16, 17, 21-25, 28-32, 35-40, 43, 45, 46, 48-51, 53, 55, 56 and 59-72 of Table B, or a pharmaceutically acceptable salt thereof.

Uses or Methods of Treatment

Some embodiments provide a method of inhibiting the activity of a protein in a biological sample, comprising contacting an effective amount of a compound of Formula (I) (including (Ia) and (Ib)), a compound of Formula (II) (including (II'), (IIa), (IIb) and (IIb')), or a pharmaceutically acceptable salt thereof with one or more cells in the biological sample. Some embodiments provide the use of a compound of Formula (I) (including (Ia) and (Ib)), a compound of Formula (II) (including (II'), (IIa), (IIb) and (IIb')) or a pharmaceutically acceptable salt thereof, for inhibiting the activity of a protein in a biological sample, comprising contacting an effective amount of the compound or the pharmaceutically salt thereof with one or more cells in the biological sample. In some embodiments, the protein is CDK, GSPT1, CK1α, Ikaros, TNFα, or a cytokine such as IL-1β, IL-2 and IL-6. In some further embodiments, the protein is a CDK protein, for example, CDK9 or CDK16.

Some embodiments provide a method of decreasing cellular levels of a protein, comprising contacting one or more cells with an effective amount a compound of Formula (I) (including (Ia) and (Ib)), a compound of Formula (II) (including (II'), (IIa), (IIb) and (IIb')), or a pharmaceutically acceptable salt thereof. Some embodiments provide the use of a compound of Formula (I) (including (Ia) and (Ib)), a compound of Formula (II) (including (II'), (IIa), (IIb) and (IIb')), or a pharmaceutically acceptable salt thereof for decreasing cellular levels of a CDK, comprising contacting one or more cells with an effective amount of the compound or the pharmaceutical salt thereof. In some embodiments, the protein is CDK, GSPT1, CK1α, Ikaros, TNFα, or a cytokine such as IL-1β, IL-2 and IL-6. In some further embodiments, the protein is a CDK protein, for example, CDK9 or CDK16.

Additional embodiments provide a method of inducing the activity of IL-2, comprising contacting one or more cells with an effective amount of a compound of Formula (I) (including (Ia) and (Ib)), a compound of Formula (II) (including (II'), (IIa), (IIb) and (IIb')), or a pharmaceutically acceptable salt thereof. Other embodiments provide a method of increasing the cellular levels of IL-2, comprising contacting a cell with an effective amount a compound of Formula (I) (including (Ia) and (Ib)), a compound of Formula (II) (including (II'), (IIa), (IIb) and (IIb')), or a pharmaceutically acceptable salt thereof.

In some embodiments of the methods or the uses described herein, the cell is a cancer cell. The cancer cell may be selected from the group consisting of small cell lung cancer cell, non-small cell lung cancer cell, breast cancer cell, prostate cancer cell, head and neck cancer cell, pancreatic cancer cell, rectal cancer cell, colon cancer cell, teratoma cell, gastric cancer cell, ovarian cancer cell, endometrial cancer cell, brain cancer cell, retinoblastoma cell, leukemia cell, skin cancer cell, melanoma cell, squamous cell carcinoma cell, liposarcoma cell, lymphoma cell, multiple myeloma cell, testicular cancer cell, liver cancer cell, esophageal cancer cell, kidney carcinoma cell, astrogliosis cell, relapsed/refractory multiple myeloma cell, and neuroblastoma cell. In some further embodiments, the cancer cell is leukemia cell, lymphoma cell or multiple myeloma cell (including relapsed/refractory).

Some embodiments provide a method of treating or ameliorating a disease, disorder, or condition associated with a protein malfunction in a subject; the method comprising administering a therapeutically effective amount of a compound of Formula (I) (including (Ia) and (Ib)), a compound of Formula (II) (including (II'), (IIa), (IIb) and (IIb')), or a pharmaceutically acceptable salt thereof, or a pharmaceutical composition thereof to the subject; wherein the disease, disorder, or condition is cancer. Some embodiments provide the use of a compound of Formula (I) (including (Ia) and (Ib)), a compound of Formula (II) (including (II'), (IIa), (IIb) and (IIb')), or a pharmaceutically acceptable salt thereof, or a pharmaceutical composition thereof for treating or ameliorating a disease, disorder, or condition associated with a protein malfunction; wherein the disease, disorder, or condition is cancer. In some embodiments, the protein is CDK, GSPT1, CK1α, Ikaros, TNFα, or a cytokine such as IL-1β, IL-2 and IL-6. In some further embodiments, the protein is a CDK protein, for example, CDK9 or CDK16.

Some embodiments provide a method of treating or ameliorating cancer in a subject, comprising administering a therapeutically effective amount of a compound of Formula (I) (including (Ia) and (Ib)), a compound of Formula (II) (including (II'), (IIa), (IIb) and (IIb')), or a pharmaceutically acceptable salt thereof, or a pharmaceutical composition thereof to the subject. Some embodiments provide the use of a compound of Formula (I) (including (Ia) and (Ib)), a compound of Formula (II) (including (II'), (IIa), (IIb) and (IIb')), or a pharmaceutically acceptable salt thereof, or a pharmaceutical composition thereof for treating or ameliorating cancer. In some embodiments, the cancer is associated with one or more protein malfunction, including CDK, GSPT1, CK1α, Ikaros, TNFα, or a cytokine such as IL-1β, IL-2 and IL-6. In some further embodiments, the cancer is associated with a CDK protein.

In any embodiments of the methods or uses described herein, the cancer may include small cell lung cancer, non-small cell lung cancer, breast cancer, prostate cancer, head and neck cancer, pancreatic cancer, colon cancer, rectal cancer, teratoma, gastric cancer, ovarian cancer, endometrial cancer, brain cancer, retinoblastoma, leukemia, skin cancer, melanoma, squamous cell carcinoma, liposarcoma, lymphoma, multiple myeloma, testicular cancer, liver cancer, esophageal cancer, kidney carcinoma, astrogliosis, relapsed/refractory multiple myeloma, or neuroblastoma. In some further embodiments, the cancer is leukemia, lymphoma, or multiple myeloma (including relapsed/refractory).

In any embodiments of the methods or uses described herein, the CDK protein is CDK1. In other embodiments, the CDK protein is CDK2. In still other embodiments, the CDK protein is CDK4. In some embodiments, the CDK protein is CDK5. In some embodiments, the CDK protein is CDK6. In other embodiments, the CDK protein is CDK9. In some other embodiments, the CDK protein is CDK16. In still other embodiments, the CDK protein is a combination of one or more of CDK proteins. In some embodiments, the CDK protein is wild-type. In other embodiments, the CDK protein is a mutant form of the CDK protein. In some embodiments, the CDK protein is overexpressed.

Some embodiments provide a method of treating, ameliorating, or preventing an inflammatory disease, disorder or condition in a subject, comprising administering a therapeutically effective amount of a compound of Formula (I) (including (Ia) and (Ib)), a compound of Formula (II) (including (II'), (IIa), (IIb) and (IIb')), or a pharmaceutically acceptable salt thereof, or a pharmaceutical composition thereof to the subject. Some embodiments provide the use of a compound of Formula (I) (including (Ia) and (Ib)), a compound of Formula (II) (including (II'), (IIa), (IIb) and (IIb')), or a pharmaceutically acceptable salt thereof, or a pharmaceutical composition thereof for treating, ameliorating, or preventing an inflammatory disease, disorder or condition. In some embodiments, the inflammatory disease, disorder or condition is a neurodegenerative disease (such as multiple sclerosis, Alzheimer's disease, Parkinson's disease), fibrosis (such as pulmonary fibrosis), lupus, fibromyalgia, rheumatoid arthritis, osteoarthritis, ankylosing spondylitis, psoriasis, psoriatic arthritis, inflammatory bowel disease, Crohn's disease, ulcerative colitis, uveitis, or chronic obstructive pulmonary disease. In some embodiments, the inflammatory disease, disorder or condition is associated with a protein, wherein the protein is IL-1β, IL-2, IL-6, TNFα, CK1α, GSPT1, or ikaros, combinations of any of the foregoing. In some embodiments, the protein is wild-type. In other embodiments, the protein is a mutant form of the protein. In some embodiments, the protein is overexpressed.

Additional Therapeutic Agents

Some embodiments provide pharmaceutical compositions comprising a compound of Formula (I), a compound of Formula (II), or a pharmaceutically acceptable salt of any of the foregoing and a second therapeutic agent. In some embodiments, the second therapeutic agent is an anti-inflammatory agent. In some embodiments, the second therapeutic agent is a non-steroidal anti-inflammatory agent. In some embodiments, the second therapeutic agent is an anti-cancer agent. In some embodiments, the second therapeutic agent is an immunostimulatory agent. In some embodiments, the second therapeutic agent is an immunosuppressive agent. In some embodiments, the second therapeutic agent is an antibody.

In some embodiments, the second therapeutic agent is selected from aspirin; diflunisal; salsalate; acetaminophen; ibuprofen; dexibuprofen; naproxen; fenoprofen; ketoprofen; dexketoprofen; flurbiprofen; oxaprozin; loxoprofen; indomethacin; tolmetin; sulindac; etodolac; ketorolac; diclofenac; aceclofenac; nabumetone; enolic acid; piroxicam; meloxicam; tenoxicam; droxicam; lornoxicam; isoxicam; mefenamic acid; meclofenamic acid; flufenamic acid; tolfenamic acid; sulfonanilides; clonixin; licofelone; dexamethasone; and prednisone. In some embodiments, the second therapeutic agent is mechlorethamine; cyclophosphamide; melphalan; chlorambucil; ifosfamide; busulfan; N-nitroso-N-methylurea (MNU); carmustine (BCNU); lomustine (CCNU); semustine (MeCCNU); fotemustine; streptozotocin; dacarbazine; mitozolomide; temozolomide; thiotepa; mytomycin; diaziquone (AZQ); cisplatin; carboplatin; or oxaliplatin. In some embodiments, the second therapeutic agent is vincristine; vinblastine; vinorelbine; vindesine; vinflunine; paclitaxel; docetaxel; etoposide; teniposide; tofacitinib; ixabepilone; irinotecan; topotecan; camptothecin; doxorubicin; mitoxantrone; or teniposide. In some embodiments, the second therapeutic agent is actinomycin; bleomycin; plicamycin; mitomycin; daunorubicin; epirubicin; idarubicin; pirarubicin; aclarubicin; mitoxantrone; cyclophosphamide; methotrexate; 5-fluorouracil; prednisolone; folinic acid; methotrexate; melphalan; capecitabine; mechlorethamine; uramustine; melphalan; chlorambucil; ifosfamide; bendamustine; 6-mercaptopurine; or procarbazine. In some embodiments, the second therapeutic agent is cladribine; pemetrexed; fludarabine; gemcitabine; hydroxyurea; nelarabine; cladribine; clofarabine; ytarabine; decitabine; cytarabine; cytarabine liposomal; pralatrexate; floxuridine; fludarabine; colchicine; thioguanine; cabazitaxel; larotaxel; ortataxel; tesetaxel; aminopterin; pemetrexed; pralatrexate; raltitrexed; pemetrexed; carmofur; or floxuridine. In some embodiments, the second therapeutic agent is azacitidine; decitabine; hydroxycarbamide; topotecan; irinotecan; belotecan; teniposide; aclarubicin; epirubicin; idarubicin; amrubicin; pirarubicin; valrubicin; zorubicin; mitoxantrone; pixantrone; mechlorethamine; chlorambucil; prednimustine; uramustine; estramustine; carmustine; lomustine; fotemustine; nimustine; ranimustine; carboquone; thioTEPA; triaziquone; or triethylenemelamine. In some embodiments, the second therapeutic agent is nedaplatin; satraplatin; procarbazine; dacarbazine; temozolomide; altretamine; mitobronitol; pipobroman; actinomycin; bleomycin; plicamycin; aminolevulinic acid; methyl aminolevulinate; efaproxiral; talaporfin; temoporfin; verteporfin; alvocidib; seliciclib; palbociclib; bortezomib; carfilzomib; anagrelide; masoprocol; olaparib; belinostat; panobinostat; romidepsin; vorinosta; idelalisib; atrasentan; bexarotene; testolactone; amsacrine; trabectedin; alitretinoin; tretinoin; demecolcine; elsamitrucin; etoglucid; lonidamine; lucanthone; mitoguazone; mitotane; oblimersen; omacetaxine mepesuccinate; or eribulin. In some embodiments, the second therapeutic agent is azathioprine; mycophenolic acid; leflunomide; teriflunomide; tacrolimus; cyclosporin; pimecrolimus; abetimus; gusperimus; lenalidomide; pomalidomide; thalidomide; anakinra; sirolimus; everolimus; ridaforolimus; temsirolimus; umirolimus; zotarolimus; eculizumab; adalimumab; afelimomab; certolizumab pegol; golimumab; infliximab; nerelimomab; mepolizumab; omalizumab; faralimomab; elsilimomab; lebrikizumab; ustekinumab; etanercept; otelixizumab; teplizumab; visilizumab; clenoliximab; keliximab; zanolimumab; efalizumab; erlizumab; obinutuzumab; rituximab; or ocrelizumab. In some embodiments, the second therapeutic agent is pascolizumab; gomiliximab; lumiliximab; tenelixmab; toralizumab; aselizumab; galiximab; gavilimomab; ruplizumab; belimumab; blisibimod; ipilimumab; tremelimumab; bertilimumab; lerdelimumab; metelimumab; natalizumab; tocilizumab; odulimomab; basiliximab; daclizumab; inolimomab; zolimoma; atorolimumab; cedelizumab; fontolizumab; maslimomab; morolimumab; pexelizumab; reslizumab; rovelizumab; siplizumab; talizumab; telimomab; vapaliximab; vepalimomab; abatacept; belatacept; pegsunercept; aflibercept; alefacept; or rilonacept.

Dosing Regimes

In some embodiments, about 1 mg to about 5 grams, or any amount in between, of a compound of Formula (I), a compound of Formula (II), or a pharmaceutically acceptable salt of any of the foregoing is administered each day, each week, or each cycle of treatment.

In some embodiments, a compound of Formula (I), a compound of Formula (II), or a pharmaceutically acceptable salt of any of the foregoing is administered once per day, twice per day, three times per day, four times per day, or more than four times per day. In some embodiments, a compound of Formula (I), a compound of Formula (II), or a pharmaceutically acceptable salt of any of the foregoing is administered once per day, twice per day, three times per day, four times per day, or more than four times per cycle of treatment.

In some embodiments, each cycle of treatment lasts from 1 day to 14 days, or any value in between. In some embodiments, each cycle of treatment has from at least one day up to fourteen days, or any value in between, between administration. In some embodiments, each cycle of treatment includes one or more additional therapeutic agents, as described herein. In some embodiments, a compound of Formula (I), a compound of Formula (II), or a pharmaceutically acceptable salt of any of the foregoing is provided intravenously over about 10 minutes to over about 4 h, or any value in between.

Pharmaceutical Compositions

Some embodiments provide a pharmaceutical composition, comprising a compound of Formula (I) (including Formula (Ia) and (Ib)), a compound of Formula (II) (including Formula (II'), (IIa), (IIb) and (IIb')), or a pharmaceutically acceptable salt thereof, and at least one pharmaceutically acceptable carrier or excipient.

One or more of the compounds of preferred embodiments can be provided in the form of pharmaceutically acceptable salts, active metabolites, or tautomers thereof. Some embodiments can be provided in pharmaceutical compositions comprising a therapeutically effective amount of the compound. In some embodiments, the pharmaceutical composition also contains at least one pharmaceutically acceptable inactive ingredient. The pharmaceutical composition can be formulated for intravenous injection, subcutaneous injection, oral administration, buccal administration, inhalation, nasal administration, topical administration, transdermal administration, ophthalmic administration, or otic administration. The pharmaceutical composition can be in the form of a tablet, a pill, a capsule, a liquid, an inhalant, a nasal spray solution, a suppository, a suspension, a gel, a colloid, a dispersion, a solution, an emulsion, an ointment, a lotion, an eye drop, or an ear drop.

The term "pharmaceutical composition" refers to a mixture of one or more compounds and/or salts disclosed herein with other chemical components, such as one or more excipients. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

As used herein, an "excipient" refers to essentially inert substances that are added to a pharmaceutical composition to provide, without limitation, bulk, consistency, stability, binding ability, lubrication, disintegrating ability etc., to the composition. For example, stabilizers such as anti-oxidants and metal-chelating agents are excipients. Excipients also include ingredients in a pharmaceutical composition that lack appreciable pharmacological activity but may be pharmaceutically necessary or desirable. For example, to increase the bulk of a potent drug whose mass is too small for manufacture and/or administration. It may also be a liquid for the dissolution of a drug to be administered by injection, ingestion or inhalation. For example, a buffered aqueous solution such as, without limitation, phosphate buffered saline that mimics the pH and isotonicity of human blood.

The pharmaceutical compositions described herein can be administered to a human patient per se, or in pharmaceutical compositions where they are mixed with other active ingredients, as in combination therapy, or excipients, or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound, salt and/or composition exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections. In some embodiments, a compound of Formula (I), a compound of Formula (II), or a pharmaceutically acceptable salt of any of the foregoing, can be administered orally.

One may also administer the compound, salt and/or composition in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory disease or condition may be desirable.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound and/or salt described herein formulated in a compatible pharmaceutical excipient may also be prepared, placed in an appropriate container, and labeled for treatment of an indicated condition.

Other objects, features, and advantages of the compounds, methods, and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

EXAMPLES

Additional embodiments are disclosed in further detail in the following schemes, which are not in any way intended to limit the scope of the claims.

Characterization of the compounds disclosed herein is performed with Bruker AV-500 and Bruker DRX-500 NMR spectrometers and a Perkin Elmer PE-SCIEX API-150 mass spectrometer.

Example 1

Compound 1: 3-[8-Oxo-3-({3-[5-(2-{4-[(5-{[5-(tert-butyl)-1,3-oxazol-2-yl]methylthio}-1,3-thiazol-2-ylamino)carbonyl]-1-piperidyl}acetylamino)pentyl]ureido}methyl)-2-thia-7-azabicyclo[3.3.0]octa-1(5),3-dien-7-yl]-2,6-piperidinedione To a solution of 2-(4-((5-(((5-(tert-butyl)oxazol-2-yl)methyl)thio)thiazol-2-yl) carbamoyl)piperidin-1-yl)acetic acid (100 mg, 0.228 mmol) in DMF (8 mL) at RT was added tert-butyl (2-(2-aminoethoxy)ethyl)carbamate (56 mg, 0.274 mmol) followed by HOBt (46.2 mg, 0.342 mmol), EDCI (66 mg, 0.342 mmol) and DIEA (59 mg, 0.456 mmol). The mixture was stirred at RT for 10 h then diluted with H$_2$O (10 mL) and extracted with EA. The combined organic layers were washed with H$_2$O (10 mL), dried over anhydrous Na$_2$SO$_4$, filtered, and concentrated. The residue was purified using silica gel eluting with DCM/MeOH (0% to 7%) to give tert-butyl (2-(2-(2-(4-((5-(((5-(tert-butyl)oxazol-2-yl)methyl)thio)thiazol-2-yl)carbamoyl)piperidin-1-yl)acetamido)ethoxy)ethyl)carbamate (120 mg, 84% yield) as a solid. MS (ESI) m/z 625.1 [M+H]$^+$.

To a solution of tert-butyl ((5-(2,6-dioxopiperidin-3-yl)-4-oxo-5,6-dihydro-4H-thieno[3,4-c]pyrrol-1-yl)methyl)carbamate (85 mg, 0.224 mmol) in DCM (8 mL) at RT was added TFA (2 mL). The mixture was stirred at RT for 1 h then concentrated to give the amine TFA salt (90 mg, crude) as an oil. The amine TFA salt was dissolved in THF (5 mL), then TEA (45.2 mg, 0.448 mmol) was added followed by 4-nitrobenzyl chloroformate (54.2 mg, 0.269 mmol). The mixture was stirred at RT for 1 h then concentrated to give 4-nitrophenyl ((5-(2,6-dioxopiperidin-3-yl)-4-oxo-5,6-dihydro-4H-thieno[3,4-c]pyrrol-1-yl)methyl)carbamate (110 mg, crude). MS (ESI) m/z 445.1 [M+H]$^+$.

To a solution of tert-butyl (2-(2-(2-(4-((5-(((5-(tert-butyl)oxazol-2-yl)methyl)thio)thiazol-2-yl)carbamoyl)piperidin-1-yl)acetamido)ethoxy)ethyl)carbamate (120 mg, 0.192 mmol) in DCM (8 mL) at RT was added TFA (2 mL). The mixture was stirred at RT for 1 h then concentrated to give 1-(2-((2-(2-aminoethoxy)ethyl)amino)-2-oxoethyl)-N-(5-(((5-(tert-butyl)oxazol-2-yl)methyl)thio)thiazol-2-yl)piperidine-4-carboxamide TFA salt (120 mg, crude) as an oil. This was dissolved in THF (10 mL) and TEA (155 mg, 1.54 mmol) was added. A suspension of 4-nitrophenyl((5-(2,6-dioxopiperidin-3-yl)-4-oxo-5,6-dihydro-4H-thieno[3,4-c]pyrrol-1-yl)methyl)carbamate (110 mg, crude) in THF (2 mL) was added and the mixture was stirred at RT for 3 h then concentrated. The residue was purified using silica gel eluting with DCM/MeOH (0% to 10%) followed by prep-HPLC using 0.1% TFA in water and 0.1% TFA in ACN with a gradient of 95% to 5% of the 0.1% TFA water to afford Compound 1 (59.2 mg, 37% yield) as a solid.

Example 2

Compound 2: 3-{6-Oxo-2-[(3-{2-[2-(2-{4-[(5-{[5-(tert-butyl)-1,3-oxazol-2-yl]methylthio}-1,3-thiazol-2-ylamino)carbonyl]-1-piperidyl}acetylamino)ethoxy]ethyl}ureido)methyl]-3-thia-7-azabicyclo[3.3.0]octa-1,4-dien-7-yl}-2,6-piperidinedione To a solution of 2-(4-((5-(((5-(tert-butyl)oxazol-2-yl)methyl)thio)thiazol-2-yl) carbamoyl)piperidin-1-yl)acetic acid (100 mg, 0.228 mmol) in DMF (8 mL) at RT was added tert-butyl (2-(2-aminoethoxy)ethyl)carbamate (56 mg, 0.274 mmol) followed by HOBt (46.2 mg, 0.342 mmol), EDCI (66 mg, 0.342 mmol) and DIEA (59 mg, 0.456 mmol). The mixture was stirred at RT for 10 h then diluted with H$_2$O and extracted with EA. The combined organic layers were washed with H$_2$O, dried over anhydrous Na$_2$SO$_4$, filtered, and concentrated. The crude product was purified using silica gel eluting with DCM/MeOH (0% to 7%) to give tert-butyl (2-(2-(2-(4-((5-(((5-(tert-butyl)oxazol-2-yl)methyl)thio)thiazol-2-yl)carbamoyl)piperidin-1-yl)acetamido)ethoxy)ethyl) carbamate (120 mg, 84% yield) as a solid. MS (ESI) m/z 625.1 [M+H]$^+$.

To a solution of tert-butyl ((5-(2,6-dioxopiperidin-3-yl)-4-oxo-5,6-dihydro-4H-thieno[3,4-c]pyrrol-1-yl)methyl)carbamate (85 mg, 0.224 mmol) in DCM (8 mL) at RT was added TFA (2 mL). The mixture was stirred at RT for 1 h and concentrated to give the amine TFA salt (90 mg, crude) as an oil. The amine TFA salt was dissolved in THF (5 mL) and TEA (45.2 mg, 0.448 mmol) was added followed by 4-nitrobenzyl chloroformate (54.2 mg, 0.269 mmol). The mixture was stirred at RT for 1 h then concentrated to give the crude 4-nitrophenyl ((5-(2,6-dioxopiperidin-3-yl)-4-oxo-5,6-dihydro-4H-thieno[3,4-c]pyrrol-1-yl)methyl)carbamate (110 mg, crude). MS (ESI) m/z 445.1 [M+H]$^+$.

To a solution of tert-butyl (2-(2-(2-(4-(((5-(((5-(tert-butyl)oxazol-2-yl)methyl) thio)thiazol-2-yl)carbamoyl)piperidin-1-yl)acetamido)ethoxy)ethyl)carbamate (120 mg, 0.192 mmol) in DCM (8 mL) at RT was added TFA (2 mL). The mixture was stirred at RT for 1 h then concentrated to give 1-(2-((2-(2-aminoethoxy)ethyl)amino)-2-oxoethyl)-N-(5-(((5-(tert-butyl)oxazol-2-yl)methyl)thio)thiazol-2-yl)piperidine-4-carboxamide TFA salt (120 mg, crude) as an oil. This was dissolved in THF (10 mL) and TEA (155 mg, 1.54 mmol) was added. A suspension of 4-nitrophenyl((5-(2,6-dioxopiperidin-3-yl)-4-oxo-5,6-dihydro-4H-thieno[3,4-c]pyrrol-1-yl)methyl)carbamate (110 mg, crude) in THF (2 mL) was added, and the mixture was stirred at RT for 3 h then concentrated. The residue was purified using silica gel eluting with DCM/MeOH (0% to 10%) followed by prep-HPLC using 0.1% TFA in water and 0.1% TFA in ACN with a gradient of 95% to 5% of the 0.1% TFA water to afford Compound 2 (59.2 mg, 37% yield) as a solid.

Example 3

Compound 3: 3-{8-Oxo-3-[(3-{2-[2-(2-{4-[(5-{[5-(tert-butyl)-1,3-oxazol-2-yl]methylthio}-1,3-thiazol-2-ylamino)carbonyl]-1-piperidyl}acetylamino)ethoxy]ethyl}ureido)methyl]-2-thia-7-azabicyclo[3.3.0]octa-1(5),3-dien-7-yl}-2,6-piperidinedione To a solution of tert-butyl ((5-(2,6-dioxopiperidin-3-yl)-6-oxo-5,6-dihydro-4H-thieno[2,3-c]pyrrol-2-yl)methyl)carbamate (80 mg, 0.211 mmol) in DCM (8 mL) at RT was added TFA (2 mL). The mixture was stirred at RT for 1 h then concentrated to give 3-(2-(aminomethyl)-6-oxo-4H-thieno[2,3-c]pyrrol-5(6H)-yl)piperidine-2,6-dione TFA salt (90 mg, crude) as an oil.

3-(2-(aminomethyl)-6-oxo-4H-thieno[2,3-c]pyrrol-5(6H)-yl)piperidine-2,6-dione TFA salt was dissolved in THF (5 mL) and TEA (42.6 mg, 0.422 mmol) was added followed by 4-nitrobenzyl chloroformate (50.9 mg, 0.253 mmol). The mixture was stirred at RT for 1 h then concentrated to give 4-nitrophenyl ((5-(2,6-dioxopiperidin-3-yl)-6-oxo-5,6-dihydro-4H-thieno[2,3-c]pyrrol-2-yl)methyl)carbamate (94 mg, crude). MS (ESI) m/z 445.1[M+H]$^+$.

To a solution of tert-butyl (2-(2-(2-(4-((5-(((5-(tert-butyl)oxazol-2-yl)methyl)thio)thiazol-2-yl)carbamoyl)piperidin-1-yl)acetamido)ethoxy)ethyl)carbamate (70 mg, 0.112 mmol) in DCM (4 mL) at RT was added TFA (1 mL). The mixture was stirred at RT for 1 h then concentrated to give 1-(2-((2-(2-aminoethoxy)ethyl)amino)-2-oxoethyl)-N-(5-(((5-(tert-butyl)oxazol-2-yl)methyl)thio)thiazol-2-yl)piperidine-4-carboxamide TFA salt (80 mg, crude) as an oil. 1-(2-((2-(2-Aminoethoxy) ethyl)amino)-2-oxoethyl)-N-(5-(((5-(tert-butyl)oxazol-2-yl)methyl)thio)thiazol-2-yl) piperidine-4-carboxamide TFA salt was dissolved in THF (5 mL) and TEA (90 mg, 0.896 mmol) was added. A suspension of 4-nitrophenyl ((5-(2,6-dioxopiperidin-3-yl)-6-oxo-5,6-dihydro-4H-thieno[2,3-c]pyrrol-2-yl)methyl)carbamate (94 mg, crude) in THF (2 mL) was added. The mixture was stirred at RT for 3 h then concentrated. The residue was purified using silica gel eluting with DCM/MeOH (0% to 10%) followed by prep-HPLC using 0.1% TFA in water and 0.1% TFA in ACN with a gradient of 95% to 5% of the 0.1% TFA water to afford Compound 3 (7.9 mg, 8% yield) as a solid.

Example 4

Compound 4: 3-[2-({3-[7-(4-{5-Chloro-4-[5-(cyclopropylmethyl)-1-methyl-1H-pyrazol-4-yl]-2-pyrimidinylamino}cyclohexylamino)-7-oxoheptyl]ureido}methyl)-6-oxo-3-thia-7-azabicyclo[3.3.0]octa-1,4-dien-7-yl]-2,6-piperidinedione To a solution of (1r,4r)-N1-(5-chloro-4-(5-(cyclopropylmethyl)-1-methyl-1H-pyrazol-4-yl)pyrimidin-2-yl)cyclohexane-1,4-diamine (200 mg, 0.526 mmol) in DMF (10 mL) at RT was added 7-((tert-butoxycarbonyl)amino)heptanoic acid (129 mg, 0.526 mmol) followed by HOBt (106.5 mg, 0.789 mmol), EDCI (151.5 mg, 0.789 mmol) and DIEA (136 mg, 1.052 mmol). The mixture was stirred at RT for 16 h then diluted with H$_2$O (10 mL) and extracted with EA. The combined organic layers were washed with H$_2$O (10 mL), dried over anhydrous Na$_2$SO$_4$, filtered and concentrated. The residue was purified using silica gel eluting with DCM/MeOH (0% to 8%) to give tert-butyl (7-(((1r,4r)-4-((5-chloro-4-(5-(cyclopropylmethyl)-1-methyl-1H-pyrazol-4-yl)pyrimidin-2-yl)amino)cyclohexyl)amino)-7-oxoheptyl) carbamate (260 mg, 84% yield) as a solid. MS (ESI) m/z 588.1 [M+H]$^+$.

To a solution of tert-butyl (7-(((1r,4r)-4-((5-chloro-4-(5-(cyclopropylmethyl)-1-methyl-1H-pyrazol-4-yl)pyrimidin-2-yl)amino)cyclohexyl)amino)-7-oxoheptyl)carbamate (70 mg, 0.119 mmol) in DCM (6 mL) at RT was added TFA (1.5 mL). The mixture was stirred at RT for 1 h then concentrated to give 7-amino-N-((1r,4r)-4-((5-chloro-4-(5-(cyclopropylmethyl)-1-methyl-1H-pyrazol-4-yl)pyrimidin-2-yl)amino)cyclohexyl)heptanamide as an oil. The crude 7-amino-N-((1r,4r)-4-((5-chloro-4-(5-(cyclopropylmethyl)-1-methyl-1H-pyrazol-4-yl)pyrimidin-2-yl)amino)cyclohexyl)heptanamide was dissolved in THF (5 mL) and TEA (71.4 mg, 0.714 mmol) was added. A suspension of 4-nitrophenyl ((5-(2,6-dioxopiperidin-3-yl)-4-oxo-5,6-dihydro-4H-thieno[3,4-c]pyrrol-1-yl)methyl)carbamate (29.7 mg, 0.148 mmol) in THF (1 mL) was added and the mixture was stirred at RT for 1 h then concentrated. The residue was purified using silica gel eluting with DCM/MeOH (0% to 10%) to afford Compound 4 (28.6 mg, 30% yield) as a solid.

Example 5

Compound 5: N-((1r,4r)-4-((5-chloro-4-(5-(cyclopropylmethyl)-1-methyl-1H-pyrazol-4-yl)pyrimidin-2-yl)amino)cyclohexyl)-7-(3-((5-(2,6-dioxopiperidin-3-yl)-6-oxo-5,6-dihydro-4H-thieno[2,3-c]pyrrol-2-yl)methyl)ureido)heptanamide To a solution of tert-butyl ((5-(2,6-dioxopiperidin-3-yl)-6-oxo-5,6-dihydro-4H-thieno[2,3-c]pyrrol-2-yl)methyl)carbamate (80 mg, 0.21 mmol) in DCM (8 mL) at RT was added TFA (2 mL). The mixture was stirred at RT for 1 h then concentrated to give the TFA salt of 3-(2-(aminomethyl)-6-oxo-4H-thieno[2,3-c]pyrrol-5(6H)-yl)piperidine-2,6-dione (90 mg, crude) as an oil.

To a solution of the amine TFA salt in THF (5 mL) was added TEA (42.4 mg, 0.42 mmol) and 4-nitrobenzyl chloroformate (51 mg, 0.253 mmol). The mixture was stirred at RT for 1 h and concentrated to give 4-nitrophenyl ((5-(2,6-dioxopiperidin-3-yl)-6-oxo-5,6-dihydro-4H-thieno[2,3-c]pyrrol-2-yl)methyl)carbamate (93 mg, crude). MS (ESI) m/z 445.1 [M+H]$^+$.

To a solution of tert-butyl (7-(((1r,4r)-4-((5-chloro-4-(5-(cyclopropylmethyl)-1-methyl-1H-pyrazol-4-yl)pyrimidin-2-yl)amino)cyclohexyl)amino)-7-oxoheptyl)carbamate (90 mg, 0.153 mmol) in DCM (8 mL) at RT was added TFA (2 mL). The mixture was stirred at RT for 1 h then concentrated to give the TFA salt of 7-amino-N-((1r,4r)-4-((5-chloro-4-(5-(cyclopropylmethyl)-1-methyl-1H-pyrazol-4-yl)pyrimidin-2-yl)amino)cyclohexyl)heptanamide.

To a solution of the amine TFA salt in THF (5 mL) was added TEA (124 mg, 1.224 mmol) and a suspension of 4-nitrophenyl ((5-(2,6-dioxopiperidin-3-yl)-6-oxo-5,6-dihydro-4H-thieno[2,3-c]pyrrol-2-yl)methyl)carbamate (93 mg, 0.21 mmol) in THF (1 mL). The mixture was stirred at RT for 3 h then concentrated. The residue was purified using silica gel eluting with MeOH/DCM (0% to 8%) followed by prep-HPLC using 0.1% TFA in H$_2$O, 0.1% TFA in ACN (5%-95%) to afford Compound 5 (16.5 mg, 14% yield) as a solid.

Example 6

Compound 6: (S)—N-(5-(((5-(tert-butyl)oxazol-2-yl)methyl)thio)thiazol-2-yl)-1-(1-(2-(2,7-dioxoazepan-3-yl)-1-oxoisoindolin-5-yl)-3,11-dioxo-7-oxa-2,4,10-triazadodecan-12-yl)piperidine-4-carboxamide To a solution of (S)-tert-butyl ((2-(2,7-dioxoazepan-3-yl)-1-oxoisoindolin-5-yl)methyl)carbamate (70 mg, 0.180 mmol) in DCM (4 mL) at RT was added TFA (1 mL). The solution was stirred at RT for 1 h. The solvent was removed and the residue was dried to give the amine TFA salt (90 mg, crude) as an oil.

The amine TFA salt was dissolved in THF (5 mL) and TEA (37 mg, 0.36 mmol) was added. Then 4-nitrobenzyl chloroformate (43.6 mg, 0.217 mmol) was added. The mixture was stirred at RT for 1 h. The solvent was removed to give (S)-4-nitrophenyl ((2-(2,7-dioxoazepan-3-yl)-1-oxoisoindolin-5-yl)methyl)carbamate (81.5 mg, crude). MS (ESI) m/z 453.1 [M+H]$^+$.

To a solution of tert-butyl (2-(2-(2-(4-((5-(((5-(tert-butyl)oxazol-2-yl)methyl)thio)thiazol-2-yl)carbamoyl)piperidin-1-yl)acetamido)ethoxy)ethyl)carbamate (90 mg, 0.144 mmol) in DCM (8 mL) at RT was added TFA (2 mL). The solution was stirred at RT for 1 h. The solvent was removed and the residue was dried to give the amine TFA salt (80 mg, crude) as an oil.

The amine TFA salt was dissolved in THF (5 mL) and TEA (90 mg, 0.896 mmol) was added. A suspension of (S)-4-nitrophenyl ((2-(2,7-dioxoazepan-3-yl)-1-oxoisoindolin-5-yl)methyl)carbamate (81.5 mg, crude) in THF (2 mL) was added. Then the mixture was stirred at RT for 3 h. The solvent was removed and the residue was purified using silica gel eluting with DCM/MeOH (0% to 10%) followed by prep-HPLC as previously described to afford Compound 6 (16.3 mg, 14% yield) as a solid.

Example 7

Compound 7: (S)—N-(5-(((5-(tert-butyl)oxazol-2-yl)methyl)thio)thiazol-2-yl)-1-(1-(2-(2,7-dioxoazepan-3-yl)-1-oxoisoindolin-4-yl)-3,11-dioxo-7-oxa-2,4,10-triazadodecan-12-yl)piperidine-4-carboxamide To a solution of (S)-tert-butyl ((2-(2,7-dioxoazepan-3-yl)-1-oxoisoindolin-4-yl)methyl)carbamate (100 mg, 0.258 mmol) in DCM (8 mL) at RT was added TFA (2 mL). The solution was stirred at RT for 1 h. The solvent was removed and the residue was dried to give the amine TFA salt (120 mg, crude) as an oil.

The amine TFA salt was dissolved in THF (5 mL) and TEA (52 mg, 0.516 mmol) was added. Then 4-nitrobenzyl chloroformate (62.3 mg, 0.31 mmol) was added. The mixture was stirred at RT for 1 h. The solvent was removed to give (S)-4-nitrophenyl ((2-(2,7-dioxoazepan-3-yl)-1-oxoisoindolin-4-yl)methyl)carbamate (120 mg, crude). MS (ESI) m/z 453.1 [M+H]$^+$.

To a solution of tert-butyl (2-(2-(2-(4-((5-(((5-(tert-butyl)oxazol-2-yl)methyl)thio)thiazol-2-yl)carbamoyl)piperidin-1-yl)acetamido)ethoxy)ethyl)carbamate (85 mg, 0.136 mmol) in DCM (8 mL) at RT was added TFA (2 mL). The solution was stirred at RT for 1 h. The solvent was removed and the residue was dried to give the amine TFA salt (100 mg, crude) as an oil.

The amine TFA salt was dissolved in THF (5 mL) and TEA (110 mg, 0.896 mmol) was added. Then the suspension of (S)-4-nitrophenyl ((2-(2,7-dioxoazepan-3-yl)-1-oxoisoindolin-4-yl)methyl)carbamate (120 mg, crude) in THF (2 mL) was added. Then the mixture was stirred at RT for 3 h. The solvent was removed and the residue was purified using silica gel eluting with DCM/MeOH (0% to 10%) to give the crude product compound (150 mg) as an oil. It was further purified using prep-HPLC as previously described to afford Compound 7 (79.4 mg, 70% yield) as a solid.

Example 8

Compound 8: N-((1r,4r)-4-((5-chloro-4-(5-(cyclopropylmethyl)-1-methyl-1H-pyrazol-4-yl)pyrimidin-2-yl)amino)cyclohexyl)-7-((2-((4-(((2-(2,6-dioxopiperidin-3-yl)-1-oxoisoindolin-4-yl)oxy)methyl)benzyl)amino)-2-oxoethyl)amino)heptanamide To a solution of tert-butyl (7-(((1r,4r)-4-((5-chloro-4-(5-(cyclopropylmethyl)-1-methyl-1H-pyrazol-4-yl)pyrimidin-2-yl)amino)cyclohexyl)amino)-7-oxoheptyl)carbamate (400 mg, 0.681 mmol) in DCM (8 mL) at RT was added TFA (2 mL). The solution was stirred at RT for 1 h. The solvent was removed and the residue was dried to give the amine TFA salt (300 mg, crude) as an oil.

The amine TFA salt was dissolved in N,N-dimethylamide (16 mL), and K$_2$CO$_3$ (282 mg, 2.04 mmol) was added. The suspension was cooled to 0° C. and tert-butyl bromoacetate (133 mg, 0.681 mmol) was added. The suspension was stirred at RT for 3 h. The mixture was diluted with H$_2$O (10 mL) and extracted with EA (20 mL×2). The combined organic layers were washed with H$_2$O (10 mL), dried over Na$_2$SO$_4$, filtered and concentrated. The residue was purified using silica gel eluting with MeOH/DCM (0% to 9%) to give tert-butyl 2-((7-(((1r,4r)-4-((5-chloro-4-(5-(cyclopropylmethyl)-1-methyl-1H-pyrazol-4-yl)pyrimidin-2-yl)amino)cyclohexyl)amino)-7-oxoheptyl)amino)acetate (33 mg, 8% yield) as an oil. MS (ESI) m/z 602.3 [M+H]$^+$.

To a solution of tert-butyl 2-((7-(((1r,4r)-4-((5-chloro-4-(5-(cyclopropylmethyl)-1-methyl-1H-pyrazol-4-yl)pyrimidin-2-yl)amino)cyclohexyl)amino)-7-oxoheptyl)amino)acetate (55 mg, 0.0913 mmol) in DCM (4 mL) at RT was added TFA (1 mL). The solution was stirred at RT for 10 h. The solvent was removed and the residue was dried to give 2-((7-(((1r,4r)-4-((5-chloro-4-(5-(cyclopropylmethyl)-1-methyl-1H-pyrazol-4-yl)pyrimidin-2-yl)amino)cyclohexyl)amino)-7-oxoheptyl)amino)acetic acid (56 mg, crude) as an oil. MS (ESI) m/z 546.2 [M+H]$^+$.

To a solution of tert-butyl 4-(((2-(2,6-dioxopiperidin-3-yl)-1-oxoisoindolin-4-yl)oxy)methyl)benzylcarbamate (50 mg, 0.104 mmol) in DCM (4 mL) at RT was added TFA (1 mL). The solution was stirred at RT for 1 h. The solvent was removed and the residue was dried to give the amine TFA salt (45 mg, crude) as an oil.

The amine TFA salt was dissolved in DMF (5 mL) at RT and DIEA (40 mg, 0.312 mmol) was added. Then 2-((7-(((1r,4r)-4-((5-chloro-4-(5-(cyclopropylmethyl)-1-methyl-1H-pyrazol-4-yl)pyrimidin-2-yl)amino)cyclohexyl)amino)-7-oxoheptyl)amino)acetic acid (56 mg, 0.104 mmol), HOBt (21 mg, 0.156 mmol) and EDCI (29.9 mg, 0.156 mmol) were added. The mixture was stirred at RT for 16 h. The solvent was removed and the residue was purified using prep-HPLC to afford Compound 8 (25.7 mg, 27% yield) as a solid.

Example 9

Compound 9: N-((1r,4r)-4-((5-chloro-4-(5-(cyclopropylmethyl)-1-methyl-1H-pyrazol-4-yl)pyrimidin-2-yl)amino)cyclohexyl)-7-((2-((2-((S)-2,7-dioxoazepan-3-yl)-1-oxoisoindolin-4-yl)amino)-2-oxoethyl)amino)heptanamide To a solution of (S)-3-(4-amino-1-oxoisoindolin-2-yl)azepane-2,7-dione (100 mg, 0.366 mmol) in THF (5 mL) at 0° C. was added 2-chloroacetyl chloride (82 mg, 0.733 mmol), followed by TEA (93 mg, 0.915 mmol). The mixture was stirred at RT for 30 min. The solvent was removed and the residue was purified using silica gel eluting with MeOH/DCM (0% to 6%) to give (S)-2-chloro-N-(2-(2,7-dioxoazepan-3-yl)-1-oxoisoindolin-4-yl)acetamide (122 mg, 96% yield) as a solid. MS (ESI) m/z 349.9 [M+H]$^+$.

To a solution of tert-butyl (7-(((1r,4r)-4-((5-chloro-4-(5-(cyclopropylmethyl)-1-methyl-1H-pyrazol-4-yl)pyrimidin-2-yl)amino)cyclohexyl)amino)-7-oxoheptyl)carbamate (99 mg, 0.172 mmol) in DCM (8 mL) at RT was added TFA (2 mL). The solution was stirred at RT for 1 h. The solvent was removed and the residue was dried to give the amine TFA salt as an oil.

The amine TFA salt was dissolved in DMA (5 mL), then K$_2$CO$_3$ (48 mg, 0.344 mmol) and potassium iodide (28 mg, 0.172 mmol) were added. Then (S)-2-chloro-N-(2-(2,7-dioxoazepan-3-yl)-1-oxoisoindolin-4-yl)acetamide (60 mg, 0.172 mmol) was added and the mixture was heated at 50° C. for 4 h. The solvent was removed and the residue was purified using prep-HPLC as previously described to afford Compound 9 (42.7 mg, 31% yield) as a solid.

Example 10

Compound 10: N-(5-(((5-(tert-butyl)oxazol-2-yl)methyl)thio)thiazol-2-yl)-1-(14-((2-(2,6-dioxopiperidin-3-yl)-1,3-dioxoisoindolin-4-yl)amino)-2-oxo-6,9,12-trioxa-3-azatetradecyl)piperidine-4-carboxamide To a suspension of 2-(2,6-dioxopiperidin-3-yl)-4-fluoroisoindoline-1,3-dione (500 mg, 1.81 mmol) in 1-methyl-2-pyrrolidinone (10 mL) was added tert-butyl (2-(2-(2-(2-aminoethoxy)ethoxy)ethoxy)ethyl)carbamate (636 mg, 2.17 mmol) and DIEA (700 mg, 5.43 mmol). The mixture was heated at 100° C. under microwave irradiation for 50 min, then cooled to RT, diluted with H$_2$O (20 mL) and extracted with EA. The combined organic layers were washed with H$_2$O, dried over Na$_2$SO$_4$, filtered and concentrated to give the crude product which was purified using silica gel eluting with EA/PE (10% to 88%) to give tert-butyl (2-(2-(2-(2-((2-(2,6-dioxopiperidin-3-yl)-1,3-dioxoisoindolin-4-yl)amino)ethoxy)ethoxy)ethoxy)ethyl)carbamate (502 mg, 55% yield) as an oil. MS (ESI) m/z 549.3[M+1]$^+$.

To a solution of tert-butyl (2-(2-(2-(2-((2-(2,6-dioxopiperidin-3-yl)-1,3-dioxoisoindolin-4-yl)amino)ethoxy)ethoxy)ethoxy)ethyl)carbamate (130 mg, 0.242 mmol) in DCM (8 mL) was added TFA (2 mL). The mixture was stirred at RT for 1 h and concentrated to give the amine TFA salt which was dissolved in DMF (5 mL). To the solution was added DIEA (94 mg, 0.729 mmol), EDCI (70 mg, 0.365 mmol), HOBt (49 mg, 0.365 mmol) and 2-(4-((5-(((5-(tert-butyl)oxazol-2-yl)methyl)thio)thiazol-2-yl)carbamoyl)piperidin-1-yl)acetic acid (106 mg, 0.243 mmol). After 16 h at RT, the mixture was diluted with H$_2$O and extracted with EA. The combined organic layers were washed with H$_2$O, dried over Na$_2$SO$_4$, filtered and concentrated to give the crude product which was purified using prep-TLC using DCM/MeOH (10:1) to afford Compound 10 (48.4 mg, 23% yield) as a solid.

Example 11

Compound 11: N-(5-(((5-(tert-butyl)oxazol-2-yl)methyl)thio)thiazol-2-yl)-1-(2-((5-(3-((5-(2,6-dioxopiperidin-3-yl)-4-oxo-5,6-dihydro-4H-thieno[3,4-c]pyrrol-1-yl)methyl)ureido)pentyl)amino)-2-oxoethyl)piperidine-4-carboxamide To a solution of 2-(4-((5-(((5-(tert-butyl)oxazol-2-yl)methyl)thio)thiazol-2-yl)carbamoyl)piperidin-1-yl)acetic acid (200 mg, 0.46 mmol) in DMF (5 mL) was added tert-butyl (5-aminopentyl)carbamate (111 mg, 0.55 mmol) and DIEA (118 mg, 0.92 mmol), followed by HOBt (93 mg, 0.69 mmol) and EDCI.HCl (133 mg, 0.69 mmol). The mixture was stirred at RT overnight, diluted with H$_2$O, and extracted with EA. The combined organic layers were washed with saturated NaHCO$_3$, dried over Na$_2$SO$_4$, filtered and concentrated to give the crude product, which was purified using silica gel eluting with MeOH/DCM (0% to 10%) to give tert-butyl (5-(2-(4-((5-(((5-(tert-butyl)oxazol-2-yl)methyl)thio)thiazol-2-yl)carbamoyl)piperidin-1-yl)acetamido)pentyl)carbamate (196 mg, 69% yield) as a solid. MS (ESI) m/z 623.2 [M+H]$^+$.

To a solution of tert-butyl (5-(2-(4-((5-(((5-(tert-butyl)oxazol-2-yl)methyl)thio) thiazol-2-yl)carbamoyl)piperidin-1-yl)acetamido)pentyl)carbamate (130 mg, 0.211 mmol) in DCM (6 mL) was added TFA (3 mL). The mixture was stirred at RT for 0.5 h then concentrated to give 1-(2-((5-aminopentyl)amino)-2-oxoethyl)-N-(5-(((5-(tert-butyl)oxazol-2-yl)methyl)thio)thiazol-2-yl)piperidine-4-carboxamide as a TFA salt. MS (ESI) m/z 523.2 [M+H]$^+$.

To a solution of 1-(2-((5-aminopentyl)amino)-2-oxoethyl)-N-(5-(((5-(tert-butyl)oxazol-2-yl)methyl)thio)thiazol-2-yl)piperidine-4-carboxamide (110 mg, as TFA salt) in THF (5 mL) was added 4-nitrophenyl ((5-(2,6-dioxopiperidin-3-yl)-4-oxo-5,6-dihydro-4H-thieno[3,4-c]pyrrol-1-yl)methyl)carbamate (94 mg, 0.211 mmol) and TEA (42 mg, 0.422 mmol) at RT. After 2 h, the mixture was concentrated and purified using prep-HPLC as previously described to afford Compound 11 (5.4 mg, 3% yield) as a solid.

Example 12

Compound 12: N-(5-(((5-(tert-butyl)oxazol-2-yl)methyl)thio)thiazol-2-yl)-1-(2-((3-(3-((5-(2,6-dioxopiperidin-3-yl)-6-oxo-5,6-dihydro-4H-thieno[2,3-c]pyrrol-2-yl)methyl)ureido)propyl)amino)-2-oxoethyl)piperidine-4-carboxamide To a solution of 2-(4-((5-(((5-(tert-butyl)oxazol-2-yl)methyl)thio)thiazol-2-yl) carbamoyl)piperidin-1-yl)acetic acid (200 mg, 0.46 mmol) in DMF (5 mL) was added tert-butyl (3-aminopropyl)carbamate (95 mg, 0.55 mmol) and DIEA (118 mg, 0.92 mmol), followed by HOBt (93 mg, 0.69 mmol) and EDCI.HCl (133 mg, 0.69 mmol). The mixture was stirred at RT overnight, then diluted with $H_2O$ and extracted with EA. The combined organic layers were washed with saturated $NaHCO_3$, dried over $Na_2SO_4$, filtered and concentrated to give the crude product, which was purified using silica gel eluting with MeOH/DCM (0% to 10%) to give tert-butyl (3-(2-(4-((5-(((5-(tert-butyl)oxazol-2-yl)methyl)thio)thiazol-2-yl)carbamoyl)piperidin-1-yl)acetamido)propyl)carbamate (185 mg, 68% yield) as a solid. MS (ESI) m/z 595.2 $[M+H]^+$.

To a solution of tert-butyl (3-(2-(4-((5-(((5-(tert-butyl)oxazol-2-yl)methyl)thio)thiazol-2-yl)carbamoyl)piperidin-1-yl)acetamido)propyl)carbamate (125 mg, 0.211 mmol) in DCM (4 mL) was added TFA (2 mL). The mixture was stirred at RT for 0.5 h then concentrated to give 1-(2-((3-aminopropyl)amino)-2-oxoethyl)-N-(5-(((5-(tert-butyl)oxazol-2-yl)methyl)thio)thiazol-2-yl)piperidine-4-carboxamide as a TFA salt. MS (ESI) m/z 495.2 $[M+H]^+$.

To a solution of 1-(2-((3-aminopropyl)amino)-2-oxoethyl)-N-(5-(((5-(tert-butyl)oxazol-2-yl)methyl)thio)thiazol-2-yl)piperidine-4-carboxamide (104 mg, as TFA salt) in THF (5 mL) was added 4-nitrophenyl ((5-(2,6-dioxopiperidin-3-yl)-6-oxo-5,6-dihydro-4H-thieno[2,3-c]pyrrol-2-yl)methyl)carbamate (94 mg, 0.211 mmol) and TEA (42 mg, 0.422 mmol) at RT. After 2 h, the mixture was concentrated to give the crude product, which was purified using prep-HPLC as previously described to afford Compound 12 (31.9 mg, 19% yield) as a solid.

Example 13

Compound 13: N-(5-(((5-(tert-butyl)oxazol-2-yl)methyl)thio)thiazol-2-yl)-1-(1-(5-(2,6-dioxopiperidin-3-yl)-6-oxo-5,6-dihydro-4H-thieno[2,3-c]pyrrol-2-yl)-3,14-dioxo-7,10-dioxa-2,4,13-triazapentadecan-15-yl)piperidine-4-carboxamide To a solution of 2-(4-((5-(((5-(tert-butyl)oxazol-2-yl)methyl)thio)thiazol-2-yl) carbamoyl)piperidin-1-yl)acetic acid (250 mg, 0.57 mmol) in DMF (2 mL) at RT was added tert-butyl (2-(2-(2-aminoethoxy)ethoxy)ethyl)carbamate (156 mg, 0.62 mmol), HOBT (116 mg, 0.85 mmol), EDCI (164 mg, 0.85 mmol) and DIEA (148 mg, 1.48 mmol). The mixture was stirred at RT for 4 h then concentrated and purified using silica gel eluting with DCM/MeOH (50:1 to 20:1) to give tert-butyl (2-(2-(2-(2-(4-((5-(((5-(tert-butyl)oxazol-2-yl)methyl) thio)thiazol-2-yl)carbamoyl)piperidin-1-yl)acetamido)ethoxy)ethoxy)ethyl)carbamate (350 mg, 91% yield) as an oil. MS (ESI) m/z 669.3 $[M+H]^+$.

To a solution of tert-butyl (2-(2-(2-(2-(4-((5-(((5-(tert-butyl)oxazol-2-yl)methyl) thio)thiazol-2-yl)carbamoyl)piperidin-1-yl)acetamido)ethoxy)ethoxy)ethyl)carbamate (147 mg, 0.220 mmol) in DCM (2 mL) at RT was added TFA (0.5 mL). After 1 h, the mixture was concentrated and the residue was dissolved in THF (5 mL). TEA (177 mg, 1.76 mmol) and 4-nitrophenyl ((5-(2,6-dioxopiperidin-3-yl)-4-oxo-5,6-dihydro-4H-thieno[3,4-c]pyrrol-1-yl)methyl)carbamate (160 mg, 0.264 mmol) were added at RT. After 3 h, the mixture was concentrated and purified using prep-HPLC to afford Compound 13 (36.7 mg, 19% yield) as a solid.

Example 14

Compound 14: N-(5-(((5-(tert-butyl)oxazol-2-yl)methyl)thio)thiazol-2-yl)-1-(2-((4-((2-(((5-(2,6-dioxopiperidin-3-yl)-6-oxo-5,6-dihydro-4H-thieno[2,3-c]pyrrol-2-yl)methyl)amino)-2-oxoethyl)amino)butyl)amino)-2-oxoethyl)piperidine-4-carboxamide To a solution of 2-(4-((5-(((5-(tert-butyl)oxazol-2-yl)methyl)thio) thiazol-2-yl)carbamoyl)piperidin-1-yl)acetic acid (500 mg, 1.14 mmol) in DMF (10 mL) was added tert-butyl (4-aminobutyl) carbamate (258 mg, 1.37 mmol) and DIEA (294 mg, 2.28 mmol), followed by 2-(7-Azabenzotriazol-1-yl)-N,N,N',N'-tetramethyluronium hexafluorophosphate (HATU, 650 mg, 1.70 mmol). After 1 h, the mixture was diluted with $H_2O$ and extracted with EA. The combined organic layers were washed with saturated $NaHCO_3$, dried over $Na_2SO_4$, filtered and concentrated to give the crude product, which was purified using silica gel eluting with MeOH/DCM (0% to 10%) to give tert-butyl (4-(2-(4-((5-(((5-(tert-butyl)oxazol-2-yl)methyl)thio)thiazol-2-yl)carbamoyl)piperidin-1-yl)acetamido)butyl)carbamate (470 mg, 81% yield) as a solid. MS (ESI) m/z 609.2 $[M+H]^+$.

To a solution of tert-butyl (4-(2-(4-((5-(((5-(tert-butyl)oxazol-2-yl)methyl)thio) thiazol-2-yl)carbamoyl)piperidin-1-yl)acetamido)butyl)carbamate (470 mg, 0.773 mmol) in DCM (4 mL) was added TFA (1 mL). The mixture was stirred at RT for 0.5 h. The solvent was removed and the residue was dried to give the amine TFA salt. MS (ESI) m/z 509.2 $[M+H]^+$.

To a solution of 1-(2-((5-aminopentyl)amino)-2-oxoethyl)-N-(5-(((5-(tert-butyl)oxazol-2-yl)methyl)thio)thiazol-2-yl)piperidine-4-carboxamide (392 mg, as the TFA salt) in DMF (20 mL) was added tert-butyl 2-bromoacetate (150 mg, 0.77 mmol) and $K_2CO_3$ (106 mg, 0.77 mmol) at RT. After 16 h, the mixture was diluted with $H_2O$ and extracted with EA. The combined organic layers were washed with saturated $NaHCO_3$, dried over $Na_2SO_4$, filtered and concentrated to give the crude product, which was purified using silica gel eluting with MeOH/DCM (0% to 10%) to give tert-butyl 2-((4-(2-(4-((5-(((5-(tert-butyl) oxazol-2-yl)methyl)thio)thiazol-2-yl)carbamoyl)piperidin-1-yl)acetamido)butyl)amino)acetate (120 mg, 25% yield) as a solid. MS (ESI) m/z 623.2 $[M+H]^+$.

To a solution of tert-butyl 2-((4-(2-(4-((5-(((5-(tert-butyl)oxazol-2-yl) methyl)thio)thiazol-2-yl)carbamoyl)piperidin-1-yl)acetamido)butyl)amino)acetate (120 mg, 0.193 mmol) in DCM (8 mL) was added TFA (2 mL). The mixture was stirred at RT for 16 h. The solvent was removed and the residue was dried to give 2-((4-(2-(4-((5-(((5-(tert-butyl) oxazol-2-yl) methyl)thio)thiazol-2-yl)carbamoyl)piperidin-1-yl)acetamido)butyl)amino)acetic acid (120 mg crude). MS (ESI) m/z 509.2 $[M+H]^+$.

To a solution of 2-((4-(2-(4-((5-(((5-(tert-butyl)oxazol-2-yl) methyl)thio)thiazol-2-yl)carbamoyl)piperidin-1-yl)acetamido)butyl)amino)acetic acid (120 mg crude, 0.193 mmol) in DMF (10 mL) was added 3-(2-(aminomethyl)-6-oxo-4H-thieno[2,3-c]pyrrol-5(6H)-yl)piperidine-2,6-dione (71 mg, 0.254 mmol) and TEA (64 mg, 0.636 mmol), followed by propanephosphonicacidanhydride (T₃P, 135 mg, 0.424 mmol). After 2 h, the mixture was diluted with H$_2$O and extracted with DCM. The combined organic layers were washed with brine, dried over Na$_2$SO$_4$, filtered and concentrated to give the crude product, which was purified using prep-TLC using DCM/MeOH (20:1) to afford Compound 14 (20 mg, 12% yield) as a solid.

Example 15

Compound 15: N-(5-(((5-(tert-butyl)oxazol-2-yl) methyl)thio)thiazol-2-yl)-1-(1-(5-(2,6-dioxopiperidin-3-yl)-6-oxo-5,6-dihydro-4H-thieno[2,3-c]pyrrol-2-yl)-7-methyl-3,11-dioxo-2,4,7,10-tetraazadodecan-12-yl)piperidine-4-carboxamide To a solution of N-(2-aminoethyl)-N$^1$-methylethane-1,2-diamine (1.1 g, 9.4 mmol) in DCM (24 mL) at 0° C. was slowly added (Boc)$_2$O (614 mg, 2.8 mmol in 4 mL DCM). The mixture was stirred at 0° C. for 1 h then warmed to RT. After 2 h, the mixture was diluted with DCM and washed with brine. The organic layer was dried over Na$_2$SO$_4$, filtered and concentrated to give tert-butyl (2-((2-aminoethyl)(methyl)amino)ethyl)carbamate (600 mg, 30% yield) as an oil.

To a solution of 2-(4-((5-(((5-(tert-butyl)oxazol-2-yl) methyl)thio)thiazol-2-yl)carbamoyl)piperidin-1-yl)acetic acid (250 mg, 0.57 mmol) in DMF (2 mL) at RT was added tert-butyl (2-((2-aminoethyl)(methyl)amino)ethyl) carbamate (161 mg, 0.74 mmol), HOBT (116 mg, 0.85 mmol), EDCI (164 mg, 0.85 mmol) and DIEA (148 mg, 1.48 mmol). The mixture was stirred at RT for 5 h then concentrated. The residue was purified using silica gel eluting with DCM/MeOH (50:1 to 20:1) to give tert-butyl (2-((2-(2-(4-((5-(((5-(tert-butyl)oxazol-2-yl)methyl)thio)thiazol-2-yl)carbamoyl) piperidin-1-yl)acetamido)ethyl)(methyl)amino)ethyl) carbamate (210 mg, 57% yield) as a solid. MS (ESI) m/z 638.3 [M+H]$^+$.

To a solution of tert-butyl (2-((2-(2-(4-((5-(((5-(tert-butyl) oxazol-2-yl) methyl)thio)thiazol-2-yl)carbamoyl)piperidin-1-yl)acetamido)ethyl)(methyl)amino)ethyl)carbamate (150 mg, 0.235 mmol) in DCM (4 mL) at RT was added TFA (1 mL). After 1 h, the mixture was concentrated to give the amine TFA salt (6 mL).

To a solution of the amine TFA salt in THF was added TEA (190 mg, 1.88 mmol) and 4-nitrophenyl((5-(2,6-dioxopiperidin-3-yl)-4-oxo-5,6-dihydro-4H-thieno[3,4-c]pyrrol-1-yl)methyl)carbamate (140 mg, 0.237 mmol) at RT. The mixture was stirred for 4 h and concentrated to give the crude product, which was purified using prep-HPLC as previously described to afford Compound 15 (6.5 mg, 3% yield) as a solid.

Example 16

Compound 16: 2-(((1r,4r)-4-((5-chloro-4-(5-(cyclopropylmethyl)-1-methyl-1H-pyrazol-4-yl)pyrimidin-2-yl)amino)cyclohexyl)amino)-N-(5-(3-((5-(2,6-dioxopiperidin-3-yl)-6-oxo-5,6-dihydro-4H-thieno[2,3-c]pyrrol-2-yl)methyl)ureido)pentyl)acetamide To a solution of (1r,4r)-N$^1$-(5-chloro-4-(5-(cyclopropylmethyl)-1-methyl-1H-pyrazol-4-yl)pyrimidin-2-yl)cyclohexane-1,4-diamine (200 mg, 0.504 mmol) in DMF (8 mL) at RT was added K$_2$CO$_3$ (208 mg, 1.51 mmol) followed by tert-butyl 2-bromoacetate (100 mg, 0.504 mmol). The mixture was stirred at RT for 5 h, then diluted with H$_2$O and extracted with EA. The combined organic layers were washed with H$_2$O, dried over Na$_2$SO$_4$, filtered and concentrated to give the crude product which was purified using prep-TLC eluting with DCM/MeOH (15:1) to give tert-butyl 2-(((1r,4r)-4-((5-chloro-4-(5-(cyclopropylmethyl)-1-methyl-1H-pyrazol-4-yl)pyrimidin-2-yl)amino)cyclohexyl) amino)acetate (139 mg, 58% yield) as an oil. MS (ESI) m/z 475.2 [M+H]$^+$.

To a solution of tert-butyl 2-(((1r,4r)-4-((5-chloro-4-(5-(cyclopropylmethyl)-1-methyl-1H-pyrazol-4-yl)pyrimidin-2-yl)amino)cyclohexyl)amino)acetate (139 mg, 0.293 mmol) in DCM (8 mL) was added TFA (2 mL). The mixture was stirred at RT overnight. The solvent was removed and the residue was dried to give 2-(((1r,4r)-4-((5-chloro-4-(5-(cyclopropylmethyl)-1-methyl-1H-pyrazol-4-yl)pyrimidin-2-yl)amino)cyclohexyl)amino)acetic acid (123 mg, crude) as the TFA salt. MS (ESI) m/z 419.2 [M+H]$^+$.

To a solution of tert-butyl ((5-(2,6-dioxopiperidin-3-yl)-6-oxo-5,6-dihydro-4H-thieno[2,3-c]pyrrol-2-yl)methyl)carbamate (130 mg, 0.343 mmol) in DCM (8 mL) at RT was added TFA (2 mL). The solution was stirred at RT for 1 h. The solvent was removed and the residue was dried to give the amine TFA salt (120 mg, crude) as an oil.

To a solution of the amine TFA salt in THF (5 mL) was added TEA (87 mg, 0.858 mmol) and 4-nitrobenzyl chloroformate (104 mg, 0.515 mmol). The mixture was stirred at RT for 2 h. The solvent was removed to afford 4-nitrophenyl ((5-(2,6-dioxopiperidin-3-yl)-6-oxo-5,6-dihydro-4H-thieno [2,3-c]pyrrol-2-yl)methyl)carbamate (153 mg, crude). MS (ESI) m/z 445.1 [M+H]$^+$.

To a solution of 4-nitrophenyl ((5-(2,6-dioxopiperidin-3-yl)-6-oxo-5,6-dihydro-4H-thieno[2,3-c]pyrrol-2-yl)methyl) carbamate (153 mg, 0.343 mmol) in THF (5 mL) at 0° C. was added TEA (173 mg, 1.72 mmol) followed by tert-butyl (5-aminopentyl)carbamate (69 mg, 0.343 mmol). After 1 h, the mixture was concentrated and the residue was purified using silica gel eluting with MeOH/DCM (0% to 8%) to give the crude product (150 mg) which was dissolved in DCM and washed with H$_2$O, dried over Na$_2$SO$_4$, filtered and concentrated to give tert-butyl (5-(3-((5-(2,6-dioxopiperidin-3-yl)-6-oxo-5,6-dihydro-4H-thieno[2,3-c]pyrrol-2-yl) methyl)ureido)pentyl)carbamate (61 mg, 35% yield) as an oil. MS (ESI) m/z 408.2 [M-Boc+H]$^+$.

To a solution of tert-butyl (5-(3-((5-(2,6-dioxopiperidin-3-yl)-6-oxo-5,6-dihydro-4H-thieno[2,3-c]pyrrol-2-yl) methyl)ureido)pentyl)carbamate (61 mg, 0.12 mmol) in DCM (8 mL) was added TFA (2 mL). After 1 h, the mixture was concentrated to give the amine TFA salt which was dissolved in DMF (5 mL). DIEA (47 mg, 0.36 mmol), 2-(((1r,4r)-4-((5-chloro-4-(5-(cyclopropylmethyl)-1-methyl-1H-pyrazol-4-yl)pyrimidin-2-yl)amino)cyclohexyl) amino)acetic acid (56 mg, 0.12 mmol), HOBt (24 mg, 0.18 mmol) and EDCI.HCl (35 mg, 0.18 mmol) were added. The mixture was stirred at RT overnight. The solvent was removed and the residue was purified using prep-HPLC as previously described to afford Compound 16 (17.6 mg, 18% yield) as a solid.

Example 17

Compound 17: 2-(((1r,4r)-4-((4-(5-(cyclopropylmethyl)-1-methyl-1H-pyrazol-4-yl)-5-fluoropyrimidin-2-yl)amino)cyclohexyl)amino)-N-(5-(3-((5-(2,6-dioxopiperidin-3-yl)-6-oxo-5,6-dihydro-4H-thieno[2,3-c]pyrrol-2-yl)methyl)ureido)pentyl)acetamide To a solution of tert-butyl (5-(3-((5-(2,6-dioxopiperidin-3-yl)-6-oxo-5,6-dihydro-4H-thieno[2,3-c]pyrrol-2-yl)

methyl)ureido)pentyl)carbamate (53 mg, 0.105 mmol) in DCM (4 mL) was added TFA (1 mL). After 1 h, the mixture was concentrated to give the amine TFA salt which was dissolved in DMF (5 mL). DIEA (40 mg, 0.315 mmol), ((1r,4r)-4-((4-(5-(cyclopropylmethyl)-1-methyl-1H-pyrazol-4-yl)-5-fluoropyrimidin-2-yl)amino)cyclohexyl)glycine (see experimental for Compound 25), 42 mg, 0.105 mmol), HOBt (22 mg, 0.158 mmol) and EDCI.HCl (31 mg, 0.158 mmol) were added. The mixture was stirred at RT overnight. The solvent was removed and the residue was purified using prep-HPLC as previously described to afford Compound 17 (13.3 mg, 16% yield) as a solid.

Example 18

Compound 18: N-(5-(((5-(tert-butyl)oxazol-2-yl)methyl)thio)thiazol-2-yl)-1-(2-((7-(3-((5-(2,6-dioxopiperidin-3-yl)-6-oxo-5,6-dihydro-4H-thieno[2,3-c]pyrrol-2-yl)methyl)ureido)heptyl)amino)-2-oxoethyl)piperidine-4-carboxamide To a solution of 2-(4-((5-(((5-(tert-butyl)oxazol-2-yl)methyl)thio)thiazol-2-yl)carbamoyl)piperidin-1-yl)acetic acid (200 mg, 0.46 mmol) in DMF (5 mL) was added tert-butyl (7-aminoheptyl)carbamate (126 mg, 0.55 mmol) and DIEA (118 mg, 0.92 mmol), followed by HOBt (93 mg, 0.69 mmol) and EDCI.HCl (133 mg, 0.69 mmol). After overnight at RT, the mixture was diluted with H$_2$O and extracted with EA. The combined organic layers were washed with saturated NaHCO$_3$, dried over Na$_2$SO$_4$, filtered and concentrated to give the crude product, which was purified using silica gel eluting with MeOH/DCM (0% to 10%) to give tert-butyl (7-(2-(4-((5-(((5-(tert-butyl)oxazol-2-yl)methyl)thio)thiazol-2-yl)carbamoyl)piperidin-1-yl)acetamido)heptyl)carbamate (243 mg, 82% yield) as a solid. MS (ESI) m/z 651.2 [M+H]$^+$.

To a solution of tert-butyl (7-(2-(4-((5-(((5-(tert-butyl)oxazol-2-yl)methyl)thio) thiazol-2-yl)carbamoyl)piperidin-1-yl)acetamido)heptyl)carbamate (186 mg, 0.286 mmol) in DCM (5 mL) was added TFA (2 mL). The mixture was stirred at RT for 0.5 h. After removing the solvent, the crude amine was used for the next step directly as the TFA salt. MS (ESI) m/z 551.2 [M+H]$^+$.

To a solution of 1-(2-((7-aminoheptyl)amino)-2-oxoethyl)-N-(5-(((5-(tert-butyl)oxazol-2-yl)methyl)thio)thiazol-2-yl)piperidine-4-carboxamide (116 mg, as TFA salt) in THF (5 mL) was added 4-nitrophenyl ((5-(2,6-dioxopiperidin-3-yl)-6-oxo-5,6-dihydro-4H-thieno[2,3-c]pyrrol-2-yl)methyl)carbamate (94 mg, 0.211 mmol) and TEA (42 mg, 0.422 mmol) at RT. The solution was stirred for 2 h then concentrated to give the crude product, which was purified using prep-HPLC as previously described to afford Compound 18 (6.2 mg, 3% yield) as a solid.

Example 19

Compound 19: N-(5-(((5-(tert-butyl)oxazol-2-yl)methyl)thio)thiazol-2-yl)-1-(1-(5-(2,6-dioxopiperidin-3-yl)-6-oxo-5,6-dihydro-4H-thieno[2,3-c]pyrrol-2-yl)-3-oxo-7,10-dioxa-2,4-diazadodecan-12-yl)piperidine-4-carboxamide To a solution of N-(5-(((5-(tert-butyl)oxazol-2-yl)methyl)thio)thiazol-2-yl) piperidine-4-carboxamide (100 mg, 026 mmol) in DMF (6 mL) at RT was added tert-butyl (2-(2-(2-bromoethoxy)ethoxy)ethyl)carbamate (81.8 mg, 0.26 mmol) and K$_2$CO$_3$ (71.8 mg, 0.52 mmol). The mixture was stirred at RT overnight then the mixture was diluted with water and extracted with DCM. The organic layer was dried over Na$_2$SO$_4$, filtered and concentrated. The residue was purified using silica gel eluting with MeOH/DCM (0% to 10%) to give tert-butyl (2-(2-(2-(4-((5-(((5-(tert-butyl)oxazol-2-yl)methyl)thio)thiazol-2-yl)carbamoyl)piperidin-1-yl)ethoxy)ethoxy)ethyl)carbamate (121 mg, 75% yield) as a solid. MS (ESI) m/z 612.1 [M+H]$^+$.

To a solution of tert-butyl (2-(2-(2-(4-((5-(((5-(tert-butyl)oxazol-2-yl)methyl)thio) thiazol-2-yl)carbamoyl)piperidin-1-yl)ethoxy)ethoxy)ethyl)carbamate (121 mg, 0.198 mmol) in DCM (6 mL) was added TFA (3 mL) at 0° C. The solution was then stirred at RT for 2 h and concentrated to give the TFA salt of 1-(2-(2-(2-aminoethoxy)ethoxy)ethyl)-N-(5-(((5-(tert-butyl) oxazol-2-yl)methyl) thio)thiazol-2-yl)piperidine-4-carboxamide (100 mg crude) as an oil. MS (ESI) m/z 512.0 [M+H]$^+$.

To a solution of 1-(2-(2-(2-aminoethoxy)ethoxy)ethyl)-N-(5-(((5-(tert-butyl)oxazol-2-yl)methyl)thio)thiazol-2-yl) piperidine-4-carboxamide (100 mg, as the TFA salt) in THF (5 mL) was added 4-nitrophenyl ((5-(2,6-dioxopiperidin-3-yl)-6-oxo-5,6-dihydro-4H-thieno[2,3-c]pyrrol-2-yl)methyl) carbamate and TEA (52.6 mg, 0.526 mmol) at RT. The solution was stirred for 2 h and concentrated to give the crude product, which was purified using prep-HPLC as previously described to afford Compound 19 (39.4 mg, 18% yield) as a solid.

Example 20

Compound 20: N-(5-(((5-(tert-butyl)oxazol-2-yl)methyl)thio)thiazol-2-yl)-1-(8-(3-((5-(2,6-dioxopiperidin-3-yl)-6-oxo-5,6-dihydro-4H-thieno[2,3-c]pyrrol-2-yl)methyl)ureido)octyl)piperidine-4-carboxamide To a solution of N-(5-(((5-(tert-butyl)oxazol-2-yl)methyl)thio)thiazol-2-yl) piperidine-4-carboxamide (100 mg, 0.263 mmol) in DMF (5 mL) was added tert-butyl (8-iodooctyl)carbamate (93 mg, 0.263 mmol) and K$_2$CO$_3$ (73 mg, 0.526 mmol). The mixture was diluted with H$_2$O and extracted with EA. The combined organic layers were dried over Na$_2$SO$_4$, filtered and concentrated. The residue was purified using prep-HPLC as previously described to give tert-butyl (8-(4-((5-(((5-(tert-butyl)oxazol-2-yl)methyl)thio)thiazol-2-yl)carbamoyl)piperidin-1-yl)octyl)carbamate (136 mg, 86% yield) as an oil. MS (ESI) m/z 608.2 [M+H]$^+$.

To a solution of tert-butyl (8-(4-((5-(((5-(tert-butyl)oxazol-2-yl)methyl)thio) thiazol-2-yl)carbamoyl)piperidin-1-yl)octyl)carbamate (128 mg, 0.211 mmol) in DCM (6 mL) was added TFA (3 mL) at 0° C. The solution was stirred at RT for 2 h. The solvent was removed to give 1-(8-aminooctyl)-N-(5-(((5-(tert-butyl)oxazol-2-yl)methyl)thio)thiazol-2-yl)piperidine-4-carboxamide (107 mg, as the TFA salt) as an oil. MS (ESI) m/z 508.2 [M+H]$^+$.

To a solution of 1-(8-aminooctyl)-N-(5-(((5-(tert-butyl) oxazol-2-yl) methyl)thio)thiazol-2-yl)piperidine-4-carboxamide (107 mg, as TFA salt) in THF (5 mL) was added 4-nitrophenyl((5-(2,6-dioxopiperidin-3-yl)-6-oxo-5,6-dihydro-4H-thieno[2,3-c]pyrrol-2-yl)methyl)carbamate and TEA (42 mg, 0.211 mmol) at RT. The mixture was stirred for 2 h then concentrated to give the crude product which was purified using prep-HPLC as previously described to afford Compound 20 (37.3 mg, 22% yield) as a solid.

Example 21

Compound 21: 1-(6-(((1r,4r)-4-((4-(5-(cyclopropyl-methyl)-1-methyl-1H-pyrazol-4-yl)-5-fluoropyrimidin-2-yl)amino)cyclohexyl)amino)hexyl)-3-((5-(2,6-dioxopiperidin-3-yl)-6-oxo-5,6-dihydro-4H-thieno[2,3-c]pyrrol-2-yl)methyl)urea To a solution of (1r,4r)-$N^1$-(4-(5-(cyclopropylmethyl)-1-methyl-1H-pyrazol-4-yl)-5-fluoropyrimidin-2-yl)cyclohexane-1,4-diamine (600 mg, 1.44 mmol) in DMF (15 mL) at RT was added $K_2CO_3$ (497 mg, 3.6 mmol), followed by tert-butyl (6-bromohexyl)carbamate (403 mg, 1.44 mmol). The mixture was stirred at 70° C. for 7 h, then diluted with $H_2O$ (10 mL) and extracted with EA (30 mL×2). The combined organic layers were washed with $H_2O$ (20 mL), dried over $Na_2SO_4$, filtered and concentrated to give the crude product, which was purified using silica gel eluting with MeOH/DCM (0% to 10%) to give tert-butyl (6-(((1r,4r)-4-((4-(5-(cyclopropylmethyl)-1-methyl-1H-pyrazol-4-yl)-5-fluoropyrimidin-2-yl)amino)cyclohexyl)amino)hexyl)carbamate (259 mg, 33% yield) as an oil. MS (ESI) m/z 544.4 [M+H]$^+$.

To a solution of tert-butyl (6-(((1r,4r)-4-((4-(5-(cyclopropylmethyl)-1-methyl-1H-pyrazol-4-yl)-5-fluoropyrimidin-2-yl)amino)cyclohexyl)amino)hexyl)carbamate (259 mg, 0.477 mmol) in THF/$H_2O$ (15 mL/4.5 mL) at 0° C. was added sodium carbonate (76 mg, 0.716 mmol), followed by Cbz-Cl (203 mg, 1.19 mmol). The mixture was stirred at RT overnight, then diluted with $H_2O$ (10 mL) and extracted with EA (15 mL×2). The combined organic layers were dried over $Na_2SO_4$, filtered and concentrated to give the crude product, which was purified using silica gel eluting with MeOH/DCM (0% to 5%) to give benzyl (6-((tert-butoxycarbonyl)amino)hexyl)((1r,4r)-4-((4-(5-(cyclopropylmethyl)-1-methyl-1H-pyrazol-4-yl)-5-fluoropyrimidin-2-yl)amino)cyclohexyl)carbamate (288 mg, 89% yield) as an oil. MS (ESI) m/z 678.4 [M+H]$^+$.

To a solution of benzyl (6-((tert-butoxycarbonyl)amino)hexyl) ((1r,4r)-4-((4-(5-(cyclopropylmethyl)-1-methyl-1H-pyrazol-4-yl)-5-fluoropyrimidin-2-yl)amino)cyclohexyl)carbamate (89 mg, 0.132 mmol) in DCM (4 mL) at 0° C. was added TFA (1 mL). The mixture was stirred at RT for 1 h then concentrated. The resulting amine TFA salt was dissolved in THF (5 mL) and TEA (41 mg, 0.396 mmol) was added. The mixture was stirred at 0° C. for 5 min. Then the suspension of 4-nitrophenyl ((5-(2,6-dioxopiperidin-3-yl)-6-oxo-5,6-dihydro-4H-thieno[2,3-c]pyrrol-2-yl)methyl)carbamate (117 mg, crude) in THF (1 mL) was added. The mixture was stirred at RT for 1 h, then diluted with $H_2O$ (10 mL) and extracted with DCM (15 mL×2). The combined organic layers were dried over $Na_2SO_4$, filtered and concentrated to give the crude product, which was purified using silica gel eluting with EA in PE from 10% to 50% to give benzyl ((1r,4r)-4-((4-(5-(cyclopropylmethyl)-1-methyl-1H-pyrazol-4-yl)-5-fluoropyrimidin-2-yl)amino)cyclohexyl)(6-(3-((5-(2,6-dioxopiperidin-3-yl)-6-oxo-5,6-dihydro-4H-thieno[2,3-c]pyrrol-2-yl)methyl)ureido)hexyl)carbamate (44 mg, 38% yield) as a solid.

To a solution of benzyl ((1r,4r)-4-((4-(5-(cyclopropylmethyl)-1-methyl-1H-pyrazol-4-yl)-5-fluoropyrimidin-2-yl)amino)cyclohexyl)(6-(3-((5-(2,6-dioxopiperidin-3-yl)-6-oxo-5,6-dihydro-4H-thieno[2,3-c]pyrrol-2-yl)methyl)ureido)hexyl)carbamate (48 mg, 0.057 mmol) in AcOH (1.5 mL) at RT was added HBr (33% in AcOH, 1.5 mL). The mixture was stirred at RT for 10 min. The solvent was removed and the residue was dried to give the crude product which was dissolved in DMF (2 mL) and adjusted to pH about 7 with TEA. The solvent was removed and the residue was purified using prep-HPLC as previously described to afford Compound 21 (21.2 mg, 50% yield) as a solid.

Example 22

Compound 22: 1-(8-(((1r,4r)-4-((5-chloro-4-(5-(cyclopropylmethyl)-1-methyl-1H-pyrazol-4-yl)pyrimidin-2-yl)amino)cyclohexyl)amino)octyl)-3-((5-(2,6-dioxopiperidin-3-yl)-6-oxo-5,6-dihydro-4H-thieno[2,3-c]pyrrol-2-yl)methyl)urea To a solution of (1r,4r)-$N^1$-(5-chloro-4-(5-(cyclopropylmethyl)-1-methyl-1H-pyrazol-4-yl)pyrimidin-2-yl)cyclohexane-1,4-diamine (360 mg, 0.56 mmol) in DMF (10 mL) was added tert-butyl (8-bromooctyl)carbamate (188 mg, 0.611 mmol) and $K_2CO_3$ (191 mg, 1.39 mmol). The mixture was stirred at 70° C. for 16 h. The mixture was diluted with $H_2O$ (10 mL) and extracted with DCM (15 mL×2). The combined organic layers were washed with brine, dried over $Na_2SO_4$, filtered and concentrated to give the crude product, which was purified using silica gel eluting with MeOH/DCM (0% to 10%) to give tert-butyl (8-(((1r,4r)-4-((5-chloro-4-(5-(cyclopropylmethyl)-1-methyl-1H-pyrazol-4-yl)pyrimidin-2-yl)amino)cyclohexyl)amino)octyl)carbamate (200 mg, 61% yield) as a solid. MS (ESI) m/z 588.2 [M+H]$^+$.

To a solution of tert-butyl (8-(((1r,4r)-4-((5-chloro-4-(5-(cyclopropylmethyl)-1-methyl-1H-pyrazol-4-yl)pyrimidin-2-yl)amino)cyclohexyl)amino)octyl)carbamate (180 mg, 0.31 mmol) in THF (10 mL) and water (3 mL) was added Benzyl chloroformate (157 mg, 0.92 mml) and $Na_2CO_3$ (93.2 mg, 0.92 mml). The mixture was stirred at RT for 16 h, then diluted with $H_2O$ (10 mL) and extracted with DCM (15 mL×2). The combined organic layers were washed with brine, dried over $Na_2SO_4$, filtered and concentrated to give the crude product, which was purified using silica gel eluting with MeOH/DCM (0% to 10%) to give benzyl (8-((tert-butoxycarbonyl)amino)octyl)((1r,4r)-4-((5-chloro-4-(5-(cyclopropylmethyl)-1-methyl-1H-pyrazol-4-yl)pyrimidin-2-yl)amino)cyclohexyl)carbamate (210 mg, 85% yield) as an oil. MS (ESI) m/z 694.2 [M+H]$^+$.

To a solution of benzyl (8-((tert-butoxycarbonyl)amino)octyl)((1r,4r)-4-((5-chloro-4-(5-(cyclopropylmethyl)-1-methyl-1H-pyrazol-4-yl)pyrimidin-2-yl)amino)cyclohexyl)carbamate (190 mg, 0.264 mmol) in DCM (6 mL) at RT was added TFA (1.5 mL). After 2 h, the mixture was concentrated to give the amine TFA salt (200 mg, crude) as an oil.

To a solution of the amine TFA salt in THF (10 mL) was added TEA (67 mg, 0.66 mmol) and 4-nitrobenzyl chloroformate (80 mg, 0.396 mmol). The mixture was stirred at RT for 16 h. The solvent was removed to give benzyl ((1r,4r)-4-((5-chloro-4-(5-(cyclopropylmethyl)-1-methyl-1H-pyrazol-4-yl)pyrimidin-2-yl)amino)cyclohexyl)(8-(((4-nitrophenoxy)carbonyl)amino)octyl)carbamate (229 mg, crude). MS (ESI) m/z 759.1 [M+H]$^+$.

To a solution of tert-butyl ((5-(2,6-dioxopiperidin-3-yl)-6-oxo-5,6-dihydro-4H-thieno[2,3-c]pyrrol-2-yl)methyl)carbamate (92 mg, 0.24 mmol) in DCM (4 mL) was added TFA (1 mL). After 2 h, the mixture was concentrated to give the amine TFA salt.

To a solution of the amine TFA salt in THF (5 mL).was added TEA (49 mg, 0.484 mmol) and benzyl ((1r,4r)-4-((5-chloro-4-(5-(cyclopropylmethyl)-1-methyl-1H-pyrazol-4-yl)pyrimidin-2-yl)amino)cyclohexyl)(8-(((4-nitrophenoxy)carbonyl)amino)octyl)carbamate (190 mg, 0.242 mmol).

The mixture was stirred at RT for 16 h. The solvent was removed and the residue was purified using silica gel eluting with MeOH/DCM (0% to 10%) to give benzyl ((1r,4r)-4-((5-chloro-4-(5-(cyclopropylmethyl)-1-methyl-1H-pyrazol-4-yl)pyrimidin-2-yl)amino)cyclohexyl)(8-(3-((5-(2,6-dioxopiperidin-3-yl)-6-oxo-5,6-dihydro-4H-thieno[2,3-c]pyrrol-2-yl)methyl)ureido)octyl)carbamate (40 mg, 18% yield) as a solid. MS (ESI) m/z 927.2 [M+H]+.

To a solution of benzyl ((1r,4r)-4-((5-chloro-4-(5-(cyclopropylmethyl)-1-methyl-1H-pyrazol-4-yl)pyrimidin-2-yl)amino)cyclohexyl)(8-(3-((5-(2,6-dioxopiperidin-3-yl)-6-oxo-5,6-dihydro-4H-thieno[2,3-c]pyrrol-2-yl)methyl)ureido)octyl)carbamate (40 mg, 0.043 mmol) in AcOH (1.5 mL) was added HBr (1.5 mL, 33% in AcOH). The mixture was stirred at RT for 2 h then diluted with H$_2$O and TEA and extracted with DCM. The combined organic layers were washed with brine, dried over Na$_2$SO$_4$, filtered and concentrated to give the crude product, which was purified using prep-HPLC as previously described to afford Compound 22 (7.5 mg, 22% yield) as a solid.

Example 23

Compound 23: 1-(8-(((1r,4r)-4-((4-(5-(cyclopropylmethyl)-1-methyl-1H-pyrazol-4-yl)-5-fluoropyrimidin-2-yl)amino)cyclohexyl)amino)octyl)-3-((5-(2,6-dioxopiperidin-3-yl)-6-oxo-5,6-dihydro-4H-thieno[2,3-c]pyrrol-2-yl)methyl)urea To a solution of (1r,4r)-N$^1$-(4-(5-(cyclopropylmethyl)-1-methyl-1H-pyrazol-4-yl)-5-fluoropyrimidin-2-yl)cyclohexane-1,4-diamine (500 mg, 1.20 mmol) in DMF (10 mL) was added K$_2$CO$_3$ (414 mg, 3.00 mmol), followed by tert-butyl (8-bromooctyl)carbamate (336 mg, 1.09 mmol). The mixture was stirred at 70° C. overnight. The mixture was diluted with H$_2$O and extracted with DCM. The combined organic layers were washed with H$_2$O, dried over Na$_2$SO$_4$, filtered and concentrated to give the crude product, which was purified using silica gel eluting with MeOH/DCM (0% to 10%) to give tert-butyl (8-(((1r,4r)-4-((4-(5-(cyclopropylmethyl)-1-methyl-1H-pyrazol-4-yl)-5-fluoropyrimidin-2-yl)amino)cyclohexyl)amino)octyl)carbamate (198 mg, 29% yield) as an oil. MS (ESI) m/z 571.7 [M+H]+.

To a solution of tert-butyl (8-(((1r,4r)-4-((4-(5-(cyclopropylmethyl)-1-methyl-1H-pyrazol-4-yl)-5-fluoropyrimidin-2-yl)amino)cyclohexyl)amino)octyl)carbamate (198 mg, 0.35 mmol) in THF/H$_2$O (12 mL/3.6 mL) at RT was added sodium carbonate (112 mg, 1.05 mmol), followed by benzyl chloroformate (298 mg, 1.75 mmol). The mixture was stirred at RT overnight, diluted with H$_2$O, and extracted with EA. The combined organic layers were dried over Na$_2$SO$_4$, filtered and concentrated to give the crude product, which was purified using silica gel eluting with MeOH/DCM (0% to 10%) to give benzyl (8-((tert-butoxycarbonyl)amino)octyl)((1r,4r)-4-((4-(5-(cyclopropylmethyl)-1-methyl-1H-pyrazol-4-yl)-5-fluoropyrimidin-2-yl)amino)cyclohexyl)carbamate (100 mg, 41% yield) as an oil. MS (ESI) m/z 705.9 [M+H]+.

To a solution of benzyl (8-((tert-butoxycarbonyl)amino)octyl)((1r,4r)-4-((4-(5-(cyclopropylmethyl)-1-methyl-1H-pyrazol-4-yl)-5-fluoropyrimidin-2-yl)amino)cyclohexyl)carbamate (100 mg, 0.142 mmol) in DCM (4 mL) at 0° C. was added TFA (1 mL). After 1 h at RT, the mixture was concentrated to give the amine TFA salt, which was dissolved in THF (5 mL).

To the solution of amine TFA salt in THF was added TEA (43 mg, 0.426 mmol) and 4-nitrobenzyl chloroformate (57.2 mg, 0.284 mmol). The mixture was stirred at RT for 1 h. The solvent was removed to give the crude product, which was purified using silica gel eluting with EA/PE (0% to 50%) to give benzyl ((1r,4r)-4-((4-(5-(cyclopropylmethyl)-1-methyl-1H-pyrazol-4-yl)-5-fluoropyrimidin-2-yl)amino)cyclohexyl)(8-(((4-nitrophenoxy)carbonyl)amino)octyl)carbamate (84 mg, 77% yield) as an oil. MS (ESI) m/z 770.8 [M+H]+.

To a solution of benzyl ((1r,4r)-4-((4-(5-(cyclopropylmethyl)-1-methyl-1H-pyrazol-4-yl)-5-fluoropyrimidin-2-yl)amino)cyclohexyl)(8-(((4-nitrophenoxy)carbonyl)amino)octyl)carbamate (84 mg, 0.109 mmol) in THF (5 mL) at RT was added 3-(2-(aminomethyl)-6-oxo-4H-thieno[2,3-c]pyrrol-5(6H)-yl)piperidine-2,6-dione (30.4 mg, 0.109 mmol) and TEA (34 mg, 0.327 mmol). The mixture was stirred at 40° C. for 2 h. The solvent was removed and the residue was purified using silica gel eluting with MeOH/DCM (0% to 10%) to give benzyl ((1r,4r)-4-((4-(5-(cyclopropylmethyl)-1-methyl-1H-pyrazol-4-yl)-5-fluoropyrimidin-2-yl)amino)cyclohexyl)(8-(3-((5-(2,6-dioxopiperidin-3-yl)-6-oxo-5,6-dihydro-4H-thieno[2,3-c]pyrrol-2-yl)methyl)ureido)octyl)carbamate (45 mg) as a solid. MS (ESI) m/z 911.1 [M+H]+.

To a solution of benzyl ((1r,4r)-4-((4-(5-(cyclopropylmethyl)-1-methyl-1H-pyrazol-4-yl)-5-fluoropyrimidin-2-yl)amino)cyclohexyl)(8-(3-((5-(2,6-dioxopiperidin-3-yl)-6-oxo-5,6-dihydro-4H-thieno[2,3-c]pyrrol-2-yl)methyl)ureido)octyl)carbamate (45 mg, 0.049 mmol) in AcOH (1.5 mL) at RT was added HBr (33% in AcOH, 1.5 mL). The mixture was stirred at RT for 30 min. Upon removal of solvent, the residue was dissolved in DMF (2 mL). After adjusting to pH about 7 with TEA, the mixture was concentrated and the residue was purified using prep-HPLC as previously described to afford Compound 23 (10 mg, 26% yield) as a solid.

Example 24

Compound 24: 1-(6-(((1r,4r)-4-((5-chloro-4-(5-(cyclopropylmethyl)-1-methyl-1H-pyrazol-4-yl)pyrimidin-2-yl)amino)cyclohexyl)amino)hexyl)-3-((5-(2,6-dioxopiperidin-3-yl)-6-oxo-5,6-dihydro-4H-thieno[2,3-c]pyrrol-2-yl)methyl)urea To a solution of (1r,4r)-N-(5-chloro-4-(5-(cyclopropylmethyl)-1-methyl-1H-pyrazol-4-yl)pyrimidin-2-yl)cyclohexane-1,4-diamine (220 mg, 0.611 mmol) in DMF (8 mL) was added tert-butyl (6-bromohexyl)carbamate (188 mg, 0.672 mmol) and K$_2$CO$_3$ (169 mg, 1.22 mmol). The mixture was stirred at 70° C. for 16 h then diluted with H$_2$O and extracted with DCM. The combined organic layers were washed with brine, dried over Na$_2$SO$_4$, filtered and concentrated. The residue was purified using silica gel eluting with MeOH/DCM (0% to 10%) to give tert-butyl (6-(((1r,4r)-4-((5-chloro-4-(5-(cyclopropylmethyl)-1-methyl-1H-pyrazol-4-yl)pyrimidin-2-yl)amino)cyclohexyl)amino)hexyl)carbamate (150 mg, 44% yield) as a solid. MS (ESI) m/z 560.2 [M+H]+.

To a solution of tert-butyl (6-(((1r,4r)-4-((5-chloro-4-(5-(cyclopropylmethyl)-1-methyl-1H-pyrazol-4-yl)pyrimidin-2-yl)amino)cyclohexyl)amino)hexyl)carbamate (150 mg, 0.268 mmol) in THF (4 mL) and water (1 mL) was added benzyl chloroformate (137 mg, 0.805 mml) and Na$_2$CO$_3$ (85 mg, 0.805 mml). The mixture was stirred at RT for 16 h then diluted with H$_2$O and extracted with DCM. The combined organic layers were washed with brine, dried over Na$_2$SO$_4$, filtered and concentrated to give the crude product, which was purified using silica gel eluting with MeOH/DCM (0% to 10%) to give benzyl (6-((tert-butoxycarbonyl)amino)hexyl)((1r,4r)-4-((5-chloro-4-(5-(cyclopropylmethyl)-1-methyl-1H-pyrazol-4-yl)pyrimidin-2-yl)amino)cyclohexyl)carbamate (160 mg, 86% yield) as an oil. MS (ESI) m/z 694.2 [M+H]+.

To a solution of benzyl (6-((tert-butoxycarbonyl)amino)hexyl)((1r,4r)-4-((5-chloro-4-(5-(cyclopropylmethyl)-1-methyl-1H-pyrazol-4-yl)pyrimidin-2-yl)amino)cyclohexyl)carbamate (150 mg, 0.216 mmol) in DCM (4 mL) at RT was added TFA (1 mL). After 1 h, the mixture was concentrated to give the amine TFA salt (130 mg, crude) as an oil, which was dissolved in THF (4 mL). TEA (55 mg, 0.54 mmol) and 4-nitrobenzyl chloroformate (65 mg, 0.324 mmol) were added. The mixture was stirred at RT for 16 h. The solvent was removed to give benzyl ((1r,4r)-4-((5-chloro-4-(5-(cyclopropylmethyl)-1-methyl-1H-pyrazol-4-yl)pyrimidin-2-yl)amino)cyclohexyl)(6-(((4-nitrophenoxy)carbonyl)amino)hexyl)carbamate (163.7 mg, crude). MS (ESI) m/z 759.1 [M+H]+.

To a solution of tert-butyl ((5-(2,6-dioxopiperidin-3-yl)-6-oxo-5,6-dihydro-4H-thieno[2,3-c]pyrrol-2-yl)methyl)carbamate (58 mg, 0.15 mmol) in DCM (4 mL) was added TFA (1 mL). After 2 h at RT, the mixture was concentrated to give the amine TFA salt, which was dissolved in THF (4 mL). TEA (51 mg, 0.508 mmol) and benzyl ((1r,4r)-4-((5-chloro-4-(5-(cyclopropylmethyl)-1-methyl-1H-pyrazol-4-yl)pyrimidin-2-yl)amino)cyclohexyl)(6-(((4-nitrophenoxy)carbonyl)amino)hexyl)carbamate (77 mg, 0.101 mmol) were added. The mixture was stirred at RT for 16 h. The solvent was removed to give the crude compound which was purified using silica gel eluting with MeOH/DCM (0% to 10%) to give benzyl ((1r,4r)-4-((5-chloro-4-(5-(cyclopropylmethyl)-1-methyl-1H-pyrazol-4-yl)pyrimidin-2-yl)amino)cyclohexyl)(6-(3-((5-(2,6-dioxopiperidin-3-yl)-6-oxo-5,6-dihydro-4H-thieno[2,3-c]pyrrol-2-yl)methyl)ureido)hexyl)carbamate (55 mg, 60% yield) as a solid. MS (ESI) m/z 899.2 [M+H]+.

To a solution of benzyl ((1r,4r)-4-((5-chloro-4-(5-(cyclopropylmethyl)-1-methyl-1H-pyrazol-4-yl)pyrimidin-2-yl)amino)cyclohexyl)(6-(3-((5-(2,6-dioxopiperidin-3-yl)-6-oxo-5,6-dihydro-4H-thieno[2,3-c]pyrrol-2-yl)methyl)ureido)hexyl)carbamate (55 mg, 0.061 mmol) in AcOH (1.5 mL) was added HBr (1.5 mL, 33% in AcOH). The mixture was stirred at RT for 2 h then diluted with H2O (10 ml). TEA (1 mL) was added and the mixture was extracted with DCM. The combined organic layers were washed with brine, dried over Na2SO4, filtered and concentrated to give the crude product, which was purified using prep-HPLC as previously described to afford Compound 24 (18 mg, 39% yield) as a solid.

Example 25

Compound 25: 2-(((1r,4r)-4-((4-(5-(cyclopropylmethyl)-1-methyl-1H-pyrazol-4-yl)-5-fluoropyrimidin-2-yl)amino)cyclohexyl)amino)-N-(5-((2-(((5-(2,6-dioxopiperidin-3-yl)-6-oxo-5,6-dihydro-4H-thieno[2,3-c]pyrrol-2-yl)methyl)amino)-2-oxoethyl)amino)pentyl)acetamide To a solution of (1r,4r)-N1-(4-(5-(cyclopropylmethyl)-1-methyl-1H-pyrazol-4-yl)-5-fluoropyrimidin-2-yl)cyclohexane-1,4-diamine (1.0 g, 2.4 mmol) in DMF (10 mL) at RT was added K2CO3 (994 mg, 7.2 mmol), followed by tert-butyl 2-bromoacetate (468 mg, 2.4 mmol). The mixture was stirred at RT for 7 h, diluted with H2O and extracted with EA. The combined organic layers were washed with H2O, dried over Na2SO4, filtered and concentrated to give the crude product, which was purified using silica gel eluting with MeOH/DCM (0% to 10%) to give tert-butyl 2-(((1r,4r)-4-((4-(5-(cyclopropylmethyl)-1-methyl-1H-pyrazol-4-yl)-5-fluoropyrimidin-2-yl)amino)cyclohexyl)amino)acetate (832 mg, 77% yield) as an oil. MS (ESI) m/z 459.3 [M+H]+.

To a solution of tert-butyl 2-(((1r,4r)-4-((4-(5-(cyclopropylmethyl)-1-methyl-1H-pyrazol-4-yl)-5-fluoropyrimidin-2-yl)amino)cyclohexyl)amino)acetate (832 mg, 1.82 mmol) in DCM (16 mL) was added TFA (4 mL). The mixture was stirred at RT overnight. The solvent was removed and the residue was dissolved in tert-butyl methyl ether (10 mL). The suspension was stirred at RT for 30 min. The suspension was filtered and the filter cake was dried to give 2-(((1r,4r)-4-((4-(5-(cyclopropylmethyl)-1-methyl-1H-pyrazol-4-yl)-5-fluoropyrimidin-2-yl)amino)cyclohexyl)amino)acetic acid (1.08 g, crude) as the TFA salt. MS (ESI) m/z 403.2 [M+H]+.

To a solution of 2-(((1r,4r)-4-((4-(5-(cyclopropylmethyl)-1-methyl-1H-pyrazol-4-yl)-5-fluoropyrimidin-2-yl)amino)cyclohexyl)amino)acetic acid (300 mg, 0.466 mmol, as TFA salt) in DMF (10 mL) was added DIEA (178 mg, 1.38 mmol), followed by tert-butyl (5-aminopentyl)carbamate (113 mg, 0.559 mmol), HOBt (94 mg, 0.699 mmol) and EDCI.HCl (134 mg, 0.699 mmol). The mixture was stirred at RT overnight, diluted with H2O and extracted with EA. The combined organic layers were washed with H2O, dried over Na2SO4, filtered and concentrated to give the crude product, which was purified using silica gel eluting with MeOH/DCM (0% to 10%) to give tert-butyl (5-(2-(((1r,4r)-4-((4-(5-(cyclopropylmethyl)-1-methyl-1H-pyrazol-4-yl)-5-fluoropyrimidin-2-yl)amino)cyclohexyl)amino)acetamido)pentyl)carbamate (201 mg, 74% yield) as an oil. MS (ESI) m/z 587.4 [M+H]+.

To a solution of tert-butyl (5-(2-(((1r,4r)-4-((4-(5-(cyclopropylmethyl)-1-methyl-1H-pyrazol-4-yl)-5-fluoropyrimidin-2-yl)amino)cyclohexyl)amino)acetamido)pentyl)carbamate (195 mg, 0.333 mmol) in THF/H2O (12.5 mL/5 mL) at 0° C. was added sodium carbonate (106 mg, 0.999 mmol), followed by benzyl chloroformate (113 mg, 0.666 mmol). The mixture was stirred at RT for 30 min, diluted with H2O and extracted with EA. The combined organic layers were dried over Na2SO4, filtered and concentrated to give the crude product, which was purified using silica gel eluting with MeOH/DCM (0% to 6%) to give benzyl (2-((5-((tert-butoxycarbonyl)amino)pentyl)amino)-2-oxoethyl)((1r,4r)-4-((4-(5-(cyclopropylmethyl)-1-methyl-1H-pyrazol-4-yl)-5-fluoropyrimidin-2-yl)amino)cyclohexyl)carbamate (237 mg, 99% yield) as a solid. MS (ESI) m/z 721.4 [M+H]+.

To a solution of benzyl (2-((5-((tert-butoxycarbonyl)amino)pentyl)amino)-2-oxoethyl)((1r,4r)-4-((4-(5-(cyclopropylmethyl)-1-methyl-1H-pyrazol-4-yl)-5-fluoropyrimidin-2-yl)amino)cyclohexyl)carbamate (181 mg, 0.251 mmol) in DCM (8 mL) was added TFA (2 mL). The mixture was stirred at RT for 1 h then concentrated. The resulting amine TFA salt was dissolved in DMF (7 mL) and cooled to 0° C., then K2CO3 (87 mg, 0.628 mmol) was added, followed by tert-butyl bromoacetate (49 mg, 0.251 mmol). The mixture was stirred at RT for 6 h, diluted with H2O and extracted with DCM. The organic layer was concentrated to give the crude product, which was purified using prep-TLC eluting with DCM/MeOH (10:1) to give tert-butyl 4-((1r,4r)-4-((4-(5-(cyclopropylmethyl)-1-methyl-1H-pyrazol-4-yl)-5-fluoropyrimidin-2-yl)amino)cyclohexyl)-3,6-dioxo-1-phenyl-2-oxa-4,7,13-triazapentadecan-15-oate (30 mg, 16% yield) as an oil. MS (ESI) m/z 735.4 [M+H]+.

To a solution of tert-butyl 4-((1r,4r)-4-((4-(5-(cyclopropylmethyl)-1-methyl-1H-pyrazol-4-yl)-5-fluoropyrimidin-2-yl)amino)cyclohexyl)-3,6-dioxo-1-phenyl-2-oxa-4,7,13-triazapentadecan-15-oate (30 mg, 0.041 mmol) in DCM (4 mL) was added TFA (1 mL). The mixture was stirred at RT overnight then concentrated to give 4-((1r,4r)-4-((4-(5-(cyclopropylmethyl)-1-methyl-1H-pyrazol-4-yl)-5-fluoropyrimidin-2-yl)amino)cyclohexyl)-3,6-dioxo-1-phenyl-2-oxa-4,7,13-triazapentadecan-15-oic acid (30 mg, crude) as a TFA salt. MS (ESI) m/z 679.4 [M+H]$^+$.

To a solution of tert-butyl ((5-(2,6-dioxopiperidin-3-yl)-6-oxo-5,6-dihydro-4H-thieno[2,3-c]pyrrol-2-yl)methyl)carbamate (38 mg, 0.1 mmol) in DCM (4 mL) was added TFA (1 mL). The mixture was stirred at RT for 1 h then concentrated to give the amine TFA salt. DMF (5 mL) and DIEA (32 mg, 0.249 mmol) were added. Then 4-((1r,4r)-4-((4-(5-(cyclopropylmethyl)-1-methyl-1H-pyrazol-4-yl)-5-fluoropyrimidin-2-yl)amino)cyclohexyl)-3,6-dioxo-1-phenyl-2-oxa-4,7,13-triazapentadecan-15-oic acid (56 mg, 0.083 mmol), HOBt (17 mg, 0.124 mmol) and EDCI.HCl (24 mg, 0.124 mmol) were added. The mixture was stirred at RT overnight. The solvent was removed and the residue was purified using prep-TLC eluting with DCM/MeOH (10:1) to give benzyl ((1r,4r)-4-((4-(5-(cyclopropylmethyl)-1-methyl-1H-pyrazol-4-yl)-5-fluoropyrimidin-2-yl)amino)cyclohexyl)(2-((5-((2-(((5-(2,6-dioxopiperidin-3-yl)-6-oxo-5,6-dihydro-4H-thieno[2,3-c]pyrrol-2-yl)methyl)amino)-2-oxoethyl)amino)pentyl)amino)-2-oxoethyl)carbamate (65 mg, 83% yield) as a solid.

To a solution of benzyl ((1r,4r)-4-((4-(5-(cyclopropylmethyl)-1-methyl-1H-pyrazol-4-yl)-5-fluoropyrimidin-2-yl)amino)cyclohexyl)(2-((5-((2-(((5-(2,6-dioxopiperidin-3-yl)-6-oxo-5,6-dihydro-4H-thieno[2,3-c]pyrrol-2-yl)methyl)amino)-2-oxoethyl)amino)pentyl)amino)-2-oxoethyl)carbamate (65 mg, 0.069 mmol) in AcOH (2 mL) was added HBr (33% in AcOH, 2 mL). The mixture was stirred at RT for 1 h then concentrated. The residue was dissolved in DMF (2 mL), adjusted to a pH of about 7 with TEA, then concentrated. The residue was purified using prep-HPLC as previously described to afford Compound 25 (10.1 mg, 18% yield) as a solid.

Example 26

Compound 26: N-(5-(((5-(tert-butyl)oxazol-2-yl)methyl)thio)thiazol-2-yl)-1-(1-(5-(2,6-dioxopiperidin-3-yl)-4-oxo-5,6-dihydro-4H-thieno[3,4-c]pyrrol-1-yl)-3,15-dioxo-8,11-dioxa-2,5,14-triazahexadecan-16-yl)piperidine-4-carboxamide To a solution of 2-(4-((5-(((5-(tert-butyl)oxazol-2-yl)methyl)thio)thiazol-2-yl)carbamoyl)piperidin-1-yl)acetic acid (510 mg, 1.16 mmol) in DMF (5 mL) was added tert-butyl (2-(2-(2-aminoethoxy)ethoxy)ethyl)carbamate (347 mg, 1.39 mmol) and DIEA (300 mg, 2.32 mmol), followed by HOBt (236 mg, 1.75 mmol) and EDCI.HCl (336 mg, 1.75 mmol). The mixture was stirred at RT for 12 h then diluted with H$_2$O and extracted with EA. The combined organic layers were washed with saturated NaHCO$_3$, dried over Na$_2$SO$_4$, filtered and concentrated to give the crude product, which was purified using silica gel eluting with DCM/MeOH (0% to 10%) to give tert-butyl (2-(2-(2-(2-(4-((5-(((5-(tert-butyl)oxazol-2-yl)methyl)thio)thiazol-2-yl)carbamoyl)piperidin-1-yl)acetamido)ethoxy)ethoxy)ethyl)carbamate (521 mg, 68% yield) as a solid. MS (ESI) m/z 669.2 [M+H]$^+$.

To a solution of tert-butyl (2-(2-(2-(2-(4-((5-(((5-(tert-butyl)oxazol-2-yl)methyl)thio)thiazol-2-yl)carbamoyl)piperidin-1-yl)acetamido)ethoxy)ethoxy)ethyl)carbamate (521 mg, 0.779 mmol) in DCM (10 mL) was added TFA (4 mL). The mixture was stirred at RT for 1 h then concentrated to give the amine TFA salt, which was dissolved in DMF (8 mL) and cooled to 0° C. K$_2$CO$_3$ (322 mg, 2.337 mmol) was added followed by tert-butyl bromoacetate (152 mg, 0.779 mmol). The mixture was stirred at RT for 3 h then diluted with H$_2$O and extracted with DCM. The organic layer was concentrated and the residue was purified using prep-TLC eluting with DCM/MeOH (10:1) to give tert-butyl14-(4-((5-(((5-(tert-butyl)oxazol-2-yl)methyl)thio)thiazol-2-yl)carbamoyl)piperidin-1-yl)-13-oxo-6,9-dioxa-3,12-diazatetradecan-1-oate (117 mg, 22% yield) as an oil. MS (ESI) m/z 683.2 [M+H]$^+$.

To a solution of tert-butyl14-(4-((5-(((5-(tert-butyl)oxazol-2-yl)methyl)thio)thiazol-2-yl)carbamoyl)piperidin-1-yl)-13-oxo-6,9-dioxa-3,12-diazatetradecan-1-oate (117 mg, 0.171 mmol) in DCM (4 mL) was added TFA (2 mL). The mixture was stirred at RT for 4 h then concentrated. The residue was dissolved in DMF (8 mL) and DIEA (44 mg, 0.342 mmol) was added. Then 3-(1-(aminomethyl)-4-oxo-4H-thieno[3,4-c]pyrrol-5(6H)-yl)piperidine-2,6-dione (57 mg, 0.205 mmol), HOBt (35 mg, 0.257 mmol) and EDCI.HCl (49 mg, 0.257 mmol) were added. The mixture was stirred at RT overnight. The solvent was removed and the residue was purified using prep-HPLC as previously described to afford Compound 26 (25.3 mg, 17% yield) as a solid.

Example 27

Compound 27: N-(5-(((5-(tert-butyl)oxazol-2-yl)methyl)thio)thiazol-2-yl)-1-(2-((5-(3-((5-(2,6-dioxopiperidin-3-yl)-4,6-dioxo-5,6-dihydro-4H-thieno[2,3-c]pyrrol-2-yl)methyl)ureido)pentyl)amino)-2-oxoethyl)piperidine-4-carboxamide To a solution of 2-(4-((5-(((5-(tert-butyl)oxazol-2-yl)methyl)thio)thiazol-2-yl)carbamoyl)piperidin-1-yl)acetic acid (510 mg, 1.16 mmol) in DMF (5 mL) was added tert-butyl (2-(2-(2-aminoethoxy)ethoxy)ethyl)carbamate (347 mg, 1.39 mmol) and DIEA (300 mg, 2.32 mmol), followed by HOBt (236 mg, 1.75 mmol) and EDCI.HCl (336 mg, 1.75 mmol). The mixture was stirred at RT for 12 h. The mixture was diluted with H$_2$O and extracted with EA. The combined organic layers were washed with saturated NaHCO$_3$, dried over Na$_2$SO$_4$, filtered and concentrated to give the crude product, which was purified using silica gel eluting with DCM/MeOH (0% to 10%) to give tert-butyl (2-(2-(2-(2-(4-((5-(((5-(tert-butyl)oxazol-2-yl)methyl)thio)thiazol-2-yl)carbamoyl)piperidin-1-yl)acetamido)ethoxy)ethoxy)ethyl)carbamate (521 mg, 68% yield) as a solid. MS (ESI) m/z 669.2 [M+H]$^+$.

To a solution of tert-butyl (2-(2-(2-(2-(4-((5-(((5-(tert-butyl)oxazol-2-yl)methyl)thio)thiazol-2-yl)carbamoyl)piperidin-1-yl)acetamido)ethoxy)ethoxy)ethyl)carbamate (521 mg, 0.779 mmol) in DCM (10 mL) was added TFA (4 mL). The mixture was stirred at RT for 1 h then concentrated to give the amine TFA salt which was dissolved in DMF (8 mL) and cooled to 0° C. K$_2$CO$_3$ (322 mg, 2.337 mmol) was added, followed by tert-butyl bromoacetate (152 mg, 0.779 mmol). The mixture was stirred at RT for 3 h then diluted with H$_2$O and extracted with DCM. The organic layer was concentrated and the residue was purified using prep-TLC eluting with DCM/MeOH (10:1) to give tert-butyl14-(4-((5-

(((5-(tert-butyl)oxazol-2-yl)methyl)thio)thiazol-2-yl)carbamoyl)piperidin-1-yl)-13-oxo-6,9-dioxa-3,12-diazatetradecan-1-oate (117 mg, 22% yield) as an oil. MS (ESI) m/z 683.2 [M+H]$^+$.

To a solution of tert-butyl14-(4-((5-(((5-(tert-butyl)oxazol-2-yl)methyl)thio)thiazol-2-yl)carbamoyl)piperidin-1-yl)-13-oxo-6,9-dioxa-3,12-diazatetradecan-1-oate (117 mg, 0.171 mmol) in DCM (4 mL) was added TFA (2 mL). The mixture was stirred at RT for 4 h then concentrated. The residue was dissolved in DMF (8 mL) and DIEA (44 mg, 0.342 mmol) was added. Then 3-(1-(aminomethyl)-4-oxo-4H-thieno[3,4-c]pyrrol-5(6H)-yl)piperidine-2,6-dione (57 mg, 0.205 mmol), HOBt (35 mg, 0.257 mmol) and EDCI.HCl (49 mg, 0.257 mmol) were added. The mixture was stirred at RT overnight. The solvent was removed and the residue was purified using prep-HPLC as previously described to afford Compound 27 (25.3 mg, 17% yield) as a solid.

Example 28

Compound 28: 2-(((1r,4r)-4-((5-chloro-4-(5-(cyclopropylmethyl)-1-methyl-1H-pyrazol-4-yl)pyrimidin-2-yl)amino)cyclohexyl)amino)-N-(2-(2-(2-((4-(((2-(2,6-dioxopiperidin-3-yl)-1-oxoisoindolin-4-yl)oxy)methyl)benzyl)amino)-2-oxoethoxy)ethoxy)ethyl) acetamide To a solution of methyl 3-hydroxy-2-methylbenzoate (10.0 g, 0.06 mol) in DMF (50 mL) was added imidazole. The mixture was stirred at RT for 5 h. The mixture was filtered and the filtrate was concentrated. The residue was purified using silica gel eluting with PE/EA (10:1) to give methyl 3-(((tert-butyldimethylsilyl)oxy)-2-methylbenzoate (17.5 g, crude) as an oil.

To a solution of methyl 3-((tert-butyldimethylsilyl)oxy)-2-methylbenzoate (9.0 g, 32.1 mmol) in CCl$_4$ (30 mL) was added NBS (6.2 g, 35.0 mmol) and azodiisobutyronitrile (1.0 g, 6.4 mmol). The mixture was stirred at 70° C. for 18 h then diluted with water. The organic layer was dried over Na$_2$SO$_4$, filtered and concentrated. The residue was purified using silica gel eluting with PE/EA (10:1) to give methyl 2-(bromomethyl)-3-((tert-butyldimethylsilyl)oxy)benzoate (11.7 g crude) as an oil.

To a solution of methyl 2-(bromomethyl)-3-((tert-butyldimethylsilyl)oxy)benzoate (2.0 g, 5.587 mmol) in DMF (20 mL) was added tert-butyl 4,5-diamino-5-oxopentanoate (1.24 g, 6.145 mmol) and trimethylamine (1.4 g, 13.97 mmol). The mixture was stirred at RT for 16 h. Tetrabutylammonium fluoride (0.88 g, 3.35 mmol) was added dropwise then the mixture was stirred at 60° C. for 2 h. The mixture was diluted with sat. NaHCO$_3$ and extracted with EA. The organic layer was dried over Na$_2$SO$_4$, filtered and concentrated. The residue was purified using silica gel eluting with PE/EA (1:1) to give tert-butyl 5-amino-4-(4-hydroxy-1-oxoisoindolin-2-yl)-5-oxopentanoate (1.82 g, 98% yield) as a solid. MS (ESI) m/z 335.1 [M+H]$^+$.

To a solution of tert-butyl 5-amino-4-(4-hydroxy-1-oxoisoindolin-2-yl)-5-oxopentanoate (900 mg, 2.69 mmol) in DMF (8 mL) was added 4-(bromomethyl)benzonitrile (581 mg, 2.96 mmol) and K$_2$CO$_3$ (742 mg, 5.38 mml). The mixture was stirred at RT for 16 h. The mixture was diluted with water and extracted with EA. The organic layer was dried over Na$_2$SO$_4$, filtered and concentrated. The residue was purified using silica gel eluting with PE/EA (1:1) to give tert-butyl 5-amino-4-(4-((4-cyanobenzyl)oxy)-1-oxoisoindolin-2-yl)-5-oxopentanoate (1.0 g, 83% yield) as a solid. MS (ESI) m/z 450.1 [M+H]$^+$.

To a solution of tert-butyl 5-amino-4-(4-((4-cyanobenzyl)oxy)-1-oxoisoindolin-2-yl)-5-oxopentanoate (1.0 g, 2.23 mmol) in THF (20 mL) was added Raney Ni (100 mg) and di-tert-butyl dicarbonate (730 mg, 3.34 mmol). The mixture was degassed and purged with H$_2$. After 16 h at RT, the mixture was filtered and the filtrate was concentrated. The residue was purified using silica gel eluting with PE/EA (1:1) to give tert-butyl 5-amino-4-(4-((4-(((tert-butoxycarbonyl)amino)methyl)benzyl)oxy)-1-oxoisoindolin-2-yl)-5-oxopentanoate (1.08 g, 88% yield) as a solid. MS (ESI) m/z 554.2 [M+H]$^+$.

To a solution of tert-butyl 5-amino-4-(4-((4-(((tert-butoxycarbonyl)amino)methyl) benzyl)oxy)-1-oxoisoindolin-2-yl)-5-oxopentanoate (1.08 g, 1.95 mmol) in DCM (8 mL) was added TFA (2 mL). The mixture was stirred at RT for 2 h then concentrated to give 5-amino-4-(4-((4-(aminomethyl)benzyl)oxy)-1-oxoisoindolin-2-yl)-5-oxopentanoic acid (0.775 mg, quant.) as a solid. MS (ESI) m/z 398.0 [M+H]$^+$.

To a solution of 5-amino-4-(4-((4-(aminomethyl)benzyl)oxy)-1-oxoisoindolin-2-yl)-5-oxopentanoic acid (775 mg, 1.85 mmol) and trimethylamine (591 mg, 5.85 mmol) in THF (15 mL) was added di-tert-butyl dicarbonate (638 mg, 2.93 mmol). The mixture was stirred at RT for 3 h then concentrated to give 5-amino-4-(4-((4-(((tert-butoxycarbonyl)amino)methyl)benzyl)oxy)-1-oxoisoindolin-2-yl)-5-oxopentanoic acid (950 mg, quant.) as an oil. MS (ESI) m/z 498.1 [M+H]$^+$.

To a solution of 5-amino-4-(4-((4-(((tert-butoxycarbonyl)amino)methyl) benzyl)oxy)-1-oxoisoindolin-2-yl)-5-oxopentanoic acid (900 mg, 1.8 mmol) in CAN (25 mL) was added CDI (1.17 g, 7.2 mmol). After 16 h at 100° C., the mixture was filtered and the filtrate was concentrated. The residue was purified using silica gel eluting with PE/EA (1:1) to give tert-butyl 4-(((2-(2,6-dioxopiperidin-3-yl)-1-oxoisoindolin-4-yl)oxy)methyl)benzylcarbamate (710 mg, 74% yield) as a solid. MS (ESI) m/z 480.2 [M+H]$^+$.

To a solution of tert-butyl 4-(((2-(2,6-dioxopiperidin-3-yl)-1-oxoisoindolin-4-yl)oxy)methyl)benzylcarbamate (110 mg, 0.229 mmol) in DCM (4 mL) was added TFA (1 mL). The mixture was stirred at RT for 2 h and concentrated to give the TFA salt of 3-(4-((4-(aminomethyl)benzyl)oxy)-1-oxoisoindolin-2-yl)piperidine-2,6-dione which was dissolved in DMF (5 mL). 2,2-Dimethyl-4-oxo-3,8,11-trioxa-5-azatridecan-13-oic acid (76 mg, 0.2756 mmol), HATU (174 mg, 0.4592 mmol) and DIEA (89 mg, 0.688 mmol) were added. After 16 h at RT, the mixture was concentrated. The residue was purified using silica gel eluting with DCM/MeOH (10:1) to give tert-butyl (2-(2-(2-((4-(((2-(2,6-dioxopiperidin-3-yl)-1-oxoisoindolin-4-yl)oxy)methyl)benzyl)amino)-2-oxoethoxy)ethoxy)ethyl)carbamate (130 mg, 90% yield) as a solid. MS (ESI) m/z 625.2 [M+H]$^+$.

To a solution of tert-butyl (2-(2-(2-((4-(((2-(2,6-dioxopiperidin-3-yl)-1-oxoisoindolin-4-yl)oxy)methyl)benzyl) amino)-2-oxoethoxy)ethoxy)ethyl)carbamate (100 mg, 0.16 mmol) in DCM (4 mL) was added TFA (1 mL). The mixture was stirred at RT for 2 h then concentrated to give the amine TFA salt which was dissolved in DMF (4 mL). 2-(((1r,4r)-4-((5-Chloro-4-(5-(cyclopropylmethyl)-1-methyl-1H-pyrazol-4-yl)pyrimidin-2-yl)amino)cyclohexyl)amino)acetic acid (67 mg, 0.16 mmol), T3P (153 mg, 0.48 mmol) and TEA (48 mg, 0.48 mmol) were added. The mixture was stirred at RT for 16 h then concentrated, and the residue was purified using prep-TLC eluting with DCM/MeOH (10:1) to afford Compound 28 (34.1 mg, yield 23% yield) as a solid.

Example 29

Compound 29: 2-(((1r,4r)-4-((4-(5-(cyclopropylmethyl)-1-methyl-1H-pyrazol-4-yl)-5-fluoropyrimidin-2-yl)amino)cyclohexyl)amino)-N-(4-((2-(((5-(2,6-dioxopiperidin-3-yl)-6-oxo-5,6-dihydro-4H-thieno[2,3-c]pyrrol-2-yl)methyl)amino)-2-oxoethyl)amino)butyl)acetamide To a solution of 2-(((1r,4r)-4-((4-(5-(cyclopropylmethyl)-1-methyl-1H-pyrazol-4-yl)-5-fluoropyrimidin-2-yl)amino)cyclohexyl)amino)acetic acid (350 mg, 0.678 mmol) in DMF (4 mL) was added DIEA (262 mg, 2.03 mmol), followed by tert-butyl (4-aminobutyl)carbamate (153 mg, 0.814 mmol), HOBt (137 mg, 1.02 mmol) and EDCI.HCl (195 mg, 1.02 mmol). The mixture was stirred at RT overnight, diluted with H$_2$O and extracted with EA. The combined organic layers were washed with H$_2$O, dried over Na$_2$SO$_4$, filtered and concentrated to give the crude product, which was purified using silica gel eluting with MeOH/DCM (0% to 10%) to give tert-butyl (4-(2-(((1r,4r)-4-((4-(5-(cyclopropylmethyl)-1-methyl-1H-pyrazol-4-yl)-5-fluoropyrimidin-2-yl)amino)cyclohexyl)amino)acetamido)butyl)carbamate (240 mg, 71% yield) as a solid. MS (ESI) m/z 573.1 [M+H]$^+$.

To a solution of tert-butyl (4-(2-(((1r,4r)-4-((4-(5-(cyclopropylmethyl)-1-methyl-1H-pyrazol-4-yl)-5-fluoropyrimidin-2-yl)amino)cyclohexyl)amino)acetamido)butyl)carbamate (240 mg, 0.42 mmol) in THF/H$_2$O (4 mL:1 mL) at 0° C. was added sodium carbonate (133 mg, 1.26 mmol), followed by benzyl chloroformate (108 mg, 0.63 mmol). The mixture was stirred at RT for 2 h. The mixture was diluted with H$_2$O and extracted with EA. The combined organic layers were dried over Na$_2$SO$_4$, filtered and concentrated to give the crude product, which was purified using silica gel eluting with MeOH/DCM (0% to 6%) to give benzyl (2-((4-(((tert-butoxycarbonyl)amino)butyl)amino)-2-oxoethyl)((1r,4r)-4-((4-(5-(cyclopropylmethyl)-1-methyl-1H-pyrazol-4-yl)-5-fluoropyrimidin-2-yl)amino)cyclohexyl)carbamate (300 mg, 100% yield) as a solid. MS (ESI) m/z 707.1 [M+H]$^+$.

To a solution of benzyl (2-((4-((tert-butoxycarbonyl)amino)butyl)amino)-2-oxoethyl)((1r,4r)-4-((4-(5-(cyclopropylmethyl)-1-methyl-1H-pyrazol-4-yl)-5-fluoropyrimidin-2-yl)amino)cyclohexyl)carbamate (300 mg, 0.425 mmol) in DCM (4 mL) was added TFA (1 mL). The mixture was stirred at RT for 3 h then concentrated. The resulting amine TFA salt was dissolved in DMF (4 mL) and cooled to 0° C., then K$_2$CO$_3$ (196 mg, 1.275 mmol) was added, followed by tert-butyl bromoacetate (83 mg, 0.425 mmol). The mixture was stirred at RT for 16 h then diluted with H$_2$O and extracted with DCM. The organic layer was concentrated and the residue was purified using silica gel eluting with MeOH/DCM (0% to 6%) to give tert-butyl 4-((1r,4r)-4-((4-(5-(cyclopropylmethyl)-1-methyl-1H-pyrazol-4-yl)-5-fluoropyrimidin-2-yl)amino)cyclohexyl)-3,6-dioxo-1-phenyl-2-oxa-4,7,12-triazatetradecan-14-oate (135 mg, 44% yield) as solid. MS (ESI) m/z 721.4 [M+H]$^+$.

To a solution of tert-butyl 4-((1r,4r)-4-((4-(5-(cyclopropylmethyl)-1-methyl-1H-pyrazol-4-yl)-5-fluoropyrimidin-2-yl)amino)cyclohexyl)-3,6-dioxo-1-phenyl-2-oxa-4,7,12-triazatetradecan-14-oate (135 mg, 0.188 mmol) in DCM (4 mL) was added TFA (1 mL). The mixture was stirred at RT overnight then concentrated to give 4-((1r, 4r)-4-((4-(5-(cyclopropylmethyl)-1-methyl-1H-pyrazol-4-yl)-5-fluoropyrimidin-2-yl)amino)cyclohexyl)-3,6-dioxo-1-phenyl-2-oxa-4,7,12-triazatetradecan-14-oic acid (124.5 mg, crude) as the TFA salt. MS (ESI) m/z 665.4 [M+H]$^+$.

To a solution of tert-butyl ((5-(2,6-dioxopiperidin-3-yl)-6-oxo-5,6-dihydro-4H-thieno[2,3-c]pyrrol-2-yl) methyl) carbamate (30 mg, 0.08 mmol) in DCM (4 mL) was added TFA (1 mL). The mixture was stirred at RT for 2 h then concentrated. The resulting amine TFA salt was dissolved in DMF (4 mL) then TEA (24 mg, 0.237 mmol) was added, followed by 4-((1r,4r)-4-((4-(5-(cyclopropylmethyl)-1-methyl-1H-pyrazol-4-yl)-5-fluoropyrimidin-2-yl)amino)cyclohexyl)-3,6-dioxo-1-phenyl-2-oxa-4,7,12-triazatetradecan-14-oic acid (52 mg, 0.153 mmol) and propanephosphonicacidanhydride (75 mg, 0.458 mmol). The mixture was stirred at RT for 16 h. The solvent was removed and the residue was purified using prep-TLC eluting with DCM/MeOH (10:1) to give benzyl ((1r,4r)-4-((4-(5-(cyclopropylmethyl)-1-methyl-1H-pyrazol-4-yl)-5-fluoropyrimidin-2-yl)amino)cyclohexyl)(2-((4-((2-(((5-(2,6-dioxopiperidin-3-yl)-6-oxo-5,6-dihydro-4H-thieno[2,3-c]pyrrol-2-yl)methyl)amino)-2-oxoethyl)amino)butyl)amino)-2-oxoethyl)carbamate (50 mg, 68% yield) as an oil. MS (ESI) m/z 926.4 [M+H]$^+$.

To a solution of benzyl ((1r,4r)-4-((4-(5-(cyclopropylmethyl)-1-methyl-1H-pyrazol-4-yl)-5-fluoropyrimidin-2-yl)amino)cyclohexyl)(2-((4-((2-(((5-(2,6-dioxopiperidin-3-yl)-6-oxo-5,6-dihydro-4H-thieno[2,3-c]pyrrol-2-yl)methyl)amino)-2-oxoethyl)amino)butyl)amino)-2-oxoethyl)carbamate (50 mg, 0.054 mmol) in AcOH (1.5 mL) was added HBr (33% in AcOH, 1.5 mL). The mixture was stirred at RT for 1 h then concentrated, dissolved in DMF (2 mL), and adjusted to a pH of about 7 with TEA. The mixture was concentrated and the residue was purified using prep-HPLC as previously described to afford Compound 29 (7.3 mg, 17% yield) as a solid.

Example 30

Compound 30: 2-(((1r,4r)-4-((5-chloro-4-(5-(cyclopropylmethyl)-1-methyl-1H-pyrazol-4-yl)pyrimidin-2-yl)amino)cyclohexyl)amino)-N-(5-((2-(((5-(2,6-dioxopiperidin-3-yl)-6-oxo-5,6-dihydro-4H-thieno[2,3-c]pyrrol-2-yl)methyl)amino)-2-oxoethyl)amino)pentyl)acetamide To a solution of tert-butyl 4-((1r,4r)-4-((5-chloro-4-(5-(cyclopropylmethyl)-1-methyl-1H-pyrazol-4-yl)pyrimidin-2-yl)amino)cyclohexyl)-3,6-dioxo-1-phenyl-2-oxa-4,7,13-triazapentadecan-15-oate (60 mg, 0.08 mmol) in DCM (2 mL) at RT was added TFA (0.5 mL). The mixture was stirred at RT overnight then concentrated and dissolved in DMF (2 mL). DIEA (51 mg, 0.24 mmol) was added followed by 3-(2-(aminomethyl)-6-oxo-4H-thieno[2,3-c]pyrrol-5(6H)-yl)piperidine-2,6-dione (46 mg, 0.12 mmol), HOBT (16 mg, 0.12 mmol) and EDCI.HCl (24 mg, 0.12 mmol). The mixture was stirred at RT overnight then concentrated. The residue was purified using prep-TLC eluting with DCM/MeOH (10:1) to give the benzyl ((1r,4r)-4-((5-chloro-4-(5-(cyclopropylmethyl)-1-methyl-1H-pyrazol-4-yl)pyrimidin-2-yl)amino)cyclohexyl)(2-((5-((2-(((5-(2,6-dioxopiperidin-3-yl)-6-oxo-5,6-dihydro-4H-thieno[2,3-c]pyrrol-2-yl)methyl)amino)-2-oxoethyl)amino)pentyl)amino)-2-oxoethyl)carbamate (65 mg, 84% yield) as a solid. MS (ESI) m/z 478.8 [M/2+H]$^+$.

To a solution of benzyl ((1r,4r)-4-((5-chloro-4-(5-(cyclopropylmethyl)-1-methyl-1H-pyrazol-4-yl)pyrimidin-2-yl)

amino)cyclohexyl)(2-((5-((2-(((5-(2,6-dioxopiperidin-3-yl)-6-oxo-5,6-dihydro-4H-thieno[2,3-c]pyrrol-2-yl)methyl)amino)-2-oxoethyl)amino)pentyl)amino)-2-oxoethyl)carbamate (65 mg, 0.067 mmol) in AcOH (2 mL) at RT was added HBr (2 mL, 33% in AcOH). The mixture was stirred at RT for 1 h then concentrated, dissolved in DMF (2 mL), and adjusted to a pH of about 7 with TEA. The mixture was concentrated and the residue was purified using prep-HPLC as previously described to afford Compound 30 (17.8 mg, 32% yield) as a solid.

Example 31

Compound 31: 2-(((1r,4r)-4-((5-chloro-4-(5-(cyclopropylmethyl)-1-methyl-1H-pyrazol-4-yl)pyrimidin-2-yl)amino)cyclohexyl)amino)-N-(5-((2-(((5-(2,6-dioxopiperidin-3-yl)-4-oxo-5,6-dihydro-4H-thieno[3,4-c]pyrrol-1-yl)methyl)amino)-2-oxoethyl)amino)pentyl)acetamide To a solution of 2-(((1r,4r)-4-((5-chloro-4-(5-(cyclopropylmethyl)-1-methyl-1H-pyrazol-4-yl)pyrimidin-2-yl)amino)cyclohexyl)amino)acetic acid (300 mg, 0.717 mmol) in DMF (10 mL) at RT was added tert-butyl (5-aminopentyl)carbamate (159 mg, 0.788 mmol), HOBT (145 mg, 1.075 mmol), EDCI.HCl (206 mg, 1.08 mmol) and DIEA (277 mg, 2.15 mmol). The mixture was stirred at RT overnight then concentrated and the residue was purified using silica gel eluting with MeOH/DCM (0% to 5%) to give tert-butyl (5-(2-(((1r,4r)-4-((5-chloro-4-(5-(cyclopropylmethyl)-1-methyl-1H-pyrazol-4-yl)pyrimidin-2-yl)amino)cyclohexyl)amino)acetamido)pentyl)carbamate (420 mg, crude) as a solid. MS (ESI) m/z 603.4 [M+H]$^+$.

To a solution of tert-butyl (5-(2-(((1r,4r)-4-((5-chloro-4-(5-(cyclopropylmethyl)-1-methyl-1H-pyrazol-4-yl)pyrimidin-2-yl)amino)cyclohexyl)amino)acetamido)pentyl)carbamate (420 mg, 0.717 mmol) in THF/H$_2$O (12.5 mL/5 mL) at 0° C. was added sodium carbonate (228 mg, 2.15 mmol), followed by benzyl chloroformate (245 mg, 1.434 mmol). The mixture was stirred at RT for 2 h, diluted with H$_2$O and extracted with EA. The combined organic layers were dried over Na$_2$SO$_4$, filtered and concentrated to give the crude product, which was purified using silica gel eluting with MeOH/DCM (0% to 6%) to give benzyl (2-((5-((tert-butoxycarbonyl)amino)pentyl)amino)-2-oxoethyl)((1r,4r)-4-((5-chloro-4-(5-(cyclopropylmethyl)-1-methyl-1H-pyrazol-4-yl)pyrimidin-2-yl)amino)cyclohexyl)carbamate (190 mg, 36% yield) as a solid. MS (ESI) m/z 737.4 [M+H]$^+$.

To a solution of benzyl (2-((5-((tert-butoxycarbonyl)amino)pentyl)amino)-2-oxoethyl)((1 r,4r)-4-((5-chloro-4-(5-(cyclopropylmethyl)-1-methyl-1H-pyrazol-4-yl)pyrimidin-2-yl)amino)cyclohexyl)carbamate (190 mg, 0.258 mmol) in DCM (4 mL) at RT was added TFA (1 mL). The mixture was stirred at RT for 30 min then concentrated. The resulting amine TFA salt was dissolved in DMF (7 mL) and cooled to 0° C., then K$_2$CO$_3$ (52 mg, 0.375 mmol) was added, followed by tert-butyl bromoacetate (50 mg, 0.258 mmol). The mixture was stirred at RT for 3 h, diluted with H$_2$O and extracted with DCM. The organic layer was concentrated and the residue was purified using prep-TLC eluting with DCM/MeOH (10:1) to give tert-butyl 4-((1r,4r)-4-((5-chloro-4-(5-(cyclopropylmethyl)-1-methyl-1H-pyrazol-4-yl)pyrimidin-2-yl)amino)cyclohexyl)-3,6-dioxo-1-phenyl-2-oxa-4,7,13-triazapentadecan-15-oate (90 mg, 46%) as a solid. MS (ESI) m/z 751.4 [M+H]$^+$.

To a solution of tert-butyl 4-((1r,4r)-4-((5-chloro-4-(5-(cyclopropylmethyl)-1-methyl-1H-pyrazol-4-yl)pyrimidin-2-yl)amino)cyclohexyl)-3,6-dioxo-1-phenyl-2-oxa-4,7,13-triazapentadecan-15-oate (50 mg, 0.06 mmol) in DCM (2 mL) at RT was added TFA (0.5 mL). The mixture was stirred at RT overnight. The solvent was removed and the residue was dissolved in DMF (5 mL). Then DIEA (20 mg, 0.15 mmol), 3-(1-(aminomethyl)-4-oxo-4H-thieno[3,4-c]pyrrol-5(6H)-yl)piperidine-2,6-dione (25 mg, 0.08 mmol), HOBT (13 mg, 0.09 mmol) and EDCI.HCl (18 mg, 0.09 mmol) were added. The suspension was stirred at RT overnight and concentrated, then the residue was purified using prep-TLC eluting with DCM/MeOH (10:1) to give to give benzyl ((1r,4r)-4-((5-chloro-4-(5-(cyclopropylmethyl)-1-methyl-1H-pyrazol-4-yl)pyrimidin-2-yl)amino)cyclohexyl)(2-((5-((2-(((5-(2,6-dioxopiperidin-3-yl)-4-oxo-5,6-dihydro-4H-thieno[3,4-c]pyrrol-1-yl)methyl)amino)-2-oxoethyl)amino)pentyl)amino)-2-oxoethyl)carbamate (60 mg, 92% yield) as a solid. MS (ESI) m/z 478.8 [M/2+H]$^+$.

To a solution of benzyl ((1r,4r)-4-((5-chloro-4-(5-(cyclopropylmethyl)-1-methyl-1H-pyrazol-4-yl)pyrimidin-2-yl)amino)cyclohexyl)(2-((5-((2-(((5-(2,6-dioxopiperidin-3-yl)-4-oxo-5,6-dihydro-4H-thieno[3,4-c]pyrrol-1-yl)methyl)amino)-2-oxoethyl)amino)pentyl)amino)-2-oxoethyl)carbamate (60 mg, 0.06 mmol) in AcOH (2 mL) at RT was added HBr (2 mL, 33% in AcOH). The mixture was stirred at RT for 2 h then concentrated, and the residue was dissolved in DMF (2 mL) and adjusted to a pH of about 7 with TEA. The mixture was concentrated and the residue was purified using prep-HPLC as previously described to afford Compound 31 (14.1 mg, 27% yield) as a solid.

Example 32

Compound 32: 2-(((1r,4r)-4-((4-(5-(cyclopropylmethyl)-1-methyl-1H-pyrazol-4-yl)-5-fluoropyrimidin-2-yl)amino)cyclohexyl)amino)-N-(5-((2-(((5-(2,6-dioxopiperidin-3-yl)-4-oxo-5,6-dihydro-4H-thieno[3,4-c]pyrrol-1-yl)methyl)amino)-2-oxoethyl)amino)pentyl)acetamide To a solution of tert-butyl ((5-(2,6-dioxopiperidin-3-yl)-4-oxo-5,6-dihydro-4H-thieno[3,4-c]pyrrol-1-yl)methyl)carbamate (77 mg, 0.203 mmol) in DCM (4 mL) was added TFA (1 mL). The mixture was stirred at RT for 1 h. The mixture was concentrated to give the amine as the trifluoroacetate salt. The amine was dissolved in DMF (5 mL) and DIEA (78 mg, 0.254 mmol) was added. Then 4-((1r,4r)-4-((4-(5-(cyclopropylmethyl)-1-methyl-1H-pyrazol-4-yl)-5-fluoropyrimidin-2-yl)amino)cyclohexyl)-3,6-dioxo-1-phenyl-2-oxa-4,7,13-triazapentadecan-15-oic acid (115 mg, 0.169 mmol), HOBt (35 mg, 0.254 mmol) and EDCI.HCl (49 mg, 0.254 mmol) was added. The mixture was stirred at RT overnight. The solvent was removed and the residue was purified using prep-TLC eluting with DCM/MeOH (10:1) to give benzyl ((1r,4r)-4-((4-(5-(cyclopropylmethyl)-1-methyl-1H-pyrazol-4-yl)-5-fluoropyrimidin-2-yl)amino)cyclohexyl)(2-((5-((2-(((5-(2,6-dioxopiperidin-3-yl)-4-oxo-5,6-dihydro-4H-thieno[3,4-c]pyrrol-1-yl)methyl)amino)-2-oxoethyl)amino)pentyl)amino)-2-oxoethyl)carbamate (70 mg, 44% yield) as a solid.

To a solution of benzyl ((1r,4r)-4-((4-(5-(cyclopropylmethyl)-1-methyl-1H-pyrazol-4-yl)-5-fluoropyrimidin-2-yl)amino)cyclohexyl)(2-((5-((2-(((5-(2,6-dioxopiperidin-3-yl)-4-oxo-5,6-dihydro-4H-thieno[3,4-c]pyrrol-1-yl)methyl)amino)-2-oxoethyl)amino)pentyl)amino)-2-oxoethyl)carbamate (70 mg, 0.075 mmol) in AcOH (2 mL) was added HBr (33% in AcOH, 2 mL). The mixture was stirred at RT for 1 h. The solvent was removed and the residue was dissolved in DMF (2 mL) and adjusted to a pH of about 7 with TEA. The mixture was concentrated and the residue was purified using prep-HPLC as previously described to afford Compound 32 (21.3 mg, 36% yield) as a solid.

Example 33

Compound 33: N-(5-(((5-(tert-butyl)oxazol-2-yl) methyl)thio)thiazol-2-yl)-1-(2-((5-((2-(((5-(2,6-di-oxopiperidin-3-yl)-4-oxo-5,6-dihydro-4H-thieno[3,4-c]pyrrol-1-yl)methyl)amino)-2-oxoethyl)amino) pentyl)amino)-2-oxoethyl)piperidine-4-carboxamide To a solution of 2-(4-((5-(((5-(tert-butyl)oxazol-2-yl) methyl)thio)thiazol-2-yl)carbamoyl)piperidin-1-yl)acetic acid (300 mg, 0.68 mmol) in DMF (10 mL) was added tert-butyl (5-aminopentyl)carbamate (166 mg, 0.82 mmol) and DIEA (196 mg, 1.36 mmol), followed by HOBt (137 mg, 1.02 mmol) and EDCI.HCl (196 mg, 1.02 mmol). The mixture was stirred at RT overnight then diluted with $H_2O$ and extracted with EA. The combined organic layers were washed with saturated $NaHCO_3$, dried over $Na_2SO_4$, filtered and concentrated to give the crude product, which was purified using silica gel eluting with DCM/MeOH (0% to 10%) to give tert-butyl(5-(2-(4-((5-(((5-(tert-butyl)oxazol-2-yl)methyl)thio)thiazol-2-yl)carbamoyl)piperidin-1-yl)ac-etamido)pentyl)carbamate (409 mg, 96% yield) as a solid. MS (ESI) m/z 623.2 [M+H]$^+$.

To a solution of tert-butyl(5-(2-(4-((5-(((5-(tert-butyl) oxazol-2-yl)methyl)thio)thiazol-2-yl)carbamoyl)piperidin-1-yl)acetamido)pentyl)carbamate (409 mg, 0.658 mmol) in DCM (10 mL) was added TFA (5 mL). The mixture was stirred at RT for 1 h then concentrated. The resulting amine TFA salt was dissolved in DMF (10 mL) and cooled to 0° C., then $K_2CO_3$ (209 mg, 1.974 mmol) was added, followed by tert-butyl bromoacetate (128 mg, 0.658 mmol). After 3 h, the mixture was diluted with $H_2O$ and extracted with DCM. The organic layer was concentrated to give the crude product which was purified using prep-TLC eluting with DCM/MeOH (10:1) to give tert-butyl 2-((5-(2-(4-((5-(((5-(tert-butyl)oxazol-2-yl)methyl)thio)thiazol-2-yl)carbamoyl)piperidin-1-yl)acetamido)pentyl)amino)acetate (120 mg, 29% yield) as an oil. MS (ESI) m/z 637.2 [M+H]$^+$.

To a solution of tert-butyl 2-((5-(2-(4-((5-(((5-(tert-butyl) oxazol-2-yl)methyl)thio)thiazol-2-yl)carbamoyl)piperidin-1-yl)acetamido)pentyl)amino)acetate (120 mg, 0.189 mmol) in DCM (4 mL) was added TFA (2 mL). The mixture was stirred at RT for 4 h. The solvent was removed and the residue was dissolved in DMF (6 mL). DIEA (48.8 mg, 0.378 mmol) was added followed by 3-(1-(aminomethyl)-4-oxo-4H-thieno[3,4-c]pyrrol-5(6H)-yl)piperidine-2,6-dione (53 mg, 0.189 mmol), HOBt (38.3 mg, 0.284 mmol) and EDCI.HCl (54.5 mg, 0.284 mmol). The mixture was stirred at RT overnight. The solvent was removed and the residue was purified using prep-HPLC as previously described to afford Compound 33 (12.1 mg, 8% yield) as a solid.

Example 34

Compound 34: N-(5-(((5-(tert-butyl)oxazol-2-yl) methyl)thio)thiazol-2-yl)-1-(1-(5-(2,6-dioxopiperi-din-3-yl)-6-oxo-5,6-dihydro-4H-thieno[2,3-c]pyrrol-2-yl)-3,15-dioxo-8,11-dioxa-2,5,14-triazahexadecan-16-yl)piperidine-4-carboxamide To a solution of 2-(4-((5-(((5-(tert-butyl)oxazol-2-yl) methyl)thio)thiazol-2-yl)carbamoyl)piperidin-1-yl)acetic acid (510 mg, 1.16 mmol) in DMF (5 mL) was added tert-butyl (2-(2-(2-aminoethoxy)ethoxy)ethyl)carbamate (347 mg, 1.39 mmol) and DIEA (300 mg, 2.32 mmol), followed by HOBt (236 mg, 1.75 mmol) and EDCI.HCl (336 mg, 1.75 mmol). The mixture was stirred at RT for 12 h, diluted with $H_2O$ and extracted with EA. The combined organic layers were washed with saturated $NaHCO_3$, dried over $Na_2SO_4$, filtered and concentrated to give the crude product, which was purified using silica gel eluting with DCM/MeOH (0% to 10%) to give tert-butyl (2-(2-(2-(2-(4-((5-(((5-(tert-butyl)oxazol-2-yl)methyl)thio)thiazol-2-yl) carbamoyl)piperidin-1-yl)acetamido)ethoxy)ethoxy)ethyl) carbamate (521 mg, 68% yield) as a solid. MS (ESI) m/z 669.2 [M+H]$^+$.

To a solution of tert-butyl (2-(2-(2-(2-(4-((5-(((5-(tert-butyl)oxazol-2-yl)methyl)thio)thiazol-2-yl)carbamoyl)pip-eridin-1-yl)acetamido)ethoxy)ethoxy)ethyl)carbamate (521 mg, 0.779 mmol) in DCM (10 mL) was added TFA (4 mL). The mixture was stirred at RT for 1 h then concentrated. The resulting amine TFA salt was dissolved in DMF (8 mL) and cooled to 0° C., then $K_2CO_3$ (322 mg, 2.337 mmol) was added, followed by tert-butyl bromoacetate (152 mg, 0.779 mmol). The mixture was stirred at RT for 3 h, diluted with $H_2O$, and extracted with DCM. The organic layer was concentrated and the residue was purified using prep-TLC eluting with DCM/MeOH (10:1) to give tert-butyl 14-(4-((5-(((5-(tert-butyl)oxazol-2-yl)methyl)thio)thiazol-2-yl) carbamoyl)piperidin-1-yl)-13-oxo-6,9-dioxa-3,12-diazatet-radecan-1-oate (117 mg, 22% yield) as an oil. MS (ESI) m/z 683.2 [M+H]$^+$.

To a solution of tert-butyl14-(4-((5-(((5-(tert-butyl)oxa-zol-2-yl)methyl)thio)thiazol-2-yl)carbamoyl)piperidin-1-yl)-13-oxo-6,9-dioxa-3,12-diazatetradecan-1-oate (75 mg, 0.11 mmol) in DCM (4 mL) was added TFA (2 mL). The mixture was stirred at RT for 4 h then concentrated. The residue was dissolved in DMF (5 mL) and DIEA (28 mg, 0.22 mmol) was added. Then 3-(2-(aminomethyl)-6-oxo-4H-thieno[2,3-c]pyrrol-5(6H)-yl)piperidine-2,6-dione (30.7 mg, 0.11 mmol), HOBt (23 mg, 0.17 mmol) and EDCI.HCl (33 mg, 0.17 mmol) were added. The mixture was stirred at RT overnight. The solvent was removed and the residue was purified using prep-HPLC as previously described to afford Compound 34 (8.1 mg, 8% yield) as a solid.

Example 35

Compound 35: 2-(((1r,4r)-4-((5-chloro-4-(5-(cyclo-propylmethyl)-1-methyl-1H-pyrazol-4-yl)pyrimidin-2-yl)amino)cyclohexyl)amino)-N-(4-((2-(((5-(2,6-dioxopiperidin-3-yl)-6-oxo-5,6-dihydro-4H-thieno[2,3-c]pyrrol-2-yl)methyl)amino)-2-oxoethyl)amino) butyl)acetamide To a solution of 2-(((1r,4r)-4-((5-chloro-4-(5-(cyclopro-pylmethyl)-1-methyl-1H-pyrazol-4-yl)pyrimidin-2-yl) amino)cyclohexyl)amino)acetic acid (300 mg, 0.564 mmol) in DMF (6 mL) was added DIEA (254.6 mg, 1.974 mmol), followed by tert-butyl (4-aminobutyl)carbamate (148.4 mg, 0.789 mmol) and HATU (321.4 mg, 0.846 mmol). The mixture was stirred at RT overnight, then diluted with $H_2O$ and extracted with EA. The combined organic layers were washed with $H_2O$ and saturated $NaHCO_3$, dried over $Na_2SO_4$, filtered and concentrated to give tert-butyl (4-(2-(((1r,4r)-4-((5-chloro-4-(5-(cyclopropylmethyl)-1-methyl-1H-pyrazol-4-yl)pyrimidin-2-yl)amino)cyclohexyl)amino) acetamido)butyl)carbamate (300 mg crude). MS (ESI) m/z 589.4 [M+H]$^+$.

To a solution of tert-butyl (4-(2-(((1r,4r)-4-((5-chloro-4-(5-(cyclopropylmethyl)-1-methyl-1H-pyrazol-4-yl)pyrimidin-2-yl)amino)cyclohexyl)amino)acetamido)butyl)carbamate (254 mg, 0.432 mmol) in THF/H$_2$O (4 mL:1 mL) at RT was added sodium carbonate (137.4 mg, 1.296 mmol), followed by benzyl chloroformate (110.5 mg, 0.648 mmol). After 30 min at RT, the mixture was concentrated and the residue was diluted with H$_2$O then extracted with EA. The combined organic layers were dried over Na$_2$SO$_4$, filtered and concentrated to give the crude product, which was purified using silica gel eluting with MeOH/DCM (0% to 6%) to give benzyl (2-((4-((tert-butoxycarbonyl)amino)butyl)amino)-2-oxoethyl)((1r,4r)-4-((5-chloro-4-(5-(cyclopropylmethyl)-1-methyl-1H-pyrazol-4-yl)pyrimidin-2-yl)amino)cyclohexyl)carbamate (277.5 mg, 89% yield) as a solid. MS (ESI) m/z 723.4 [M+H]$^+$.

To a solution of benzyl (2-((4-((tert-butoxycarbonyl)amino)butyl)amino)-2-oxoethyl)((1r,4r)-4-((5-chloro-4-(5-(cyclopropylmethyl)-1-methyl-1H-pyrazol-4-yl)pyrimidin-2-yl)amino)cyclohexyl)carbamate (277 mg, 0.383 mmol) in DCM (4 mL) was added TFA (1 mL). The mixture was stirred at RT for 30 min then concentrated to give benzyl (2-((4-aminobutyl)amino)-2-oxoethyl)((1r,4r)-4-((5-chloro-4-(5-(cyclopropylmethyl)-1-methyl-1H-pyrazol-4-yl)pyrimidin-2-yl)amino)cyclohexyl)carbamate (230 mg, 96% yield) as the TFA salt.

To a solution of benzyl (2-((4-aminobutyl)amino)-2-oxoethyl)((1r,4r)-4-((5-chloro-4-(5-(cyclopropylmethyl)-1-methyl-1H-pyrazol-4-yl)pyrimidin-2-yl)amino)cyclohexyl)carbamate (220 mg, 0.354 mmol, as TFA salt) in DMF (8 mL) at 0° C. was added K$_2$CO$_3$ (146.4 mg, 1.06 mmol), followed by tert-butyl bromoacetate (68.9 mg, 0.354 mmol). The mixture was stirred at RT for 4 h, then diluted with H$_2$O and extracted with DCM. The organic layer was concentrated to give the crude product which was purified using silica gel eluting with MeOH/DCM (0% to 8% to give tert-butyl 4-((1r,4r)-4-((5-chloro-4-(5-(cyclopropylmethyl)-1-methyl-1H-pyrazol-4-yl)pyrimidin-2-yl)amino)cyclohexyl)-3,6-dioxo-1-phenyl-2-oxa-4,7,12-triazatetradecan-14-oate (63 mg, 24% yield) as a solid. MS (ESI) m/z 737.3 [M+H]$^+$.

To a solution of tert-butyl 4-((1r,4r)-4-((5-chloro-4-(5-(cyclopropylmethyl)-1-methyl-1H-pyrazol-4-yl)pyrimidin-2-yl)amino)cyclohexyl)-3,6-dioxo-1-phenyl-2-oxa-4,7,12-triazatetradecan-14-oate (133 mg, 0.180 mmol) in DCM (4 mL) was added TFA (1 mL). The mixture was stirred at RT overnight. The solvent was removed to give the crude product as residue which was used for the next step directly. The residue was dissolved in DMF (4 mL). Then 3-(2-(aminomethyl)-6-oxo-4H-thieno[2,3-c]pyrrol-5(6H)-yl)piperidine-2,6-dione (50.47 mg, 0.181 mmol, HCl salt) and DIEA (46.7 mg, 0.362 mmol) was added and stirred for 5 min. Then HOBt (24.4 mg, 0.181 mmol) and EDCI.HCl (34.7 mg, 0.181 mmol) was added. The mixture was stirred at RT overnight. The solvent was removed and the residue was purified using prep-TLC eluting with DCM/MeOH (10:1) to give benzyl ((1r,4r)-4-((5-chloro-4-(5-(cyclopropylmethyl)-1-methyl-1H-pyrazol-4-yl)pyrimidin-2-yl)amino)cyclohexyl)(2-((4-((2-(((5-(2,6-dioxopiperidin-3-yl)-6-oxo-5,6-dihydro-4H-thieno[2,3-c]pyrrol-2-yl)methyl)amino)-2-oxoethyl)amino)butyl)amino)-2-oxoethyl)carbamate (93 mg, 66% yield) as a solid. MS (ESI) m/z 943.2 [M+H]$^+$.

To a solution of benzyl ((1r,4r)-4-((5-chloro-4-(5-(cyclopropylmethyl)-1-methyl-1H-pyrazol-4-yl)pyrimidin-2-yl)amino)cyclohexyl)(2-((4-((2-(((5-(2,6-dioxopiperidin-3-yl)-6-oxo-5,6-dihydro-4H-thieno[2,3-c]pyrrol-2-yl)methyl)amino)-2-oxoethyl)amino)butyl)amino)-2-oxoethyl)carbamate (93 mg, 0.098 mmol) in AcOH (2 mL) was added HBr (33% in AcOH, 2 mL). The mixture was stirred at RT for 1 h. The solvent was removed and the residue was dried to give the crude product. It was dissolved in DMF (2 mL) and adjusted to pH about 7 with TEA. The solvent was removed and the residue was purified using prep-HPLC as previously described to afford Compound 35 (6.2 mg, 8% yield) as a solid.

Example 36

Compound 36: 2-(((1r,4r)-4-((5-chloro-4-(5-(cyclopropylmethyl)-1-methyl-1H-pyrazol-4-yl)pyrimidin-2-yl)amino)cyclohexyl)amino)-N-(4-((2-(((5-(2,6-dioxopiperidin-3-yl)-4,6-dioxo-5,6-dihydro-4H-thieno[2,3-c]pyrrol-2-yl)methyl)amino)-2-oxoethyl)amino)butyl)acetamide To a solution of 2-(((1r,4r)-4-((5-chloro-4-(5-(cyclopropylmethyl)-1-methyl-1H-pyrazol-4-yl) pyrimidin-2-yl)amino)cyclohexyl)amino)acetic acid (300 mg, 0.56 mmol) in N,N-dimethylamide (8 mL) at RT was added tert-butyl (4-aminobutyl)carbamate (106 mg, 0.56 mmol), followed by HATU (319 mg, 0.84 mmol) and N,N-diisopropylethylamine (217 mg, 1.68 mmol) added. The mixture was stirred at RT for 2 h, diluted with H$_2$O (10 mL), and extracted with EA (15 mL×2). The combined organic layers were washed with H$_2$O (10 mL), dried over Na$_2$SO$_4$, filtered and concentrated to give the crude tert-butyl (4-(2-(((1r,4r)-4-((5-chloro-4-(5-(cyclopropylmethyl)-1-methyl-1H-pyrazol-4-yl) pyrimidin-2-yl) amino)cyclohexyl)amino)acetamido)butyl)carbamate (330 mg, crude) as a solid. MS (ESI) m/z 589.3 [M+H]$^+$.

To a solution of tert-butyl (4-(2-(((1r,4r)-4-((5-chloro-4-(5-(cyclopropylmethyl)-1-methyl-1H-pyrazol-4-yl)pyrimidin-2-yl)amino)cyclohexyl)amino)acetamido)butyl)carbamate (330 mg, 0.56 mmol) in THF/H$_2$O (15 mL/4.5 mL) at 0° C. was added sodium carbonate (178 mg, 1.68 mmol), followed by benzyl carbonochloridate (126 mg, 0.84 mmol) added. The mixture was stirred at RT for overnight and then the suspension was diluted with H$_2$O (10 mL), extracted with EA (15 mL×2). The combined organic layers were dried over Na$_2$SO$_4$, filtered and concentrated to give the crude product, which was purified using silica gel eluting with MeOH/DCM (0% to 5%) to give benzyl (2-((4-((tert-butoxycarbonyl)amino)butyl)amino)-2-oxoethyl)((1r,4r)-4-((5-chloro-4-(5-(cyclopropylmethyl)-1-methyl-1H-pyrazol-4-yl)pyrimidin-2-yl)amino)cyclohexyl)carbamate (342 mg, 83% yield) as a solid. MS (ESI) m/z 724.2 [M+H]$^+$ To a solution of benzyl (2-((4-((tert-butoxycarbonyl)amino)butyl)amino)-2-oxoethyl) ((1r,4r)-4-((5-chloro-4-(5-(cyclopropylmethyl)-1-methyl-1H-pyrazol-4-yl)pyrimidin-2-yl)amino)cyclohexyl)carbamate (342 mg, 0.47 mmol) in DCM (8 mL) was added TFA (2 mL). The mixture was stirred at RT for 1 h then concentrated. The resulting amine TFA salt was dissolved in DMF (7 mL) and cooled to 0° C., then K$_2$CO$_3$ (138 mg, 2.35 mmol) was added, followed by tert-butyl bromoacetate (92 mg, 0.47 mmol) added. The mixture was stirred at RT for 6 h, diluted with H$_2$O (5 mL), and extracted with DCM (20 mL). The organic layer was concentrated to give the crude product which was purified using prep-TLC eluting with DCM/MeOH (10:1) to give tert-butyl 4-((1r,4r)-4-((5-chloro-4-(5-(cyclopropylmethyl)-1-methyl-1H-pyrazol-4-yl)pyrimidin-2-yl)amino)cyclohexyl)-3,6-dioxo-1-phenyl-2-oxa-4,7,12-triazatetradecan-14-oate (225 mg, 62% yield) as an oil. MS (ESI) m/z 737.4 [M+H]$^+$.

To a solution of tert-butyl 4-((1r,4r)-4-((5-chloro-4-(5-(cyclopropylmethyl)-1-methyl-1H-pyrazol-4-yl)pyrimidin-2-yl)amino)cyclohexyl)-3,6-dioxo-1-phenyl-2-oxa-4,7,12-triazatetradecan-14-oate (74 mg, 0.1 mmol) in DCM (8 mL) at RT was added TFA (2 mL). The mixture was stirred at RT for 1 h. The solvent was removed and the residue was dried to give acid (68 mg, crude) as an oil. The oil was dissolved in DMF (4 mL) and TEA (50 mg, 0.50 mmol) was added. Then 2-(aminomethyl)-5-(2,6-dioxopiperidin-3-yl)-4H-thieno[2,3-c]pyrrole-4,6(5H)-dione (60 mg, 0.2 mmol) and propanephosphonicacidanhydride (95 mg, 0.3 mmol) added. The mixture was stirred at RT for 2 h. The solvent was removed and the residue was purified using prep-TLC eluting with DCM/MeOH (10:1) to give benzyl ((1r,4r)-4-((5-chloro-4-(5-(cyclopropylmethyl)-1-methyl-1H-pyrazol-4-yl)pyrimidin-2-yl)amino)cyclohexyl)(2-((4-((2-(((5-(2,6-dioxopiperidin-3-yl)-4,6-dioxo-5,6-dihydro-4H-thieno[2,3-c]pyrrol-2-yl)methyl)amino)-2-oxoethyl)amino)butyl)amino)-2-oxoethyl)carbamate (96 mg, crude) as a solid. MS (ESI) m/z 956.4 [M+H]$^+$.

To a solution of benzyl ((1r,4r)-4-((5-chloro-4-(5-(cyclopropylmethyl)-1-methyl-1H-pyrazol-4-yl)pyrimidin-2-yl)amino)cyclohexyl)(2-((4-((2-(((5-(2,6-dioxopiperidin-3-yl)-4,6-dioxo-5,6-dihydro-4H-thieno[2,3-c]pyrrol-2-yl)methyl)amino)-2-oxoethyl)amino)butyl)amino)-2-oxoethyl)carbamate (96 mg, 0.10 mmol) in AcOH (2 mL) was added HBr (33% in AcOH, 2 mL). The mixture was stirred at RT for 1 h. The solvent was removed and the residue was dried to give the crude product which was dissolved in DMF (2 mL) and adjusted to a pH of about 7 with TEA. The solvent was removed and the residue was purified using prep-HPLC as previously described to afford Compound 36 (10.2 mg, 12% yield) as a solid.

Example 37

Compound 37: 2-(((1r,4r)-4-((4-(5-(cyclopropylmethyl)-1-methyl-1H-pyrazol-4-yl)-5-fluoropyrimidin-2-yl)amino)cyclohexyl)amino)-N-(4-((2-(((5-(2,6-dioxopiperidin-3-yl)-4,6-dioxo-5,6-dihydro-4H-thieno[2,3-c]pyrrol-2-yl)methyl)amino)-2-oxoethyl)amino)butyl)acetamide To a solution of 2-(((1r,4r)-4-((4-(5-(cyclopropylmethyl)-1-methyl-1H-pyrazol-4-yl)-5-fluoropyrimidin-2-yl)amino)cyclohexyl)amino)acetic acid (350 mg, 0.678 mmol) in DMF (4 mL) was added DIEA (262 mg, 2.03 mmol), followed by tert-butyl (4-aminobutyl)carbamate (153 mg, 0.814 mmol), HOBt (137 mg, 1.02 mmol) and EDCI.HCl (195 mg, 1.02 mmol) was added. The mixture was stirred at RT overnight, diluted with H$_2$O (10 mL), and extracted with EA (15 mL×2). The combined organic layers were washed with H$_2$O (10 mL), dried over Na$_2$SO$_4$, filtered and concentrated to give the crude product, which was purified using silica gel eluting with MeOH/DCM (0% to 10%) to give tert-butyl (4-(2-(((1r,4r)-4-((4-(5-(cyclopropylmethyl)-1-methyl-1H-pyrazol-4-yl)-5-fluoropyrimidin-2-yl)amino)cyclohexyl)amino)acetamido)butyl)carbamate (240 mg, 71% yield) as a solid. MS (ESI) m/z 573.1 [M+H]$^+$.

To a solution of tert-butyl (4-(2-(((1r,4r)-4-((4-(5-(cyclopropylmethyl)-1-methyl-1H-pyrazol-4-yl)-5-fluoropyrimidin-2-yl)amino)cyclohexyl)amino)acetamido)butyl)carbamate (240 mg, 0.42 mmol) in THF/H$_2$O (4 mL/1 mL) at 0° C. was added sodium carbonate (133 mg, 1.26 mmol), followed by benzyl chloroformate (108 mg, 0.63 mmol) added. The mixture was stirred at RT for 2 h, diluted with H$_2$O (10 mL), and extracted with EA (15 mL×2). The combined organic layers were dried over Na$_2$SO$_4$, filtered and concentrated to give the crude product, which was purified using silica gel eluting with MeOH/DCM (0% to 6% to give benzyl (2-((4-((tert-butoxycarbonyl)amino)butyl)amino)-2-oxoethyl)((1r,4r)-4-((4-(5-(cyclopropylmethyl)-1-methyl-1H-pyrazol-4-yl)-5-fluoropyrimidin-2-yl)amino)cyclohexyl)carbamate (300 mg, 100% yield) as a solid. MS (ESI) m/z 707.1 [M+H]$^+$.

To a solution of benzyl (2-((4-((tert-butoxycarbonyl)amino)butyl)amino)-2-oxoethyl)((1r,4r)-4-((4-(5-(cyclopropylmethyl)-1-methyl-1H-pyrazol-4-yl)-5-fluoropyrimidin-2-yl)amino)cyclohexyl)carbamate (300 mg, 0.425 mmol) in DCM (4 mL) was added TFA (1 mL). The mixture was stirred at RT for 3 h then concentrated. The resulting amine TFA salt was dissolved in DMF (4 mL) and cooled to 0° C., then K$_2$CO$_3$ (196 mg, 1.275 mmol) was added, followed by tert-butyl bromoacetate (83 mg, 0.425 mmol). The mixture was stirred at RT for 16 h, diluted with H$_2$O and extracted with DCM. The organic layer was concentrated to give the crude product which was purified using silica gel eluting with MeOH/DCM (0% to 6%) to give tert-butyl 4-((1r,4r)-4-((4-(5-(cyclopropylmethyl)-1-methyl-1H-pyrazol-4-yl)-5-fluoropyrimidin-2-yl)amino)cyclohexyl)-3,6-dioxo-1-phenyl-2-oxa-4,7,12-triazatetradecan-14-oate (135 mg, 44% yield) as solid. MS (ESI) m/z 721.4 [M+H]$^+$.

To a solution of tert-butyl 4-((1r,4r)-4-((4-(5-(cyclopropylmethyl)-1-methyl-1H-pyrazol-4-yl)-5-fluoropyrimidin-2-yl)amino)cyclohexyl)-3,6-dioxo-1-phenyl-2-oxa-4,7,12-triazatetradecan-14-oate (135 mg, 0.188 mmol) in DCM (4 mL) was added TFA (1 mL). The mixture was stirred at RT overnight. The solvent was removed and the residue was dried to give 4-((1r, 4r)-4-((4-(5-(cyclopropylmethyl)-1-methyl-1H-pyrazol-4-yl)-5-fluoropyrimidin-2-yl)amino)cyclohexyl)-3,6-dioxo-1-phenyl-2-oxa-4,7,12-triazatetradecan-14-oic acid (124.5 mg, crude) as the TFA salt. MS (ESI) m/z 665.4 [M+H]$^+$.

To a solution of tert-butyl ((5-(2,6-dioxopiperidin-3-yl)-4,6-dioxo-5,6-dihydro-4H-thieno[2,3-c]pyrrol-2-yl)methyl)carbamate (60 mg, 0.153 mmol) in DCM (4 mL) was added TFA (1 mL). The mixture was stirred at RT for 2 h then concentrated. The resulting amine TFA salt was dissolved in DMF (4 mL), then TEA (46 mg, 0.458 mmol) was added, followed by 4-((1r,4r)-4-((4-(5-(cyclopropylmethyl)-1-methyl-1H-pyrazol-4-yl)-5-fluoropyrimidin-2-yl)amino)cyclohexyl)-3,6-dioxo-1-phenyl-2-oxa-4,7,12-triazatetradecan-14-oic acid (101 mg, 0.153 mmol) and propanephosphonic acid anhydride (146 mg, 0.458 mmol). The mixture was stirred at RT for 16 h. The solvent was removed and the residue was purified using prep-TLC eluting with DCM/MeOH (10:1) to give benzyl ((1r,4r)-4-((4-(5-(cyclopropylmethyl)-1-methyl-1H-pyrazol-4-yl)-5-fluoropyrimidin-2-yl)amino)cyclohexyl)(2-((4-((2-(((5-(2,6-dioxopiperidin-3-yl)-4,6-dioxo-5,6-dihydro-4H-thieno[2,3-c]pyrrol-2-yl)methyl)amino)-2-oxoethyl)amino)butyl)amino)-2-oxoethyl)carbamate (90 mg, 47% yield) as a solid. MS (ESI) m/z 939.4 [M+H]$^+$.

To a solution of benzyl ((1r,4r)-4-((4-(5-(cyclopropylmethyl)-1-methyl-1H-pyrazol-4-yl)-5-fluoropyrimidin-2-yl)amino)cyclohexyl)(2-((4-((2-(((5-(2,6-dioxopiperidin-3-yl)-4,6-dioxo-5,6-dihydro-4H-thieno[2,3-c]pyrrol-2-yl)methyl)amino)-2-oxoethyl)amino)butyl)amino)-2-oxoethyl)carbamate (45 mg, 0.048 mmol) in AcOH (1.5 mL) was added HBr (33% in AcOH, 1.5 mL). The mixture was stirred at RT for 1 h then concentrated, and the residue was dissolved in DMF (2 mL) and adjusted to a pH of about 7 with TEA. The solvent was removed and the residue was purified using prep-HPLC as previously described to afford Compound 37 (7.5 mg, 20% yield) as a solid.

Example 38

Compound 38: 2-(((1r,4r)-4-((5-chloro-4-(5-(cyclopropylmethyl)-1-methyl-1H-pyrazol-4-yl)pyrimidin-2-yl)amino)cyclohexyl)amino)-N-(4-((2-(((5-(2,6-dioxopiperidin-3-yl)-4-oxo-5,6-dihydro-4H-thieno[3,4-c]pyrrol-1-yl)methyl)amino)-2-oxoethyl)amino)butyl)acetamide To a solution of 2-(((1r,4r)-4-((5-chloro-4-(5-(cyclopropylmethyl)-1-methyl-1H-pyrazol-4-yl)pyrimidin-2-yl)amino)cyclohexyl)amino)acetic acid (300 mg, 0.564 mmol) in DMF (6 mL) was added DIEA (254.6 mg, 1.974 mmol), followed by tert-butyl (4-aminobutyl)carbamate (148.4 mg, 0.789 mmol) and HATU (321.4 mg, 0.846 mmol). The mixture was stirred at RT overnight, then diluted with $H_2O$ and extracted with EA. The combined organic layers were washed with $H_2O$ and saturated $NaHCO_3$, dried over $Na_2SO_4$, filtered and concentrated to give tert-butyl (4-(2-(((1r,4r)-4-((5-chloro-4-(5-(cyclopropylmethyl)-1-methyl-1H-pyrazol-4-yl)pyrimidin-2-yl)amino)cyclohexyl)amino)acetamido)butyl)carbamate (300 mg crude). MS (ESI) m/z 589.4 $[M+H]^+$.

To a solution of tert-butyl (4-(2-(((1r,4r)-4-((5-chloro-4-(5-(cyclopropylmethyl)-1-methyl-1H-pyrazol-4-yl)pyrimidin-2-yl)amino)cyclohexyl)amino)acetamido)butyl)carbamate (254 mg, 0.432 mmol) in $THF/H_2O$ (4 mL:1 mL) at RT was added sodium carbonate (137.4 mg, 1.296 mmol), followed by benzyl chloroformate (110.5 mg, 0.648 mmol). After 30 min at RT, the mixture was concentrated and the residue was diluted with $H_2O$ then extracted with EA. The combined organic layers were dried over $Na_2SO_4$, filtered and concentrated to give the crude product, which was purified using silica gel eluting with MeOH/DCM (0% to 6%) to give benzyl (2-((4-((tert-butoxycarbonyl)amino)butyl)amino)-2-oxoethyl)((1r,4r)-4-((5-chloro-4-(5-(cyclopropylmethyl)-1-methyl-1H-pyrazol-4-yl)pyrimidin-2-yl)amino)cyclohexyl)carbamate (277.5 mg, 89% yield) as a solid. MS (ESI) m/z 723.4 $[M+H]^+$.

To a solution of benzyl (2-((4-((tert-butoxycarbonyl)amino)butyl)amino)-2-oxoethyl)((1r,4r)-4-((5-chloro-4-(5-(cyclopropylmethyl)-1-methyl-1H-pyrazol-4-yl)pyrimidin-2-yl)amino)cyclohexyl)carbamate (277 mg, 0.383 mmol) in DCM (4 mL) was added TFA (1 mL). The mixture was stirred at RT for 30 min then concentrated to give benzyl (2-((4-aminobutyl)amino)-2-oxoethyl)((1r,4r)-4-((5-chloro-4-(5-(cyclopropylmethyl)-1-methyl-1H-pyrazol-4-yl)pyrimidin-2-yl)amino)cyclohexyl)carbamate (230 mg, 96% yield) as the TFA salt.

To a solution of benzyl (2-((4-aminobutyl)amino)-2-oxoethyl)((1r,4r)-4-((5-chloro-4-(5-(cyclopropylmethyl)-1-methyl-1H-pyrazol-4-yl)pyrimidin-2-yl)amino)cyclohexyl)carbamate (220 mg, 0.354 mmol, as TFA salt) in DMF (8 mL) at 0° C. was added $K_2CO_3$ (146.4 mg, 1.06 mmol), followed by tert-butyl bromoacetate (68.9 mg, 0.354 mmol). The mixture was stirred at RT for 4 h, then diluted with $H_2O$ and extracted with DCM. The organic layer was concentrated to give the crude product which was purified using silica gel eluting with MeOH/DCM (0% to 8%) to give tert-butyl 4-((1r,4r)-4-((5-chloro-4-(5-(cyclopropylmethyl)-1-methyl-1H-pyrazol-4-yl)pyrimidin-2-yl)amino)cyclohexyl)-3,6-dioxo-1-phenyl-2-oxa-4,7,12-triazatetradecan-14-oate (63 mg, 24% yield) as a solid. MS (ESI) m/z 737.3 $[M+H]^+$.

To a solution of tert-butyl 4-((1r,4r)-4-((5-chloro-4-(5-(cyclopropylmethyl)-1-methyl-1H-pyrazol-4-yl)pyrimidin-2-yl)amino)cyclohexyl)-3,6-dioxo-1-phenyl-2-oxa-4,7,12-triazatetradecan-14-oate (63 mg, 0.086 mmol) in DCM (4 mL) was added TFA (1 mL). The mixture was stirred at RT overnight then concentrated and dissolved in DMF (4 mL). 3-(1-(Aminomethyl)-4-oxo-4H-thieno[3,4-c]pyrrol-5(6H)-yl)piperidine-2,6-dione (35.7 mg, 0.128 mmol) and DIEA (33.0 mg, 0.256 mmol) were added. The solution was stirred for 5 min then HOBt (17.3 mg, 0.128 mmol) and EDCI.HCl (24.6 mg, 0.128 mmol) were added at the same time. The mixture was stirred at RT overnight. The solvent was removed and the residue was purified using prep-TLC eluting with DCM/MeOH (10:1) to give benzyl ((1r,4r)-4-((5-chloro-4-(5-(cyclopropylmethyl)-1-methyl-1H-pyrazol-4-yl)pyrimidin-2-yl)amino)cyclohexyl)(2-((4-((2-(((5-(2,6-dioxopiperidin-3-yl)-4-oxo-5,6-dihydro-4H-thieno[3,4-c]pyrrol-1-yl)methyl)amino)-2-oxoethyl)amino)butyl)amino)-2-oxoethyl)carbamate (55 mg, 51% yield) as a solid. MS (ESI) m/z 943.2 $[M+H]^+$.

To a solution of benzyl ((1r,4r)-4-((5-chloro-4-(5-(cyclopropylmethyl)-1-methyl-1H-pyrazol-4-yl)pyrimidin-2-yl)amino)cyclohexyl)(2-((4-((2-(((5-(2,6-dioxopiperidin-3-yl)-4-oxo-5,6-dihydro-4H-thieno[3,4-c]pyrrol-1-yl)methyl)amino)-2-oxoethyl)amino)butyl)amino)-2-oxoethyl)carbamate (55 mg, 0.058 mmol) in AcOH (1.5 mL) was added HBr (33% in AcOH, 1.5 mL). The mixture was stirred at RT for 30 min. The solvent was removed and the residue was dried to give the crude product which was dissolved in DMF (2 mL) and adjusted to pH about 7 with TEA. The solvent was removed and the residue was purified using prep-HPLC as previously described to afford Compound 38 (20.9 mg, 44% yield) as a solid.

Example 39

Compound 39: 2-(((1r,4r)-4-((4-(5-(cyclopropylmethyl)-1-methyl-1H-pyrazol-4-yl)-5-fluoropyrimidin-2-yl)amino)cyclohexyl)amino)-N-(4-((2-(((5-(2,6-dioxopiperidin-3-yl)-4-oxo-5,6-dihydro-4H-thieno[3,4-c]pyrrol-1-yl)methyl)amino)-2-oxoethyl)amino)butyl)acetamide To a solution of 2-(((1r,4r)-4-((4-(5-(cyclopropylmethyl)-1-methyl-1H-pyrazol-4-yl)-5-fluoropyrimidin-2-yl)amino)cyclohexyl)amino)acetic acid (350 mg, 0.678 mmol) in DMF (4 mL) was added DIEA (262 mg, 2.03 mmol), followed by tert-butyl (4-aminobutyl)carbamate (153 mg, 0.814 mmol), HOBt (137 mg, 1.02 mmol) and EDCI.HCl (195 mg, 1.02 mmol) was added. The mixture was stirred at RT overnight, diluted with $H_2O$ (10 mL), and extracted with EA (15 mL×2). The combined organic layers were washed with $H_2O$ (10 mL), dried over $Na_2SO_4$, filtered and concentrated to give the crude product, which was purified using silica gel eluting with MeOH/DCM (0% to 10%) to give tert-butyl (4-(2-(((r,4r)-4-((4-(5-(cyclopropylmethyl)-1-methyl-1H-pyrazol-4-yl)-5-fluoropyrimidin-2-yl)amino)cyclohexyl)amino)acetamido)butyl)carbamate (240 mg, 71% yield) as a solid. MS (ESI) m/z 573.1 $[M+H]^+$.

To a solution of tert-butyl (4-(2-(((1r,4r)-4-((4-(5-(cyclopropylmethyl)-1-methyl-1H-pyrazol-4-yl)-5-fluoropyrimidin-2-yl)amino)cyclohexyl)amino)acetamido)butyl)carbamate (240 mg, 0.42 mmol) in $THF/H_2O$ (4 mL/1 mL) at 0° C. was added sodium carbonate (133 mg, 1.26 mmol), followed by benzyl chloroformate (108 mg, 0.63 mmol) added. The mixture was stirred at RT for 2 h, diluted with $H_2O$ (10 mL), and extracted with EA (15 mL×2). The combined organic layers were dried over Na$_2$SO$_4$, filtered and concentrated to give the crude product, which was purified using silica gel eluting with MeOH/DCM (0% to 6% to give benzyl (2-((4-((tert-butoxycarbonyl)amino)butyl)amino)-2-oxoethyl)((1r,4r)-4-((4-(5-(cyclopropylmethyl)-1-methyl-1H-pyrazol-4-yl)-5-fluoropyrimidin-2-yl)amino)cyclohexyl)carbamate (300 mg, 100% yield) as a solid. MS (ESI) m/z 707.1 [M+H]$^+$.

To a solution of benzyl (2-((4-((tert-butoxycarbonyl)amino)butyl)amino)-2-oxoethyl)((1r,4r)-4-((4-(5-(cyclopropylmethyl)-1-methyl-1H-pyrazol-4-yl)-5-fluoropyrimidin-2-yl)amino)cyclohexyl)carbamate (300 mg, 0.425 mmol) in DCM (4 mL) was added TFA (1 mL). The mixture was stirred at RT for 3 h then concentrated. The resulting amine TFA salt was dissolved in DMF (4 mL) and cooled to 0° C., then K$_2$CO$_3$ (196 mg, 1.275 mmol) was added, followed by tert-butyl bromoacetate (83 mg, 0.425 mmol). The mixture was stirred at RT for 16 h, diluted with H$_2$O and extracted with DCM. The organic layer was concentrated to give the crude product which was purified using silica gel eluting with MeOH/DCM (0% to 6% to give tert-butyl 4-((1r,4r)-4-((4-(5-(cyclopropylmethyl)-1-methyl-1H-pyrazol-4-yl)-5-fluoropyrimidin-2-yl)amino)cyclohexyl)-3,6-dioxo-1-phenyl-2-oxa-4,7,12-triazatetradecan-14-oate (135 mg, 44% yield) as solid. MS (ESI) m/z 721.4 [M+H]$^+$.

To a solution of tert-butyl 4-((1r,4r)-4-((4-(5-(cyclopropylmethyl)-1-methyl-1H-pyrazol-4-yl)-5-fluoropyrimidin-2-yl)amino)cyclohexyl)-3,6-dioxo-1-phenyl-2-oxa-4,7,12-triazatetradecan-14-oate (135 mg, 0.188 mmol) in DCM (4 mL) was added TFA (1 mL). The mixture was stirred at RT overnight. The solvent was removed and the residue was dried to give 4-((1r, 4r)-4-((4-(5-(cyclopropylmethyl)-1-methyl-1H-pyrazol-4-yl)-5-fluoropyrimidin-2-yl)amino)cyclohexyl)-3,6-dioxo-1-phenyl-2-oxa-4,7,12-triazatetradecan-14-oic acid (124.5 mg, crude) as the TFA salt. MS (ESI) m/z 665.4 [M+H]$^+$.

To a solution of tert-butyl ((5-(2,6-dioxopiperidin-3-yl)-4-oxo-5,6-dihydro-4H-thieno[3,4-c]pyrrol-1-yl)methyl)carbamate (70 mg, 0.185 mmol) in DCM (4 mL) was added TFA (1 mL). The mixture was stirred at RT for 2 h. The solvent was removed to give the amine TFA salt which was dissolved in DMF (4 mL), then TEA (56 mg, 0.458 mmol) was added, followed by 4-((1r,4r)-4-((4-(5-(cyclopropylmethyl)-1-methyl-1H-pyrazol-4-yl)-5-fluoropyrimidin-2-yl)amino)cyclohexyl)-3,6-dioxo-1-phenyl-2-oxa-4,7,12-triazatetradecan-14-oic acid (123 mg, 0.185 mmol) and propanephosphonic acid anhydride (176 mg, 0.554 mmol). The mixture was stirred at RT for 16 h. The solvent was removed and the residue was purified using prep-TLC (DCM/MeOH=10/1) to give benzyl ((1r,4r)-4-((4-(5-(cyclopropylmethyl)-1-methyl-1H-pyrazol-4-yl)-5-fluoropyrimidin-2-yl)amino)cyclohexyl)(2-((4-((2-(((5-(2,6-dioxopiperidin-3-yl)-4-oxo-5,6-dihydro-4H-thieno[3,4-c]pyrrol-1-yl)methyl)amino)-2-oxoethyl)amino)butyl)amino)-2-oxoethyl)carbamate (100 mg, 46% yield) as a solid. MS (ESI) m/z 926.4 [M+H]$^+$.

To a solution of benzyl ((1r,4r)-4-((4-(5-(cyclopropylmethyl)-1-methyl-1H-pyrazol-4-yl)-5-fluoropyrimidin-2-yl)amino)cyclohexyl)(2-((4-((2-(((5-(2,6-dioxopiperidin-3-yl)-4-oxo-5,6-dihydro-4H-thieno[3,4-c]pyrrol-1-yl)methyl)amino)-2-oxoethyl)amino)butyl)amino)-2-oxoethyl)carbamate (50 mg, 0.054 mmol) in AcOH (1.5 mL) was added HBr (33% in AcOH, 1.5 mL). The mixture was stirred at RT for 1 h. The solvent was removed and the residue was dried to give the crude product. It was dissolved in DMF (2 mL) and adjusted to pH about 7 with TEA. The solvent was removed and the residue was purified using prep-HPLC as previously described to afford Compound 39 (31.4 mg, 64% yield) as a solid.

Example 40

Compound 40: 2-(((1r,4r)-4-((5-chloro-4-(5-(cyclopropylmethyl)-1-methyl-1H-pyrazol-4-yl)pyrimidin-2-yl)amino)cyclohexyl)amino)-N-(2-((2-(((5-(2,6-dioxopiperidin-3-yl)-6-oxo-5,6-dihydro-4H-thieno[2,3-c]pyrrol-2-yl)methyl)amino)-2-oxoethyl)amino)ethyl)acetamide To a solution of 2-(((1r,4r)-4-((5-chloro-4-(5-(cyclopropylmethyl)-1-methyl-1H-pyrazol-4-yl)pyrimidin-2-yl)amino)cyclohexyl)amino)acetic acid (300 mg, 0.56 mmol) in DCM (15 mL) at RT was added DIEA (216.7 mg, 1.628 mmol), tert-butyl (2-aminoethyl)carbamate (99.2 mg, 0.62 mmol) and HATU (319.2 mg, 0.84 mmol). The mixture was stirred at RT for 3 h. It was concentrated and purified using silica gel eluting with MeOH/DCM (0 to 7% to give tert-butyl (2-(2-(((1r,4r)-4-((5-chloro-4-(5-(cyclopropylmethyl)-1-methyl-1H-pyrazol-4-yl)pyrimidin-2-yl)amino)cyclohexyl)amino)acetamido)ethyl)carbamate (324 mg, 100%) as an oil. MS (ESI) m/z 561.3 [M+H]$^+$.

To a solution of tert-butyl (2-(2-(((1r,4r)-4-((5-chloro-4-(5-(cyclopropylmethyl)-1-methyl-1H-pyrazol-4-yl)pyrimidin-2-yl)amino)cyclohexyl)amino)acetamido)ethyl)carbamate (324 mg, 0.578 mmol) in THF/H$_2$O (10 mL/3 mL) at RT was added sodium carbonate (184 mg, 1.734 mmol), followed by benzyl carbonochloridate (148 mg, 0.867 mmol) added. The mixture was stirred at RT for 0.5 h and then the suspension was diluted with H$_2$O and extracted with EA. The combined organic layers were dried over Na$_2$SO$_4$, filtered and concentrated to give the crude product, which was purified using silica gel eluting with MeOH/DCM (0% to 5% to give benzyl (2-((2-((tert-butoxycarbonyl)amino)ethyl)amino)-2-oxoethyl)((1 r,4r)-4-((5-chloro-4-(5-(cyclopropylmethyl)-1-methyl-1H-pyrazol-4-yl)pyrimidin-2-yl)amino)cyclohexyl)carbamate (309 mg, 77% yield) as an oil. MS (ESI) m/z 695.3 [M+H]$^+$.

To a solution of benzyl (2-((2-((tert-butoxycarbonyl)amino)ethyl)amino)-2-oxoethyl)((1r,4r)-4-((5-chloro-4-(5-(cyclopropylmethyl)-1-methyl-1H-pyrazol-4-yl)pyrimidin-2-yl)amino)cyclohexyl)carbamate (309 mg, 0.445 mmol) in DCM (8 mL) was added TFA (2 mL). The mixture was stirred at RT for 0.5 h then concentrated. The resulting amine TFA salt was dissolved in DMF (12 mL) at RT, then K$_2$CO$_3$ (185 mg, 1.335 mmol) was added, followed by tert-butyl bromoacetate (87 mg, 0.445 mmol) added. The mixture was stirred at RT for 4 h. The mixture was diluted with H$_2$O and extracted with DCM. The organic layer was concentrated to give the crude product which was purified using prep-TLC eluting with DCM/MeOH (10:1) to give tert-butyl 2-((2-(2-(((1 r,4r)-4-((5-chloro-4-(5-(cyclopropylmethyl)-1-methyl-1H-pyrazol-4-yl)pyrimidin-2-yl)amino)cyclohexyl)amino)acetamido)ethyl)amino)acetate (103 mg, 33% yield). MS (ESI) m/z 575.3 [M+H]$^+$.

To a solution of tert-butyl 2-((2-(2-(((1r,4r)-4-((5-chloro-4-(5-(cyclopropylmethyl)-1-methyl-1H-pyrazol-4-yl)pyrimidin-2-yl)amino)cyclohexyl)amino)acetamido)ethyl)amino)acetate (103 mg, 0.145 mmol) in DCM (4 mL) was added TFA (1 mL). The mixture was stirred at RT overnight. The solvent was removed and the residue was dried to give the intermediated product. 3-(2-(aminomethyl)-6-oxo-4H-thieno[2,3-c]pyrrol-5(6H)-yl)piperidine-2,6-dione (52 mg, 0.188 mmol) was dissolved in DMF (5 mL) and DIEA (56 mg, 0.435 mmol) added. Then the intermediated product, HOBt (30 mg, 0.217 mmol) and EDCI.HCl (42 mg, 0.217 mmol) was added. The mixture was stirred at RT overnight. The solvent was removed and the residue was purified using prep-TLC eluting with DCM/MeOH (10:1) to give benzyl ((1r,4r)-4-((5-chloro-4-(5-(cyclopropylmethyl)-1-methyl-1H-pyrazol-4-yl)pyrimidin-2-yl)amino)cyclohexyl)(2-((2-((2-(((5-(2,6-dioxopiperidin-3-yl)-6-oxo-5,6-dihydro-4H-thieno[2,3-c]pyrrol-2-yl)methyl)amino)-2-oxoethyl)amino) ethyl)amino)-2-oxoethyl)carbamate (110 mg, 83% yield) as a solid. MS (ESI) m/z 914.3 [M+H]$^+$.

To a solution of benzyl ((1r,4r)-4-((5-chloro-4-(5-(cyclopropylmethyl)-1-methyl-1H-pyrazol-4-yl)pyrimidin-2-yl) amino)cyclohexyl)(2-((2-((2-(((5-(2,6-dioxopiperidin-3-yl)-6-oxo-5,6-dihydro-4H-thieno[2,3-c]pyrrol-2-yl)methyl) amino)-2-oxoethyl)amino)ethyl)amino)-2-oxoethyl) carbamate (110 mg, 0.120 mmol) in AcOH (1.5 mL) was added HBr (33% in AcOH, 1.5 mL). The mixture was stirred at RT for 0.5 h. The solvent was removed and the residue was dried to give the crude product which was dissolved in DMF (2 mL) and adjusted to a pH of about 7 with TEA. The solvent was removed and the residue was purified using prep-HPLC as previously described to afford Compound 40 (28.5 mg, 31% yield) as a solid.

Example 41

Compound 41: N-(5-(((5-(tert-butyl)oxazol-2-yl) methyl)thio)thiazol-2-yl)-1-(1-(5-(2,6-dioxopiperidin-3-yl)-4-oxo-5,6-dihydro-4H-thieno[3,4-c]pyrrol-1-yl)-3,18-dioxo-8,11,14-trioxa-2,5,17-triazanonadecan-19-yl)piperidine-4-carboxamide To a solution of 2-(4-((5-(((5-(tert-butyl)oxazol-2-yl) methyl)thio)thiazol-2-yl)carbamoyl)piperidin-1-yl)acetic acid (400 mg, 0.91 mmol) in DMF (10 mL) at RT was added DIEA (352 mg, 2.73 mmol), followed by tert-butyl (2-(2-(2-(2-aminoethoxy)ethoxy)ethoxy)ethyl) carbamate (320 mg, 1.09 mmol), HOBt (185 mg, 1.37 mmol) and EDCI.HCl (263 mg, 1.37 mmol) were added. The mixture was stirred at RT overnight, diluted with H$_2$O and extracted with EA. The combined organic layers were washed with brine, dried over Na$_2$SO$_4$, filtered and concentrated to give the crude product, which was purified using silica gel eluting with MeOH/DCM (0% to 10%) to give tert-butyl (1-(4-((5-(((5-(tert-butyl)oxazol-2-yl)methyl)thio)thiazol-2-yl)carbamoyl) piperidin-1-yl)-2-oxo-6,9,12-trioxa-3-azatetradecan-14-yl) carbamate (538 mg, 83% yield) as an oil. MS (ESI) m/z 713.3 [M+H]$^+$.

To a solution of tert-butyl (1-(4-((5-(((5-(tert-butyl)oxazol-2-yl)methyl)thio)thiazol-2-yl)carbamoyl)piperidin-1-yl)-2-oxo-6,9,12-trioxa-3-azatetradecan-14-yl)carbamate (538 mg, 0.76 mmol) in DCM (8 mL) was added TFA (2 mL). The mixture was stirred at RT for 1 h then concentrated. The resulting amine TFA salt was dissolved in DMF (7 mL) and cooled to 0° C., then K$_2$CO$_3$ (210 mg, 1.52 mmol) was added, followed by tert-butyl bromoacetate (132 mg, 0.68 mmol) added. The mixture was stirred at RT for 6 h. The mixture was diluted with H$_2$O and extracted with DCM. The organic layer was concentrated to give the crude product which was purified using prep-TLC eluting with DCM/MeOH (10:1) to give tert-butyl 17-(4-((5-(((5-(tert-butyl)oxazol-2-yl)methyl)thio)thiazol-2-yl)carbamoyl)piperidin-1-yl)-16-oxo-6,9,12-trioxa-3,15-diazaheptadecan-1-oate (137 mg, 25% yield) as a solid. MS (ESI) m/z 727.3 [M+H]$^+$.

To a solution of tert-butyl 17-(4-((5-(((5-(tert-butyl)oxazol-2-yl)methyl)thio)thiazol-2-yl)carbamoyl)piperidin-1-yl)-16-oxo-6,9,12-trioxa-3,15-diazaheptadecan-1-oate (65 mg, 0.09 mmol) in DCM (4 mL) was added TFA (1 mL). The mixture was stirred at RT for 3 h. The solvent was removed and the residue was dried to give acid as an oil which was dissolved in DMF (4 mL) and then added DIEA (35 mg, 0.27 mmol), followed by 3-(1-(aminomethyl)-4-oxo-4H-thieno [3,4-c]pyrrol-5(6H)-yl)piperidine-2,6-dione (31 mg, 0.11 mmol), HOBt (18 mg, 0.135 mmol) and EDCI.HCl (26 mg, 0.135 mmol). The mixture was stirred at RT overnight, diluted with H$_2$O and extracted with EA. The combined organic layers were washed with brine, dried over Na$_2$SO$_4$, filtered and concentrated to give the crude product, which was purified using prep-HPLC as previously described to afford Compound 41 (2.0 mg, 2% yield) as a solid.

Example 42

Compound 42: N-(5-(((5-(tert-butyl)oxazol-2-yl) methyl)thio)thiazol-2-yl)-1-(1-(5-(2,6-dioxopiperidin-3-yl)-6-oxo-5,6-dihydro-4H-thieno[2,3-c]pyrrol-2-yl)-3,18-dioxo-8,11,14-trioxa-2,5,17-triazanonadecan-19-yl)piperidine-4-carboxamide To a solution of 2-(4-((5-(((5-(tert-butyl)oxazol-2-yl) methyl)thio)thiazol-2-yl)carbamoyl)piperidin-1-yl)acetic acid (400 mg, 0.91 mmol) in DMF (10 mL) at RT was added DIEA (352 mg, 2.73 mmol), followed by tert-butyl (2-(2-(2-(2-aminoethoxy)ethoxy)ethoxy)ethyl) carbamate (320 mg, 1.09 mmol), HOBt (185 mg, 1.37 mmol) and EDCI.HCl (263 mg, 1.37 mmol) were added. The mixture was stirred at RT overnight, diluted with H$_2$O and extracted with EA. The combined organic layers were washed with brine, dried over Na$_2$SO$_4$, filtered and concentrated to give the crude product, which was purified using silica gel eluting with MeOH/DCM (0% to 10%) to give tert-butyl (1-(4-((5-(((5-(tert-butyl)oxazol-2-yl)methyl)thio)thiazol-2-yl)carbamoyl) piperidin-1-yl)-2-oxo-6,9,12-trioxa-3-azatetradecan-14-yl) carbamate (538 mg, 83% yield) as an oil. MS (ESI) m/z 713.3 [M+H]$^+$.

To a solution of tert-butyl (1-(4-((5-(((5-(tert-butyl)oxazol-2-yl)methyl)thio)thiazol-2-yl)carbamoyl)piperidin-1-yl)-2-oxo-6,9,12-trioxa-3-azatetradecan-14-yl)carbamate (538 mg, 0.76 mmol) in DCM (8 mL) was added TFA (2 mL). The mixture was stirred at RT for 1 h then concentrated. The resulting amine TFA salt was dissolved in DMF (7 mL) and cooled to 0° C., then K$_2$CO$_3$ (210 mg, 1.52 mmol) was added, followed by tert-butyl bromoacetate (132 mg, 0.68 mmol) added. The mixture was stirred at RT for 6 h. The mixture was diluted with H$_2$O and extracted with DCM. The organic layer was concentrated to give the crude product which was purified using prep-TLC eluting with DCM/MeOH (10:1) to give tert-butyl 17-(4-((5-(((5-(tert-butyl) oxazol-2-yl)methyl)thio)thiazol-2-yl)carbamoyl)piperidin-1-yl)-16-oxo-6,9,12-trioxa-3,15-diazaheptadecan-1-oate (137 mg, 25% yield) as a solid. MS (ESI) m/z 727.3 [M+H]$^+$.

To a solution of tert-butyl 17-(4-((5-(((5-(tert-butyl)oxazol-2-yl)methyl)thio) thiazol-2-yl)carbamoyl)piperidin-1-yl)-16-oxo-6,9,12-trioxa-3,15-diazaheptadecan-1-oate (72 mg, 0.10 mmol) in DCM (4 mL) was added TFA (1 mL). The mixture was stirred at RT for 3 h. The solvent was removed and the residue was dried to give acid as an oil. It was dissolved in DMF (4 mL) and DIEA (38.7 mg, 0.30 mmol) was added. Then 3-(2-(aminomethyl)-6-oxo-4H-thieno[2,3-c]pyrrol-5(6H)-yl)piperidine-2,6-dione (31 mg, 0.11 mmol), HOBt (18 mg, 0.135 mmol) and EDCI.HCl (26 mg, 0.135 mmol) were added. The mixture was stirred at RT overnight, diluted with H₂O and extracted with EA. The combined organic layers were washed with brine, dried over Na₂SO₄, filtered and concentrated to give the crude product, which was purified using prep-HPLC as previously described to afford Compound 42 (25.1 mg, 27% yield) as a solid.

Example 43

Compound 43: 14-(2-(((1r,4r)-4-((5-chloro-4-(5-(cyclopropylmethyl)-1-methyl-1H-pyrazol-4-yl)pyrimidin-2-yl)amino)cyclohexyl)amino)acetamido)-N-((5-(2,6-dioxopiperidin-3-yl)-6-oxo-5,6-dihydro-4H-thieno[2,3-c]pyrrol-2-yl)methyl)-6,9,12-trioxa-3-azatetradecanamide To a solution of 2-(((1r,4r)-4-((5-chloro-4-(5-(cyclopropylmethyl)-1-methyl-1H-pyrazol-4-yl)pyrimidin-2-yl)amino)cyclohexyl)amino)acetic acid (400 mg, 0.752 mmol) in N,N-dimethylformamide (12 mL) was added N,N-diisopropylethylamine (291 mg, 2.253 mmol), followed by tert-butyl (2-(2-(2-(2-aminoethoxy)ethoxy)ethoxy)ethyl)carbamate (264 mg, 0.901 mmol), HOBt (152 mg, 1.126 mmol) and EDCI.HCl (216 mg, 1.126 mmol). The mixture was stirred at RT overnight, diluted with H₂O and extracted with EA. The combined organic layers were washed with brine, dried over Na₂SO₄, filtered and concentrated to give the crude product, which was purified using silica gel eluting with MeOH/DCM (0% to 10%) to give tert-butyl (1-(((1r,4r)-4-((5-chloro-4-(5-(cyclopropylmethyl)-1-methyl-1H-pyrazol-4-yl)pyrimidin-2-yl)amino)cyclohexyl)amino)-2-oxo-6,9,12-trioxa-3-azatetradecan-14-yl)carbamate (452 mg, 87% yield) as an oil. MS (ESI) m/z 693.2 [M+H]⁺.

To a solution of tert-butyl (1-(((1r,4r)-4-((5-chloro-4-(5-(cyclopropylmethyl)-1-methyl-1H-pyrazol-4-yl)pyrimidin-2-yl)amino)cyclohexyl)amino)-2-oxo-6,9,12-trioxa-3-azatetradecan-14-yl)carbamate (452 mg, 0.653 mmol) in THF/H₂O (10 mL/3 mL) at RT was added sodium carbonate (207 mg, 1.959 mmol), followed by benzyl chloroformate (167 mg, 0.980 mmol) added. The mixture was stirred at RT for 30 min, diluted with H₂O and extracted with EA. The combined organic layers were dried over Na₂SO₄, filtered and concentrated to give the crude product, which was purified using silica gel eluting with MeOH/DCM (0% to 6% to give benzyl ((1r,4r)-4-((5-chloro-4-(5-(cyclopropylmethyl)-1-methyl-1H-pyrazol-4-yl)pyrimidin-2-yl)amino)cyclohexyl)(2,2-dimethyl-4,18-dioxo-3,8,11,14-tetraoxa-5,17-diazanonadecan-19-yl)carbamate (487 mg, 90% yield) as an oil. MS (ESI) m/z 827.4 [M+H]⁺.

To a solution of benzyl ((1r,4r)-4-((5-chloro-4-(5-(cyclopropylmethyl)-1-methyl-1H-pyrazol-4-yl)pyrimidin-2-yl)amino)cyclohexyl)(2,2-dimethyl-4,18-dioxo-3,8,11,14-tetraoxa-5,17-diazanonadecan-19-yl)carbamate (487 mg, 0.589 mmol) in DCM (12 mL) was added TFA (3 mL). The mixture was stirred at RT for 0.5 h then concentrated. The resulting amine TFA salt was dissolved in DMF (10 mL) and at RT was added K₂CO₃ (249 mg, 1.80 mmol), followed by tert-butyl bromoacetate (106 mg, 0.54 mmol) added. The mixture was stirred at RT for 3 h. The mixture was diluted with H₂O and extracted with DCM. The organic layer was concentrated to give the crude product which was purified using prep-TLC eluting with DCM/MeOH (10:1) to give tert-butyl 4-((1r,4r)-4-((5-chloro-4-(5-(cyclopropylmethyl)-1-methyl-1H-pyrazol-4-yl)pyrimidin-2-yl)amino)cyclohexyl)-3,6-dioxo-1-phenyl-2,10,13,16-tetraoxa-4,7,19-triazahenicosan-21-oate (169 mg, 39% yield) as an oil. MS (ESI) m/z 841.4 [M+H]⁺.

To a solution of tert-butyl 4-((1r,4r)-4-((5-chloro-4-(5-(cyclopropylmethyl)-1-methyl-1H-pyrazol-4-yl)pyrimidin-2-yl)amino)cyclohexyl)-3,6-dioxo-1-phenyl-2,10,13,16-tetraoxa-4,7,19-triazahenicosan-21-oate (169 mg, 0.201 mmol) in DCM (8 mL) was added TFA (2 mL). The mixture was stirred at RT overnight. The solvent was removed and the residue was dried to give the intermediated acid as an oil, which was dissolved in DMF (6 mL) and DIEA (77.4 mg, 0.600 mmol) was added. Then HOBt (40.5 mg, 0.300 mmol), EDCI.HCl (57.6 mg, 0.300 mmol) and 3-(2-(aminomethyl)-6-oxo-4H-thieno[2,3-c]pyrrol-5(6H)-yl)piperidine-2,6-dione (72.5 mg, 0.260 mmol) were added. The mixture was stirred at RT overnight. The solvent was removed and the residue was purified using prep-TLC eluting with DCM/MeOH (10:1) to give benzyl ((1r,4r)-4-((5-chloro-4-(5-(cyclopropylmethyl)-1-methyl-1H-pyrazol-4-yl)pyrimidin-2-yl)amino)cyclohexyl)(1-(5-(2,6-dioxopiperidin-3-yl)-6-oxo-5,6-dihydro-4H-thieno[2,3-c]pyrrol-2-yl)-3,18-dioxo-8,11,14-trioxa-2,5,17-triazanonadecan-19-yl)carbamate (109 mg, 52% yield) as an oil. MS (ESI) m/z 1046.6 [M+H]⁺.

To a solution of compound benzyl ((1r,4r)-4-((5-chloro-4-(5-(cyclopropylmethyl)-1-methyl-1H-pyrazol-4-yl)pyrimidin-2-yl)amino)cyclohexyl)(1-(5-(2,6-dioxopiperidin-3-yl)-6-oxo-5,6-dihydro-4H-thieno[2,3-c]pyrrol-2-yl)-3,18-dioxo-8,11,14-trioxa-2,5,17-triazanonadecan-19-yl)carbamate (109 mg, 0.104 mmol) in AcOH (1.5 mL) was added HBr (33% in AcOH, 1.5 mL). The mixture was stirred at RT for 0.5 h. The solvent was removed and the residue was dried to give the crude product which was dissolved in DMF (2 mL) and adjusted to a pH of about 7 with TEA. The solvent was removed and the residue was purified using prep-HPLC as previously described to afford Compound 43 (28 mg, 30% yield) as a solid.

Example 44

Compound 44: N-(5-(((5-(tert-butyl)oxazol-2-yl)methyl)thio)thiazol-2-yl)-1-(1-(5-(2,6-dioxopiperidin-3-yl)-4-oxo-5,6-dihydro-4H-thieno[3,4-c]pyrrol-1-yl)-8-methyl-3,12-dioxo-2,5,8,11-tetraazatridecan-13-yl)piperidine-4-carboxamide To a solution of tert-butyl (2-((2-(2-(4-((5-(((5-(tert-butyl)oxazol-2-yl)methyl)thio)thiazol-2-yl)carbamoyl)piperidin-1-yl)acetamido)ethyl)(methyl)amino)ethyl)carbamate (Synthetic procedure see Example 15) (400 mg, 0.628 mmol) in DCM (4 mL) was added TFA (1 mL). The mixture was stirred at RT for 0.5 h. The solvent was removed and the residue was dried to give 1-(2-((2-((2-aminoethyl)(methyl)amino)ethyl)amino)-2-oxoethyl)-N-(5-(((5-(tert-butyl)oxazol-2-yl)methyl)thio)thiazol-2-yl)piperidine-4-carboxamide as the TFA salt. MS (ESI) m/z 538.2 [M+H]⁺.

To a solution of 1-(2-((2-((2-aminoethyl)(methyl)amino)ethyl)amino)-2-oxoethyl)-N-(5-(((5-(tert-butyl)oxazol-2-yl)methyl)thio)thiazol-2-yl)piperidine-4-carboxamide (480 mg, as the TFA salt) in DMF (10 mL) at RT was added tert-butyl 2-bromoacetate (144 mg, 0.74 mmol) and K₂CO₃ (153 mg, 1.11 mmol), then the mixture was stirred at RT for 5 h. The mixture was then diluted with H₂O and extracted with EA. The combined organic layers were dried over Na₂SO₄, filtered and concentrated to give the crude product, which was purified using silica gel eluting with DCM/MeOH (0% to 10%) to give tert-butyl 2-((2-((2-(2-(4-((5-

(((5-(tert-butyl)oxazol-2-yl)methyl)thio)thiazol-2-yl)carbamoyl)piperidin-1-yl)acetamido)ethyl)(methyl)amino) ethyl)amino)acetate (110 mg, 22% yield) as a solid. MS (ESI) m/z 651.2 [M+H]$^+$.

To a solution of tert-butyl 2-((2-((2-(2-(4-((5-(((5-(tert-butyl)oxazol-2-yl)methyl)thio)thiazol-2-yl)carbamoyl)piperidin-1-yl)acetamido)ethyl)(methyl)amino)ethyl)amino) acetate (60 mg, 0.093 mmol) in DCM (1.5 mL) was added TFA (0.5 mL). The mixture was stirred at RT for 3 h. The solvent was removed and the residue was dried to give 2-((2-((2-(2-(4-((5-(((5-(tert-butyl)oxazol-2-yl)methyl)thio) thiazol-2-yl)carbamoyl)piperidin-1-yl)acetamido)ethyl) (methyl)amino)ethyl)amino)acetic acid (80 mg, crude) as an oil. MS (ESI) m/z 509.2 [M+H]$^+$.

To a solution of 2-((2-((2-(2-(4-((5-(((5-(tert-butyl)oxazol-2-yl)methyl)thio)thiazol-2-yl)carbamoyl)piperidin-1-yl) acetamido)ethyl)(methyl)amino)ethyl)amino)acetic acid (75 mg, 0.126 mmol) in DMF (4 mL) was added TEA (38 mg, 0.378 mmol), then 3-(1-(aminomethyl)-4-oxo-4H-thieno[3,4-c]pyrrol-5(6H)-yl)piperidine-2,6-dione (75 mg, 0.126 mmol) and propanephosphonic acid anhydride (120 mg, 0.378 mmol) were added. The mixture was stirred at RT for 2 h. The solvent was removed and the residue was purified using prep-TLC eluting with DCM/MeOH (10:1) to afford Compound 44 (35 mg, 32% yield) as a solid.

Example 45

Compound 45: 2-(((1r,4r)-4-((5-chloro-4-(5-(cyclopropylmethyl)-1-methyl-1H-pyrazol-4-yl)pyrimidin-2-yl)amino)cyclohexyl)amino)-N-(2-(3-((5-(2,6-dioxopiperidin-3-yl)-6-oxo-5,6-dihydro-4H-thieno[2,3-c]pyrrol-2-yl)methyl)ureido)ethyl)acetamide To a solution of 2-(((1r,4r)-4-((5-chloro-4-(5-(cyclopropylmethyl)-1-methyl-1H-pyrazol-4-yl)pyrimidin-2-yl) amino)cyclohexyl)amino)acetic acid (250 mg, 0.469 mmol) in DMF (6 mL) was added DIEA (181.5 mg, 1.407 mmol), followed by tert-butyl (2-aminoethyl)carbamate (90.2 mg, 0.563 mmol), HOBt (95 mg, 0.703 mmol) and EDCI.HCl (135 mg, 0.703 mmol) were added. The mixture was stirred at RT overnight, diluted with H$_2$O and extracted with EA. The combined organic layers were washed with brine, dried over Na$_2$SO$_4$, filtered and concentrated to give the crude product, which was purified using silica gel eluting with MeOH/DCM (0% to 10%) to give tert-butyl (2-(2-(((1r,4r)-4-((5-chloro-4-(5-(cyclopropylmethyl)-1-methyl-1H-pyrazol-4-yl)pyrimidin-2-yl)amino)cyclohexyl)amino)acetamido)ethyl)carbamate (174 mg, 66% yield) as an oil. MS (ESI) m/z 561.1 [M+H]$^+$.

To a solution of tert-butyl (2-(2-(((1r,4r)-4-((5-chloro-4-(5-(cyclopropylmethyl)-1-methyl-1H-pyrazol-4-yl)pyrimidin-2-yl)amino)cyclohexyl)amino)acetamido)ethyl)carbamate (174 mg, 0.310 mmol) in THF/H$_2$O (8 mL/2.4 mL) at RT was added sodium carbonate (98.5 mg, 0.930 mmol), followed by benzyl chloroformate (79.5 mg, 0.466 mmol) added. The mixture was stirred at RT for 1 h, diluted with H$_2$O (10 mL), and extracted with EA (15 mL×2). The combined organic layers were dried over Na$_2$SO$_4$, filtered and concentrated to give the crude product, which was purified using silica gel eluting with MeOH/DCM (0% to 6% to give benzyl (2-((2-(((tert-butoxycarbonyl)amino) ethyl)amino)-2-oxoethyl)((1r,4r)-4-((5-chloro-4-(5-(cyclopropylmethyl)-1-methyl-1H-pyrazol-4-yl)pyrimidin-2-yl) amino)cyclohexyl)carbamate (189 mg, 88% yield) as an oil. MS (ESI) m/z 695.2 [M+H]$^+$.

To a solution of tert-butyl ((5-(2,6-dioxopiperidin-3-yl)-6-oxo-5,6-dihydro-4H-thieno[2,3-c]pyrrol-2-yl)methyl)carbamate (103 mg, 0.272 mmol) in DCM (6 mL) at RT was added TFA (1.5 mL). The mixture was stirred at RT for 1 h and concentrated to give the amine TFA salt which was dissolved in THF (4 mL) and TEA (60.3 mg, 0.597 mmol) was added. Then 4-nitrobenzyl chloroformate (60.2 mg, 0.299 mmol) was added. The mixture was stirred at RT for 30 min. The solvent was removed to give the crude 4-nitrophenyl ((5-(2,6-dioxopiperidin-3-yl)-6-oxo-5,6-dihydro-4H-thieno[2,3-c]pyrrol-2-yl)methyl)carbamate (120 mg, crude). MS (ESI) m/z 445.4 [M+H]$^+$.

To a solution of benzyl (2-((2-((tert-butoxycarbonyl) amino)ethyl)amino)-2-oxoethyl)((1r,4r)-4-((5-chloro-4-(5-(cyclopropylmethyl)-1-methyl-1H-pyrazol-4-yl)pyrimidin-2-yl)amino)cyclohexyl)carbamate (189 mg, 0.272 mmol) in DCM (8 mL) at RT was added TFA (2 mL). The mixture was stirred at RT for 1 h. The solvent was removed and the residue was dried to give the amine TFA salt which was dissolved in THF (5 mL) and TEA (82.4 mg, 0.816 mmol) was added. The mixture was stirred at RT for 5 min. Then the suspension of 4-nitrophenyl ((5-(2,6-dioxopiperidin-3-yl)-6-oxo-5,6-dihydro-4H-thieno[2,3-c]pyrrol-2-yl)methyl) carbamate (120 mg, crude) in THF (1 mL) was added and the mixture was stirred at RT for 12 h. The mixture was then diluted with H$_2$O and extracted with DCM. The combined organic layers were dried over Na$_2$SO$_4$, filtered and concentrated to give the crude product, which was purified using silica gel eluting with EA in PE from 10% to 50% to give benzyl ((1r,4r)-4-((5-chloro-4-(5-(cyclopropylmethyl)-1-methyl-1H-pyrazol-4-yl)pyrimidin-2-yl)amino)cyclohexyl) (2-((2-(3-((5-(2,6-dioxopiperidin-3-yl)-6-oxo-5,6-dihydro-4H-thieno[2,3-c]pyrrol-2-yl)methyl)ureido)ethyl)amino)-2-oxoethyl)carbamate (159 mg, 66% yield) as an oil. MS (ESI) m/z 900.4 [M+H]$^+$.

To a solution of benzyl ((1r,4r)-4-((5-chloro-4-(5-(cyclopropylmethyl)-1-methyl-1H-pyrazol-4-yl)pyrimidin-2-yl) amino)cyclohexyl)(2-((2-(3-((5-(2,6-dioxopiperidin-3-yl)-6-oxo-5,6-dihydro-4H-thieno[2,3-c]pyrrol-2-yl)methyl) ureido)ethyl)amino)-2-oxoethyl)carbamate (159 mg, 0.176 mmol) in AcOH (2 mL) at RT was added HBr (33% in AcOH, 2 mL). The mixture was stirred at RT for 30 min. The solvent was removed and the residue was dried to give the crude product which was dissolved in DMF (2 mL) and adjusted to a pH of about 7 with TEA. The solvent was removed and the residue was purified using prep-HPLC as previously described to afford Compound 45 (33.6 mg, 25% yield) as a solid.

Example 46

Compound 46: 2-(((1r,4r)-4-((5-chloro-4-(5-(cyclopropylmethyl)-1-methyl-1H-pyrazol-4-yl)pyrimidin-2-yl)amino)cyclohexyl)amino)-N-(1-(5-(2,6-dioxopiperidin-3-yl)-6-oxo-5,6-dihydro-4H-thieno[2,3-c]pyrrol-2-yl)-3-oxo-7,10,13-trioxa-2,4-diazapentadecan-15-yl)acetamide To a solution of tert-butyl ((5-(2,6-dioxopiperidin-3-yl)-6-oxo-5,6-dihydro-4H-thieno[2,3-c]pyrrol-2-yl)methyl)carbamate (100 mg, 0.263 mmol) in DCM (6 mL) at RT was added TFA (1.5 mL). The mixture was stirred at RT for 1 h. The solvent was removed and the residue was dried to give the amine TFA salt, which was dissolved in THF (5 mL) and TEA (58 mg, 0.578 mmol) was added. Then 4-nitrobenzyl chloroformate (58 mg, 0.289 mmol) was added. The mixture was stirred at RT for 0.5 h. The solvent was removed to give the crude 4-nitrophenyl ((5-(2,6-dioxopiperidin-3-yl)-6-oxo-5,6-dihydro-4H-thieno[2,3-c]pyrrol-2-yl)methyl)carbamate (116 mg, crude). MS (ESI) m/z 445.4 [M+H]$^+$.

To a solution of benzyl ((1r,4r)-4-((5-chloro-4-(5-(cyclopropylmethyl)-1-methyl-1H-pyrazol-4-yl)pyrimidin-2-yl)amino)cyclohexyl)(2,2-dimethyl-4,18-dioxo-3,8,11,14-tetraoxa-5,17-diazanonadecan-19-yl)carbamate (synthetic procedure see Example 43) (269 mg, 0.325 mmol) in DCM (12 mL) at RT was added TFA (3 mL). The mixture was stirred at RT for 1 h then concentrated. The resulting amine TFA salt was dissolved in THF (4 mL) and TEA (48.4 mg, 0.479 mmol) was added. The mixture was stirred at RT for 5 min. Then the suspension of 4-nitrophenyl ((5-(2,6-dioxopiperidin-3-yl)-6-oxo-5,6-dihydro-4H-thieno[2,3-c]pyrrol-2-yl)methyl)carbamate (61 mg) in THF (1 mL) was added and the mixture was stirred at RT for 12 h. The mixture was then diluted with H$_2$O and extracted with DCM. The combined organic layers were dried over Na$_2$SO$_4$, filtered and concentrated to give the crude product, which was purified using silica gel eluting with EA in PE from 10% to 50% to give benzyl ((1r,4r)-4-((5-chloro-4-(5-(cyclopropylmethyl)-1-methyl-1H-pyrazol-4-yl)pyrimidin-2-yl)amino)cyclohhexyl)(1-(5-(2,6-dioxopiperidin-3-yl)-6-oxo-5,6-dihydro-4H-thieno[2,3-c]pyrrol-2-yl)-3,17-dioxo-7,10,13-trioxa-2,4,16-triazaoctadecan-18-yl)carbamate (112 mg, 79% yield) as an oil. MS (ESI) m/z 1032.6 [M+H]$^+$.

To a solution of benzyl ((1r,4r)-4-((5-chloro-4-(5-(cyclopropylmethyl)-1-methyl-1H-pyrazol-4-yl)pyrimidin-2-yl)amino)cyclohexyl)(1-(5-(2,6-dioxopiperidin-3-yl)-6-oxo-5,6-dihydro-4H-thieno[2,3-c]pyrrol-2-yl)-3,17-dioxo-7,10,13-trioxa-2,4,16-triazaoctadecan-18-yl)carbamate (112 mg, 0.108 mmol) in AcOH (2 mL) at RT was added HBr (33% in AcOH, 2 mL). The mixture was stirred at RT for 30 min. The solvent was removed and the residue was dried to give the crude product, which was dissolved in DMF (2 mL) and adjusted to a pH of about 7 with TEA. The solvent was removed and the residue was purified using prep-HPLC as previously described to afford Compound 46 (34.9 mg, 36% yield) as a solid.

Example 47

Compound 47: N-(5-(((5-(tert-butyl)oxazol-2-yl)methyl)thio)thiazol-2-yl)-1-(1-(5-(2,6-dioxopiperidin-3-yl)-6-oxo-5,6-dihydro-4H-thieno[2,3-c]pyrrol-2-yl)-8-methyl-3,12-dioxo-2,5,8,11-tetraazatridecan-13-yl)piperidine-4-carboxamide To a solution of tert-butyl (2-((2-(2-(4-((5-(((5-(tert-butyl)oxazol-2-yl)methyl)thio)thiazol-2-yl)carbamoyl)piperidin-1-yl)acetamido)ethyl)(methyl)amino)ethyl)carbamate (synthetic procedure see Example 15) (400 mg, 0.628 mmol) in DCM (4 mL) was added TFA (1 mL). The mixture was stirred at RT for 0.5 h. The solvent was removed and the residue was dried to give 1-(2-((2-((2-aminoethyl)(methyl)amino)ethyl)amino)-2-oxoethyl)-N-(5-(((5-(tert-butyl)oxazol-2-yl)methyl)thio)thiazol-2-yl)piperidine-4-carboxamide as the TFA salt. MS (ESI) m/z 538.2 [M+H]$^+$.

To a solution of 1-(2-((2-((2-aminoethyl)(methyl)amino)ethyl)amino)-2-oxoethyl)-N-(5-(((5-(tert-butyl)oxazol-2-yl)methyl)thio)thiazol-2-yl)piperidine-4-carboxamide (480 mg, as the TFA salt) in DMF (10 mL) at RT was added tert-butyl 2-bromoacetate (144 mg, 0.74 mmol) and K$_2$CO$_3$ (153 mg, 1.11 mmol), then the mixture was stirred at RT for 5 h. The mixture was then diluted with H$_2$O and extracted with EA. The combined organic layers were dried over Na$_2$SO$_4$, filtered and concentrated to give the crude product, which was purified using silica gel eluting with DCM/MeOH (0% to 10%) to give tert-butyl 2-((2-((2-(2-(4-((5-(((5-(tert-butyl)oxazol-2-yl)methyl)thio)thiazol-2-yl)carbamoyl)piperidin-1-yl)acetamido)ethyl)(methyl)amino)ethyl)amino)acetate (110 mg, 22% yield) as a solid. MS (ESI) m/z 651.2 [M+H]$^+$.

To a solution of tert-butyl 2-((2-((2-(2-(4-((5-(((5-(tert-butyl)oxazol-2-yl)methyl)thio)thiazol-2-yl)carbamoyl)piperidin-1-yl)acetamido)ethyl)(methyl)amino)ethyl)amino)acetate (60 mg, 0.093 mmol) in DCM (1.5 mL) was added TFA (0.5 mL). The mixture was stirred at RT for 3 h. The solvent was removed and the residue was dried to give 2-((2-((2-(2-(4-((5-(((5-(tert-butyl)oxazol-2-yl)methyl)thio)thiazol-2-yl)carbamoyl)piperidin-1-yl)acetamido)ethyl)(methyl)amino)ethyl)amino)acetic acid (80 mg, crude) as an oil. MS (ESI) m/z 509.2 [M+H]$^+$.

To a solution of 2-((2-((2-(2-(4-((5-(((5-(tert-butyl)oxazol-2-yl)methyl)thio)thiazol-2-yl)carbamoyl)piperidin-1-yl)acetamido)ethyl)(methyl)amino)ethyl)amino)acetic acid (120 mg, 0.202 mmol) in DMF (5 mL) was added TEA (51 mg, 0.505 mmol) then 3-(2-(aminomethyl)-6-oxo-4H-thieno[2,3-c]pyrrol-5(6H)-yl)piperidine-2,6-dione (80 mg, 0.242 mmol) and propanephosphonic acid anhydride (160 mg, 0.505 mmol) were added. The mixture was stirred at RT for 2 h. The solvent was removed and the residue was purified using prep-TLC eluting with DCM/MeOH (10:1) to afford Compound 47 (14.6 mg, 8% yield) as a solid.

Example 48

Compound 48: 2-(((1r,4r)-4-((4-(5-(cyclopropylmethyl)-1-methyl-1H-pyrazol-4-yl)-5-fluoropyrimidin-2-yl)amino)cyclohexyl)amino)-N-(4-((2-(((5-(2,6-dioxopiperidin-3-yl)-4,6-dioxo-5,6-dihydro-4H-thieno[3,4-c]pyrrol-1-yl)methyl)amino)-2-oxoethyl)amino)butyl)acetamide To a solution of tert-butyl 4-((1r,4r)-4-((4-(5-(cyclopropylmethyl)-1-methyl-1H-pyrazol-4-yl)-5-fluoropyrimidin-2-yl)amino)cyclohexyl)-3,6-dioxo-1-phenyl-2-oxa-4,7,12-triazatetradecan-14-oate (synthetic procedure see Example 36) (166 mg, 0.23 mmol) in DCM (4 mL) was added TFA (1 mL). The mixture was stirred at RT for 1 h then concentrated. The resulting amine TFA salt was dissolved in DMF (5 mL) and DIEA (89 mg, 0.69 mmol) added. Then 1-(aminomethyl)-5-(2,6-dioxopiperidin-3-yl)-4H-thieno[3,4-c]pyrrole-4,6(5H)-dione (84 mg, 0.23 mmol), HOBt (39 mg, 0.29 mmol) and EDCI.HCl (56 mg, 0.29 mmol) were added. The mixture was stirred at RT overnight. The solvent was removed and the residue was purified using prep-TLC eluting with DCM/MeOH (10:1) to give benzyl ((1r,4r)-4-((4-(5-(cyclopropylmethyl)-1-methyl-1H-pyrazol-4-yl)-5-fluoropyrimidin-2-yl)amino)cyclohexyl)(2-((4-((2-(((5-(2,6-dioxopiperiidin-3-yl)-4,6-dioxo-5,6-dihydro-4H-thieno[3,4-c]pyrrol-1-yl)methyl)amino)-2-oxoethyl)amino)butyl)amino)-2-oxoethyl)carbamate (110 mg, 51% yield) as a solid. MS (ESI) m/z 940.4 [M+H]$^+$.

To a solution of benzyl ((1r,4r)-4-((4-(5-(cyclopropylmethyl)-1-methyl-1H-pyrazol-4-yl)-5-fluoropyrimidin-2-yl)amino)cyclohexyl)(2-((4-((2-(((5-(2,6-dioxopiperidin-3-yl)-4,6-dioxo-5,6-dihydro-4H-thieno[3,4-c]pyrrol-1-yl)methyl)amino)-2-oxoethyl)amino)butyl)amino)-2-oxoethyl)carbamate (110 mg, 0.117 mmol) in AcOH (2 mL) was added HBr (33% in AcOH, 2 mL). The mixture was stirred at RT for 1 h. The solvent was removed and the residue was dried to give the crude product, which was dissolved in DMF (2 mL) and adjusted to a pH of about 7 with TEA. The solvent was removed and the residue was purified using prep-HPLC as previously described to afford Compound 48 (36.8 mg, 39% yield) as a solid.

Example 49

Compound 49: 2-(((1r,4r)-4-((5-chloro-4-(5-(cyclopropylmethyl)-1-methyl-1H-pyrazol-4-yl)pyrimidin-2-yl)amino)cyclohexyl)amino)-N-(2-(2-(2-(2-((2-(2,6-dioxopiperidin-3-yl)-1,3-dioxoisoindolin-4-yl)amino)ethoxy)ethoxy)ethoxy)ethyl)acetamide To a solution of (1r,4r)-N$^1$-(5-chloro-4-(5-(cyclopropylmethyl)-1-methyl-1H-pyrazol-4-yl)pyrimidin-2-yl)cyclohexane-1,4-diamine (200 mg, 0.56 mmol) in N,N-dimethylformamide (8 mL) at RT was added potassium carbonate (155 mg, 1.12 mmol) and tert-butyl 2-bromoacetate (129 mg, 0.67 mmol) added. After 7 h, the mixture was diluted with H$_2$O and extracted with EA. The combined organic layers were washed with brine, dried over Na$_2$SO$_4$, filtered and concentrated to give the crude product, which was purified using silica gel eluting with MeOH/DCM (0% to 10%) to give tert-butyl 2-(((1r,4r)-4-((5-chloro-4-(5-(cyclopropylmethyl)-1-methyl-1H-pyrazol-4-yl)pyrimidin-2-yl)amino)cyclohexyl)amino)acetate (196 mg, 74% yield) as an oil. MS (ESI) m/z 475.3[M+H]$^+$.

To a solution of tert-butyl 2-(((1r,4r)-4-((5-chloro-4-(5-(cyclopropylmethyl)-1-methyl-1H-pyrazol-4-yl)pyrimidin-2-yl)amino)cyclohexyl)amino)acetate (85 mg, 0.18 mmol) in DCM (4 mL) was added TFA (2 mL). The mixture was stirred at RT overnight. The solvent was removed and the residue was dissolved in tert-butyl methyl ether (5 mL). After 30 min, the suspension was filtered and the filter cake was dried in vacuum to give 2-(((1r,4r)-4-((5-chloro-4-(5-(cyclopropylmethyl)-1-methyl-1H-pyrazol-4-yl)pyrimidin-2-yl)amino)cyclohexyl)amino)acetic acid (75 mg, crude) as trifluoroacetate salt. MS (ESI) m/z 419.2[M+H]$^+$.

To a solution of 2-(((1r,4r)-4-((5-chloro-4-(5-(cyclopropylmethyl)-1-methyl-1H-pyrazol-4-yl)pyrimidin-2-yl)amino)cyclohexyl)amino)acetic acid (75 mg, 0.18 mmol) in N,N-dimethylformamide (6 mL) was added N,N-diisopropylethylamine (46 mg, 0.36 mmol), 4-((2-(2-(2-(2-aminoethoxy)ethoxy)ethoxy)ethyl)amino)-2-(2,6-dioxopiperidin-3-yl)isoindoline-1,3-dione (82 mg, 0.18 mmol), HOBt (36 mg, 0.27 mmol) and EDCI.HCl (52 mg, 0.27 mmol). The mixture was stirred at RT overnight. The solvent was removed and the residue was purified using prep-HPLC as previously described to afford Compound 49 (24.3 mg, 16% yield) as a solid.

Example 50

Compound 50: 2-(((1r,4r)-4-((4-(5-(cyclopropylmethyl)-1-methyl-1H-pyrazol-4-yl)-5-fluoropyrimidin-2-yl)amino)cyclohexyl)amino)-N-(2-(2-(2-(2-((2-(2,6-dioxopiperidin-3-yl)-1,3-dioxoisoindolin-4-yl)amino)ethoxy)ethoxy)ethoxy)ethyl)acetamido To a solution of (1r,4r)-N$^1$-(4-(5-(cyclopropylmethyl)-1-methyl-1H-pyrazol-4-yl)-5-fluoropyrimidin-2-yl)cyclohexane-1,4-diamine (200 mg, 0.58 mmol) in N,N-dimethylformamide (8 mL) at RT was added potassium carbonate (160 mg, 1.16 mmol) and tert-butyl 2-bromoacetate (134 mg, 0.69 mmol). After 7 h, the mixture was diluted with H$_2$O and extracted with EA. The combined organic layers were washed with brine, dried over Na$_2$SO$_4$, filtered and concentrated to give the crude product, which was purified using silica gel eluting with MeOH/DCM (0% to 10%) to give tert-butyl 2-(((1r,4r)-4-((4-(5-(cyclopropylmethyl)-1-methyl-1H-pyrazol-4-yl)-5-fluoropyrimidin-2-yl)amino)cyclohexyl)amino)acetate (188 mg, 71% yield) as an oil. MS (ESI) m/z 459.3[M+H]$^+$.

To a solution of tert-butyl 2-(((1r,4r)-4-((4-(5-(cyclopropylmethyl)-1-methyl-1H-pyrazol-4-yl)-5-fluoropyrimidin-2-yl)amino)cyclohexyl)amino)acetate (124 mg, 0.27 mmol) in DCM (4 mL) was added TFA (2 mL). The mixture was stirred at RT overnight. The solvent was removed and the residue was dissolved in tert-butyl methyl ether (5 mL). After 30 min, the suspension was filtered and the filter cake was dried in vacuum to give 2-(((1r,4r)-4-((4-(5-(cyclopropylmethyl)-1-methyl-1H-pyrazol-4-yl)-5-fluoropyrimidin-2-yl)amino)cyclohexyl)amino)acetic acid (108 mg, crude) as trifluoroacetate salt. MS (ESI) m/z 403.2 [M+H]$^+$.

To a solution of 2-(((1r,4r)-4-((4-(5-(cyclopropylmethyl)-1-methyl-1H-pyrazol-4-yl)-5-fluoropyrimidin-2-yl)amino)cyclohexyl)amino)acetic acid (108 mg, 0.27 mmol) in N,N-dimethylformamide (5 mL) was added N,N-diisopropylethylamine (69 mg, 0.54 mmol), 4-((2-(2-(2-(2-aminoethoxy)ethoxy)ethoxy)ethyl)amino)-2-(2,6-dioxopiperidin-3-yl)isodoline-1,3-dione (122 mg, 0.27 mmol), HOBt (55 mg, 0.41 mmol) and EDCI.HCl (78 mg, 0.41 mmol). The mixture was stirred at RT overnight. The solvent was removed and the residue was purified using prep-HPLC as previously described to afford Compound 50 (39.9 mg, 18% yield) as a solid.

Example 51

Compound 51: 2-(((1r,4r)-4-((5-chloro-4-(5-(cyclopropylmethyl)-1-methyl-1H-pyrazol-4-yl)pyrimidin-2-yl)amino)cyclohexyl)amino)-N-(4-((2-(((5-(2,6-dioxopiperidin-3-yl)-4,6-dioxo-5,6-dihydro-4H-thieno[3,4-c]pyrrol-1-yl)methyl)amino)-2-oxoethyl)amino)butyl)acetamide To a solution of tert-butyl 4-((r,4r)-4-((5-chloro-4-(5-(cyclopropylmethyl)-1-methyl-1H-pyrazol-4-yl)pyrimidin-2-yl)amino)cyclohexyl)-3,6-dioxo-1-phenyl-2-oxa-4,7,12-triazatetradecan-14-oate (see experimental for Compound 36) (214 mg, 0.29 mmol) in DCM (4 mL) was added TFA (1 mL). The mixture was stirred at RT for 1 h then concentrated. The resulting amine TFA salt was dissolved in DMF (5 mL) and DIEA (93 mg, 0.722 mmol) added. Then 1-(aminomethyl)-5-(2,6-dioxopiperidin-3-yl)-4H-thieno[3,4-c]pyrrole-4,6(5H)-dione (162 mg, 0.55 mmol), HOBt (50 mg, 0.36 mmol) and EDCI.HCl (70 mg, 0.36 mmol) were added. The mixture was stirred at RT overnight. The solvent was removed and the residue was purified using prep-TLC eluting with DCM/MeOH (10:1) to give benzyl ((1r,4r)-4-((5-chloro-4-(5-(cyclopropylmethyl)-1-methyl-1H-pyrazol-4-yl)pyrimidin-2-yl)amino)cyclohexyl)(2-((4-((2-(((5-(2,6-dioxopiperidin-3-yl)-4,6-dioxo-5,6-dihydro-4H-thieno[3,4-c]pyrrol-1-yl)methyl)amino)-2-oxoethyl)amino)butyl)amino)-2-oxoethyl)carbamate (185 mg, 67% yield) as a solid. MS (ESI) m/z 956.4 [M+H]$^+$.

To a solution of benzyl ((1r,4r)-4-((5-chloro-4-(5-(cyclopropylmethyl)-1-methyl-1H-pyrazol-4-yl)pyrimidin-2-yl)amino)cyclohexyl)(2-((4-((2-(((5-(2,6-dioxopiperidin-3-yl)-4,6-dioxo-5,6-dihydro-4H-thieno[3,4-c]pyrrol-1-yl)methyl)amino)-2-oxoethyl)amino)butyl)amino)-2-oxoethyl)carbamate (185 mg, 0.19 mmol) in AcOH (2 mL) was added HBr (33% in AcOH, 2 mL). The mixture was stirred at RT for 1 h then concentrated, dissolved in DMF (2 mL), and adjusted to a pH of about 7 with TEA. The mixture was concentrated and the residue was purified using prep-HPLC as previously described to afford Compound 51 (25.4 mg, 16% yield) as a solid.

Example 52

Compound 52: N-(5-(((5-(tert-butyl)oxazol-2-yl)methyl)thio)thiazol-2-yl)-1-(2-((3-((2-(((5-(2,6-dioxopiperidin-3-yl)-6-oxo-5,6-dihydro-4H-thieno[2,3-c]pyrrol-2-yl)methyl)amino)-2-oxoethyl)amino)propyl)amino)-2-oxoethyl)piperidine-4-carboxamide To a solution of 2-(4-((5-(((5-(tert-butyl)oxazol-2-yl)methyl)thio)thiazol-2-yl)carbamoyl)piperidin-1-yl)acetic acid (250 mg, 0.452 mmol) in DMF (5 mL) was added DIEA (174.9 mg, 1.356 mmol), followed by tert-butyl (3-aminopropyl)carbamate (117.9 mg, 0.678 mmol) and HATU (343.5 mg, 0.904 mmol). The mixture was stirred at RT for 2 h, diluted with H$_2$O and extracted with EA. The combined organic layers were washed with brine, dried over Na$_2$SO$_4$, filtered and concentrated to give the crude product, which was purified using silica gel eluting with MeOH/DCM (0% to 10%) to give tert-butyl (3-(2-(4-((5-(((5-(tert-butyl)oxazol-2-yl)methyl)thio)thiazol-2-yl)carbamoyl)piperidin-1-yl)acetamido)propyl)carbamate (234 mg, 87% yield) as a solid. MS (ESI) m/z 595.7 [M+H]$^+$.

To a solution of tert-butyl (3-(2-(4-((5-(((5-(tert-butyl)oxazol-2-yl)methyl)thio)thiazol-2-yl)carbamoyl)piperidin-1-yl)acetamido)propyl)carbamate (234 mg, 0.393 mmol) in DCM (8 mL) was added TFA (2 mL). The mixture was stirred at RT for 1 h then concentrated. The resulting amine TFA salt was dissolved in DMF (5 mL) at RT, then K$_2$CO$_3$ (162 mg, 1.179 mmol) was added, followed by tert-butyl bromoacetate (76 mg, 0.393 mmol). The mixture was stirred at RT overnight, diluted with H$_2$O and extracted with DCM. The organic layer was concentrated to give the crude product which was purified using silica gel eluting with MeOH/DCM (0% to 10%) to give tert-butyl 2-((3-(2-(4-((5-(((5-(tert-butyl)oxazol-2-yl)methyl)thio)thiazol-2-yl)carbamoyl)piperidin-1-yl)acetamido)propyl)amino)acetate (70 mg, 29% yield) as an oil. MS (ESI) m/z 609.8 [M+H]$^+$.

To a solution of tert-butyl 2-((3-(2-(4-((5-(((5-(tert-butyl)oxazol-2-yl)methyl)thio)thiazol-2-yl)carbamoyl)piperidin-1-yl)acetamido)propyl)amino)acetate (70 mg, 0.114 mmol) in DCM (4 mL) was added TFA (1 mL). The mixture was stirred at RT overnight then concentrated, and the residue was dissolved in DMF (2 mL). DIEA (44.1 mg, 0.342 mmol) was added followed by 3-(2-(aminomethyl)-6-oxo-4H-thieno[2,3-c]pyrrol-5(6H)-yl)piperidine-2,6-dione (36 mg, 0.114 mmol) and HATU (86.6 mg, 0.228 mmol). The mixture was stirred at RT for 2 h. The solvent was removed and the residue was purified using prep-HPLC as previously described to afford Compound 52 (16 mg, 17% yield) as a solid.

Example 53

Compound 53: 2-((7-(((1r,4r)-4-((5-chloro-4-(5-(cyclopropylmethyl)-1-methyl-1H-pyrazol-4-yl)pyrimidin-2-yl)amino)cyclohexyl)amino)heptyl)amino)-N-((5-(2,6-dioxopiperidin-3-yl)-6-oxo-5,6-dihydro-4H-thieno[2,3-c]pyrrol-2-yl)methyl)acetamide To a solution of compound 7-((tert-butoxycarbonyl)amino)heptanoic acid (1.0 g, 4.08 mmol) in DCM (20 mL) at RT was added EDAC.HCl (1.17 g, 6.12 mmol) and TEA (824 mg, 8.16 mmol) followed by N,O-dimethylhydroxylamine (437 mg, 4.48 mmol) and N,N-dimethylpyridin-4-amine (52 mg, 0.408 mmol). The mixture was stirred at RT overnight then diluted with water and extracted with DCM. The organic layers were dried over Na$_2$SO$_4$, filtered, and concentrated. The residue was purified using silica gel eluting with MeOH/DCM (0% to 8%) to give tert-butyl (7-(methoxy(methyl)amino)-7-oxoheptyl)carbamate (1.071 g, 91% yield) as an oil. MS (ESI) m/z 289.2 [M+H]$^+$.

Tert-butyl (7-(methoxy(methyl)amino)-7-oxoheptyl)carbamate (1.07 g, 3.72 mmol) was dissolved in THF (20 mL) and cooled to −70° C., then lithium aluminium hydride (5.6 mL, 1 M in THF) was added slowly. After addition, the solution was warmed to 0° C. and stirred at this temperature for 30 min then was quenched with saturated ammonium chloride and extracted with EA. The organic layers were dried over Na$_2$SO$_4$, filtered and concentrated to give tert-butyl (7-oxoheptyl)carbamate (839 mg crude). MS (ESI) m/z 252.2 [M+Na]$^+$.

To a stirred solution of (1r,4r)-N-(5-chloro-4-(5-(cyclopropylmethyl)-1-methyl-1H-pyrazol-4-yl)pyrimidin-2-yl)cyclohexane-1,4-diamine (450 mg, 1.25 mmol) and tert-butyl (7-oxoheptyl)carbamate (290 mg, 1.25 mmol) in MeOH (20 mL) was added AcOH (4 drops) followed by sodium cyanoborohydride (315 mg, 5 mmol). The mixture was stirred at RT for 4 h then concentrated and the residue was purified using prep-TLC eluting with DCM/MeOH (10:1) to give tert-butyl (7-(((1r,4r)-4-((5-chloro-4-(5-(cyclopropylmethyl)-1-methyl-1H-pyrazol-4-yl)pyrimidin-2-yl)amino)cyclohexyl)amino)heptyl)carbamate (440 mg, 61% yield) as a solid. MS (ESI) m/z=574.4 [M+H]$^+$.

To a stirred solution of tert-butyl (7-(((1r,4r)-4-((5-chloro-4-(5-(cyclopropylmethyl)-1-methyl-1H-pyrazol-4-yl)pyrimidin-2-yl)amino)cyclohexyl)amino)heptyl)carbamate (440 mg, 0.77 mmol) in THF (7 mL) and water (0.4 mL) was added sodium carbonate (244 mg, 2.3 mmol) and benzyl chloroformate (200 mg, 1.17 mmol). The mixture was stirred at RT for 2 h then water was added and the mixture was extracted with EA. The organic layers were washed with brine, dried over Na$_2$SO$_4$, and concentrated to give benzyl (7-((tert-butoxycarbonyl)amino)heptyl)((1r,4r)-4-((5-chloro-4-(5-(cyclopropylmethyl)-1-methyl-1H-pyrazol-4-yl)pyrimidin-2-yl)amino)cyclohexyl)carbamate (590 mg crude) as an oil. MS (ESI) m/z=708.4 [M+H]$^+$.

To a stirred solution of benzyl (7-((tert-butoxycarbonyl)amino)heptyl)((1r,4r)-4-((5-chloro-4-(5-(cyclopropylmethyl)-1-methyl-1H-pyrazol-4-yl)pyrimidin-2-yl)amino)cyclohexyl)carbamate (0.83 mmol) in DCM (8 mL) was added TFA (4 mL). The mixture was stirred at RT for 2 h then concentrated, dissolved in DMF (2 mL), and adjusted to a pH of about 7 with aqueous K$_2$CO$_3$. The mixture was concentrated and the residue was purified using prep-TLC eluting with DCM/MeOH (10:1) to give benzyl (7-aminoheptyl)((1r,4r)-4-((5-chloro-4-(5-(cyclopropylmethyl)-1-methyl-1H-pyrazol-4-yl)pyrimidin-2-yl)amino)cyclohexyl)carbamate (210 mg) as a solid. MS (ESI) m/z=608.4 [M+H]$^+$.

To a stirred solution of benzyl (7-aminoheptyl)((1r,4r)-4-((5-chloro-4-(5-(cyclopropylmethyl)-1-methyl-1H-pyrazol-4-yl)pyrimidin-2-yl)amino)cyclohexyl)carbamate (210 mg, 0.34 mmol) in DMF (4 mL) was added K$_2$CO$_3$ (71 mg, 0.51 mmol) and tert-butyl 2-bromoacetate (67 mg, 0.34 mmol). The mixture was stirred at RT for 2 h then water was added and the mixture was extracted with EA. The organic layers were washed with brine, dried over Na$_2$SO$_4$, evaporated and purified using prep-TLC (EA) to give tert-butyl 2-((7-(((benzyloxy)carbonyl)((1r,4r)-4-((5-chloro-4-(5-(cyclopropylmethyl)-1-methyl-1H-pyrazol-4-yl)pyrimidin-2-yl) amino)cyclohexyl)amino)heptyl)amino)acetate (80 mg, 32% yield) as an oil. MS (ESI) m/z=722.4 [M+H]$^+$.

To a stirred solution of tert-butyl 2-((7-(((benzyloxy) carbonyl)((1r,4r)-4-((5-chloro-4-(5-(cyclopropylmethyl)-1-methyl-1H-pyrazol-4-yl)pyrimidin-2-yl)amino)cyclohexyl) amino)heptyl)amino)acetate (80 mg, 0.11 mmol) in DCM (6 mL) was added TFA (1.5 mL). The mixture was stirred at RT overnight then concentrated to give crude 2-((7-(((benzyloxy)carbonyl)((1r,4r)-4-((5-chloro-4-(5-(cyclopropylmethyl)-1-methyl-1H-pyrazol-4-yl)pyrimidin-2-yl)amino)cyclohexyl)amino)heptyl)amino)acetic acid. MS (ESI) m/z=666.4 [M+H]$^+$.

To a stirred solution of 2-((7-(((benzyloxy)carbonyl)((1r,4r)-4-((5-chloro-4-(5-(cyclopropylmethyl)-1-methyl-1H-pyrazol-4-yl)pyrimidin-2-yl)amino)cyclohexyl)amino)heptyl)amino)acetic acid (0.11 mmol, crude) and 3-(2-(aminomethyl)-6-oxo-4H-thieno[2,3-c]pyrrol-5(6H)-yl) piperidine-2,6-dione hydrochloride (42 mg, 0.13 mmol) in DMF (5 mL) was added DIEA (43 mg, 0.33 mmol), HOBt (23 mg, 0.17 mmol) and EDCI.HCl (33 mg, 0.17 mmol). The mixture was stirred at RT overnight then water was added and the mixture and extracted with EA. The combined organic layers were washed with brine, dried over Na$_2$SO$_4$, evaporated and purified using prep-TLC eluting with DCM/MeOH (10/1) to give benzyl ((1r,4r)-4-((5-chloro-4-(5-(cyclopropylmethyl)-1-methyl-1H-pyrazol-4-yl)pyrimidin-2-yl)amino)cyclohexyl)(7-((2-(((5-(2,6-dioxopiperidin-3-yl)-6-oxo-5,6-dihydro-4H-thieno[2,3-c]pyrrol-2-yl)methyl) amino)-2-oxoethyl)amino)heptyl)carbamate (40 mg, 39% yield) as a solid. MS (ESI) m/z=464.3 [M/2+H]$^+$.

To a stirred solution of benzyl ((1r,4r)-4-((5-chloro-4-(5-(cyclopropylmethyl)-1-methyl-1H-pyrazol-4-yl)pyrimidin-2-yl)amino)cyclohexyl)(7-((2-(((5-(2,6-dioxopiperidin-3-yl)-6-oxo-5,6-dihydro-4H-thieno[2,3-c]pyrrol-2-yl)methyl) amino)-2-oxoethyl)amino)heptyl)carbamate (40 mg, 0.043 mmol) in AcOH (1 mL) was added HBr in AcOH (1 mL). The mixture was stirred at RT for 30 min then concentrated. The residue was dissolved in DMF, adjusted to a pH of about 7 with TEA, then evaporated and purified using prep-HPLC as previously described to afford Compound 53 (9.3 mg, 27% yield) as a solid.

Example 54

Compound 54: N-(5-(((5-(tert-butyl)oxazol-2-yl) methyl)thio)thiazol-2-yl)-1-(2-((4-((4-((5-(2,6-dioxopiperidin-3-yl)-4-oxo-5,6-dihydro-4H-thieno[3,4-c]pyrrol-1-yl)methoxy)benzyl)amino)butyl) amino)-2-oxoethyl)piperidine-4-carboxamide Compound 54 was prepared following similar procedure described in Examples 1 and 67.

Example 55

Compound 55: 2-(((1r,4r)-4-((5-chloro-4-(5-(cyclopropylmethyl)-1-methyl-1H-pyrazol-4-yl)pyrimidin-2-yl)amino)cyclohexyl)amino)-N-(2-(2-(2-(2-((2-(2,6-dioxopiperidin-3-yl)-1-oxoisoindolin-4-yl)amino) ethoxy)ethoxy)ethoxy)ethyl)acetamide Compound 55 was prepared following similar procedure described in Example 49.

Example 56

Compound 56: 2-(((1r,4r)-4-((4-(5-(cyclopropylmethyl)-1-methyl-1H-pyrazol-4-yl)-5-fluoropyrimidin-2-yl)amino)cyclohexyl)amino)-N-(2-(2-(2-(2-((2-(2,6-dioxopiperidin-3-yl)-1-oxoisoindolin-4-yl)amino) ethoxy)ethoxy)ethoxy)ethyl)acetamide Compound 56 was prepared following similar procedure described in Example 50.

Example 57

Compound 57: N-(5-(((5-(tert-butyl)oxazol-2-yl) methyl)thio)thiazol-2-yl)-1-(7-((2-(((5-(2,6-dioxopiperidin-3-yl)-6-oxo-5,6-dihydro-4H-thieno[2,3-c] pyrrol-2-yl)methyl)amino)-2-oxoethyl)amino)heptyl) piperidine-4-carboxamide Compound 57 was prepared following similar procedure described in Examples 20 and 33.

Example 58

Compound 58: N-(5-(((5-(tert-butyl)oxazol-2-yl) methyl)thio)thiazol-2-yl)-1-(1-(5-(2,6-dioxopiperidin-3-yl)-4-oxo-5,6-dihydro-4H-thieno[3,4-c]pyrrol-1-yl)-3-oxo-8,11,14,17-tetraoxa-2,5-diazanonadecan-19-yl)piperidine-4-carboxamide Compound 58 was prepared following similar procedure described in Examples 31 and 34.

Example 59

Compound 59: 1-(8-(((1r,4r)-4-((4-(5-(cyclopropylmethyl)-1-methyl-1H-pyrazol-4-yl)-5-fluoropyridin-2-yl)amino)cyclohexyl)amino)octyl)-3-((5-(2,6-dioxopiperidin-3-yl)-6-oxo-5,6-dihydro-4H-thieno[2,3-c]pyrrol-2-yl)methyl)urea Compound 59 was prepared following similar procedure described in Example 23.

Example 60

Compound 60: 2-((5-(((1r,4r)-4-((5-chloro-4-(5-(cyclopropylmethyl)-1-methyl-1H-pyrazol-4-yl)pyrimidin-2-yl)amino)cyclohexyl)amino)pentyl) amino)-N-((5-(2,6-dioxopiperidin-3-yl)-6-oxo-5,6-dihydro-4H-thieno[2,3-c]pyrrol-2-yl)methyl) acetamide Compound 60 was prepared following similar procedure described in Examples 53.

Example 61

Compound 61: 1-(8-(((1r,4r)-4-((5-chloro-4-(5-(cyclopropylmethyl)-1-methyl-1H-pyrazol-4-yl)pyrimidin-2-yl)amino)cyclohexyl)amino)octyl)-3-((3-(2,6-dioxopiperidin-3-yl)-2-methyl-4-oxo-3,4-dihydrothieno[3,4-d]pyrimidin-7-yl)methyl)urea To a solution of tert-butyl (8-(methoxy(methyl)amino)-8-oxooctyl)carbamate (700 mg, 2.317 mmol) in THF (10 mL) at −78° C. was added LiAlH$_4$ (3.4 mL, 1 M in THF)

dropwise over 10 min, the mixture was stirred at 0° C. for 30 min. The mixture was then quenched with saturated aqueous NH₄Cl (5 mL) slowly. The mixture was extracted with EA and the combined organic phase was washed with H₂O, dried over Na₂SO₄, filtered and concentrated to give tert-butyl (8-oxooctyl)carbamate (583 mg, crude).

To a solution of (1r,4r)-N1-(5-chloro-4-(5-(cyclopropylmethyl)-1-methyl-1H-pyrazol-4-yl)pyrimidin-2-yl)cyclohexane-1,4-diamine (300 mg, 0.833 mmol) in MeOH/HOAc (10 mL:1 mL) at RT was added tert-butyl (8-oxooctyl) carbamate (404 mg, 1.666 mmol), followed by NaBH₃CN (210 mg, 3.332 mmol). The suspension was stirred at RT overnight. The solvent was removed and the residue was purified using silica gel eluting with MeOH/DCM (0% to 4%) to give tert-butyl (8-(((1r,4r)-4-((5-chloro-4-(5-(cyclopropylmethyl)-1-methyl-1H-pyrazol-4-yl)pyrimidin-2-yl)amino)cyclohexyl)amino)octyl)carbamate (331 mg, 68% yield) as an oil. MS (ESI) m/z 588.2 [M+H]⁺.

To a solution of tert-butyl (8-(((1r,4r)-4-((5-chloro-4-(5-(cyclopropylmethyl)-1-methyl-1H-pyrazol-4-yl)pyrimidin-2-yl)amino)cyclohexyl)amino)octyl)carbamate (331 mg, 0.563 mmol) in THF/H₂O (5 mL:1.5 mL) at RT was added sodium carbonate (180 mg, 1.689 mmol), followed by benzyl carbonochloridate (288 mg, 1.689 mmol). The mixture was stirred at RT for 1 h then the suspension was diluted with H₂O and extracted with DCM. The combined organic layers were dried over Na₂SO₄, filtered and concentrated to give the crude product, which was purified using silica gel eluting with MeOH/DCM (0% to 5%) to give benzyl (8-((tert-butoxycarbonyl)amino)octyl)((1 r,4r)-4-((5-chloro-4-(5-(cyclopropylmethyl)-1-methyl-1H-pyrazol-4-yl)pyrimidin-2-yl)amino)cyclohexyl)carbamate (327 mg, 81% yield) as an oil. MS (ESI) m/z 722.4 [M+H]⁺.

To a solution of benzyl (8-((tert-butoxycarbonyl)amino) octyl)((1r,4r)-4-((5-chloro-4-(5-(cyclopropylmethyl)-1-methyl-1H-pyrazol-4-yl)pyrimidin-2-yl)amino)cyclohexyl) carbamate (327 mg, 0.453 mmol) in DCM (12 mL) at RT was added TFA (3 mL). The mixture was stirred at RT for 2 h then concentrated to give crude benzyl (8-aminooctyl)((1r,4r)-4-((5-chloro-4-(5-(cyclopropylmethyl)-1-methyl-1H-pyrazol-4-yl)pyrimidin-2-yl)amino)cyclohexyl)carbamate as the TFA salt. MS (ESI) m/z 622.3 [M+H]⁺.

3-(7-(aminomethyl)-2-methyl-4-oxothieno[3,4-d]pyrimidin-3(4H)-yl)piperidine-2,6-dione (103 mg, 0.246 mmol) was dissolved in THF (2 mL) and TEA (49 mg, 0.295 mmol) was added. Then 4-nitrobenzyl chloroformate (59 mg, 0.295 mmol) was added. The mixture was stirred at RT for 0.5 h then concentrated to give crude 4-nitrophenyl ((3-(2,6-dioxopiperidin-3-yl)-2-methyl-4-oxo-3,4-dihydrothieno[3,4-d]pyrimidin-7-yl)methyl)carbamate (115 mg, crude). MS (ESI) m/z 471.4 [M+H]⁺.

Benzyl (8-aminooctyl)((1r,4r)-4-((5-chloro-4-(5-(cyclopropylmethyl)-1-methyl-1H-pyrazol-4-yl)pyrimidin-2-yl) amino)cyclohexyl)carbamate (120 mg, 0.164 mmol) was dissolved in THF (2 mL) and TEA (83 mg, 0.820 mmol) was added. The mixture was stirred at RT for 5 min. Then the suspension of 4-nitrophenyl ((3-(2,6-dioxopiperidin-3-yl)-2-methyl-4-oxo-3,4-dihydrothieno[3,4-d]pyrimidin-7-yl) methyl)carbamate (115 mg, crude) in THF (1 mL) was added and the mixture was stirred at 25° C. for 3 h. The mixture was diluted with H₂O and extracted with DCM. The combined organic layers were dried over Na₂SO₄, filtered and concentrated to give the crude product, which was purified using silica gel to give benzyl ((1r,4r)-4-((5-chloro-4-(5-(cyclopropylmethyl)-1-methyl-1H-pyrazol-4-yl)pyrimidin-2-yl)amino)cyclohexyl)(8-(3-((3-(2,6-dioxopiperidin-3-yl)-2-methyl-4-oxo-3,4-dihydrothieno[3,4-d] pyrimidin-7-yl)methyl)ureido)octyl)carbamate (100 mg) as an oil. MS (ESI) m/z 954.5 [M+H]⁺.

To a solution of benzyl ((1r,4r)-4-((5-chloro-4-(5-(cyclopropylmethyl)-1-methyl-1H-pyrazol-4-yl)pyrimidin-2-yl) amino)cyclohexyl)(8-(3-((3-(2,6-dioxopiperidin-3-yl)-2-methyl-4-oxo-3,4-dihydrothieno[3,4-d]pyrimidin-7-yl) methyl)ureido)octyl)carbamate (100 mg, 0.104 mmol) in AcOH (1.5 mL) at RT was added HBr (33% in AcOH, 1.5 mL). The mixture was stirred at RT for 30 min then concentrated, dissolved in DMF (2 mL), and adjusted to a pH of about 7 with TEA. The mixture was concentrated and the residue was purified using prep-HPLC as previously described to afford Compound 61 (17.8 mg, 21% yield) as a solid.

Example 62

Compound 62: 2-(((1r,4r)-4-((4-(5-(cyclopropylmethyl)-1-methyl-1H-pyrazol-4-yl)-5-fluoropyrimidin-2-yl)amino)cyclohexyl)amino)-N-(1-(5-(2,6-dioxopiperidin-3-yl)-6-oxo-5,6-dihydro-4H-thieno[2,3-c]pyrrol-2-yl)-5,8,11-trioxa-2-azatridecan-13-yl) acetamide Compound 62 was prepared following similar procedure described in Examples 21 and 43.

Example 63

Compound 63: 2-(((1r,4r)-4-((4-(5-(cyclopropylmethyl)-1-methyl-1H-pyrazol-4-yl)-5-fluoropyridin-2-yl)amino)cyclohexyl)amino)-N-(2-((2-(((5-(2,6-dioxopiperidin-3-yl)-6-oxo-5,6-dihydro-4H-thieno[2,3-c]pyrrol-2-yl)methyl)amino)-2-oxoethyl)amino) ethyl)acetamide Compound 63 was prepared following similar procedure described in Example 36.

Example 64

Compound 64: 4-((14-(((1r,4r)-4-((5-chloro-4-(5-(cyclopropylmethyl)-1-methyl-1H-pyrazol-4-yl)pyrimidin-2-yl)amino)cyclohexyl)amino)-3,6,9,12-tetraoxatetradecyl)amino)-2-(2,6-dioxopiperidin-3-yl)isoindoline-1,3-dione Compound 64 was prepared following similar procedure described in Examples 10 and 22.

111

Example 65

Compound 65: 1-(8-(((1r,4r)-4-((4-(5-(cyclopropylmethyl)-1-methyl-1H-pyrazol-4-yl)-1,3,5-triazin-2-yl)amino)cyclohexyl)amino)octyl)-3-((5-(2,6-dioxopiperidin-3-yl)-6-oxo-5,6-dihydro-4H-thieno[2,3-c]pyrrol-2-yl)methyl)urea Compound 65 was prepared following similar procedure described in Example 22.

Example 66

Compound 66: 3-(2-(13-(((1r,4r)-4-((5-chloro-4-(5-(cyclopropylmethyl)-1-methyl-1H-pyrazol-4-yl)pyrimidin-2-yl)amino)cyclohexyl)amino)-5,8,11-trioxa-2-azatridecyl)-6-oxo-4,6-dihydro-5H-thieno[2,3-c]pyrrol-5-yl)piperidine-2,6-dione Compound 66 was prepared following similar procedure described in Examples 53.

Example 67

Compound 67: (S)-3-(1-((4-(((2-(2-(2-(((1r,4r)-4-((5-chloro-4-(5-(cyclopropylmethyl)-1-methyl-1H-pyrazol-4-yl)pyrimidin-2-yl)amino)cyclohexyl)amino)ethoxy)ethoxy)ethyl)amino)methyl)phenoxy)methyl)-4-oxo-4H-thieno[3,4-c]pyrrol-5(6H)-yl)piperidine-2,6-dione To a solution of 2,2-dimethyl-4-oxo-3,8,11-trioxa-5-azatridecan-13-oic acid (1.5 g, 5.7 mmol) in DCM (25 mL) at RT was added EDCI.HCl (1.64 g, 8.56 mmol) and TEA (1.15 g, 11.4 mmol). Then N,O-dimethylhydroxylamine (611 mg, 6.27 mmol) and N,N-dimethylpyridin-4-amine (69 mg, 0.57 mmol) were added and the mixture was stirred at RT overnight. The mixture was diluted with $H_2O$ and extracted with DCM. The combined organic layers were dried over $Na_2SO_4$, filtered and concentrated to give the crude product, which was purified using silica gel eluting with MeOH/DCM (0% to 5%) to give tert-butyl (3-methyl-4-oxo-2,6,9-trioxa-3-azaundecan-11-yl)carbamate (1.42 g, 82% yield) as an oil. MS (ESI) m/z 307.2 $[M+H]^+$, 207.2 $[M-Boc]^+$.

To a solution of tert-butyl (3-methyl-4-oxo-2,6,9-trioxa-3-azaundecan-11-yl)carbamate (500 mg, 1.64 mmol) in THF (15 mL) at −78° C. was added $LiAlH_4$ (3.28 mL, 1 M in THF) dropwise over 10 min. The mixture was stirred at 0° C. for 30 min then quenched with saturated $NH_4Cl$ (5 mL) aqueous slowly. The mixture was extracted with EA and washed with brine. The organic layer was dried over $Na_2SO_4$, filtered and concentrated to give tert-butyl (2-(2-(2-oxoethoxy)ethoxy)ethyl)carbamate (320 mg, crude).

To a solution of (1r,4r)-$N^1$-(5-chloro-4-(5-(cyclopropylmethyl)-1-methyl-1H-pyrazol-4-yl)pyrimidin-2-yl)cyclohexane-1,4-diamine (300 mg, 0.693 mmol, HCl salt) in MeOH (10 mL) at RT was added DIEA (89 mg, 0.693 mmol). The solution was stirred at RT for 10 min. Then tert-butyl (2-(2-(2-oxoethoxy)ethoxy)ethyl)carbamate (205 mg, 0.831 mmol) and $NaBH_3CN$ (174 mg, 2.772 mmol)

112 were added, followed by AcOH (2 drops). The suspension was stirred at RT overnight. The solvent was removed and the residue was purified using silica gel eluting with MeOH/DCM (0% to 8%) to give tert-butyl (2-(2-(2-(((1r,4r)-4-((5-chloro-4-(5-(cyclopropylmethyl)-1-methyl-1H-pyrazol-4-yl)pyrimidin-2-yl)amino)cyclohexyl)amino)ethoxy)ethoxy)ethyl)carbamate (206 mg, 50% yield) as an oil. MS (ESI) m/z 592.3 $[M+H]^+$.

To a solution of tert-butyl (2-(2-(2-(((1r,4r)-4-((5-chloro-4-(5-(cyclopropylmethyl)-1-methyl-1H-pyrazol-4-yl)pyrimidin-2-yl)amino)cyclohexyl)amino)ethoxy)ethoxy)ethyl)carbamate (100 mg, 0.169 mmol) in DCM (8 mL) was added TFA (2 mL). The mixture was stirred at RT for 1 h then concentrated. The resulting amine TFA salt was dissolved in MeOH/DCM (1 mL:4 mL) and cooled to 0° C., then DIEA (89 mg, 0.693 mmol) was added and the mixture was stirred for 5 min. Then (S)-4-((5-(2,6-dioxopiperidin-3-yl)-4-oxo-5,6-dihydro-4H-thieno[3,4-c]pyrrol-1-yl)methoxy)benzaldehyde (65 mg, 0.169 mmol) and $NaBH_3CN$ (43 mg, 0.676 mmol) were added, followed by AcOH (2 drops). The mixture was stirred at RT overnight. The solvent was removed and the residue was purified using silica gel eluting with MeOH/DCM (0% to 10%) to give the crude product (80 mg). It was further purified using prep-HPLC as previously described to afford Compound 67 (29.2 mg, 24% yield) as a solid.

Example 68

Compound 68: (S)-3-(1-((4-(((7-(((1r,4r)-4-((5-chloro-4-(5-(cyclopropylmethyl)-1-methyl-1H-pyrazol-4-yl)pyrimidin-2-yl)amino)cyclohexyl)amino)heptyl)amino)methyl)phenoxy)methyl)-4-oxo-4H-thieno[3,4-c]pyrrol-5(6H)-yl)piperidine-2,6-dione Compound 68 was prepared following similar procedure described in Example 67.

Example 69

Compound 69: (S)-3-(1-((4-(13-(((1r,4r)-4-((5-chloro-4-(5-(cyclopropylmethyl)-1-methyl-1H-pyrazol-4-yl)pyrimidin-2-yl)amino)cyclohexyl)amino)-5,8,11-trioxa-2-azatridecyl)phenoxy)methyl)-4-oxo-4H-thieno[3,4-c]pyrrol-5(6H)-yl)piperidine-2,6-dione Compound 68 was prepared following similar procedure described in Example 67.

Example 70

Compound 70: 3-(4-(1-(7-(((1r,4r)-4-((5-chloro-4-(5-(cyclopropylmethyl)-1-methyl-1H-pyrazol-4-yl)pyrimidin-2-yl)amino)cyclohexyl)amino)heptyl)piperidin-4-yl)-6-fluoro-1-oxoisoindolin-2-yl)piperidine-2,6-dione To a solution of 3-(4-bromo-6-fluoro-1-oxoisoindolin-2-yl)piperidine-2,6-dione (300 mg, 0.882 mmol) in DMF (18 ml) at RT was added tert-butyl 4-(4,4,5,5-tetramethyl-1,3, 2-dioxaborolan-2-yl)-5,6-dihydropyridine-1(2H)-carboxylate (742 mg, 2.401 mmol) and $K_2CO_3$ (365.3 mg, 2.647 mmol). The suspension was bubbled with $N_2$. Then Pd(dppf)$Cl_2$ (322.8 mg, 0.441 mmol) was added and the mixture was stirred at 100° C. for 16 h. The mixture was filtered and concentrated to afford a residue, which was purified using silica gel eluting with EA/PE (0% to 60%) to give tert-butyl 4-(2-(2,6-dioxopiperidin-3-yl)-6-fluoro-1-oxoisoindolin-4-yl)-5,6-dihydropyridine-1(2H)-carboxylate (192 mg, 49% yield) as a solid. MS (ESI) m/z 388.1 [M−55]$^+$.

To a solution of tert-butyl 4-(2-(2,6-dioxopiperidin-3-yl)-6-fluoro-1-oxoisoindolin-4-yl)-5,6-dihydropyridine-1 (2H)-carboxylate (192 mg, 0.433 mmol) in DCM/MeOH (1 ml:6 mL) at RT was added Pd/C (200 mg). The mixture was degassed and refilled with $H_2$ then stirred at RT for 18 h. The mixture was filtered and the filtrate was concentrated to give crude tert-butyl 4-(2-(2,6-dioxopiperidin-3-yl)-6-fluoro-1-oxoisoindolin-4-yl)piperidine-1-carboxylate (181 mg, 94% yield). MS (ESI) m/z 390.1 [M−55]$^+$.

To a solution of tert-butyl 4-(2-(2,6-dioxopiperidin-3-yl)-6-fluoro-1-oxoisoindolin-4-yl)piperidine-1-carboxylate (181 mg, 0.407 mmol) in DCM (4 mL) was added TFA (1 mL). The mixture was stirred at RT for 1 h then concentrated to give crude 3-(6-fluoro-1-oxo-4-(piperidin-4-yl)isoindolin-2-yl)piperidine-2,6-dione as a TFA salt. MS (ESI) m/z 346.1 [M+H]$^+$.

To a solution of (1r,4r)-N1-(5-chloro-4-(5-(cyclopropylmethyl)-1-methyl-1H-pyrazol-4-yl)pyrimidin-2-yl)cyclohexane-1,4-diamine (400 mg, 0.924 mmol) in DMF (20 mL) at RT was added $K_2CO_3$ (382.4 mg, 2.771 mmol) and 7-bromo-N-methoxy-N-methylheptanamide (232 mg, 0.924 mmol). The mixture was stirred at 75° C. overnight. The mixture was diluted with $H_2O$ and extracted with DCM. The combined organic phase was dried over $Na_2SO_4$, filtered, evaporated to afford a residue which was purified using silica gel eluting with MeOH/DCM (0% to 10%) to give 7-(((1r,4r)-4-((5-chloro-4-(5-(cyclopropylmethyl)-1-methyl-1H-pyrazol-4-yl)pyrimidin-2-yl)amino)cyclohexyl)amino)-N-methoxy-N-methylheptanamide (173 mg, 35% yield) as an oil. MS (ESI) m/z 532.3 [M+H]$^+$.

To a solution of 7-(((1r,4r)-4-((5-chloro-4-(5-(cyclopropylmethyl)-1-methyl-1H-pyrazol-4-yl)pyrimidin-2-yl)amino)cyclohexyl)amino)-N-methoxy-N-methylheptanamide (173 mg, 0.326 mmol) in THF/$H_2O$ (8 mL:2 mL) at RT was added sodium carbonate (103.6 mg, 0.977 mmol), followed by benzyl chloroformate (66.7 mg, 0.391 mmol). The mixture was stirred at RT for 1 h. The mixture was diluted with $H_2O$ and extracted with EA. The combined organic layers were dried over $Na_2SO_4$, filtered and concentrated to give the crude product, which was purified using silica gel eluting with MeOH/DCM (0% to 4%) to give benzyl ((1r,4r)-4-((5-chloro-4-(5-(cyclopropylmethyl)-1-methyl-1H-pyrazol-4-yl)pyrimidin-2-yl)amino)cyclohexyl)(7-(methoxy(methyl)amino)-7-oxoheptyl)carbamate (192 mg, 89% yield) as an oil. MS (ESI) m/z 666.3 [M+H]$^+$.

To a solution of benzyl ((1r,4r)-4-((5-chloro-4-(5-(cyclopropylmethyl)-1-methyl-1H-pyrazol-4-yl)pyrimidin-2-yl)amino)cyclohexyl)(7-(methoxy(methyl)amino)-7-oxoheptyl)carbamate (96 mg, 0.1443 mmol) in THF (5 mL) at −78° C. was added LiAlH$_4$ (0.22 mL, 1M in THF) dropwise under $N_2$. After addition, the mixture was stirred at −78° C. for 30 min. The mixture was quenched with sat. NH$_4$Cl (5 mL) and extracted with EA. The combined organic layers were dried over $Na_2SO_4$, filtered and concentrated to give crude benzyl ((1r,4r)-4-((5-chloro-4-(5-(cyclopropylmethyl)-1-methyl-1H-pyrazol-4-yl)pyrimidin-2-yl)amino)cyclohexyl)(7-oxoheptyl)carbamate. MS (ESI) m/z 607.3 [M+H]$^+$.

To a solution of 3-(6-fluoro-1-oxo-4-(piperidin-4-yl)isoindolin-2-yl)piperidine-2,6-dione (60.6 mg, 0.132 mmol) in DCM/MeOH (8 mL:2 mL) at RT was added DIEA (17.0 mg, 0.132 mmol). After 3 min, benzyl ((1r,4r)-4-((5-chloro-4-(5-(cyclopropylmethyl)-1-methyl-1H-pyrazol-4-yl)pyrimidin-2-yl)amino)cyclohexyl)(7-oxoheptyl)carbamate (80 mg, 0.132 mmol), NaBH$_3$CN (33.3 mg, 0.528 mmol) and AcOH (2 drops) were added. The mixture was stirred at RT for 5 h then concentrated to afford a residue, which was purified using prep-TLC eluting with DCM/MeOH+ (10:1) to get benzyl ((1r,4r)-4-((5-chloro-4-(5-(cyclopropylmethyl)-1-methyl-1H-pyrazol-4-yl)pyrimidin-2-yl)amino)cyclohexyl)(7-(4-(2-(2,6-dioxopiperidin-3-yl)-6-fluoro-1-oxoisoindolin-4-yl)piperidin-1-yl)heptyl)carbamate (88 mg, 53% yield) as an oil. MS (ESI) m/z 936.5 [M+H]$^+$.

To a solution of benzyl ((1r,4r)-4-((5-chloro-4-(5-(cyclopropylmethyl)-1-methyl-1H-pyrazol-4-yl)pyrimidin-2-yl)amino)cyclohexyl)(7-(4-(2-(2,6-dioxopiperidin-3-yl)-6-fluoro-1-oxoisoindolin-4-yl)piperidin-1-yl)heptyl)carbamate (88 mg, 0.094 mmol) in AcOH (2 mL) was added HBr (33% in AcOH, 2 mL). The mixture was stirred at RT for 1 h then concentrated, and the residue was dissolved in DMF (2 mL) and adjusted to a pH of about 7 with TEA. The solvent was removed and the residue was purified using prep-HPLC as previously described to afford Compound 70 (19.9 mg, 27% yield) as a solid.

Example 71

Compound 71: 4-((14-(((1r,4r)-4-((5-chloro-4-(5-(cyclopropylmethyl)-1-methyl-1H-pyrazol-4-yl)pyrimidin-2-yl)amino)cyclohexyl)amino)-3,6,9,12-tetraoxatetradecyl)amino)-2-(2,6-dioxopiperidin-3-yl)isoindoline-1,3-dione Compound 71 was prepared following similar procedure described in Examples 49 and 53.

Example 72

Compound 72: (S)-3-(4-((4-(13-(((1r,4r)-4-((5-chloro-4-(5-(cyclopropylmethyl)-1-methyl-1H-pyrazol-4-yl)pyrimidin-2-yl)amino)cyclohexyl)amino)-5,8,11-trioxa-2-azatridecyl)benzyl)oxy)-1-oxoisoindolin-2-yl)piperidine-2,6-dione Compound 72 was prepared following similar procedure described in Examples 8 and 53.

TABLE B

Exemplary Compounds of Formulas (I) and (II) and Characterization Data

| Chemical No. | Structure | MS (ESI) m/z [M + H]+ | ¹H NMR (400 MHz, DMSO-$d_6$) |
|---|---|---|---|
| 1 | 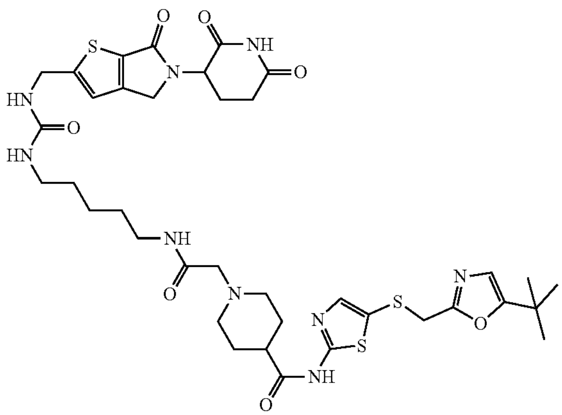 [SMILES: CC(C)(C)c1cnc(CSc2cnc(NC(=O)C3CCN(CC(=O)NCCCCCNC(=O)NCc4cc5c(s4)C(=O)N(C4CCC(=O)NC4=O)C5)CC3)s2)o1] | 830.3 | δ 10.96 (s, 1H), 7.71 (s, 1H), 7.38 (s, 1H), 7.04 (s, 1H), 6.71 (s, 1H), 6.50 (s, 1H), 6.06 (s, 1H), 4.97 (d, J = 9.2 Hz, 1H), 4.42 (s, 2H), 4.35-4.18 (m, 2H), 4.05 (s, 2H), 3.08-2.83 (m, 9H), 2.60-2.50 (m, 1H), 2.49-2.33 (m, 2H), 2.06-2.00 (m, 3H), 1.73 (s, 4H), 1.40 (s, 4H), 1.19-1.18 (m, 2H), 1.18 (s, 9H) |
| 2 | 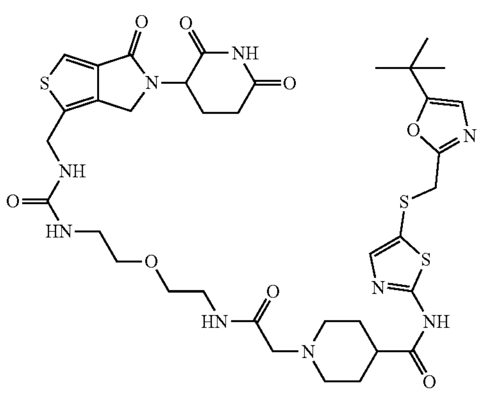 | 830.3 | δ 12.24 (s, 1H), 10.98 (s, 1H), 7.83 (s, 1H), 7.73 (t, J = 5.2 Hz, 1H), 7.38 (s, 1 H), 6.71 (s, 1H), 6.56 (t, J = 5.6 Hz, 1H), 6.10 (t, J = 5.2 Hz, 1H), 5.01 (dd, J = 4.8, 12.8 Hz, 1H), 4.33 (d, J = 6.0 Hz, 2H), 4.29-4.14 (m, 2H), 4.05 (s, 2H), 3.43-3.38 (m, 4H), 3.28-3.25 (m, 2H), 3.18-3.15 (m, 2H), 2.93-2.81 (m, 5H), 2.61-2.57 (m, 1H), 2.48-2.42 (m, 1H), 2.35-2.24 (m, 1H), 2.09-1.97 (m, 3H), 1.73-1.69 (m, 4H), 1.17 (s, 9H). |
| 3 | 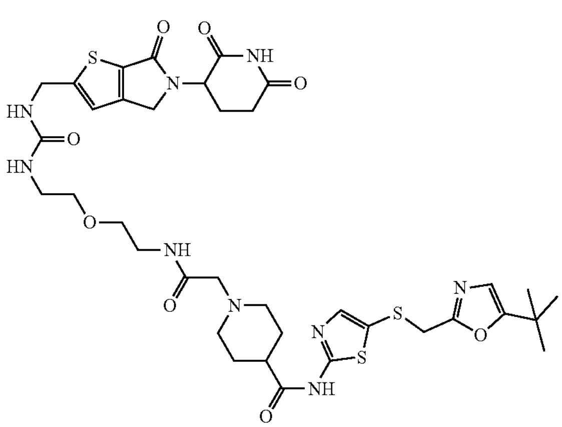 [SMILES: CC(C)(C)c1cnc(CSc2cnc(NC(=O)C3CCN(CC(=O)NCCOCCNC(=O)NCc4cc5c(s4)C(=O)N(C4CCC(=O)NC4=O)C5)CC3)s2)o1] | 830.3 | δ 12.23 (s, 1H), 10.94 (s, 1H), 7.74 (s, 1H), 7.38 (s, 1 H),7.05 (s, 1H), 6.72 (s, 1H), 6.62 (s, 1H), 6.12 (s, 1H), 4.98 (dd, J = 3.6, 12.4 Hz, 1H), 4.43 (d, J = 5.2 Hz, 2H), 4.35-4.18 (m, 2H), 4.05 (s, 2H), 3.58-3.39 (m, 6H), 3.18 (d, J = 4.8 Hz, 2H), 2.91-2.82 (m, 5H), 2.68-2.61 (m, 2H), 2.36-2.33 (m, 1H), 2.08-1.99 (m, 3H), 1.74-1.69 (m, 4H), 1.17 (s, 9H). |

TABLE B-continued

Exemplary Compounds of Formulas (I) and (II) and Characterization Data

| Chemical No. | Structure | MS (ESI) m/z [M + H]+ | 1H NMR (400 MHz, DMSO-d6) |
|---|---|---|---|
| 4 | 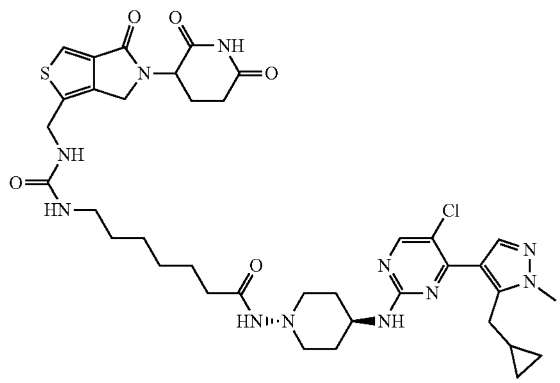 | 793.4 | δ 10.85 (s, 1H), 8.11 (s, 1H), 7.88 (s, 1H), 7.68 (s, 1H), 7.55 (d, J = 7.6 Hz, 1H), 7.06 (s, 1H), 6.30 (t, J = 6.0 Hz, 1H), 5.89 (t, J = 5.6 Hz, 1H), 4.87 (dd, J = 4.8, 12.8 Hz, 1H), 4.17 (d, J = 6.0 Hz, 2H), 4.14-3.98 (m, 2H), 3.71 (s, 3H), 3.50 (s, 1H), 3.38-3.29 (m, 1H), 2.91 (d, J = 6.0 Hz, 2H), 2.84-2.79 (m, 2H), 2.76-2.69 (m, 1H), 2.45-2.41 (m, 1H), 2.17-2.11 (m, 1H), 1.86-1.81 (m, 3H), 1.76-1.63 (m, 4H), 1.32-1.29 (m, 2H), 1.23-1.14 (m, 4H), 1.10-1.02 (m, 6H), 0.84 (s, 1H), 0.26 (s, 2H), 0.01 (s, 2H). |
| 5 | 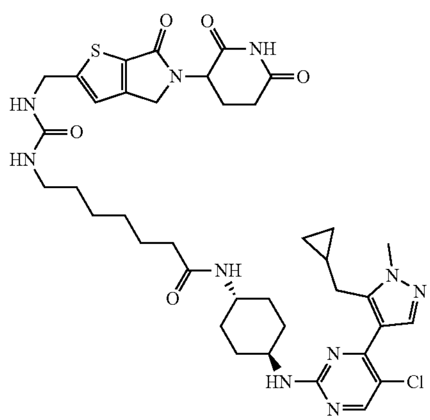 [SMILES: Cn1ncc(-c2nc(N[C@H]3CC[C@H](NC(=O)CCCCCCNC(=O)NCc4cc5c(s4)C(=O)N(C4CCC(=O)NC4=O)C5)CC3)ncc2Cl)c1CC1CC1] | 793.4 | δ 10.79 (bs, 1H), 8.11 (s, 1H), 7.87 (bs, 1H), 7.53 (m, 1H), 7.03 (bs, 1H), 6.90 (s, 1H), 6.34 (bs, 1H), 5.88 (bs, 1H), 4.83 (m, 1H), 4.27 (m, 2H), 4.03 (m, 2H), 3.71 (m, 3H), 3.18 (m 1H), 2.92 (m, 1H), 2.83 (m, 4H), 2.69 (m, 1H), 2.35 (m, 1H), 1.87 (m, 3H), 1.85 (m 4H), 1.77 (m, 2H), 1.73 (m, 2H), 1.67-1.09 (m, 14H). |
| 6 | 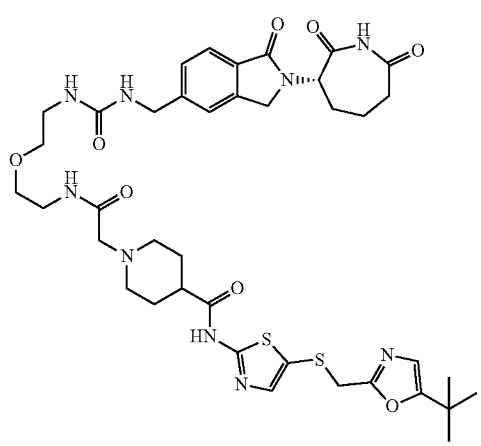 [SMILES: CC(C)(C)c1cnc(CSc2cnc(NC(=O)C3CCN(CC(=O)NCCOCCNC(=O)NCc4ccc5c(c4)CN([C@H]4CCCC(=O)NC4=O)C5=O)CC3)s2)o1] | 838.3 | δ 12.15 (s, 1H), 10.72 (s, 1H), 7.73 (t, J = 5.6 Hz, 1H), 7.66 (d, J = 8.0 Hz, 1H), 7.46 (s, 1H), 7.37 (s, 1H), 7.36 (d, J = 5.6 Hz, 1H), 6.71 (s, 1H), 6.55 (t, J = 5.6 Hz, 1H), 6.07 (t, J = 5.6 Hz, 1H), 5.22 (dd, J = 4.8, 12.4 Hz, 1H), 4.50 (s, 2H), 4.32 (d, J = 6.0 Hz, 2H), 4.04 (s, 2H), 3.56-3.27 (m, 2H), 3.20-3.17 (m, 2H), 3.11-3.04 (m, 1H), 2.90 (s, 2H), 2.82 (d, J = 11.6 Hz, 2H), 2.60-2.55 (m, 1H), 2.45-2.41 (m, 1H), 2.28-2.23 (m, 1H), 2.12-1.99 (m, 4H), 1.84-1.81 (m, 1H), 1.73-1.68 (m, 4H), 1.17 (s, 9H). |

TABLE B-continued

Exemplary Compounds of Formulas (I) and (II) and Characterization Data

| Chemical No. | Structure | MS (ESI) m/z [M + H]+ | 1H NMR (400 MHz, DMSO-d6) |
|---|---|---|---|
| 7 | 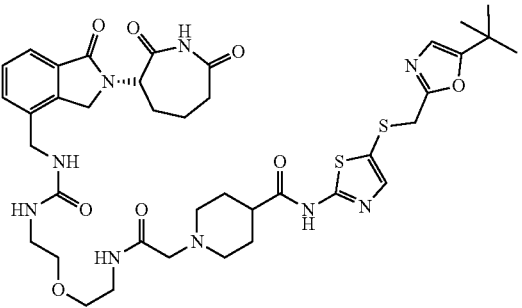 | 838.3 | δ 10.91 (s, 1H), 7.72 (t, J = 6.0 Hz, 1H), 7.61-7.57 (m, 1H), 7.48 (s, 1H), 7.46 (d, J = 2.0 Hz, 1H), 7.38 (s, 1 H), 6.71 (s, 1H), 5.25 (dd, J = 4.8, 12.4 Hz, 1H), 4.54 (s, 2H), 4.30 (d, J = 6.0 Hz, 2H), 4.05 (s, 2H), 3.44-3.37 (m, 2H), 3.19-3.14 (m, 2H), 3.13-3.05 (m, 1H), 2.89 (s, 2H), 2.82 (d, J = 11.2 Hz, 2H), 2.61-2.56 (m, 1H), 2.46-2.41 (m, 1H), 2.33-2.24 (m, 1H), 2.12-2.03 (m, 4H), 1.88-1.79 (m, 1H), 1.74-1.68 (m, 4H), 1.17 (s, 9H). |
| 8 | 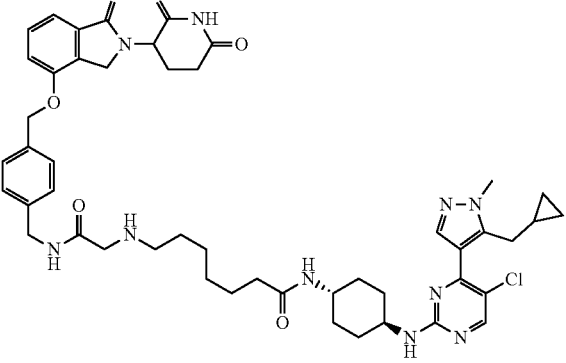 | 907.4 | δ 10.96 (s, 1H), 8.27-8.25 (m, 2H), 8.01 (s, 1H), 7.66-7.54 (m, 2H), 7.48-7.40 (m, 3H), 7.31-7.24 (m, 4H), 7.15 (s, 1H), 5.21 (s, 2H), 5.08 (dd, J = 5.2, 13.2 Hz, 1H), 4.41-4.21 (m, 4H), 3.84 (s, 3H), 3.64-3.45 (m, 2H), 3.10 (s, 2H), 3.05 (d, J = 6.4 Hz, 2H), 2.94-2.85 (m, 1H), 2.58-2.49 (m, 1H), 2.43 (t, J = 6.8 Hz, 2H), 2.02-1.97 (m, 3H), 1.90-1.87 (m, 2H), 1.80-1.77 (m, 3H), 1.47-1.44 (m, 2H), 1.37-1.30 (m, 3H), 1.27-1.19 (m, 7H), 0.98 (s, 1H), 0.39 (s, 2H), 0.13 (s, 2H). |
| 9 | 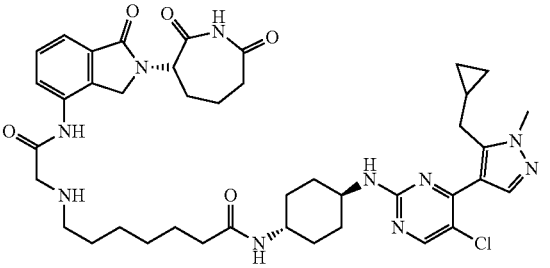 | 801.4 | δ 10.78 (s, 1H), 8.27 (s, 1H), 8.04-7.91 (m, 2H), 7.68 (d, J = 8.0 Hz, 1H), 7.51-7.47 (m, 2H), 7.21 (s, 1H), 5.27 (dd, J = 4.8, 12.0 Hz, 1H), 4.57-4.48 (m, 2H), 3.86 (s, 3H), 3.65-3.35 (m, 4H), 3.13-3.06 (m, 3H), 2.55-2.50 (m, 4H), 2.24-2.04 (m, 2H), 2.00-1.78 (m, 8H), 1.49-1.19 (m, 13 H), 0.97 (s, 1H), 0.41 (s, 2H), 0.15 (s, 2H). |
| 10 | 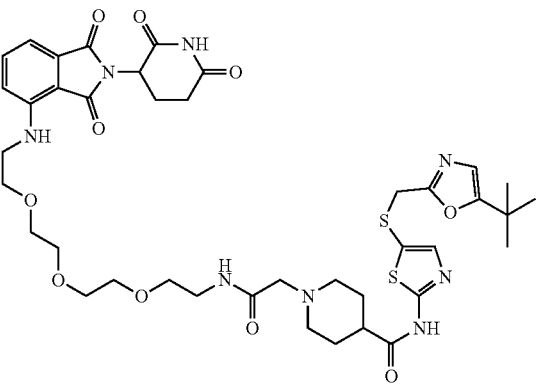 [SMILES: CC(C)(C)c1cnc(CSc2cnc(NC(=O)C3CCN(CC(=O)NCCOCCOCCOCCNc4cccc5c4C(=O)N(C4CCC(=O)NC4=O)C5=O)CC3)s2)o1] | 869.3 | δ 12.25 (s, 1H), 11.11 (s, 1H), 7.72 (s, 1H), 7.58 (t, J = 8.0 Hz, 1H), 7.38 (s, 1H), 7.13 (d, J = 8.8 Hz, 1H), 7.04 (d, J = 6.8 Hz, 1H), 6.71 (s, 1H), 6.60 (t, J = 5.2 Hz, 1H), 5.05 (dd, J = 5.2, 12.4 Hz, 1H), 4.05 (s, 2H), 3.61 (t, J = 5.2 Hz, 2H), 3.54-3.42 (m, 11H), 3.42-3.39 (m, 2H), 3.27-3.22 (m, 2H), 2.93-2.81 (m, 5H), 2.61-2.54 (m, 1H), 2.48-2.42 (m, 1H), 2.09-1.99 (m, 3H), 1.73-1.68 (m, 4H), 1.17 (s. 9H). |

TABLE B-continued
Exemplary Compounds of Formulas (I) and (II) and Characterization Data
| Chemical No. | Structure | MS (ESI) m/z [M + H]⁺ | ¹H NMR (400 MHz, DMSO-d₆) |
|---|---|---|---|
| 11 | 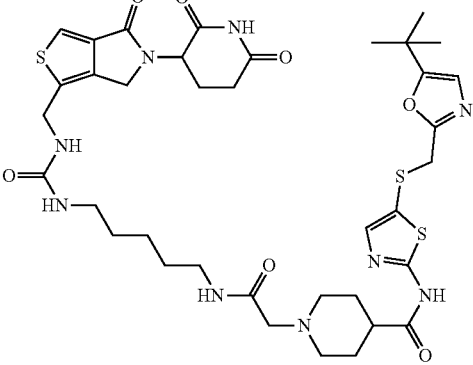 | 828.2 | δ 12.20 (s, 1H), 10.97 (s, 1H), 7.82 (s, 1H), 7.69 (t, J = 5.6 Hz, 1H), 7.34 (s, 1H), 6.71 (s, 1H), 6.43 (d, J = 5.2 Hz, 1H), 6.03 (t, J = 4.8 Hz, 1H), 5.01 (dd, J = 8.4, 13.6 Hz, 1H), 4.33-4.14 (m, 4H), 4.05 (s, 2H), 3.08-2.79 (m, 11H), 2.61-2.56 (m, 1H), 2.32-2.26 (m, 1H), 2.06-1.96 (m, 3H), 1.78-1.67 (m, 3H), 1.42-1.33 (m, 4H), 1.23-1.17 (m, 11H). |
| 12 | 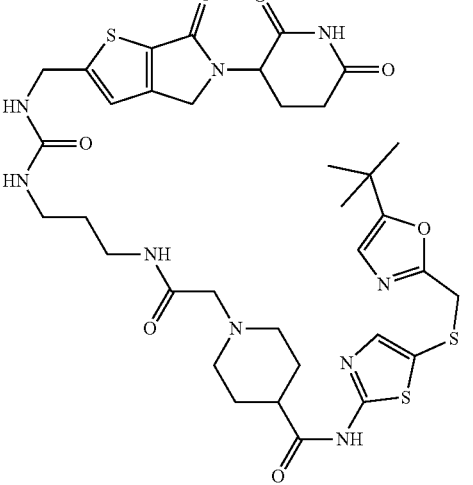 | 800.2 | δ 12.24 (s, 1H), 10.95 (s, 1H), 7.84 (s, 1H), 7.38 (s, 1H), 7.06 (s, 1H), 6.71 (s, 1H), 6.63 (t, J = 5.2 Hz, 1H), 6.11 (t, J = 6.0 Hz, 1H), 4.97 (dd, J = 8.4, 13.2 Hz, 1H), 4.43-4.17 (m, 4H), 4.05 (s, 2H), 3.11-2.81 (m, 9H), 2.59-2.55 (m, 1H), 2.35-2.31 (m, 1H), 2.09-1.97 (m, 4H), 1.77-1.70 (m, 4H), 1.51-1.48 (m, 2H), 1.17 (s, 9H). |
| 13 | 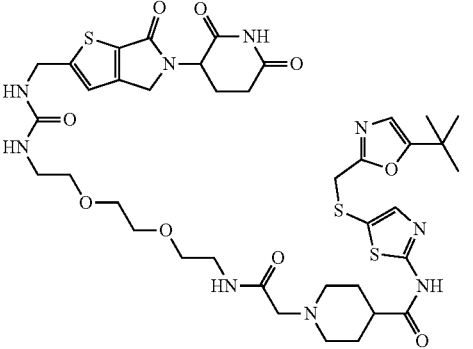 [SMILES: CC(C)(C)c1cnc(CSc2cnc(NC(=O)C3CCN(CC(=O)NCCOCCOCCNC(=O)NCc4cc5c(s4)C(=O)N(C4CCC(=O)NC4=O)C5)CC3)s2)o1] | 874.2 | δ 12.22 (s, 1H), 10.95 (s, 1H), 7.73 (t, J = 5.6 Hz, 1H), 7.38 (s, 1H), 7.05 (s, 1H), 6.71 (s, 1H), 6.66 (t, J = 6.0 Hz, 1H), 6.09 (t, J = 5.6 Hz, 1H), 4.98 (dd, J = 5.2, 13.6 Hz, 1H), 4.42 (d, J = 6.0 Hz, 2H), 4.34-4.17 (m, 2H), 4.04 (s, 2H), 3.51 (s, 4H), 3.44-3.34 (m, 4H), 3.27-3.23 (m, 2H), 3.19-3.15 (m, 2H), 2.92-2.80 (m, 5H), 2.59-2.55 (m, 1H), 2.49-2.47 (m, 1H), 2.45-2.41 (m, 1H), 2.07-1.96 (m, 3H), 1.75-1.67 (m, 4H), 1.17 (s, 9H). |

TABLE B-continued

Exemplary Compounds of Formulas (I) and (II) and Characterization Data

| Chemical No. Structure | MS (ESI) m/z [M + H]⁺ | ¹H NMR (400 MHz, DMSO-d₆) |
|---|---|---|
| 14 | 828.2 | δ 10.95 (s, 1H), 8.62 (s, 1H), 7.77 (s, 1H), 7.38 (s, 1H), 7.10 (s, 1H), 6.71 (s, 1H), 5.00-4.96 (m, 2H), 4.53 (s, 2H), 4.36-4.18 (m, 2H), 4.05 (s, 2H), 3.12-3.08 (m, 6H), 2.88-2.78 (m, 6H), 2.36-2.33 (m, 1H), 2.24-2.06 (m, 4H), 1.73 (s, 4H), 1.41 (m, 5H), 1.24-1.18 (m, 11H). |
| 15 | 843.2 | δ 12.20 (s, 1H), 10.95 (s, 1H), 7.68 (t, J = 5.6 Hz, 1H), 7.37 (s, 1H), 7.04 (s, 1H), 6.71 (s, 1H), 6.65 (t, J = 5.6 Hz, 1H), 5.97 (t, J = 5.6 Hz, 1H), 4.97 (dd, J = 5.2, 13.2 Hz, 1H), 4.60 (d, J = 4.4 Hz, 2H), 4.34-4.17 (m, 2H), 4.04 (s, 2H), 3.20-3.15 (m, 2H), 3.11-3.07 (m, 2H), 2.91-2.81 (m, 5H), 2.58-2.55 (m, 1H), 2.42-2.31 (m, 6H), 2.19 (s, 3H), 2.07-1.96 (m, 4H), 1.73-1.68 (m, 4H), 1.37-1.23 (m, 1H), 1.17 (s, 9H). |
| 16 | 808.3 | δ 10.94 (s, 1H), 8.25 (s, 1H), 8.01 (s, 1H), 7.76 (t, J = 5.2 Hz, 1H), 7.16 (s, 1H), 7.04 (s, 1H), 6.50 (t, J = 5.2 Hz, 1H), 6.05 (t, J = 5.6 Hz, 1H), 4.97 (dd, J = 4.8, 13.2 Hz, 1H), 4.43 (d, J = 5.6 Hz, 2H), 4.35-4.17 (m, 2H), 3.86 (s, 3H), 3.67-3.60 (m, 1H), 3.08-2.97 (m, 8H), 2.93-2.84 (m, 1H), 2.60-2.55 (m, 1H), 2.39-2.26 (m, 2H), 2.03-1.97 (m, 1H), 1.90-1.81 (m, 4H), 1.43-1.35 (m, 4H), 1.32-1.24 (m, 5H), 1.12-0.97 (m, 3H), 0.39 (s, 2H), 0.13 (s, 2H). |

TABLE B-continued

Exemplary Compounds of Formulas (I) and (II) and Characterization Data

| No. | Chemical Structure | MS (ESI) m/z [M + H]+ | 1H NMR (400 MHz, DMSO-d6) |
|---|---|---|---|
| 17 | 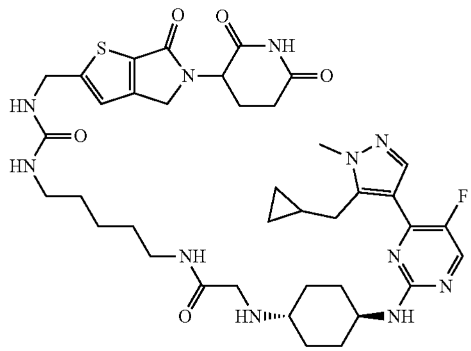 [SMILES: Cn1ncc(-c2nc(N[C@H]3CC[C@H](NCC(=O)NCCCCCNC(=O)NCc4cc5c(s4)C(=O)N(C4CCC(=O)NC4=O)C5)CC3)ncc2F)c1CC1CC1] | 792.3 | δ 10.94 (s, 1H), 8.23 (s, 1H), 7.84 (s, 1H), 7.76 (s, 1H), 7.04 (s, 1H), 6.86 (s, 1H), 6.50 (s, 1H), 6.05 (s, 1H), 4.97 (d, J = 8.8 Hz, 1H), 4.42 (s, 2H), 4.34-4.17 (m, 2H), 3.86 (s, 3H), 3.64 (s, 1H), 3.21-3.00 (m, 8H), 2.91-2.84 (m, 1H), 2.59-2.50 (m, 1H), 2.40-2.25 (m, 2H), 2.07-1.89 (m, 5H), 1.40-1.25 (m, 9H), 1.12-0.99 (m, 3H), 0.41 (s, 2H), 0.23 (s, 2H). |
| 18 | 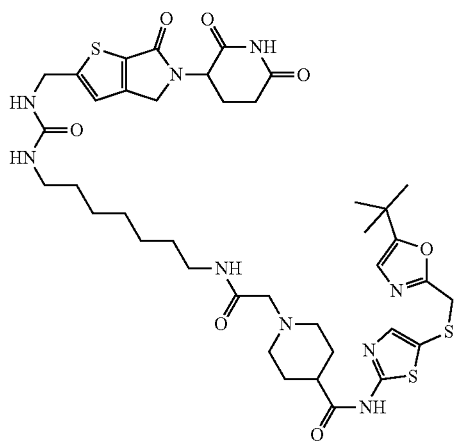 [SMILES: CC(C)(C)c1cnc(CSc2cnc(NC(=O)C3CCN(CC(=O)NCCCCCCCNC(=O)NCc4cc5c(s4)C(=O)N(C4CCC(=O)NC4=O)C5)CC3)s2)o1] | 856.3 | δ 12.21 (s, 1H), 10.94 (s, 1H), 7.69 (t, J = 6.0 Hz, 1H), 7.38 (s, 1H), 7.04 (s, 1H), 6.71 (s, 1H), 6.48 (t, J = 6.0 Hz, 1H), 6.03 (t, J = 5.6 Hz, 1H), 4.97 (dd, J = 8.4, 13.2 Hz, 1H), 4.42-4.17 (m, 4H), 4.05 (s, 2H), 3.09-2.79 (m, 9H), 2.60-2.56 (m, 1H), 2.38-2.29 (m, 1H), 2.11-1.96 (m, 4H), 1.74-1.66 (m, 4H), 1.46-1.33 (m, 4H), 1.29-1.23 (m, 6H), 1.17 (s, 9H). |
| 19 | 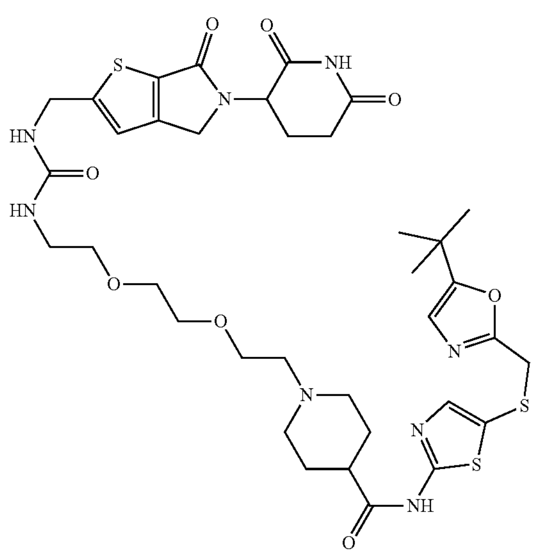 [SMILES: CC(C)(C)c1cnc(CSc2cnc(NC(=O)C3CCN(CCOCCOCCNC(=O)NCc4cc5c(s4)C(=O)N(C4CCC(=O)NC4=O)C5)CC3)s2)o1] | 817.2 | δ 10.94 (s, 1H), 7.37 (s, 1H), 7.05 (s, 1H), 6.71 (s, 1H), 6.65 (t, J = 5.6 Hz, 1H), 6.11 (t, J = 6.0 Hz, 1H), 4.97 (dd, J = 6.4, 13.2 Hz, 1H), 4.32 (d, J = 5.6 Hz, 2H), 4.42-4.17 (m, 2H), 4.04 (s, 2H), 3.50-3.48 (m, 8H), 3.19-3.15 (m, 2H), 2.91-2.84 (m, 3H), 2.60-2.55 (m, 1H), 2.46-2.31 (m, 2H), 2.00-1.90 (m, 5H), 1.71-1.56 (m, 4H), 1.17 (s, 9H). |

TABLE B-continued
Exemplary Compounds of Formulas (I) and (II) and Characterization Data
| Chemical No. Structure | MS (ESI) m/z [M + H]+ | 1H NMR (400 MHz, DMSO-d6) |
|---|---|---|
| 20 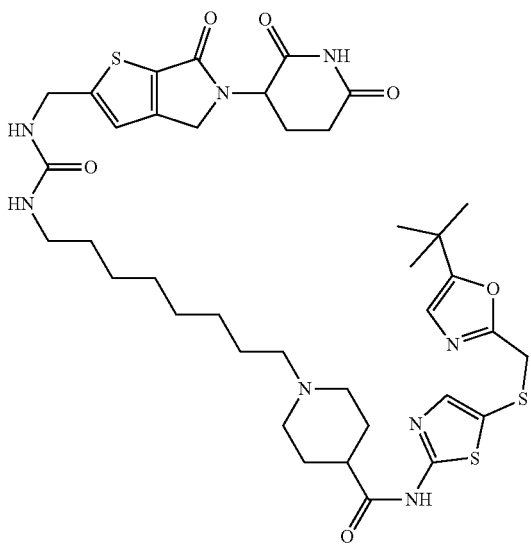 [SMILES: CC(C)(C)c1cnc(CSc2cnc(NC(=O)C3CCN(CCCCCCCCNC(=O)NCc4cc5c(s4)C(=O)N(C4CCC(=O)NC4=O)C5)CC3)s2)o1] | 813.2 | δ 12.32 (s, 1H), 10.94 (s, 1H), 7.05 (s, 1H), 7.39 (s, 1H), 7.05 (s, 1H), 6.72 (s, 1H), 6.53 (t, J = 5.6 Hz, 1H), 6.07 (t, J = 5.6 Hz, 1H), 4.97 (dd, J = 8.4, 13.6 Hz, 1H), 8.42 (d, J = 5.6 Hz, 2H), 4.35-4.17 (m, 2H), 4.05 (s, 2H), 3.02-2.84 (m, 5H), 2.60-2.55 (m, 2H), 2.36-2.32 (m, 1H), 2.00-1.54 (m, 9H), 1.37-1.34 (m, 2H), 1.27-1.24 (m, 10H), 1.18 (s, 9H). |
| 21 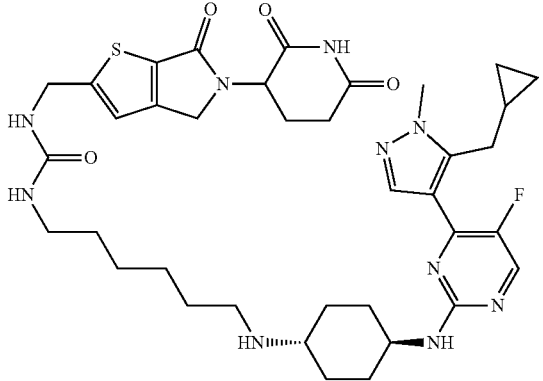 [SMILES: Cn1ncc(-c2nc(N[C@H]3CC[C@H](NCCCCCCNC(=O)NCc4cc5c(s4)C(=O)N(C4CCC(=O)NC4=O)C5)CC3)ncc2F)c1CC1CC1] | 749.3 | δ 8.24 (d, J = 2.8 Hz, 1H), 7.84 (d, J = 3.2 Hz, 1H), 7.04 (s, 1H), 6.89 (s, 1H), 6.53 (s. 1H), 6.07 (s, 1H), 4.97 (dd. J = 4.4, 13.2 Hz, 1H), 4.41 (d, J = 5.2 Hz, 2H), 4.34-4.18 (m, 2H), 3.86 (s, 3H), 3.37-3.20 (m, 5H), 3.00-2.98 (m, 2H), 2.92-2.83 (m, 1H), 2.59-2.49 (m, 1H), 2.35-2.29 (m, 2H), 1.99-1.89 (m, 5H), 1.37-1.25 (m, 10H), 1.12-1.06 (m, 3H), 0.40 (d, J = 6.4 Hz, 2H), 0.23 (d, J = 3.2 Hz, 2H). |
| 22 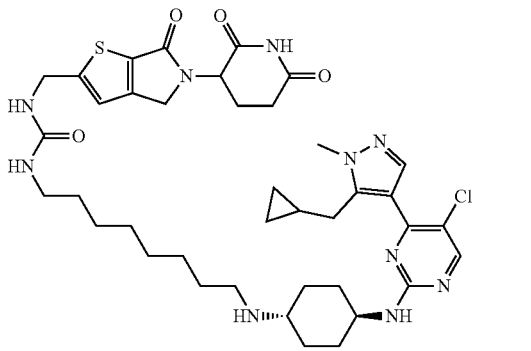 [SMILES: Cn1ncc(-c2nc(N[C@H]3CC[C@H](NCCCCCCCCNC(=O)NCc4cc5c(s4)C(=O)N(C4CCC(=O)NC4=O)C5)CC3)ncc2Cl)c1CC1CC1] | 793.2 | δ 8.25 (s, 1H), 8.01 (s, 1H), 7.17(s, 1H), 7.04 (s, 1H), 6.50 (t, J = 6.0 Hz, 1H), 6.03 (t, J = 5.6 Hz, 1H), 4.97 (dd, J = 4.8, 13.2 Hz, 1H), 4.41 (d, J = 6.0 Hz, 2H), 4.35-4.17 (m, 2H), 3.85 (s, 3H), 3.71-3.58 (m, 1H), 3.08-2.81 (m, 8H), 2.67-2.59 (m, 1H), 2.55-2.53 (m, 2H), 2.42-2.28 (m, 3H), 2.01-1.89 (m, 3H), 1.38-1.33 (m, 4H), 1.30-1.25 (m, 1H), 1.11-0.96 (m, 3H), 0.39 (s, 2H), 0.13 (s, 2H). |

TABLE B-continued

Exemplary Compounds of Formulas (I) and (II) and Characterization Data

| Chemical No. | Structure | MS (ESI) m/z [M + H]+ | 1H NMR (400 MHz, DMSO-d6) |
|---|---|---|---|
| 23 | 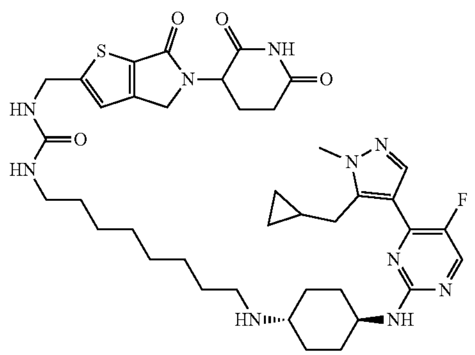 [SMILES: Cn1ncc(-c2nc(N[C@H]3CC[C@H](NCCCCCCCCNC(=O)NCc4cc5c(s4)C(=O)N(C4CCC(=O)NC4=O)C5)CC3)ncc2F)c1CC1CC1] | 776.9 | δ 8.24 (d, J = 3.6 Hz, 1H), 7.84 (d, J = 4.4 Hz, 1H), 7.04 (s, 1H), 6.86 (s, 1H), 6.51 (t, J = 6.0 Hz, 1H), 6.05 (t, J = 6.0 Hz, 1H), 4.97 (dd, J = 5.2, 13.2 Hz, 1H), 4.42 (d, J = 6.0 Hz, 2H), 4.35-4.17 (m, 2H), 3.86 (s, 3H), 3.66-3.60 (m, 1H), 3.22-3.17 (m, 4H), 3.02-2.97 (m, 2H), 2.89-2.85 (m, 1H), 2.67-2.59 (m, 1H), 2.54-2.50 (m, 2H), 2.39-2.32 (m, 3H), 1.99-1.97 (m, 1H), 1.92-1.89 (m, 4H), 1.38-1.26 (m, 14H), 1.13-1.04 (m, 3H), 0.40 (d, J = 7.2 Hz, 2H), 0.22 (dd, J = 4.8, 9.6 Hz, 2H). |
| 24 | 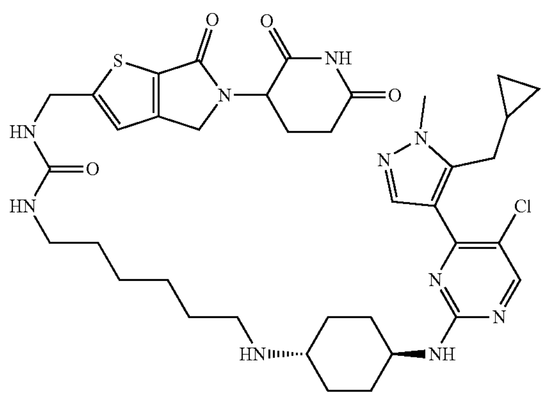 [SMILES: Cn1ncc(-c2nc(N[C@H]3CC[C@H](NCCCCCCNC(=O)NCc4cc5c(s4)C(=O)N(C4CCC(=O)NC4=O)C5)CC3)ncc2Cl)c1CC1CC1] | 765.2 | δ 10.94 (s, 1H), 8.59 (br s, 1H), 8.28 (s, 1H), 8.00 (s, 1H), 7.25 (s, 1H), 7.05 (s, 1H), 6.59 (t, J = 6.0 Hz, 1H), 6.14 (t, J = 5.6 Hz, 1H), 4.97 (dd, J = 6.0, 13.6 Hz, 1H), 4.42 (d, J = 6.0 Hz, 2H), 4.35-4.17 (m, 2H), 3.86 (s, 3H), 3.67-3.65 (m, 1H), 3.06-2.88 (m, 8H), 2.67-2.56 (m, 1H), 2.38-2.32 (m, 1H), 2.11-1.98 (m, 6H), 1.62-1.60 (m, 2H), 1.39-1.23 (m, 15H), 0.98 (s, 1H), 0.87-0.84 (m, 1H). 0.41 (s, 2H), 0.14 (s. 2H). |
| 25 | 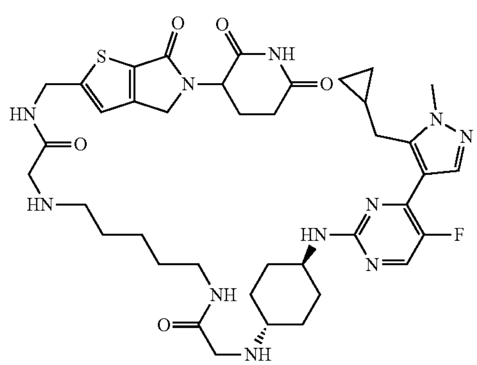 [SMILES: Cn1ncc(-c2nc(N[C@H]3CC[C@H](NCC(=O)NCCCCCNCC(=O)NCc4cc5c(s4)C(=O)N(C4CCC(=O)NC4=O)C5)CC3)ncc2F)c1CC1CC1] | 804.0 | δ 10.95 (s, 1H), 8.51 (t, J = 5.2 Hz, 1H), 8.24 (d, J = 4.0 Hz, 1H), 7.85 (d, J = 4.0 Hz, 1H), 7.76 (t, J = 5.6 Hz, 1H), 7.09 (s, 1H), 6.89 (s, 1H), 4.97 (dd, J = 5.2, 13.2 Hz, 1H), 4.52 (d, J = 5.6 Hz, 2H), 4.35-4.18 (m, 2H), 3.86 (s, 3H), 3.68-3.63 (m, 1H), 3.21 (d, J = 6.4 Hz, 2H), 3.11-3.07 (m, 6H), 2.92-2.83 (m, 1H), 2.59-2.55 (m, 2H), 2.45 (t, J = 6.8 Hz, 2H), 2.37-2.26 (m, 2H), 1.99-1.96 (m, 1H), 1.88-1.85 (m, 4H), 1.39-1.38 (m, 4H), 1.29-1.24 (m, 5H), 1.14-1.06 (m, 3H), 0.41 (d, J = 7.2 Hz, 2H), 0.23 (d, J = 4.4 Hz, 2H). |
| 26 | 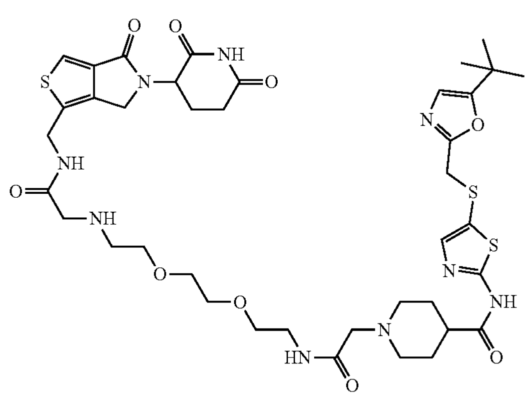 [SMILES: CC(C)(C)c1cnc(CSc2cnc(NC(=O)C3CCN(CC(=O)NCCOCCOCCNCC(=O)NCc4scc5c4CN(C4CCC(=O)NC4=O)C5=O)CC3)s2)o1] | 888.2 | δ 8.49 (t, J = 6.0 Hz, 1H), 7.85 (s, 1H), 7.71 (t, J = 5.6 Hz, 1H), 7.38 (s, 1H), 6.71 (s, 1H), 5.00 (dd, J = 8.4, 13.6 Hz, 1H), 4.43-4.15 (m, 4H), 4.05 (s, 2H), 3.49-3.15 (m, 12H), 2.89-2.80 (m, 5H), 2.63-2.56 (m, 3H), 2.46-2.29 (m, 2H), 2.09-1.95 (m, 3H), 1.77-1.68 (m, 4H), 1.17 (s, 9H). |

TABLE B-continued

Exemplary Compounds of Formulas (I) and (II) and Characterization Data

| Chemical No. | Structure | MS (ESI) m/z [M + H]+ | 1H NMR (400 MHz, DMSO-d6) |
|---|---|---|---|
| 27 | 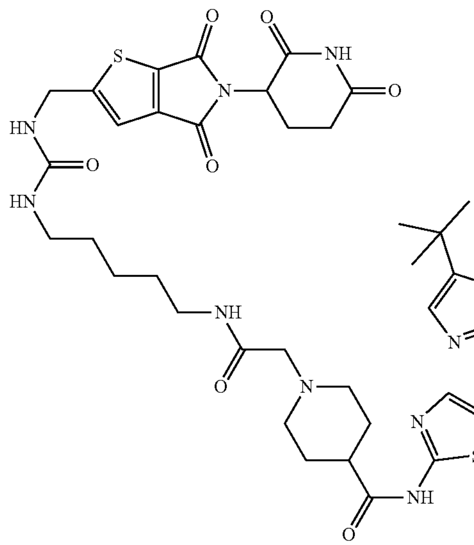 | 888.2 | δ 8.49 (t, J = 6.0 Hz, 1H), 7.85 (s, 1H), 7.71 (t, J =5.6 H, 1H), 7.38 (s, 1H), 6.71 (s, 1H), 5.00 (dd, J = 8.4, 13.6 Hz, 1H), 4.43-4.15 (m, 4H), 4.05 (s, 2H), 3.49-3.15 (m, 12H), 2.89-2.80 (m, 5H), 2.63-2.56 (m, 3H), 2.46-2.29 (m, 2H), 2.09-1.95 (m, 3H), 1.77-1.68 (m, 4H), 1.17 (s, 9H). |
| 28 | 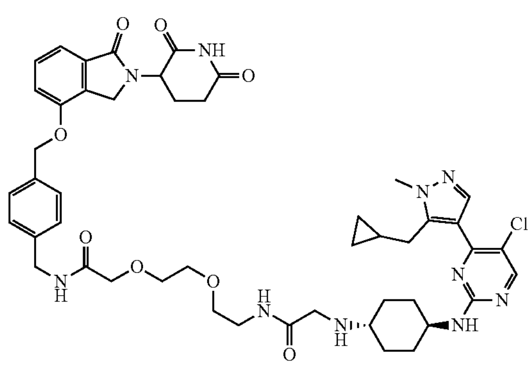 [SMILES: Cn1ncc(-c2nc(N[C@H]3CC[C@H](NCC(=O)NCCOCCOCC(=O)NCc4ccc(COc5cccc6c5CN(C5CCC(=O)NC5=O)C6=O)cc4)CC3)ncc2Cl)c1CC1CC1] | 925.2 | δ 10.96 (s, 1 H), 8.27 (s, 3 H), 8.02 (br s, 1 H), 7.49-7.42 (m, 3 H), 7.33-7.27 (m, 4 H), 7.21 (br s, 1 H), 5.21 (s, 1 H), 5.13-5.08 (m, 1 H), 4.42-4.22 (m, 4 H), 3.96 (s, 2 H), 3.85 (s, 3 H), 3.62-3.57 (m, 6 H), 3.49-3.44 (m, 4 H), 3.06-3.04 (m, 2 H), 2.95-2.86 (m, 1 H), 2.75-2.67 (m, 2 H), 2.43-2.40 (m, 1 H), 1.96 (s, 1 H), 1.31-1.26 (m, 4 H), 0.98 (br s, 1 H), 0.41(s, 2 H), 0.14 (s, 2 H). |
| 29 | 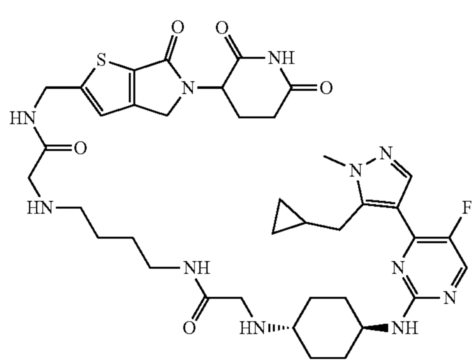 [SMILES: Cn1ncc(-c2nc(N[C@H]3CC[C@H](NCC(=O)NCCCCNCC(=O)NCc4cc5c(s4)C(=O)N(C4CCC(=O)NC4=O)C5)CC3)ncc2F)c1CC1CC1] | 792.3 | δ 10.93 (s, 1H), 8.52 (t, J = 5.6 Hz, 1H), 8.24 (d, J = 4.0 Hz, 1H), 7.85 (d, J = 4.0 Hz, 1H), 7.76 (t, J = 5.6 Hz, 1H), 7.09 (s, 1H), 6.86 (s, 1H), 4.97 (dd, J = 5.2, 13.2 Hz, 1H), 4.53 (d, J = 6.0 Hz, 2H), 4.35-4.18 (m, 2H), 3.86 (s, 3H), 3.68-3.63 (m, 1H), 3.21 (d, J = 6.4 Hz, 4H), 3.12-3.09 (m, 7H), 2.92-2.83 (m, 1H), 2.67-2.55 (m, 1H), 2.45 (t, J = 6.8 Hz, 1H), 2.39-2.28 (m, 2H), 2.00-1.96 (m, 1H), 1.89-1.86 (m, 10H), 1.42 (s, 4H), 1.28-1.24 (m, 3H), 1.15-1.06 (m, 3H), 0.41 (d, J = 7.6 Hz, 2H), 0.23 (d, J = 4.0 Hz, 2H). |

TABLE B-continued

Exemplary Compounds of Formulas (I) and (II) and Characterization Data

| Chemical No. Structure | MS (ESI) m/z [M + H]+ | $^1$H NMR (400 MHz, DMSO-d$_6$) |
|---|---|---|
| 30 | 822.3 | δ 10.94 (s, 1H), 8.50 (t, J = 6.0 Hz, 1H), 8.25 (s, 1H), 8.02 (s, 1H), 7.74 (t, J = 5.6 Hz. 1H), 7.17 (s, 1H), 7.09 (s, 1H), 4.97 (dd, J = 5.2, 13.6 Hz, 1H), 4.52 (d, J = 5.6 Hz, 2H), 4.35-4.18 (m, 2H), 3.85 (s, 3H), 3.67-3.63 (m, 1H), 3.11-3.02 (m, 9H), 2.92-2.83 (m, 1H), 2.67-2.58 (m, 1H), 2.47-2.43 (m, 3H), 2.36-2.27 (m, 3H), 2.02-1.96 (m, 2H), 1.90-1.80 (m, 4H), 1.46-1.39 (m, 4H), 1.31-1.27 (m, 2H), 1.12-0.96 (m, 3H), 0.39 (s, 2H), 0.13 (s, 2H). |
| 31 | 822.3 | δ 10.99 (s, 1H), 8.45 (t, J = 5.6 Hz, 1H), 8.25 (s, 1H), 8.02 (s, 1 H), 7.85 (s, 1H), 7.74 (t, J = 5.6 Hz, 1H), 7.18 (s, 1H), 5.00 (dd, J = 4.8, 13.2 Hz, 1H), 4.41 (d, J = 5.6 Hz, 2H), 4.30-4.15 (m, 2H), 3.85 (s, 3H), 3.66-3.61 (m, 2H), 3.10-3.04 (m, 8H), 2.93-2.84 (m, 1H), 2.60-2.54 (m, 1H), 2.43 (t, J = 6.8 Hz, 2 H), 2.36-2.25 (m, 2H), 2.02-1.95 (m, 2H), 1.89-1.85 (m, 4H), 1.47-1.35 (m, 4H), 1.31-1.22 (m, 4 H), 1.11-0.97 (m, 3H), 0.39 (s, 2 H), 0.13 (s, 2H). |
| 32 |  | δ 10.92 (s, 1H), 8.46 (t, J = 6.0 Hz, 1H), 8.24 (d, J = 3.6 Hz, 1H), 7.85 (s, 1H), 7.84 (d, J = 4.8 Hz, 1H), 7.75 (t, J = 6.4 Hz, 1H), 6.88 (s, 1H), 5.01 (dd, J = 5.2, 12.0 Hz, 1H), 4.42 (d, J = 6.0 Hz, 2H), 4.30-4.15 (m, 2H), 3.66 (s, 3H), 3.64-3.59 (m, 1H), 3.21 (d, J = 6.4 Hz, 2H), 3.10-3.05 (m, 6H), 2.93-2.84 (m, 1H), 2.60-2.56 (m, 1H), 2.43 (t, J = 7.2 Hz, 2H), 2.33-2.27 (m, 2H), 1.98-1.96 (m, 1H), 1.89-1.85 (m, 4H), 1.43-1.36 (m, 4H), 1.29-1.21 (m, 5H), 1.15-1.06 (m, 3H), 0.40 (d, J = 7.2 Hz, 2H), 0.23 (dd, J = 4.8, 10.0 Hz, 2H). |

TABLE B-continued

Exemplary Compounds of Formulas (I) and (II) and Characterization Data

| Chemical No. | Structure | MS (ESI) m/z [M + H]+ | 1H NMR (400 MHz, DMSO-d6) |
|---|---|---|---|
| 33 | 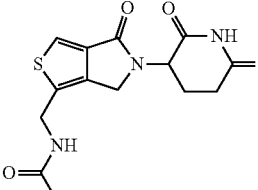 | 842.2 | δ 10.97 (s, 1H), 8.46 (t, J = 5.6 Hz, 1H), 7.85 (s, 1H), 7.69 (t, J = 5.6 Hz, 1H), 7.38 (s, 1H), 6.71 (s, 1H), 5.01 (dd, J = 8.0. 13.6 Hz, 1H), 4.41 (d, J = 5.6 Hz, 2H), 4.31-4.15 (m, 2H), 4.05 (s, 2H), 3.11-3.04 (m, 4H), 2.87-2.79 (m, 5H), 2.60-2.55 (m, 2H), 2.46-2.42 (m, 2H), 2.33-2.29 (m, 1H), 2.09-1.96 (m, 4H), 1.76-1.69 (m, 4H), 1.46-1.36 (m, 4H), 1.17 (s, 9H). |
| 34 | 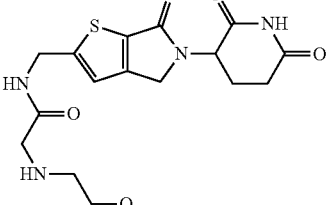 | 888.7 | δ 8.56 (t, J = 6.0 Hz, 1H), 7.72 (t, J = 6.4 Hz, 1H), 7.38 (s, 1H), 7.09 (s 1H), 6.71 (s, 1H), 4.98 (dd, J = 8.0, 13.6 Hz, 1H), 4.53-4.18 (m, 4H), 4.05 (s, 2H), 3.49-3.16 (m, 12H), 2.87-2.80 (m, 5H), 2.64-2.55 (m, 3H), 2.45-2.41 (m, 1H), 2.36-2.32 (m, 1H), 2.08-1.96 (m, 3H), 1.76-1.66 (m, 4H), 1.17 (s, 9H). |
| 35 | 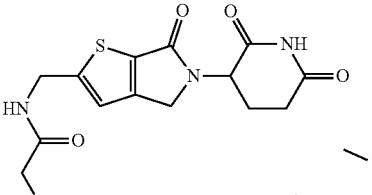 | 808.3 | δ 10.80 (s, 1H), 8.41 (t, J = 5.6 Hz, 1H), 8.12 (d, J = 3.6 Hz, 1H), 7.85 (s, 1H), 7.84 (d, J = 4.8 Hz, 1H), 7.75 (t, J = 6.4 Hz, 1H), 6.88 (s, 1H), 5.01 (dd, J = 5.2, 12.0 Hz, 1H), 4.42 (d, J = 6.0 Hz, 2H), 4.30-4.15 (m, 2H), 3.66 (s, 3H), 3.64-3.59 (m, 1H), 3.21 (d, J = 6.4 Hz, 2H), 3.10-3.05 (m, 6H), 2.93-2.84 (m, 1H), 2.60-2.56 (m, 1H), 2.43 (t, J = 7.2 Hz, 2H), 2.33-2.27 (m. 2H), 1.98-1.96 (m, 1H), 1.89-1.85 (m, 4H), 1.43-1.36 (m, 4H), 1.29-1.21 (m, 5H), 1.15-1.06 (m, 3H), 0.72 (d, J = 7.2 Hz, 2H), 0.70 (dd, J = 4.8, 10.0 Hz, 2H). |

TABLE B-continued

Exemplary Compounds of Formulas (I) and (II) and Characterization Data

| Chemical No. | Structure | MS (ESI) m/z [M + H]⁺ | ¹H NMR (400 MHz, DMSO-d₆) |
|---|---|---|---|
| 36 | 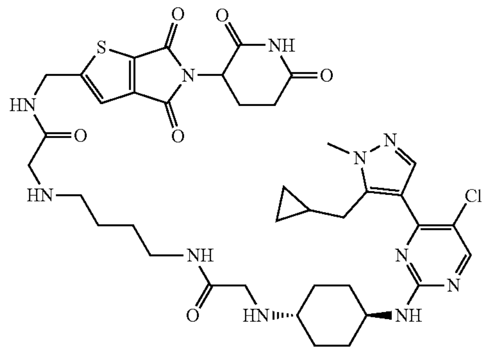 [SMILES: Cn1ncc(-c2nc(N[C@H]3CC[C@H](NCC(=O)NCCCCNCC(=O)NCc4cc5c(s4)C(=O)N(C4CCC(=O)NC4=O)C5=O)CC3)ncc2Cl)c1CC1CC1] | 822.2 | δ 11.01 (s, 1H), 9.31 (t, J = 6.0 Hz, 1H), 8.87-8.86 (m, 4H), 8.49 (t, J = 5.2 Hz, 1H), 8.29 (s, 1H), 8.03 (s, 1H), 7.45 (s, 1H), 7.27-7.24 (m, 1H), 5.04 (dd, J = 5.2, 12.8 Hz, 1H), 4.67 (d, J = 6.0 Hz, 2H), 4.56-4.53 (m, 1H), 3.86 (s, 3H), 3.17-3.12 (m, 2H), 3.04 (d, J = 6.4 Hz, 4H), 2.91-2.83 (m, 1H), 2.67-2.51 (m, 1H), 2.38-2.32 (m, 1H), 2.06-1.98 (m, 6H), 1.65-1.58 (m, 2H), 1.50-1.24 (m, 7H), 0.99 (s, 1H), 0.43 (s, 2H), 0.16 (s, 2H). |
| 37 | 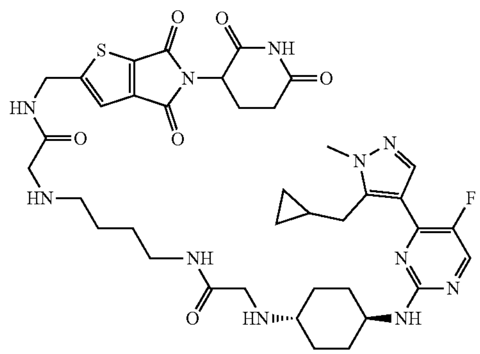 [SMILES: Cn1ncc(-c2nc(N[C@H]3CC[C@H](NCC(=O)NCCCCNCC(=O)NCc4cc5c(s4)C(=O)N(C4CCC(=O)NC4=O)C5=O)CC3)ncc2F)c1CC1CC1] | 806.2 | δ 11.09 (s, 1H), 9.27 (t, J = 6.0 Hz, 1H), 8.84 (s, 1H), 8.46 (t, J = 6.0 Hz, 1H), 8.27 (d, J = 3.6 Hz, 1H), 7.86 (d, J = 4.4 Hz, 1H), 7.45 (s, 1H), 6.98 (s, 1H), 5.03 (dd, J = 7.6, 13.2 Hz, 1H), 4.66 (d, J = 5.6 Hz, 2H), 3.87 (s, 3H), 3.82-3.80 (m, 1H), 3.72-3.70 (m, 1H), 3.64 (s, 1H), 3.20-3.15 (m, 4H), 3.03-2.94 (m, 3H), 2.88-2.83 (m, 2H), 2.67-2.49 (m, 1H), 2.07-2.01 (m, 4H), 1.65-1.59 (m, 2H), 1.49-1.44 (m, 5H), 1.34-1.06 (m, 7H), 0.42 (d, J = 7.6 Hz, 2H), 0.25 (d, J = 4.8 Hz, 2H). |
| 38 | 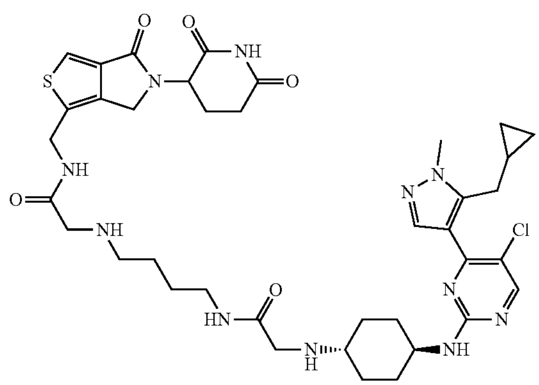 [SMILES: Cn1ncc(-c2nc(N[C@H]3CC[C@H](NCC(=O)NCCCCNCC(=O)NCc4scc5c4CN(C4CCC(=O)NC4=O)C5=O)CC3)ncc2Cl)c1CC1CC1] | 808.3 | δ 10.83 (s, 1H), 8.35 (t, J = 5.2 Hz, 1H), 8.33 (d, J = 4.0 Hz, 1H), 8.12 (d, J = 4.0 Hz, 1H), 7.76 (t, J = 5.6 Hz, 1H), 7.09 (s, 1H), 6.89 (s, 1H), 4.97 (dd, J = 5.2, 13.2 Hz, 1H), 4.52 (d, J = 5.6 Hz, 2H), 4.35-4.18 (m, 2H), 3.86 (s, 3H), 3.68-3.63 (m, 1H), 3.21 (d, J = 6.4 Hz, 2H), 3.11-3.07 (m, 6H), 2.92-2.83 (m, 1H), 2.59-2.55 (m, 2H), 2.45 (t, J = 6.8 Hz, 2H), 2.37-2.26 (m, 2H), 1.99-1.96 (m, 1H), 1.88-1.85 (m, 4H), 1.39-1.38 (m, 4H), 1.29-1.24 (m, 5H), 1.14-1.06 (m, 3H), 0.41 (d, J = 7.2 Hz, 2H), 0.23 (d, J = 4.4 Hz, 2H). |
| 39 | 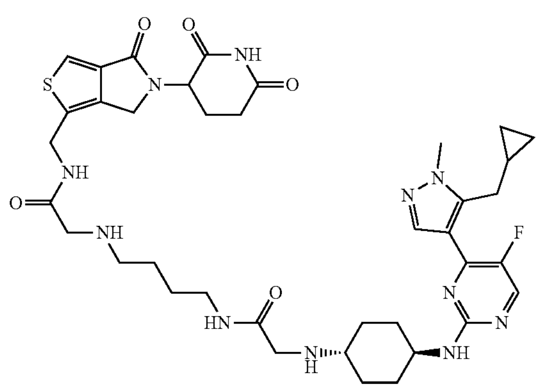 [SMILES: Cn1ncc(-c2nc(N[C@H]3CC[C@H](NCC(=O)NCCCCNCC(=O)NCc4scc5c4CN(C4CCC(=O)NC4=O)C5=O)CC3)ncc2F)c1CC1CC1] | 792.4 | δ 10.96 (s, 1H), 8.48 (t, J = 6.0 Hz, 1H), 8.24 (d, J = 4.0 Hz, 1H), 7.85-7.84 (m, 2H), 7.78 (t, J = 5.2 Hz, 1H), 6.86 (s, 1H), 5.01 (dd, J = 5.2, 13.2 Hz, 1H), 4.42 (d, J = 5.6 Hz, 2H), 4.30-4.15 (m, 2H), 3.86 (s, 3H), 3.64 (s, 1H), 3.21 (d, J = 6.8 Hz, 2H), 3.11-3.07 (m, 6H), 2.61-2.56 (m, 1H), 2.49-2.44 (m, 1H), 2.32-2.30 (m, 2H), 1.98-1.86 (m, 10H), 1.41 (s, 4H), 1.31-1.22 (m, 2H), 1.15-1.06 (m, 3H), 0.40 (d, J = 7.2 Hz, 2H), 0.23 (d, J = 4.0 Hz, 2H). |

TABLE B-continued

Exemplary Compounds of Formulas (I) and (II) and Characterization Data

| Chemical No. Structure | MS (ESI) m/z [M + H]⁺ | ¹H NMR (400 MHz, DMSO-d₆) |
|---|---|---|
| 40 | 780.3 | δ 10.93 (s, 1H), 8.56 (t, J = 6.4 Hz, 1H), 8.25 (s, 1H), 8.00 (s, 1H), 7.82 (t, J = 6.0 Hz, 1H), 7.15 (s, 1H), 7.09 (s, 1H), 4.97 (dd, J = 5.2, 13.6 Hz, 1H), 4.52 (d, J = 6.0 Hz, 2H), 4.34-4.17 (m, 2H), 3.85 (s, 3H), 3.85-3.65 (m, 1H), 3.18-3.15 (m, 5H), 3.14-3.05 (m, 4H), 2.92-2.82 (m, 1H), 2.67-2.66 (m, 3H), 2.35-2.28 (m, 3H), 2.00-1.97 (m, 1H), 1.90-1.85 (m, 8H), 1.23-1.23 (m, 3H), 1.23-0.97 (m, 4H), 0.39 (s, 2H), 0.13 (s, 2H). |
| 41 | 932.2 | δ 12.22 (s, 1H), 11.07 (s, 1H), 7.69 (s, 1H), 7.38 (s, 1H) 7.32 (s, 1H), 6.71 (s, 1H), 6.61 (t, J = 5.6 Hz, 1H), 6.15 (t, J = 5.6 Hz, 1H), 5.02 (dd, J = 5.6, 13.2 Hz, 1H), 4.46 (d, J = 5.6 Hz, 2H), 4.05 (s, 2H), 3.29-2.78 (m, 4H), 2.67-2.51 (m, 5H), 2.49-2.32 (m, 1H), 2.09-1.91 (m, 3H), 2.28-2.02(m, 2H), 1.84-1.73 (m, 4H), 1.43-1.38 (m, 4H), 1.26-1.21 (m, 2H), 1.17 (s, 9H). |
| 42 | 932.2 | δ 8.56 (t, J = 8.0 Hz, 1H), 7.71 (t, J = 8.0 Hz, 1H), 7.38 (s, 1H), 7.09 (s, 1H), 6.71 (s, 1H), 4.98 (dd, J = 6.8, 17.6 Hz, 1H), 4.52 (d, J = 8.0 Hz, 2H), 4.36-4.17 (m, 2H), 4.05 (s, 2H), 3.29-2.78 (m, 4H), 2.67-2.51 (m, 5H), 2.49-2.32 (m, 1H), 2.09-1.91 (m, 3H), 2.28-2.02 (m, 2H), 1.84-1.73 (m, 4H), 1.43-1.38 (m, 4H), 1.26-1.21 (m, 2H), 1.17 (s, 9H). |

TABLE B-continued

Exemplary Compounds of Formulas (I) and (II) and Characterization Data

| Chemical No. | Structure | MS (ESI) m/z [M + H]+ | $^1$H NMR (400 MHz, DMSO-$d_6$) |
|---|---|---|---|
| 43 | 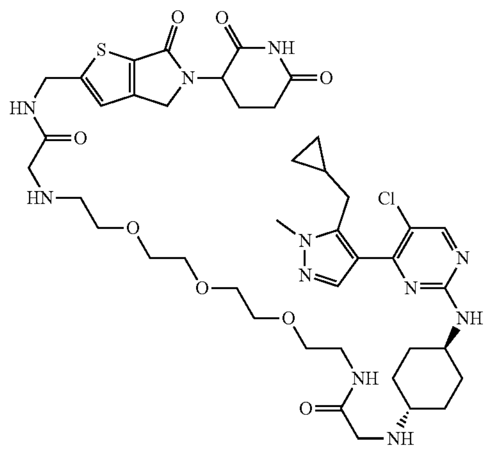 [SMILES: Cn1ncc(-c2nc(N[C@H]3CC[C@H](NCC(=O)NCCOCCOCCOCCNCC(=O)NCc4cc5c(s4)C(=O)N(C4CCC(=O)NC4=O)C5)CC3)ncc2Cl)c1CC1CC1] | 912.5 | δ 10.93 (s, 1H), 8.54 (t, J = 6.8 Hz, 1H), 8.25 (s, 1H), 8.00 (s, 1H), 7.82 (t, J = 5.6 Hz, 1H), 7.15 (s, 1H), 7.08 (s, 1H), 4.97 (dd, J = 4.8, 13.2 Hz, 1H), 4.52 (d, J = 5.6 Hz, 2H), 4.35-4.17 (m, 2H), 3.87 (s, 3H), 3.50 (s, 1H), 3.50-3.44 (m, 7H), 3.40-3.31 (m, 5H), 3.25-3.22 (m, 3H), 3.15-3.06 (m, 6H), 2.89-2.87 (m, 1H), 2.67-2.55 (m, 3H), 2.33-2.31 (m, 3H), 1.99-1.98 (m, 2H), 1.31-1.23 (m, 5H), 0.98 (s, 2H), 0.38 (s, 2H), 0.12 (s, 2H). |
| 44 | 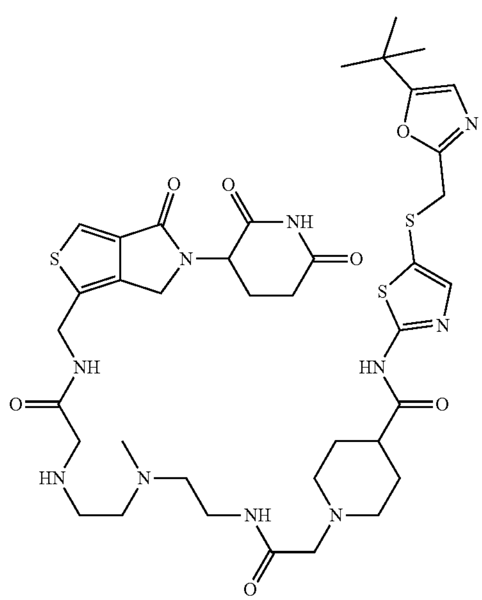 [SMILES: CN(CCNCC(=O)NCc1scc2c1CN(C1CCC(=O)NC1=O)C2=O)CCNC(=O)CN1CCC(C(=O)Nc2ncc(SCc3ncc(C(C)(C)C)o3)s2)CC1] | 856.2 | δ 12.44 (s, 1H), 11.00 (s, 1H), 9.16 (s, 1H), 8.73 (br s, 1H), 7.93 (s, 1H), 7.41 (s, 1H), 6.72 (s, 1H), 5.03 (dd, J = 5.2, 13.2 Hz, 1H), 4.51 (d, J =5.6 Hz, 2H), 4.38-4.18 (m, 2H), 4.07 (s, 2H), 3.92 (s, 2H), 3.83 (s, 2H), 3.26-3.17 (m, 4H), 3.13-3.10 (m, 4H), 2.98-2.87 (m, 1H), 2.76 (s, 1H), 2.75-2.58 (m, 3H), 2.38-2.67 (m, 1H). 2.02-1.96 (m, 5H), 1.49-1.44 (m, 5H), 1.24 (s, 1H), 1.19 (s, 9H). |

TABLE B-continued

Exemplary Compounds of Formulas (I) and (II) and Characterization Data

| Chemical No. Structure | MS (ESI) m/z [M + H]+ | $^1$H NMR (400 MHz, DMSO-$d_6$) |
|---|---|---|
| 45 | 766.3 | δ 10.96 (s, 1H), 8.25 (s, 1H) 8.02 (s, 1H), 7.87 (d, J = 5.2 Hz, 1H), 7.01 (s, 1H), 6.68 (t, J = 6.4 Hz, 1H), 6.17 (d, J = 5.2 Hz, 1H), 4.96 (dd, J = 5.2, 13.2 Hz, 1H), 4.42 (d, J = 6.0 Hz, 2H), 4.33-4.16 (m, 2H), 3.84 (s, 3H), 3.65-3.63 (m, 1H), 3.12-3.08 (m, 8H), 2.89-2.87 (m, 1H), 2.37-2.25 (m, 2H), 1.90-1.87 (m, 2H), 1.28-1.23 (m, 3H), 1.17-1.03 (m, 2H), 0.38 (s, 2H), 0.12 (s, 2H). |
| 46 | 898.4 | δ 10.93 (s, 1H), 8.23 (s, 1H), 8.01-7.07 (m, 2H), 7.17 (d, J = 7.2 Hz, 1H), 7.04 (d, J = 4.0 Hz, 1H), 6.65-6.62 (m, 1H), 6.08 (t, J = 5.6 Hz, 1H), 4.97 (dd, J = 5.2, 13.2 Hz, 1H), 4.42 (d, J = 5.6 Hz, 2H), 4.34-4.16 (m, 2H), 3.85-3.83 (m, 3H), 3.64 (s, 1H), 3.50-3.44 (m, 8H), 3.42-3.37 (m, 5H), 3.27-3.24 (m, 3H), 3.17-3.13 (m, 4H), 3.07-3.04 (m, 2H), 2.92-2.84 (m, 1H), 1.98-1.97 (m, 2H), 1.29-1.23 (m, 6H), 1.10-1.07 (m, 2H), 0.87-0.84 (m, 1H), 0.39 (s, 2H), 0.13(s, 2H). |
| 47 | 856.2 | δ 10.96 (s, 1H), 9.20 (s, 1H), 7.92 (s, 1H), 7.37 (s, 1H), 7.15 (s, 1H), 6.71 (s, 1H), 4.98 (d, J = 17.2 Hz, 1H), 4.55 (d, J = 5.2 Hz, 2H), 4.37-4.18 (m, 2H), 4.05 (s, 2H), 3.52 (s, 2H), 3.26 (s, 3H), 2.93-2.85 (m, 6H), 2.68 (s, 2H), 2.31 (m, 5H), 2.08-1.91 (m, 4H), 1.74 (s, 4H), 1.23 (s, 2H), 1.17 (s, 9H). |

TABLE B-continued

Exemplary Compounds of Formulas (I) and (II) and Characterization Data

| Chemical No. | Structure | MS (ESI) m/z [M + H]+ | 1H NMR (400 MHz, DMSO-d6) |
|---|---|---|---|
| 48 | 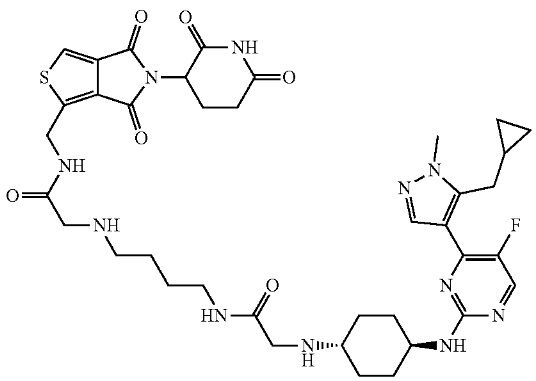 [SMILES: Cn1ncc(-c2nc(N[C@H]3CC[C@H](NCC(=O)NCCCCNCC(=O)NCc4scc5c4C(=O)N(C4CCC(=O)NC4=O)C5=O)CC3)ncc2F)c1CC1CC1] | 806.3 | δ 11.09 (s, 1H), 8.72 (s, 1H), 8.24 (t, J = 3.6 Hz, 1H), 7.84 (t, J = 4.4 Hz, 1H), 6.86 (s, 1H), 5.04 (dd, J = 5.6, 12.8 Hz, 1H), 4.67 (d, J = 4.8 Hz, 2H), 3.86 (s, 3H), 3.66-3.59 (m, 1H), 3.24-3.04 (m, 10H), 2.92-2.83 (m, 1H), 2.68-2.67 (m, 1H), 2.35-2.32 (m, 1H), 2.04-2.00 (m, 1H), 1.93-1.87 (m, 10H), 1.43 (s, 4H), 1.31-1.02 (m, 6H), 0.41 (d, J = 8.8 Hz, 2H), 0.23 (d, J = 4.8 Hz, 2H). |
| 49 | 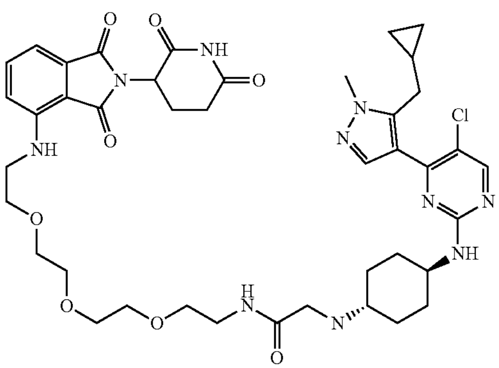 [SMILES: Cn1ncc(-c2nc(N[C@H]3CC[C@H](NCC(=O)NCCOCCOCCOCCNc4cccc5c4C(=O)N(C4CCC(=O)NC4=O)C5=O)CC3)ncc2Cl)c1CC1CC1] | 849.3 | δ 11.07 (s, 1H) 8.25 (s, 1H) 8.00-7.85 (m, 2H), 7.57 (t, J = 8.0 Hz, 1H), 7.14-7.03 (m, 3H), 6.59 (t, J = 5.6 Hz, 1H), 5.04 (dd, J = 7.6, 12.8 Hz, 1H), 3.85 (s, 3H), 3.62-3.39 (m, 16H), 3.26 (s, 2H), 3.26-3.24 (m, 2H), 3.11-3.06 (m, 4H), 2.93-2.83 (m, 1H), 2.60-2.56 (m, 1H), 2.32 (s, 1H), 2.03-1.97 (m, 1H), 1.91-1.81 (m, 3H), 1.11-0.97 (m, 3H), 0.39-0.38 (m, 2H), 0.13-0.12 (m, 2H). |
| 50 | 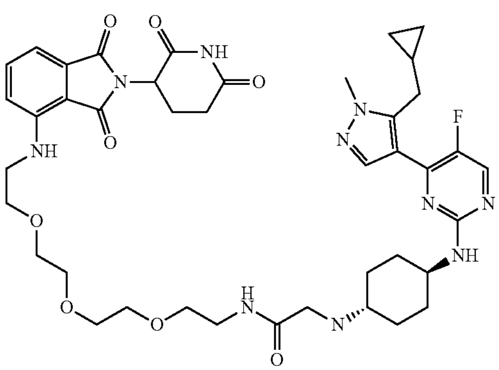 [SMILES: Cn1ncc(-c2nc(N[C@H]3CC[C@H](NCC(=O)NCCOCCOCCOCCNc4cccc5c4C(=O)N(C4CCC(=O)NC4=O)C5=O)CC3)ncc2F)c1CC1CC1] | 833.3 | δ 10.87 (s, 1H), 8.00 (d, J = 3.6 Hz, 1H), 7.61-7.60 (m, 2H), 7.34 (t, J = 7.2 Hz. 1H), 6.89 (d, J = 8.8 Hz, 1H), 6.79 (d, J = 6.8 Hz, 1H), 6.65 (s, 1H), 6.36 (t, J = 5.6 Hz, 1H), 4.81 (dd, J = 7.6, 12.8 Hz, 1H), 3.62 (s, 3H), 3.36-3.16 (m, 15H), 3.03-2.96 (m, 4H), 2.88 (s, 2H), 2.69-2.60 (m, 1H), 2.33-2.30 (m, 1H), 2.09-2.04 (m, 1H), 1.80-1.77 (m, 1H), 1.67-1.62 (m, 4H), 1.06-0.77 (m, 5H), 0.18-0.16 (m, 2H), 0.01-0 (m, 2H). |
| 51 | 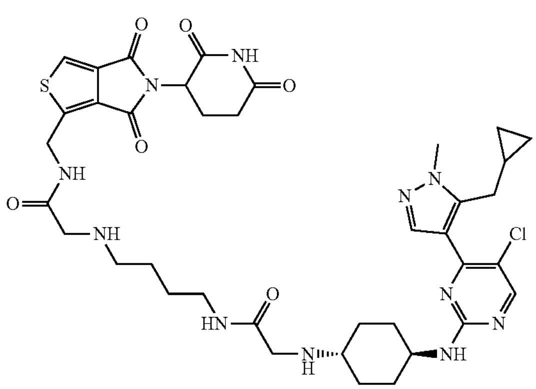 [SMILES: Cn1ncc(-c2nc(N[C@H]3CC[C@H](NCC(=O)NCCCCNCC(=O)NCc4scc5c4C(=O)N(C4CCC(=O)NC4=O)C5=O)CC3)ncc2Cl)c1CC1CC1] | 822.2 | δ 11.11 (s, 1H), 8.71-8.69 (m, 1H), 8.25-8.23 (m, 2H), 8.04-8.00 (m, 1H), 7.79-7.76 (m, 1H), 7.19-7.17 (m, 1H), 5.04 (dd, J = 4.8, 12.0 Hz, 1H), 4.67 (d, J = 4.8 Hz, 2H), 3.85 (s, 3H), 3.69-3.62 (m, 1H), 3.16 (s, 2H), 3.08 (s, 6H), 3.88-2.82 (m, 1H), 2.67-2.58 (m, 1H), 1.90-1.86 (m, 10H), 1.42 (s, 4H), 1.31-1.23 (m, 2H), 1.12-0.94 (m, 3H), 0.39 (d, J = 4.0 Hz, 2H), 0.12 (d, J = 1.6 Hz, 2H). |

TABLE B-continued

Exemplary Compounds of Formulas (I) and (II) and Characterization Data

| Chemical No. Structure | MS (ESI) m/z [M + H]+ | $^1$H NMR (400 MHz, DMSO-d$_6$) |
|---|---|---|
| 52 | 814.1 | δ 10.95 (s, 1H), 8.52 (t, J = 6.0 Hz, 1H), 7.78 (t, J = 5.2 Hz, 1H), 7.38 (s, 1H), 7.09 (s, 1H), 6.71 (s, 1H), 4.97 (t, J = 5.6 Hz, 1H), 4.97 (dd, J = 5.2, 13.2 Hz, 1H), 4.54-4.49 (m, 1H), 4.36-4.16 (m, 2H), 4.05 (m, 2H), 3.28-3.12 (m, 6H), 2.91-2.82 (m, 4H), 2.08-2.03 (m, 2H), 1.89-1.78 (m, 3H), 1.72-1.69 (m, 3H), 1.59-1.58 (m, 1H), 1.24-1.17 (m, 7H). |
| 53 | 793.3 | δ 8.49 (t, J = 6.0 Hz, 1 H), 8.25 (s, 1 H), 8.01 (brs, 1 H), 7.13 (brs, 1 H), 7.09 (s, 1 H), 4.97 (dd, J = 4.8, 13.2 Hz, 1 H), 4.52 (d, J = 6.0 Hz, 2 H), 4.35-4.17 (m, 2 H), 3.85 (s, 3 H), 3.65-3.64 (m, 2 H), 3.10-3.07 (m, 4 H), 2.90-2.84 (m, 1 H), 2.60-2.58 (m, 1 H), 2.46-2.39 (m, 3 H), 2.36-2.32 (m, 3 H), 1.99-1.96 (m, 1 H), 1.90-1.87 (m, 11 H), 1.36-1.31 (m, 4 H), 1.29-1.25 (m, 2 H), 1.10-0.97 (m, 3 H), 0.39-0.38 (m, 2 H), 0.14-0.12 (m, 2 H). |
| 54 | 877.2 | |
| 55 | 835.3 | |

TABLE B-continued

Exemplary Compounds of Formulas (I) and (II) and Characterization Data

| Chemical No. Structure | MS (ESI) m/z [M + H]+ | 1H NMR (400 MHz, DMSO-d6) |
|---|---|---|
| 56 | 819.3 | |
| 57 | 813.2 | |
| 58 | 919.2 | |

TABLE B-continued
Exemplary Compounds of Formulas (I) and (II) and Characterization Data
| Chemical No. Structure | MS (ESI) m/z [M + H]+ | 1H NMR (400 MHz, DMSO-d6) |
|---|---|---|
| 59 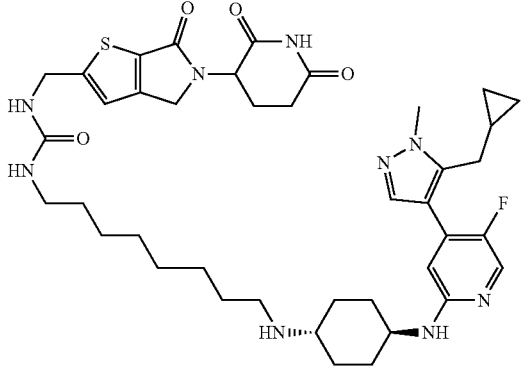 [SMILES: Cn1ncc(-c2cc(N[C@H]3CC[C@H](NCCCCCCCCNC(=O)NCc4cc5c(s4)C(=O)N(C4CCC(=O)NC4=O)C5)CC3)ncc2F)c1CC1CC1] | 776.3 | |
| 60 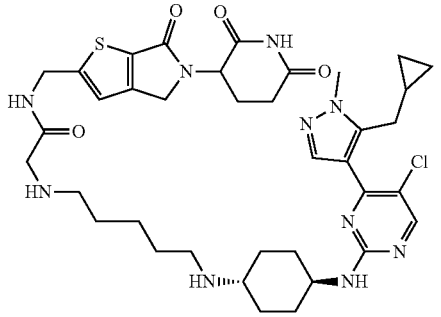 [SMILES: Cn1ncc(-c2nc(N[C@H]3CC[C@H](NCCCCCNCC(=O)NCc4cc5c(s4)C(=O)N(C4CCC(=O)NC4=O)C5)CC3)ncc2Cl)c1CC1CC1] | 765.3 [M + ]+ | |
| 61 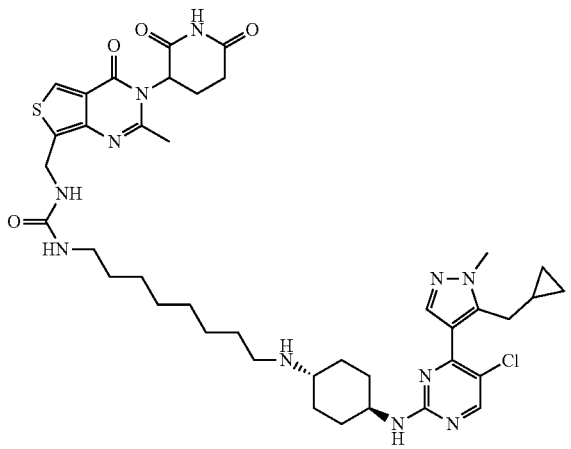 [SMILES: Cc1nc2c(CNC(=O)NCCCCCCCCN[C@H]3CC[C@H](Nc4ncc(Cl)c(-c5cnn(C)c5CC5CC5)n4)CC3)scc2c(=O)n1C1CCC(=O)NC1=O] | 820.4 | δ 8.25 (s, 1H), 8.22 (s, 1H), 7.99 (s, 1H), 7.17-7.15 (m, 1H), 6.44-6.40 (m, 1H), 5.95 (t, J = 5.6 Hz, 1H), 5.84-5.80 (m, 1H), 5.15 (dd, J = 5.6, 11.2 Hz, 1H), 4.55 (d, J = 6.0 Hz, 2H), 3.85 (s, 3H), 3.65-3.60 (m, 3H), 3.08-3.06 (m, 3H), 2.99-2.98 (m, 3H), 2.83-2.81 (m, 1H), 2.67-2.66 (m, 1H), 2.55 (s, 3H), 2.33-2.32 (m, 1H), 2.14-2.09 (m, 1H), 1.90-1.88 (m, 4H), 1.36-1.34 (m, 4H), 1.24 (s, 12H), 1.10-1.04 (m, 1H), 0.39-0.37(m, 2H), 0.12-011 (m, 2H). |

TABLE B-continued
Exemplary Compounds of Formulas (I) and (II) and Characterization Data
| Chemical No. Structure | MS (ESI) m/z [M + H]+ | 1H NMR (400 MHz, DMSO-d6) |
|---|---|---|
| 62 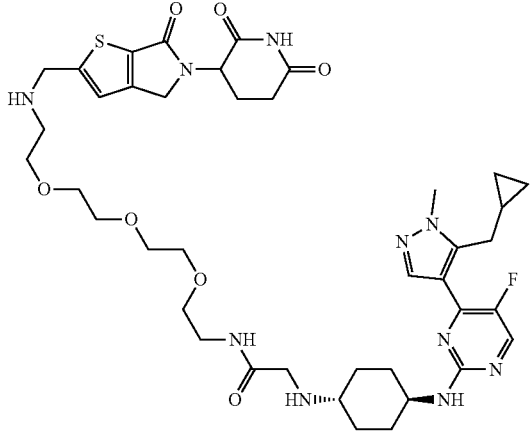 [SMILES: Cn1ncc(-c2nc(N[C@H]3CC[C@H](NCC(=O)NCCOCCOCCOCCNCc4cc5c(s4)C(=O)N(C4CCC(=O)NC4=O)C5)CC3)ncc2F)c1CC1CC1] | 839.3 | |
| 63 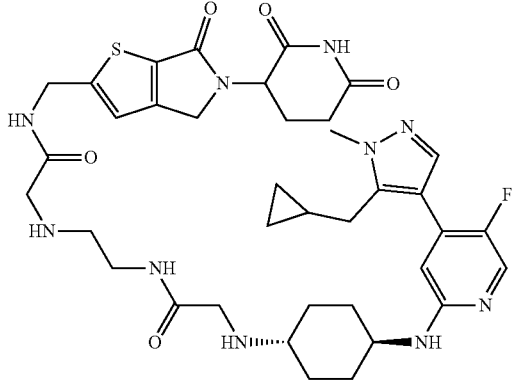 [SMILES: Cn1ncc(-c2cc(N[C@H]3CC[C@H](NCC(=O)NCCNCC(=O)NCc4cc5c(s4)C(=O)N(C4CCC(=O)NC4=O)C5)CC3)ncc2F)c1CC1CC1] | 763.3 | |
| 64 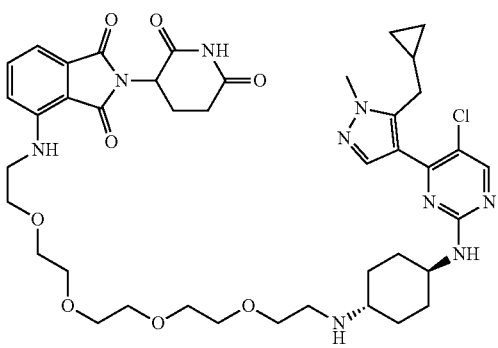 [SMILES: Cn1ncc(-c2nc(N[C@H]3CC[C@H](NCCOCCOCCOCCOCCNc4cccc5c4C(=O)N(C4CCC(=O)NC4=O)C5=O)CC3)ncc2Cl)c1CC1CC1] | 836.3 | |

TABLE B-continued
Exemplary Compounds of Formulas (I) and (II) and Characterization Data
| Chemical No. Structure | MS (ESI) m/z [M + H]+ | 1H NMR (400 MHz, DMSO-d6) |
|---|---|---|
| 65 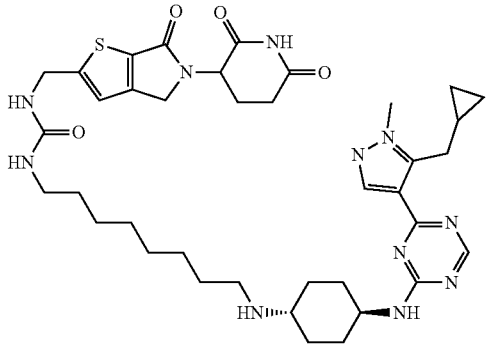 | 760.3 | |
| 66 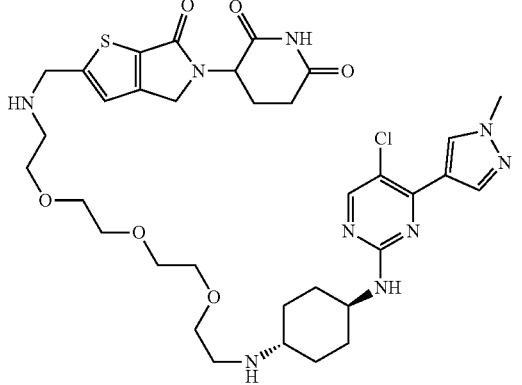 [SMILES: Cn1cc(-c2nc(N[C@H]3CC[C@H](NCCOCCOCCOCCNCc4cc5c(s4)C(=O)N(C4CCC(=O)NC4=O)C5)CC3)ncc2Cl)cn1] | 798.2 | |
| 67 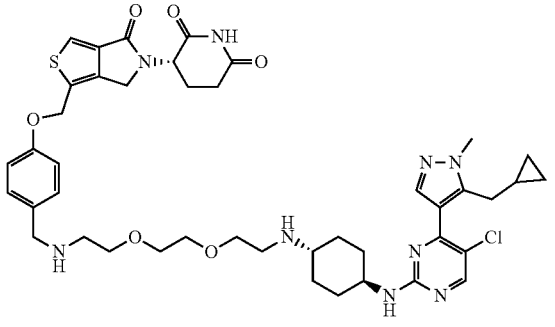 [SMILES: Cn1ncc(-c2nc(N[C@H]3CC[C@H](NCCOCCOCCNCc4ccc(OCc5scc6c5CN([C@H]5CCC(=O)NC5=O)C6=O)cc4)CC3)ncc2Cl)c1CC1CC1] | 860.3 | δ 8.25 (s, 1H), 8.00 (s, 2H), 7.24 (d, J = 8.4 Hz, 2H), 7.16 (s, 1H), 6.95 (d, J = 8.4 Hz, 2H), 5.27 (s, 2H), 5.02 (dd, J = 5.2, 13.2 Hz, 1H), 4.36-4.20 (m, 2H), 3.85 (s, 3H), 3.64 (s, 3H), 3.49-3.43 (m, 10H), 3.07 (d, J = 5.6 Hz, 2H), 2.93-2.84 (m, 1H), 2.67 (t, J = 5.2 Hz, 2H), 2.62 (t, J = 5.6 Hz, 2H), 2.57-2.55 (m, 1H), 2.39-2.31 (m, 2H), 1.99-1.97 (m, 1H), 1.90-1.87 (m, 3H), 1.34-1.24 (m, 3H), 1.06-0.97 (m, 3H), 0.39 (s, 2H), 0.12 (s, 2H). |
| 68 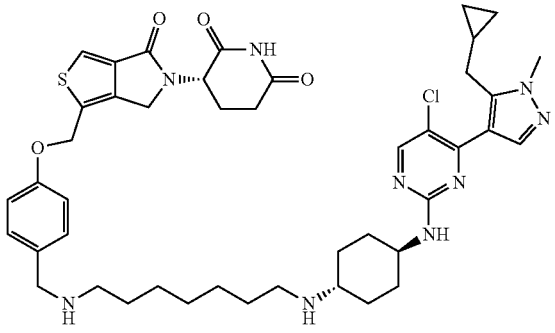 [SMILES: Cn1ncc(-c2nc(N[C@H]3CC[C@H](NCCCCCCCNCc4ccc(OCc5scc6c5CN([C@H]5CCC(=O)NC5=O)C6=O)cc4)CC3)ncc2Cl)c1CC1CC1] | 842.3 | |

TABLE B-continued

Exemplary Compounds of Formulas (I) and (II) and Characterization Data

| Chemical No. | Structure | MS (ESI) m/z [M + H]⁺ | ¹H NMR (400 MHz, DMSO-d₆) |
|---|---|---|---|
| 69 | 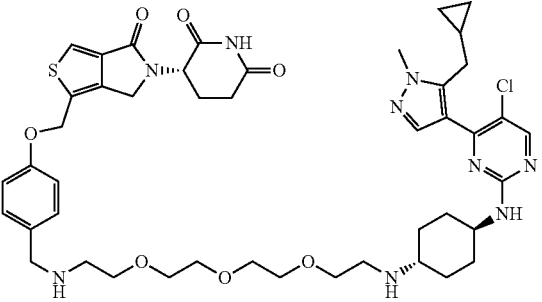 [SMILES: Cn1ncc(-c2nc(N[C@H]3CC[C@H](NCCOCCOCCOCCNCc4ccc(OCc5scc6c5CN([C@H]5CCC(=O)NC5=O)C6=O)cc4)CC3)ncc2Cl)c1CC1CC1] | 904.3 | |
| 70 | 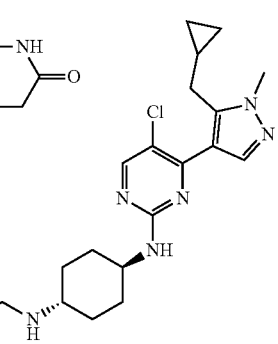 | 802.3 | δ 8.25 (s, 1H), 8.01 (s, 1H), 7.40-7.33 (m, 2H), 7.15 (d, J = 5.6 Hz, 1H), 5.15 (dd, J = 4.8 Hz, 13.2 Hz, 2H), 4.52 (dd, J = 17.2, 67.2 Hz, 1H), 3.85 (s, 3H), 3.15-3.068 (m, 2H), 2.96-2.88 (m, 3H), 2.61-2.53 (m, 4H), 2.44-2.38 (m, 2H), 2.28-2.25 (m, 2H), 2.06-1.98 (m, 8H), 1.90-1.72 (m, 4H), 1.42-1.27 (m, 4H), 1.27-1.13 (m, 8H), 1.10-1.07 (m, 2H, 0.97 (s, 1H), 0.39 (s, 2H), 0.12 (s, 2H). |
| 71 | 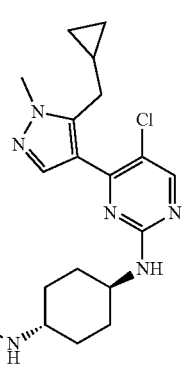 | 836.3 | |
| 72 | 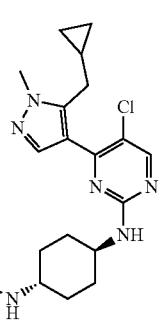 | 899.0 | |

Biological Assays

Western Blot Analysis

MV-4-11 cells were grown in RPMI 1640 media supplemented with 10% fetal bovine serum, streptomycin and penicillin.

Cells were cultured at approximately 10⁶ cells per mL and incubated in DMSO or the indicated compound for 6-8 h. Whole cell extracts were prepared using RIPA buffer according to manufacturer's protocol (Pierce). Briefly, 3×10⁶ cells were washed once in PBS, the cell pellets were resuspended in RIPA buffer and allowed to incubate for 15 minutes on ice. Cells debris was removed by centrifugation and the cleared whole cell lysates were transferred to new tubes for further analysis.

For Western blot analysis, whole cell protein extracts were separated on 4-12% SDS-polyacrylamide gels, transferred to nitrocellulose and probed with the indicated primary antibodies. Membranes were subsequently washed and probed with the appropriate IRDye secondary antibodies (LI-COR). The signal was detected using the Odyssey Imaging System (LI-COR).

The following antibodies were used in these studies: Anti-eRF3/GSPT1: Abcam, ab126090 (Cambridge, Mass.); Anti-Ikaros: Abcam, ab191394 (Cambridge, Mass.); Anti-CK1a: Abcam, ab108296 (Cambridge, Mass.); Anti-CDK9: Santa Cruz Biotechnology, sc13130 (Dallas, Tex.); Anti-CDK16: Millipore Sigma, HPA001366 (St. Louis, Mo.); β-actin (8H10comD10) mouse monoclonal antibody: Cell Signaling Technology, #3700 (Danvers, Mass.); IRDye 680RD Goat anti-rabbit antibody: LI-COR, 926-68071 (Lincoln, Nebr.); IRDye 800CW Goat anti-mouse antibody: LI-COR, 926-32210 (Lincoln, Nebr.).

IKAROS activities are shown in Table 1. CK1α activities are shown in Table 2. GSPT1 activities are shown in Table 3. CDK9 activities are shown in Table 4 at two different concentrations. CDK16 activities are shown in Table 5 at two different concentrations. In each of Tables 1-5, the % degradation values are reported as "A", "B", "C", or "D". "A" represents a % degradation value of less than 25% (value<25%). "B" represents a % degradation value of equal to or more than 25% and less than 50% (25%≤value<50%). "C" represents a % degradation value of equal to or more than 50% and less than 75% (50%≤value<75%). "D" represents a % degradation value of equal to or more than 75% (value≥75%).

TABLE 1

Activity of Compounds in IKAROS degradation assay. Compounds tested at 1 µM.

| Compound No. | IKAROS % Degradation at 1 µM |
|---|---|
| 2 | B |
| 6 | B |
| 7 | A |
| 8 | C |
| 10 | C |
| 14 | A |
| 18 | B |
| 20 | C |
| 21 | D |
| 24 | B |
| 25 | B |
| 26 | C |
| 27 | B |
| 28 | C |
| 29 | C |
| 30 | C |
| 32 | C |
| 33 | C |
| 34 | C |
| 35 | C |
| 37 | B |
| 38 | B |
| 39 | B |
| 40 | C |
| 41 | C |
| 42 | B |
| 45 | B |
| 49 | C |
| 50 | D |
| 51 | C |
| 52 | B |
| 54 | C |
| 55 | D |
| 56 | C |
| 57 | B |
| 58 | A |
| 61 | B |
| 63 | B |
| 64 | D |
| 67 | B |
| 68 | D |
| 69 | D |

TABLE 2

Activity of Compounds in CK1α degradation assay. Compounds tested at 1 µM.

| Compound No. | CK1α % Degradation at 1 µM |
|---|---|
| 3 | B |
| 6 | A |
| 7 | A |
| 9 | A |
| 11 | B |
| 18 | C |
| 22 | A |
| 30 | A |
| 33 | D |
| 34 | B |
| 35 | B |
| 37 | B |
| 39 | B |
| 40 | B |
| 41 | C |
| 45 | A |
| 50 | B |
| 51 | B |
| 52 | B |
| 54 | C |
| 55 | B |
| 56 | B |
| 58 | D |
| 64 | B |
| 65 | C |
| 67 | B |
| 69 | C |

TABLE 3

Activity of Compounds in GSPT1 degradation assay. Compounds tested at 1 µM.

| Compound No. | GSPT1 % Degradation at 1 µM |
|---|---|
| 4 | B |
| 8 | A |
| 9 | C |
| 11 | B |
| 14 | B |
| 18 | C |
| 28 | A |

TABLE 3-continued

Activity of Compounds in GSPT1 degradation assay. Compounds tested at 1 μM.

| Compound No. | GSPT1 % Degradation at 1 μM |
|---|---|
| 29 | A |
| 30 | C |
| 32 | B |
| 33 | D |
| 34 | C |
| 35 | D |
| 37 | C |
| 38 | C |
| 39 | C |
| 40 | D |
| 41 | D |
| 43 | C |
| 45 | B |
| 49 | A |
| 50 | C |
| 51 | B |
| 52 | C |
| 55 | C |
| 63 | A |
| 64 | D |
| 65 | B |
| 66 | C |
| 67 | C |
| 68 | D |

TABLE 4

Activity of Compounds in CDK9 degradation assay. Compounds tested at 0.1 μM and 1 μM.

| Compound No. | CDK9 % Degradation at 0.1 μM | CDK9 % Degradation at 1 μM |
|---|---|---|
| 12 | D | D |
| 13 | C | D |
| 14 | B | D |
| 15 | C | D |
| 16 | C | D |
| 17 | C | D |
| 22 | C | D |
| 23 | D | D |
| 24 | C | D |
| 25 | C | C |
| 26 | C | D |
| 29 | B | C |
| 30 | C | C |
| 31 | B | D |
| 32 | C | D |
| 33 | D | D |
| 34 | A | D |
| 35 | B | B |
| 36 | A | B |
| 38 | C | D |
| 39 | B | D |
| 40 | C | D |
| 41 | C | D |
| 42 | B | D |

TABLE 5

Activity of Compounds in CDK16 degradation assay. Compounds tested at 0.1 μM and 1 μM.

| Compound No. | CDK16 % Degradation at 0.1 μM | CDK16 % Degradation at 1 μM |
|---|---|---|
| 12 | B | B |
| 13 | A | A |
| 14 | A | B |
| 15 | A | A |
| 16 | D | D |
| 17 | C | C |
| 22 | A | C |
| 23 | C | D |
| 24 | C | D |
| 25 | C | C |
| 26 | B | A |
| 29 | B | C |
| 30 | B | C |
| 31 | B | D |
| 32 | C | D |
| 33 | A | C |
| 34 | B | A |
| 35 | A | C |
| 36 | A | B |
| 38 | C | D |
| 39 | A | D |
| 40 | B | C |
| 41 | A | A |
| 42 | A | A |

Cell-Based Assay

Either frozen primary blood mononuclear cells (PBMCs) or frozen CD14+ mobilized peripheral blood monocytes were purchased from AllCells (PB003F, Normal Peripheral Blood MNC (Alameda, Calif.)). Cells were quick thawed, washed 1-time with RPMI-1640 (10% FBS/1% Pen-Strep) and plated in 96 well plates at 200,000 cells per well. Cells were pretreated with DMSO only or with the indicated compound for 1 h and then induced with 100 ng/mL lipopolysaccharide (LPS) for 18-24 h. The supernatant was analyzed for IL-1β, IL-6, and TNFα, using Meso Scale assay according to manufacturer's protocol. The negative control wells were treated with DMSO.

For the IL-2 analysis, 96 well plates were precoated with 1 μg/mL anti-human CD3 antibody (OKT3, eBioscience Inc., San Diego, Calif.). After washing with PBS, the indicated compound was added (50 μL/well) followed by PBMCs diluted at 3-4 million cells/mL (150 μL/well). Plates were incubated for 24 h and the supernatants collected for Mesoscale IL-2 analysis. IL-2 activity is measured as fold difference from the DMSO control.

IL-1β, IL-6, and TNFα activities are shown in Table 6. IL-2 activities are shown in Table 7. In Table 6, the % inhibition values are reported as "A", "B", "C", or "D". "A" represents a % inhibition value of less than 50% (value<50%). "B" represents a % inhibition value of equal to or more than 50% and less than 70% (50%≤value<70%). "C" represents a % inhibition value of equal to or more than 70% and less than 90% (70%≤value<90%). "D" represents a % inhibition value of equal or more than 90% (value≥90%). In Table 7, the fold-change values are reported as "A", "B", "C", or "D". "A" represents a fold-change value of equal to or less than 0.1 (value≤0.1). "B" represents a fold-change value of more than 0.1 and equal to or less than 0.5 (0.1<value≤0.5). "C" represents a fold-change value of more than 0.5 and equal to or less than 1 (0.5<value≤1). "D" represents a fold-change value of more than 1 (value>1).

TABLE 6

Activity of Compounds in IL-1β, IL-6, and TNF-α inhibition assays. Compounds tested at 1 μM.

| Compound No. | IL-1β % Inhibition at 1 μM | IL-6 % Inhibition at 1 μM | TNF-α % Inhibition at 1 μM |
|---|---|---|---|
| 2 | D | D | C |
| 3 | D | D | C |
| 5 | D | D | C |
| 6 | A | B | A |
| 7 | A | A | A |
| 8 | A | A | A |
| 9 | B | A | B |
| 13 | D | D | D |
| 18 | D | D | C |
| 19 | D | D | C |
| 21 | A | A | A |
| 26 | D | D | C |
| 28 | D | D | D |
| 34 | C | C | C |
| 36 | C | C | C |
| 37 | D | D | C |
| 41 | D | D | C |
| 42 | D | D | A |
| 43 | A | A | A |
| 44 | B | A | B |
| 46 | C | C | B |
| 51 | D | D | D |
| 55 | D | D | D |
| 56 | D | D | D |
| 57 | D | D | D |
| 58 | D | C | A |
| 59 | C | C | A |
| 61 | D | D | D |
| 65 | A | A | A |
| 66 | A | A | A |
| 67 | D | D | D |
| 69 | C | A | C |

TABLE 7

Activity of Compounds in IL-2 fold-change assay. Compounds tested at 1 μM.

| Compound No. | IL-2 Fold-Change at 1 μM |
|---|---|
| 2 | B |
| 3 | B |
| 9 | C |
| 13 | A |
| 18 | A |
| 21 | B |
| 26 | A |
| 28 | A |
| 34 | A |
| 37 | B |
| 41 | B |
| 42 | B |
| 46 | B |
| 51 | A |
| 55 | A |
| 56 | A |
| 57 | A |
| 58 | C |
| 59 | C |
| 61 | B |
| 63 | D |
| 65 | C |
| 67 | C |

Cell Viability Assay

MOLM-13 cells were cultured in RPMI 1640 media supplemented with 10% fetal bovine serum, streptomycin and penicillin, and were plated in walled 96-well plates at 2500 cells/well. Cells were incubated in DMSO (control) or the indicated compound for 3 days at 37° C. and 5% $CO_2$. Following the incubation period, 100 μL of CellTiterGlow (CTG) reagent (CellTiter-Glo® Luminescent Cell Viability Assay, Promega (Madison, Wis.)) was added to each well. Following a 10 minutes incubation with shaking, luminescence was measured using the EnVision Multimode plate reader.

Antiproliferative activities of compounds in MOLM-13 cell viability assay are shown in Table 8. The MOLM-13 cell viability values as % DMSO are reported as "A", "B", "C", or "D". "A" represents a % viability value of less than 50% (value<50%). "B" represents a % viability value of equal to or more than 50% and less than 70% (50%≤value<70%). "C" represents a % viability value of equal to or more than 70% and less than 90% (70%≤value<90%). "D" represents a % viability value of equal or more than 90% (value≥90%). The results indicated that the compounds inhibited cancer cell viability, such as leukemia cell viability.

TABLE 8

Activity of Compounds in MOLM-13 cell viability assays. Compounds tested at 1 μM.

| Compound No. | MOLM-13 Cell Viability % DMSO at 1 μM |
|---|---|
| 1 | D |
| 2 | D |
| 3 | D |
| 4 | D |
| 5 | D |
| 6 | A |
| 7 | A |
| 8 | C |
| 9 | A |
| 11 | D |
| 12 | D |
| 13 | D |
| 14 | D |
| 15 | C |
| 16 | D |
| 18 | D |
| 19 | C |
| 20 | D |
| 21 | D |
| 22 | D |
| 23 | D |
| 24 | D |
| 25 | D |
| 26 | D |
| 27 | D |
| 28 | D |
| 29 | D |
| 30 | D |
| 31 | D |
| 32 | D |
| 33 | D |
| 34 | D |
| 35 | D |
| 36 | B |
| 37 | B |
| 38 | D |
| 39 | D |
| 40 | C |
| 41 | C |
| 42 | C |
| 43 | B |
| 44 | B |
| 45 | D |
| 46 | D |
| 47 | C |
| 48 | D |
| 49 | D |
| 50 | D |

TABLE 8-continued
Activity of Compounds in MOLM-13 cell viability assays. Compounds tested at 1 μM.
| Compound No. | MOLM-13 Cell Viability % DMSO at 1 μM |
|---|---|
| 51 | D |
| 52 | D |
| 53 | D |
| 54 | D |
| 55 | D |
| 56 | D |
| 57 | D |
| 58 | B |
| 59 | D |
| 60 | D |
| 61 | D |
| 62 | D |
| 63 | D |
| 64 | D |
| 65 | A |
| 66 | B |
| 67 | D |
| 68 | D |
| 69 | A |
What is claimed is:
1. A compound of Formula (II):
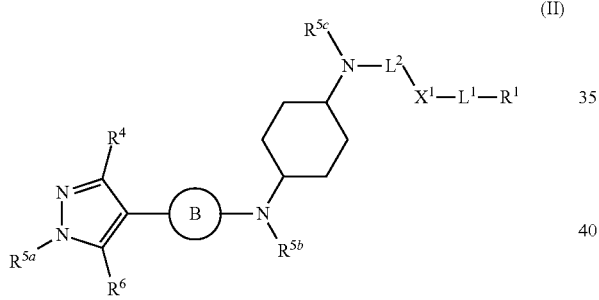
(II)
or a pharmaceutically acceptable salt thereof, wherein:
$R^1$ is
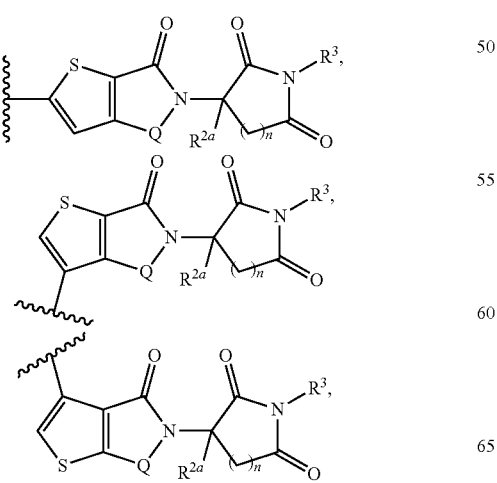
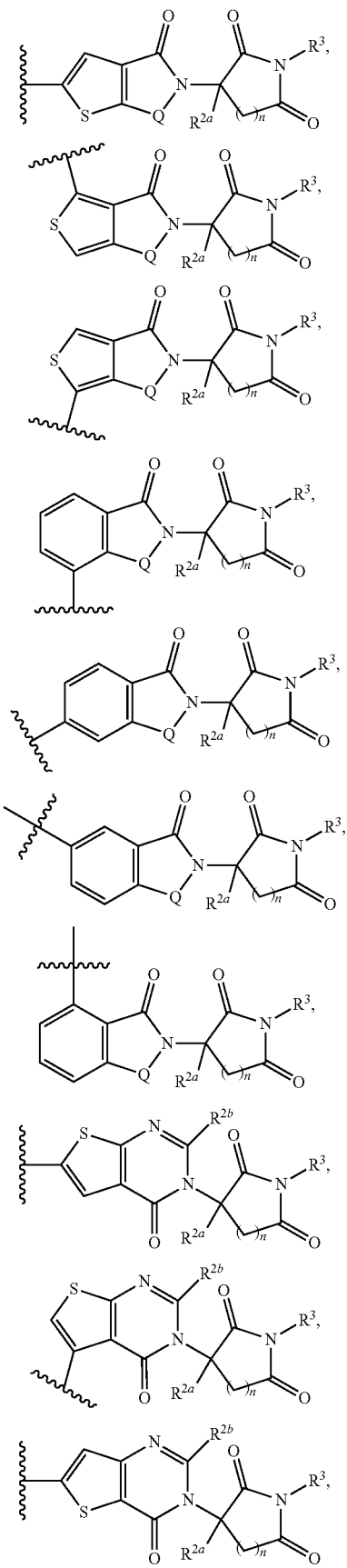

-continued

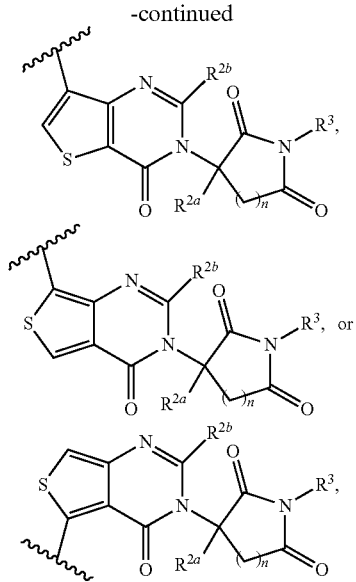

wherein $R^1$ is optionally substituted with one or more $R^4$;
each n is independently an integer of 1, 2 or 3;
each $R^{2a}$ and $R^{2b}$ is independently H, deuterium, halogen, or $C_1$-$C_6$ alkyl;
each $R^3$ is independently H, deuterium, $C_1$-$C_6$ alkyl,

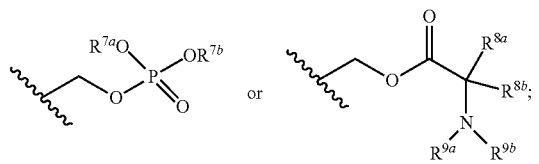

each $R^A$ is independently deuterium, hydroxyl, halogen, cyano, nitro, optionally substituted $C_1$-$C_6$ alkyl, $C_2$-$C_6$ alkenyl, $C_2$-$C_6$ alkynyl, $C_1$-$C_6$ alkoxy, $C_1$-$C_6$ haloalkyl, $C_1$-$C_6$ haloalkoxy, optionally substituted amino, $C_1$-$C_6$ alkylamino, amino($C_1$-$C_6$ alkyl), —(C=O)$NR^{10a}R^{10b}$, ($C_1$-$C_6$ alkoxy)$C_1$-$C_6$ alkyl, —O—($C_1$-$C_6$ alkoxy)$C_1$-$C_6$ alkyl, or optionally substituted $C_3$-$C_7$ cycloalkyl;
each of $R^4$ and $R^6$ is independently H, halogen, $C_1$-$C_6$ alkyl, $C_1$-$C_6$ haloalkyl, $C_1$-$C_6$ alkoxy, $C_1$-$C_6$ haloalkoxy, optionally substituted $C_3$-$C_7$ cycloalkyl ($C_1$-$C_3$ alkyl), or optionally substituted $C_3$-$C_7$ cycloalkyl;
each of $R^{5a}$, $R^{5b}$, and $R^{5c}$ is independently H or $C_1$-$C_6$ alkyl;
each of $R^{7a}$ and $R^{7b}$ is independently H, optionally substituted $C_1$-$C_6$ alkyl, optionally substituted $C_2$-$C_6$ alkenyl, optionally substituted $C_2$-$C_6$ alkynyl, optionally substituted $C_6$-$C_{10}$ aryl, optionally substituted 5 to 10 membered heteroaryl, optionally substituted $C_7$-$C_{14}$ aralkyl, optionally substituted 3 to 10 membered heterocyclyl, or optionally substituted $C_3$-$C_8$ carbocyclyl;
each of $R^{8a}$ and $R^{8b}$ is independently H, halogen, $C_1$-$C_6$ alkyl, $C_1$-$C_6$ alkoxy, $C_1$-$C_6$ haloalkyl, $C_1$-$C_6$ haloalkoxy, or $C_3$-$C_8$ carbocyclyl;
each of $R^{9a}$ and $R^{9b}$ is independently H, optionally substituted $C_1$-$C_6$ alkyl, optionally substituted $C_6$-$C_{10}$ aryl, optionally substituted $C_7$-$C_{14}$ aralkyl, or optionally substituted $C_3$-$C_8$ carbocyclyl;

each $R^{10a}$ and $R^{10b}$ is independently H or $C_1$-$C_6$ alkyl; or $R^{10a}$ and $R^{10b}$ together with the nitrogen atom to which they are attached form an optionally substituted 5 or 6 membered heterocyclyl optionally substituted with one or more $R^{11}$;
each $R^{11}$ is independently $C_1$-$C_6$ alkyl, $C_1$-$C_6$ alkoxy, $C_1$-$C_6$ haloalkyl, $C_1$-$C_6$ haloalkoxy, ($C_1$-$C_6$ alkoxy)$C_1$-$C_6$ alkyl, —O—($C_1$-$C_6$ alkoxy)$C_1$-$C_6$ alkyl, optionally substituted amino, halogen, or cyano; or two geminal $R^{11}$ form oxo;

Q is $CH_2$ or $C=O$;

$L^1$ is a bond,

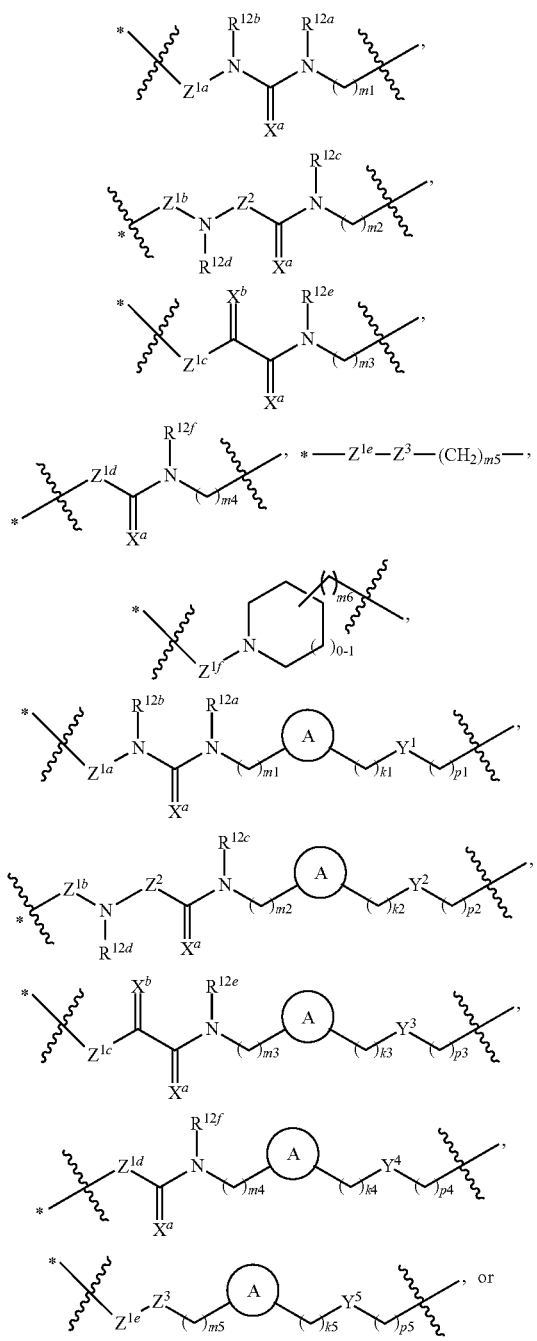

-continued

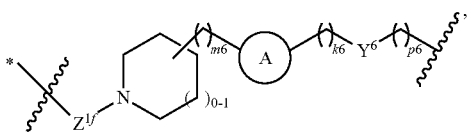

wherein the asterisk * indicates the point of connection to $X^1$;

each of $Z^{1a}$, $Z^{1b}$ $Z^{1c}$, $Z^{1d}$, $Z^{1e}$, and $Z^{1f}$ is independently a bond or —$(CR^aR^b)_{q1}$—;

$Z^2$ is —$(CR^cR^d)_{q2}$—;

$Z^3$ is a bond, O or $NR^{12g}$;

each of $R^a$, $R^b$, $R^c$ and $R^d$ is independently H, halogen, hydroxyl, $C_1$-$C_6$ alkyl, $C_1$-$C_6$ haloalkyl, $C_1$-$C_6$ alkoxy, $C_1$-$C_6$ haloalkoxy, or optionally substituted $C_3$-$C_6$ cycloalkyl;

each q1 and q2 is independently an integer of 1, 2, or 3;

each $X^a$ and $X^b$ is independently O or S;

each Ring A is independently phenyl or a five to six membered heteroaryl, each optionally substituted with one or more $R^{11}$;

each of $Y^1$, $Y^2$, $Y^3$, $Y^4$, $Y^5$ and $Y^6$ is —$NR^{12h}$—, —O—, or —S—;

each $R^{12a}$, $R^{12b}$, $R^{12c}$, $R^{12d}$, $R^{12e}$, $R^{12f}$, $R^{12g}$ and $R^{12h}$ is independently H or $C_1$-$C_6$ alkyl;

each of m1, m2, m3, m4, m5, m6, k1, k2, k3, k4, k5, k6, p1, p2, p3, p4, p5, and p6 is independently an integer of 0, 1, 2, or 3;

$L^2$ is a bond, —$(CH_2)_{1-6}NH$—, —$(CH_2)_{0-6}$—C(=O)—, or —$(CH_2)_{0-3}$—C(=O)$NR^{13}$—;

$R^{13}$ is H or $C_1$-$C_6$ alkyl;

$X^1$ is $C_1$-$C_{15}$ alkylene or heteroalkylene; and

Ring B is phenyl or a 6 membered heteroaryl, optionally substituted with one or more $R^{11}$.

2. The compound of claim 1, wherein the compound has the structure of Formula (II'):

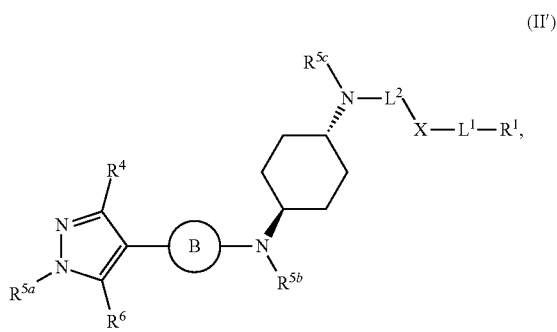

(II')

or a pharmaceutically acceptable salt thereof.

3. The compound of claim 1, wherein $R^1$ is

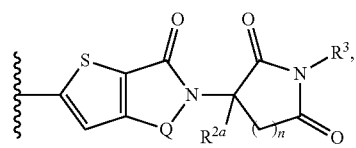

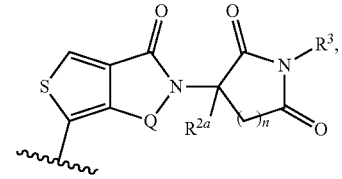

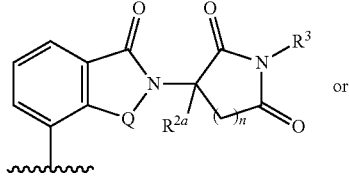

or

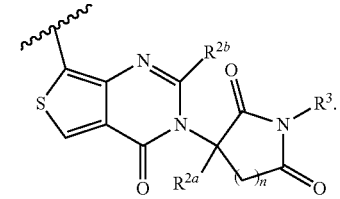

4. The compound of claim 1, wherein $R^{2a}$ is H or $R^{2b}$ is $C_1$-$C_6$ alkyl.

5. The compound of claim 1, wherein $R^3$ is H.

6. The compound of claim 1, wherein n is an integer of 2.

7. The compound of claim 1, wherein $R^1$ is substituted with one $R^4$ and wherein $R^4$ is halogen or optionally substituted $C_1$-$C_6$ alkyl.

8. The compound of claim 1, wherein each of $R^{5b}$ and $R^{5c}$ is H.

9. The compound of claim 1, wherein $L^1$ is

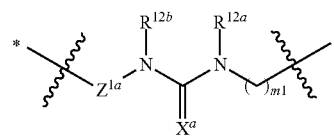

10. The compound of claim 9, wherein each of $R^{12}$ and $R^{12b}$ is H; $X^a$ is O; Zia is a bond or —$(CH_2)_{1-3}$—; and m1 is an integer of 0 or 1.

11. The compound of claim 1, wherein $L^1$ is

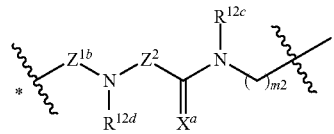

12. The compound of claim 11, wherein each of $R^{12c}$ and $R^{12d}$ is H; $X^a$ is O; $Z^2$ is —$CH_2$—; —$Z^{1b}$ is a bond or —$(CH_2)_{1-3}$—; and m2 is an integer of 0 or 1.

13. The compound of claim 1, wherein $L^1$ is *—$Z^{1e}Z^3$—$(CH_2)_{m5}$— and $Z^3$ is —$NR^{12g}$—.

14. The compound of claim 1, wherein $R^{12g}$ is H; $Z^{1e}$ is a bond or —$(CH_2)_{1-3}$—; and m5 is an integer of 0 or 1.

15. The compound of claim 1, wherein $L^1$ is

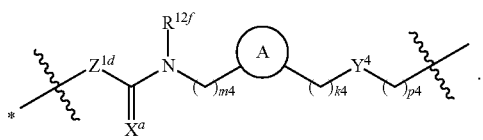

16. The compound of claim 15, wherein $R^{12f}$ is H; $Z^{1d}$ is a bond or —(CH$_2$)$_{1-3}$—; $X^a$ is O; Ring A is phenyl; $Y^4$ is —O— or —NH—; and each of k4, p4, and m4 is independently an integer of 0 or 1.

17. The compound of claim 1, wherein $L^1$ is

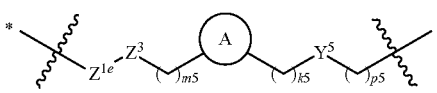

and $Z^3$ is —NR$^{12g}$—.

18. The compound of claim 17, wherein $R^{12g}$ is H; $Z^{1e}$ is a bond or —(CH$_2$)$_{1-3}$—; Ring A is phenyl; $Y^5$ is —O— or —NH—; and each of k5, p5, and m5 is independently an integer of 0 or 1.

19. The compound of claim 1, wherein $L^1$ is

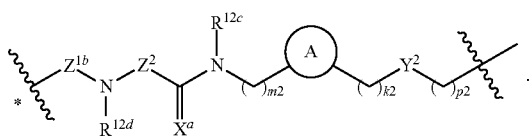

20. The compound of claim 19, wherein each of $R^{12c}$ and $R^{12d}$ is H; $X^a$ is O; $Z^{1b}$ is a bond or —(CH$_2$)$_{1-3}$—; $Z^2$ is —(CH$_2$)$_{1-3}$—; Ring A is phenyl; and each of k2, p2, and m2 is independently an integer of 0 or 1.

21. The compound of claim 1, wherein $L^1$ is

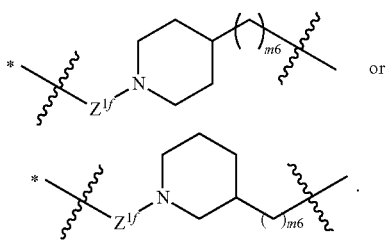

22. The compound of claim 21, wherein $Z^{1f}$ is a bond or —(CH$_2$)$_{1-3}$—; and m6 is an integer of 0 or 1.

23. The compound of claim 1, wherein $X^1$ is $C_1$-$C_8$ alkylene.

24. The compound of claim 1, wherein $X^1$ is —[(CH$_2$)$_2$O]$_{1-5}$—, —[(CH$_2$)$_2$O]$_{1-5}$(CH$_2$)$_2$—, or —(CH$_2$)$_{1-3}$—NR$^{14}$—(CH$_2$)$_{1-3}$—; and wherein $R^{14}$ is H or $C_1$-$C_6$alkyl.

25. The compound of claim 1, wherein $L^2$ is a bond, —C(O)—, or —(CH$_2$)C(O)NH—.

26. The compound of claim 1, wherein Ring B is phenyl optionally substituted with one or more $R^{11}$.

27. The compound of claim 1, wherein Ring B is a 6 membered heteroaryl selected from the group consisting of

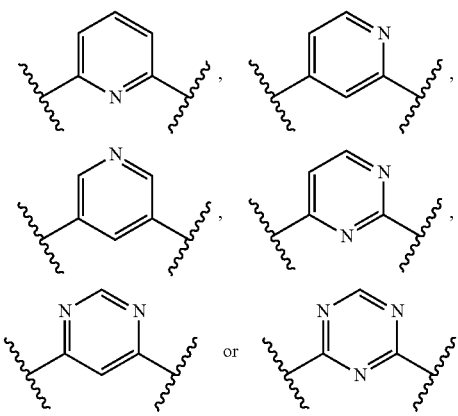

each optionally substituted with one $R^{11}$.

28. The compound of claim 27, wherein Ring B is

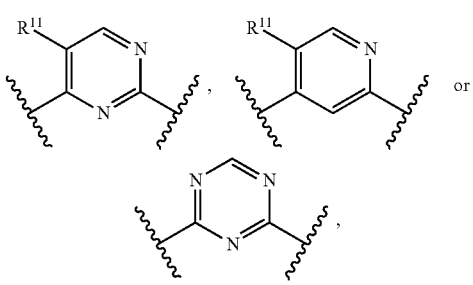

and wherein $R^{11}$ is halogen.

29. The compound of claim 1, wherein $R^{Sa}$ is methyl.

30. The compound of claim 1, one of $R^4$ and $R^6$ is H and the other of $R^4$ and $R^6$ is $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_3$-$C_6$ cycloalkyl($C_1$-$C_3$ alkyl), trifluoromethyl substituted cyclopropyl, or trifluoromethyl substituted cyclopropyl ($C_1$-$C_3$ alkyl).

31. The compound of claim 1, wherein $R^4$ is H and $R^6$ is cyclopropyl($C_1$-$C_3$ alkyl).

32. The compound of claim 1, selected from the group consisting of:

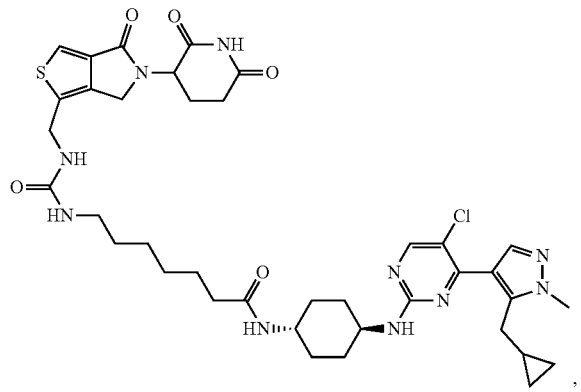

173
174
-continued
-continued
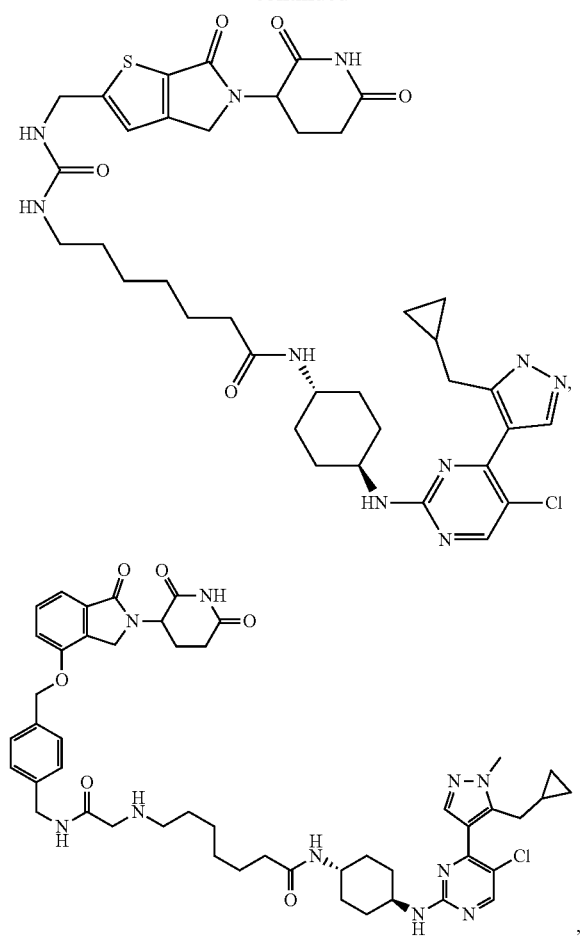
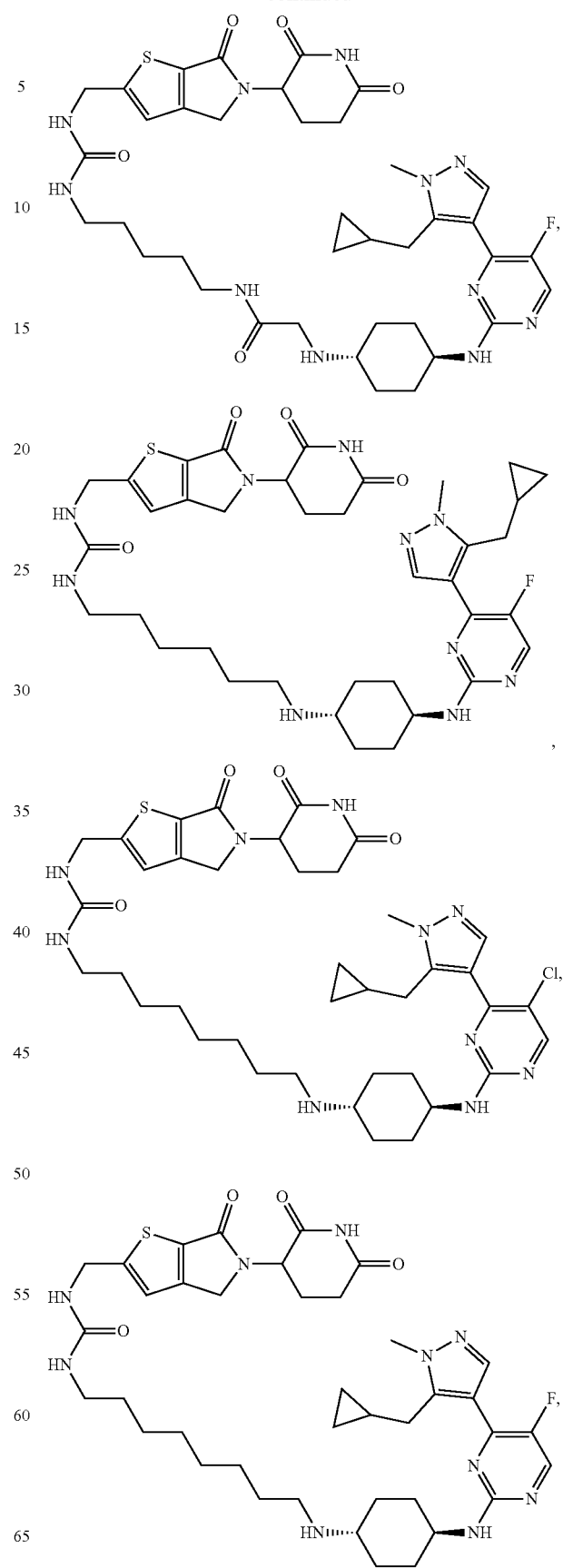

175
-continued
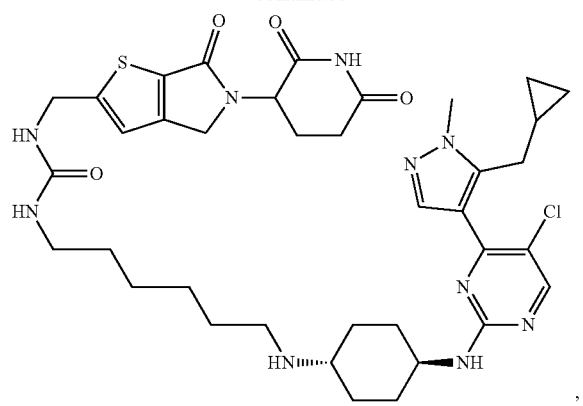
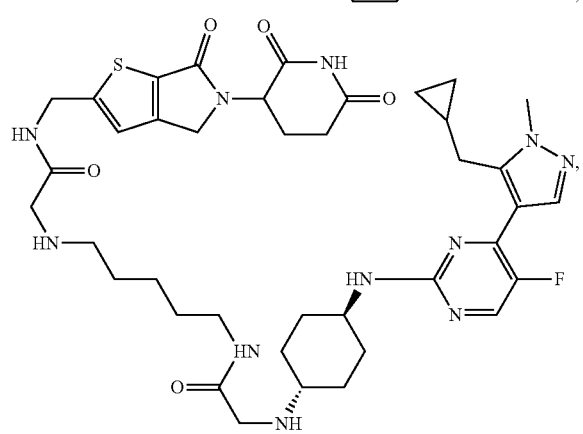
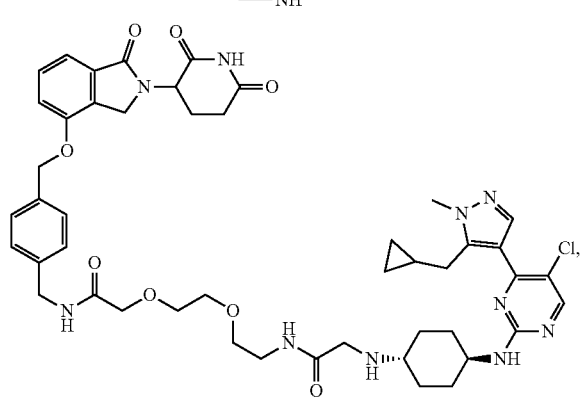
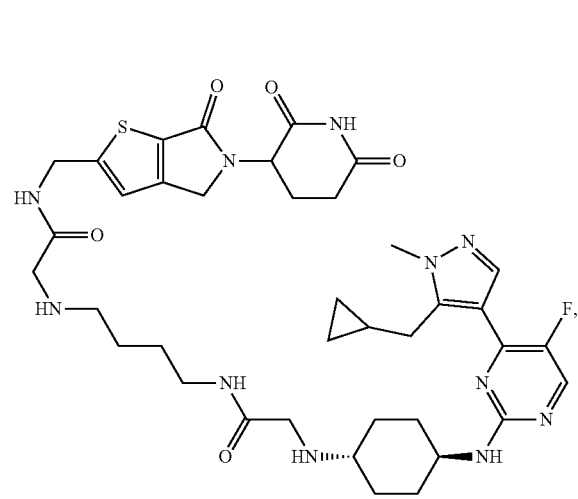
176
-continued
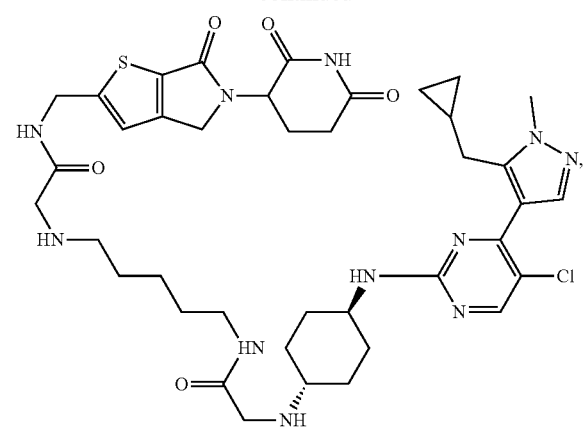
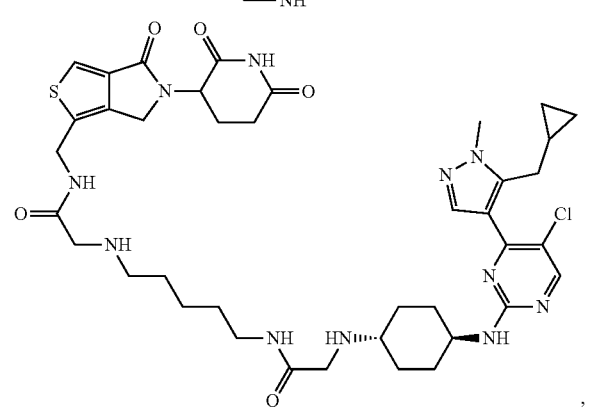
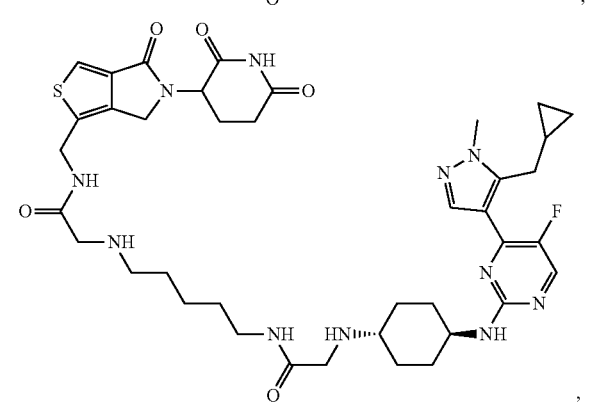
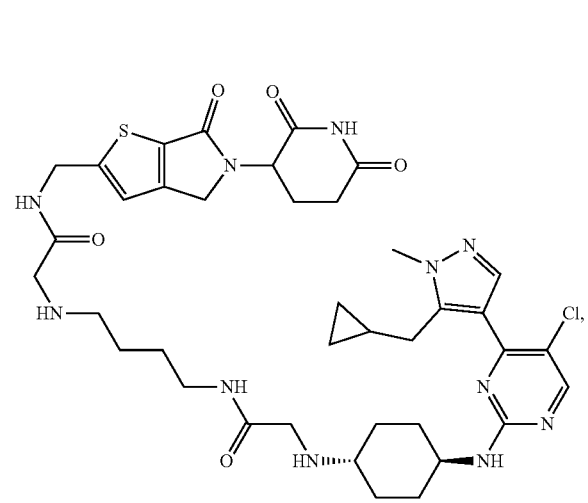

177
-continued
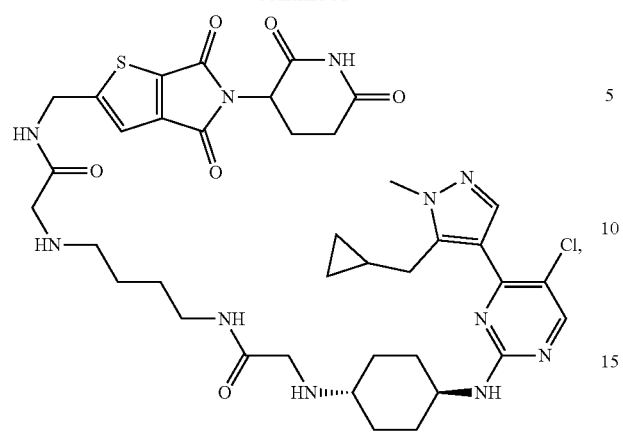
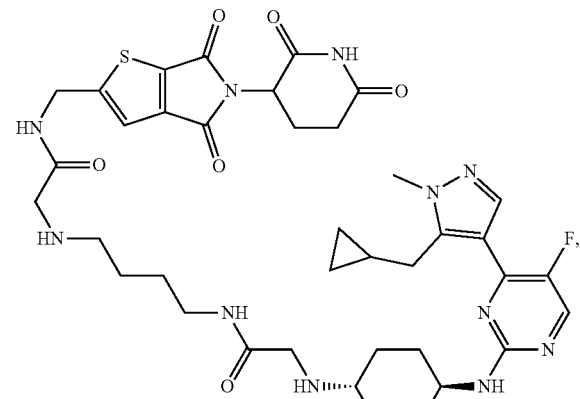
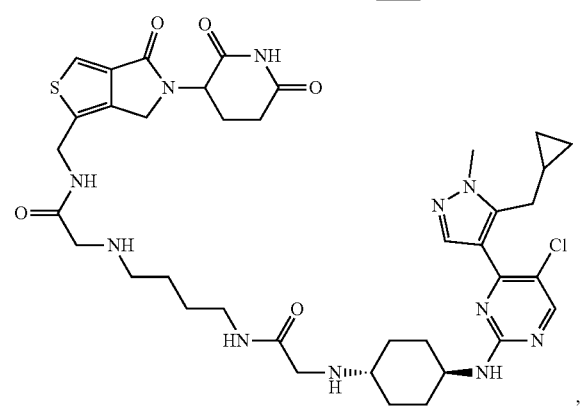
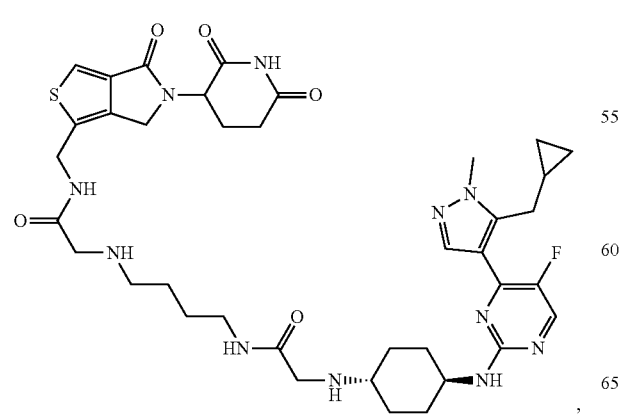
178
-continued
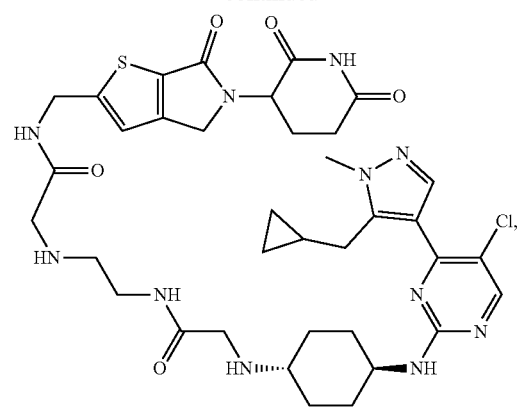
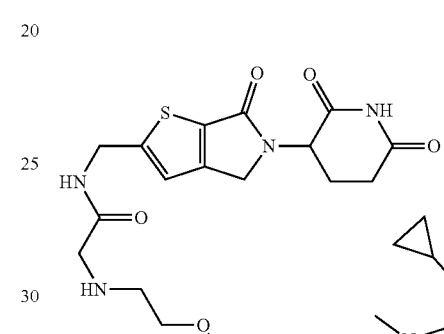
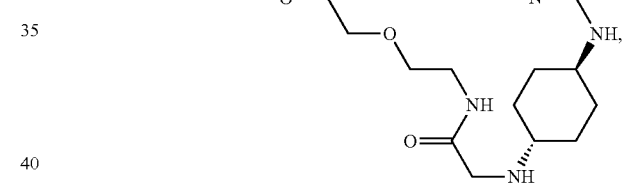
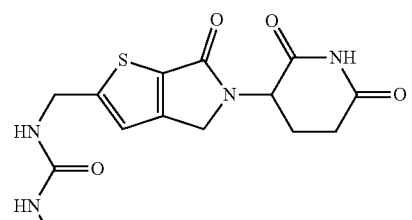
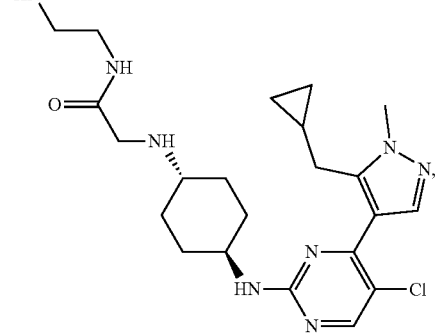

179
-continued
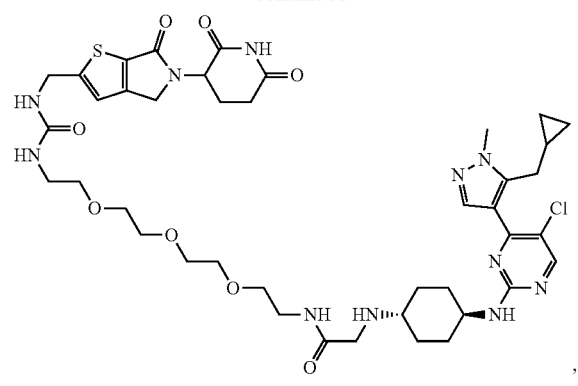
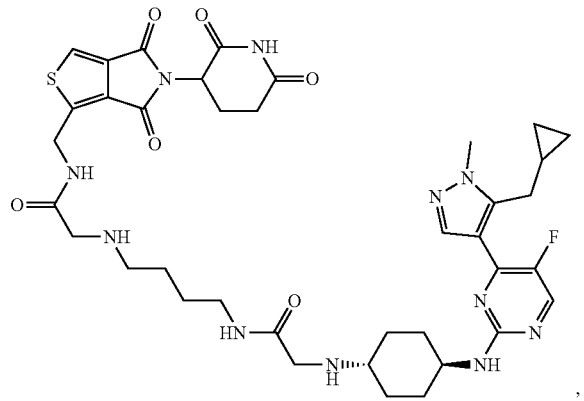
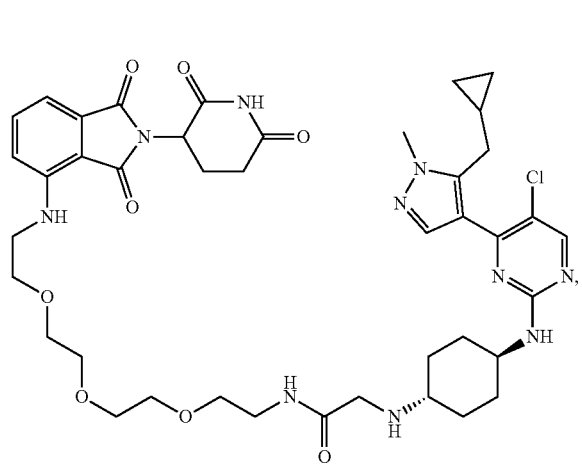
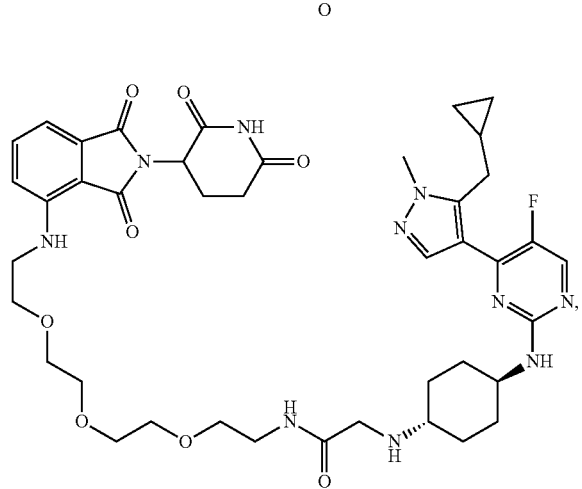
180
-continued
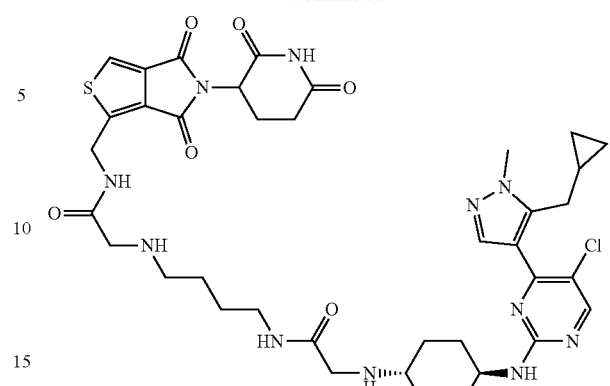
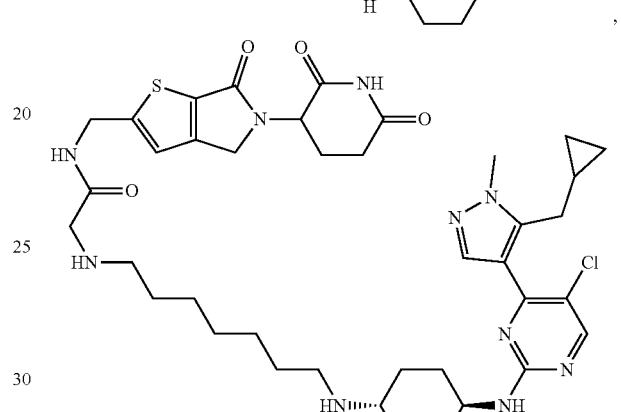
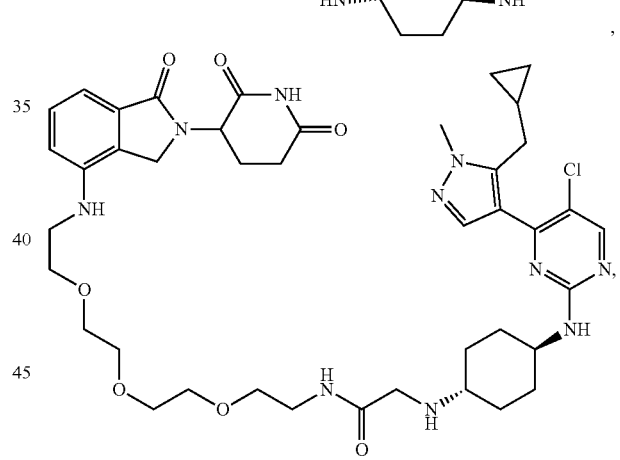
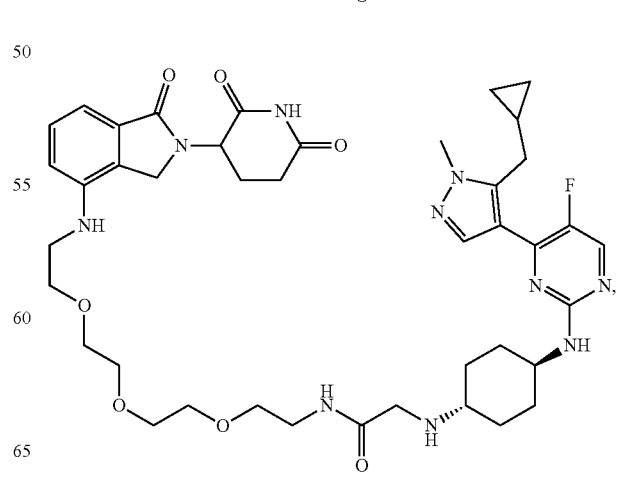

181 -continued
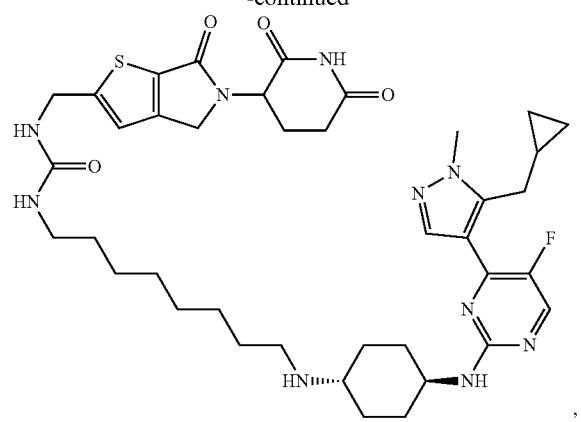
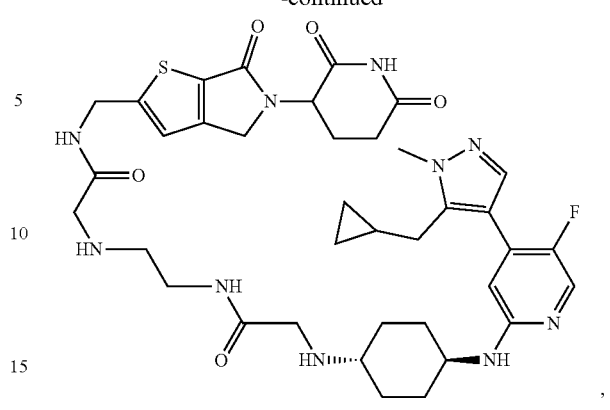
182 -continued
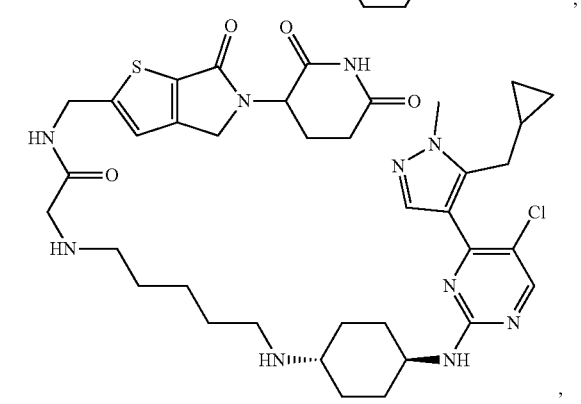
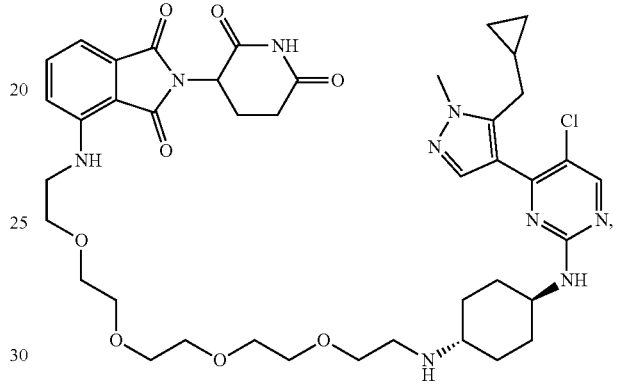
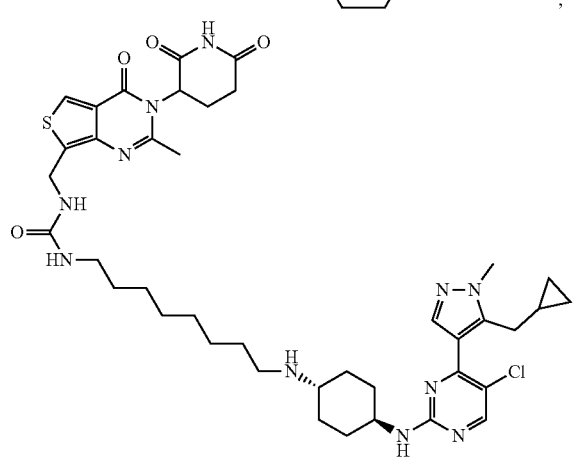
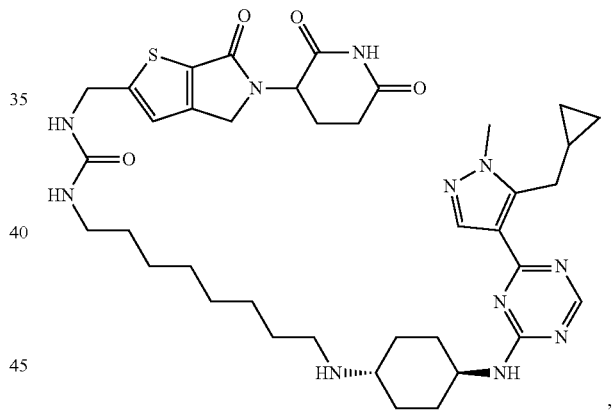
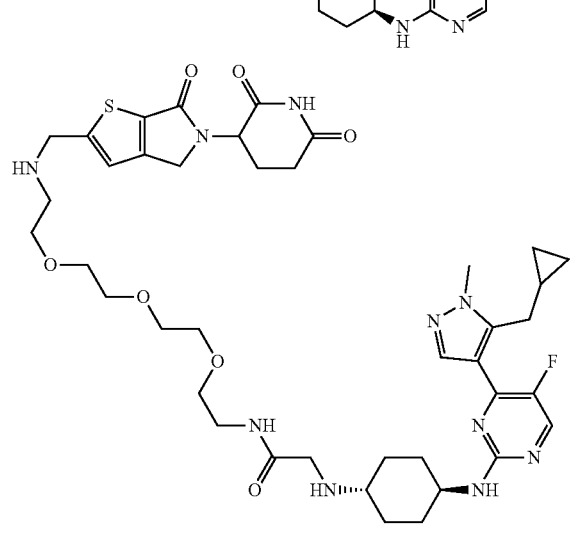
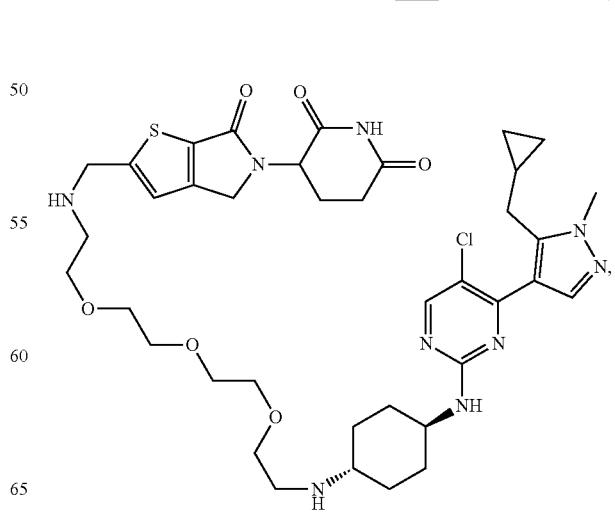

183
-continued
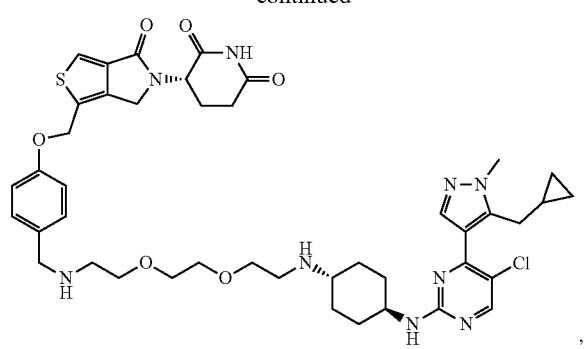
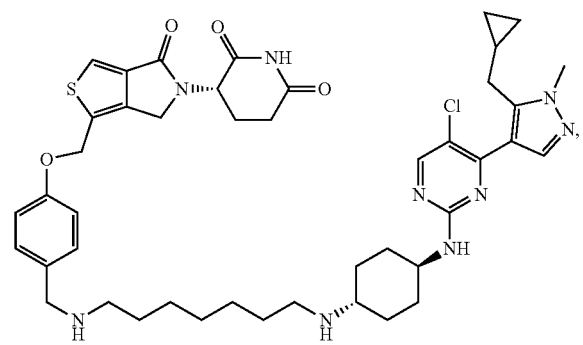
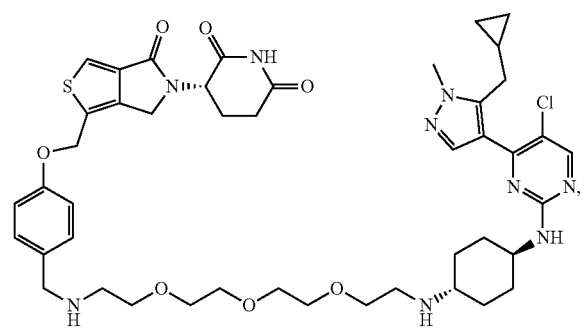
184
-continued
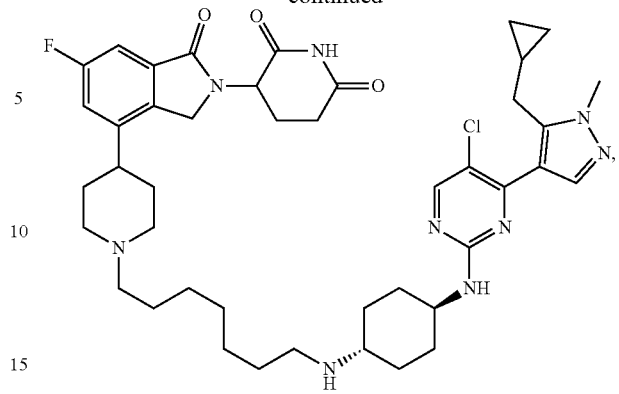
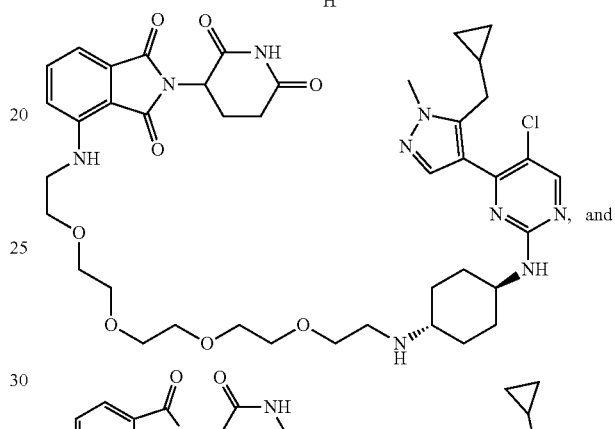
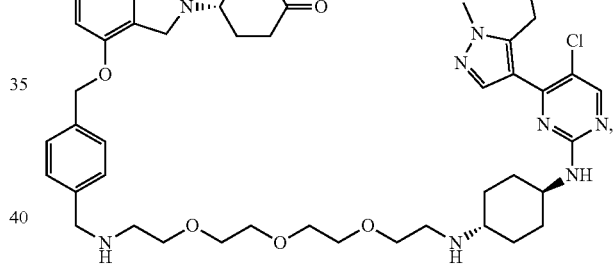
and pharmaceutically acceptable salts thereof.
33. A pharmaceutical composition comprising a compound of claim 1, or a pharmaceutically acceptable salt thereof, and at least one pharmaceutically acceptable carrier or excipient.
* * * * *